United States Patent
Zhang et al.

(10) Patent No.: US 10,961,231 B2
(45) Date of Patent: Mar. 30, 2021

(54) NTCP INHIBITORS

(71) Applicant: National Institute of Biological Sciences, Beijing, Beijing (CN)

(72) Inventors: Zhiyuan Zhang, Beijing (CN); Wenhui Li, Beijing (CN); Hanying Ruan, Beijing (CN); Yang Liu, Beijing (CN); Fengfeng Mao, Beijing (CN); Ying Li, Beijing (CN); Zhongmin Zhou, Beijing (CN)

(73) Assignee: National Institute of Biological Sciences, Beijing, Beijing (CN)

( * ) Notice: Subject to any disclaimer, the term of this patent is extended or adjusted under 35 U.S.C. 154(b) by 0 days.

(21) Appl. No.: 17/067,774

(22) Filed: Oct. 12, 2020

(65) Prior Publication Data

US 2021/0040072 A1    Feb. 11, 2021

Related U.S. Application Data

(63) Continuation of application No. PCT/CN2019/082588, filed on Apr. 19, 2019.

(30) Foreign Application Priority Data

Apr. 18, 2018  (WO) ................ PCT/CN2018/083033

(51) Int. Cl.
*C07D 405/12* (2006.01)
*C07D 307/18* (2006.01)
*A61P 1/16* (2006.01)
*C07D 409/12* (2006.01)
*C07D 407/12* (2006.01)

(52) U.S. Cl.
CPC .............. *C07D 405/12* (2013.01); *A61P 1/16* (2018.01); *C07D 307/18* (2013.01); *C07D 407/12* (2013.01); *C07D 409/12* (2013.01)

(58) Field of Classification Search
CPC .. C07D 405/12; C07D 307/18; C07D 407/12; C07D 409/12; A61P 1/16
See application file for complete search history.

(56) References Cited

U.S. PATENT DOCUMENTS

2006/0223743 A1    10/2006  Abel et al.

FOREIGN PATENT DOCUMENTS

| CN | 101120012 A | 2/2008 |
| CN | 104662036 A | 5/2015 |
| WO | WO2013159243 A1 | 10/2013 |
| WO | WO2016112321 A1 | 7/2016 |
| WO | WO20170004304 A1 | 1/2017 |

OTHER PUBLICATIONS

Eberle, Marcel K. et al. Modifications of the MeBmt Side Chain of Cyclosporin A Bioorganic & Medicinal Chemistry Letters Dec. 31, 1995(Dec. 31, 1995) No. 15 vol. 5 ISSN:0960-894Xpp. 1725-1728.

*Primary Examiner* — Robert H Havlin
(74) *Attorney, Agent, or Firm* — Richard Aron Osman

(57) ABSTRACT

The invention provides cyclosporin A analogues that are NTCP inhibitors and useful for treating HBV and/or HDV infection(s), hepatoprotection and amelioration of hypercholesterolemia, diabetes and inhibiting cancer.

20 Claims, 9 Drawing Sheets

NTCP INHIBITORS

INTRODUCTION

Figure 1A:
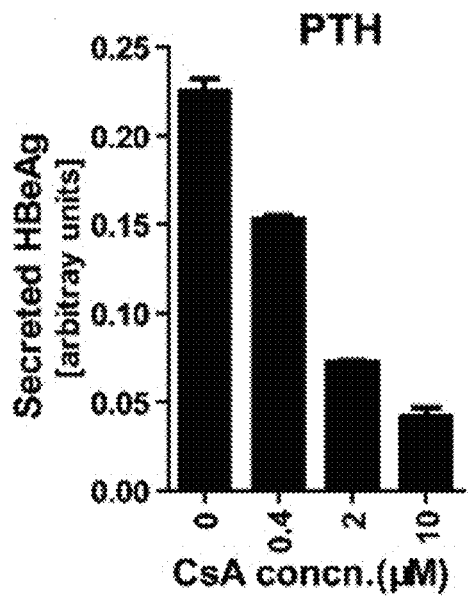

Bile acids (BAs) are molecules with endocrine activities controlling several physiological functions such as lipid metabolism, glucose homeostasis, energy metabolism and liver function. Alteration of BA homeostasis affects hepatic metabolic homeostasis and causes hepatic inflammation and pathogenesis of metabolic diseases such as non-alcoholic fatty liver disease (NAFLD), diabetes, and inflammatory bowel diseases (1), BA receptors, such as nuclear farnesoid X receptor (FXR), membrane G protein-coupled bile acid receptor-1 (Gpbar-1, also known as Takeda G protein-coupled receptor 5, or TGR5), and sphingosine-1-phosphate receptor 2 (S1PR2) have been illustrated as signaling integrators controlling glucose, lipid, and energy metabolism by binding to the nuclear hormone farnesoid X receptor (FXR) and Takeda G protein receptor 5 (TGR5) in multiple organs, leading to regulation of intestinal incretin secretion, hepatic gluconeogenesis, glycogen synthesis, energy expenditure, inflammation, and gut microbiome configuration. Alterations in BA metabolism and signaling are associated with obesity and type 2 diabetes meliitus (T2DM), whereas treatment of T2DM patients with BA sequestrants, or bariatric surgery in morbidly obese patients, results in a significant improvement in glycemic response that is associated with changes in the BA profile and signaling (1). These receptors can be targeted for the treatment of dyslipidemia, NAFLD, diabetes, and cardiovascular diseases (2).

Na$^+$-Taurocholate cotransporting peptide (NTCP, SLC10 A1) is a member of SLC10 solute carrier family. NTCP is specifically expressed in liver and in the basolateral membrane of differentiated hepatocytes. Its main function is to transport conjugated BAs from peripheral blood into hepatocytes. NTCP is a cellular receptor for hepatitis B virus (HBV) and hepatitis D virus (HDV) (3). NTCP variant rs2296651 (Ser267Phe) is reported to inversely associated with chronic hepatitis B and progression to cirrhosis and hepatocellular carcinoma in patients with HBV (4). Studies from humans carrying the SLC10 A1 variant alleles (homozygous R252H or S267F mutations) also exhibited a high level of plasma BAs, most with conjugated BAs, whereas no clinical symptoms were observed (5-7). Mouse with Ntcp deficiency (Slc10a1$^{-/-}$) also demonstrated with a good correlation between BAs levels and body weight (6). These altered BA profiles in blood under NTCP deficiency could be associated with the different activities of BA receptors in target organs and eventually affects the status of diseases, hence, blocking NTCP provides a therapeutic strategy for treating metabolic diseases (8).

Current therapies for diabetes do not ameliorate the risk of developing cardiovascular disease, specially lower the cholesterol level and related liver diseases. Thus there is a need in the art to develop new therapies to patients including those HBV and/or HDV infection(s) who suffer from diabetes and its associated diseases, and liver cancer.

SUMMARY OF THE INVENTION

The invention provides cyclosporin A analogues that are NTCP inhibitors and useful for treating HBV and/or HDV infection(s), hepatoprotection and amelioration of hypercholesterolemia, diabetes and inhibiting cancer.

In an aspect the invention provides novel compounds of formula:

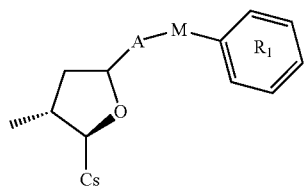

wherein:
A is O or S;
M is an optionally substituted methylene bridge, or a bond,
R1 is optionally substituted phenyl; and
Cs is cyclosporine A at position 1.
In embodiments:
M is a bond;
M is an optionally substituted methylene bridge;
M is a substituted or unsubstituted methyl-substituted methylene bridge, wherein the methyl substituents are selected from halogen, particularly F, Br, Cl or I, or an H isotope, particularly D;
A is O;
A is S;
R1 is comprises at ortho positions, independently, H, halogen, OH, Me or OMe, and at meta and para positions, independently, H, halogen, C1-C4 alkly, C1-C4 alkyoxy or a substituent disclosed herein;
the compound has a structure selected from any of Tables 1-4; and/or
the compound has Na$^+$-Taurocholate cotransporting peptide (NTCP) inhibiting activity (e.g. corresponding to an IC50 of 10 uM or less in a [$^3$H]-labeled taurocholie acid ([$^3$H]-TCA) uptake assay), inhibits HBV or HDV entry, and/or inhibits T-cell proliferation and NF-AT signaling pathway less than CsA.

In an aspect the invention provides a pharmaceutical composition comprising a therapeutically effective amount of a subject compound in unit dosage form and one or more pharmaceutically acceptable excipients.

In an aspect the invention provides a pharmaceutical composition comprising a therapeutically effective amount of a compound of subject compound and a different agent therapeutically active against HBV or HDV.

In an aspect the invention provides a method of using a subject compound or composition to treat hepatitis B virus (HBV) or hepatitis D virus HDV infection comprising: administering to a cell or person in need thereof an effective amount of a compound of claim 1, or a prodrug thereof.

In an aspect the invention provides a method of using a subject compound or composition to inhibit Na$^+$-Taurocholate cotransporting peptide (NTCP) comprising: administering to a cell or person in need thereof an effective amount of a compound of claim 1, or a prodrug thereof.

In embodiments the method further comprises antecedent step of diagnosing the infection, or the subsequent step of detecting a resultant amelioration of the infection.

The invention encompasses ail combination of the particular embodiments recited herein, as if each combination had been laboriously recited.

BRIEF DESCRIPTIONS OF THE DRAWINGS

Figure 1B:
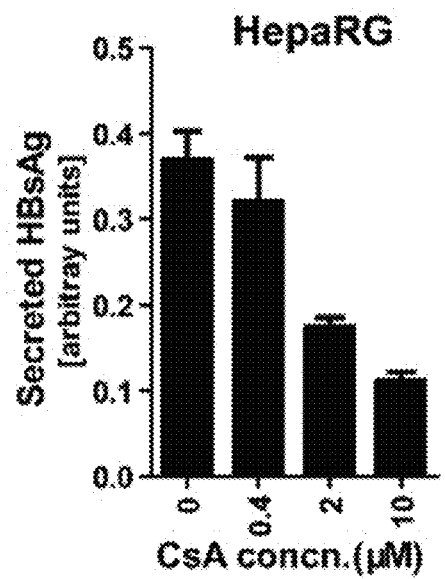

FIG. 1A. CsA inhibits HBV infection; PTH infection level was evaluated by checking HBeAg in culture medium using HBeAg ELISA kit at day 7 post infection. FIG. 1B. HepaRG infection level was evaluated by checking HBsAg in culture medium using HBsAg ELISA kit at day 11 post infection.

Figure 2A:
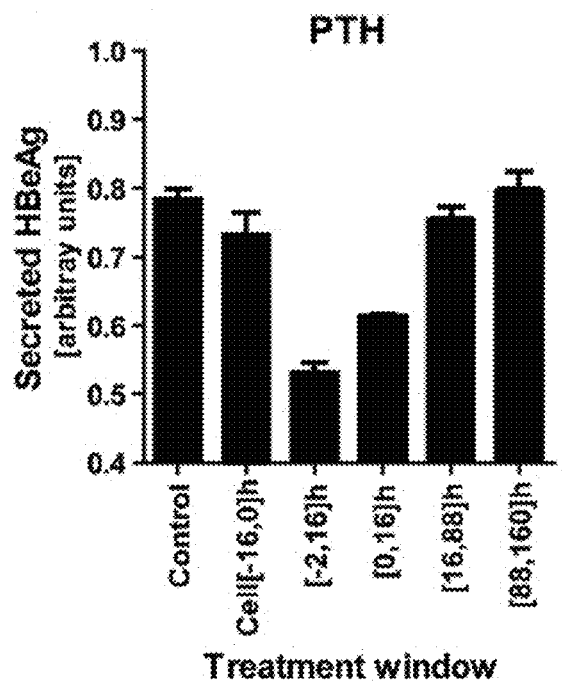
Figure 2B:
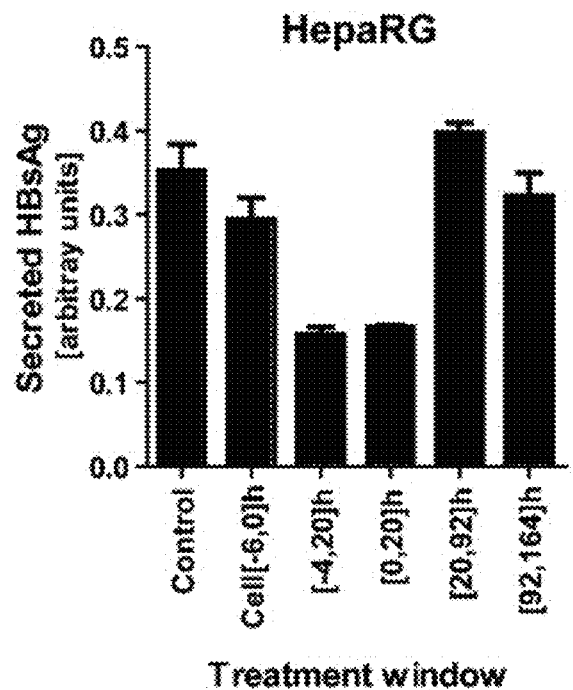

FIG. 2A. Time course of CsA inhibiting HBV and HDV; PTH infection level was evaluated by checking HBeAg in culture medium using HBeAg ELISA kit at day 7 post infection. FIG. 2B. HepaRG infection level was evaluated by checking HBsAg in culture medium using HBsAg ELISA kit at day 11 post infection.

Figure 3:
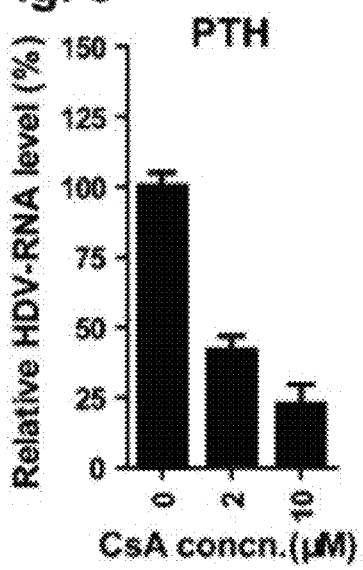

FIG. 3 CsA inhibits HDV infection.

Figure 4A:
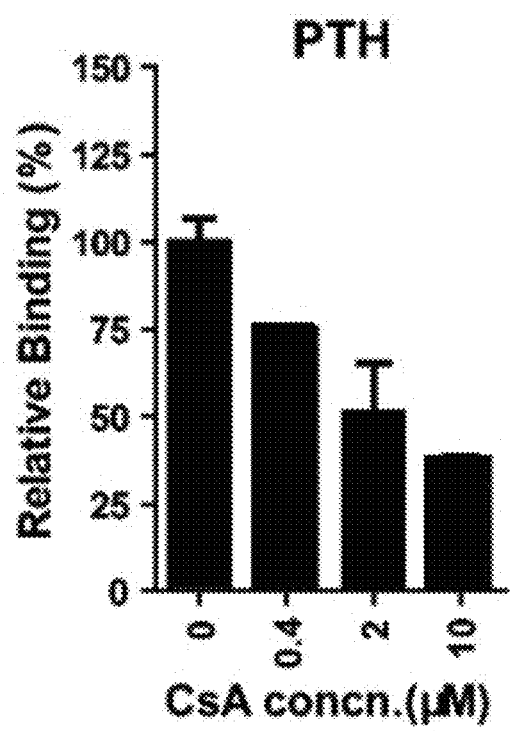
Figure 4B:
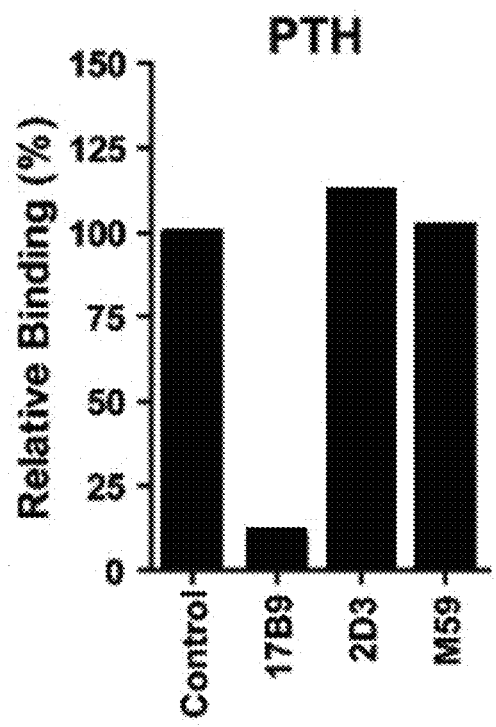
Figure 4C:
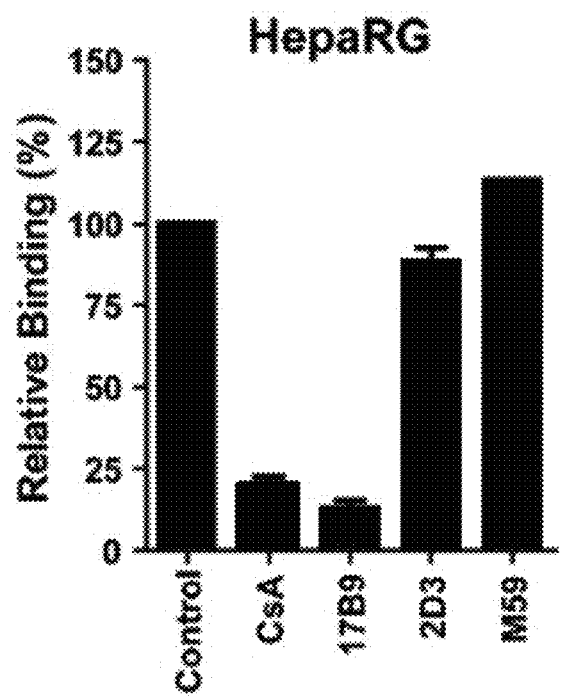

FIG. 4A. CsA inhibits HBV binding to target cells; CsA: 10 μM. FIG. 4B. 17B9: 50 μg/ml on PTH and 5 μg/ml on HepaRG. FIG. 4C, 2D3: 50 μg/ml on PTH and 5 μg/ml on HepaRG, Myr-59: 200 nM.

Figure 5:
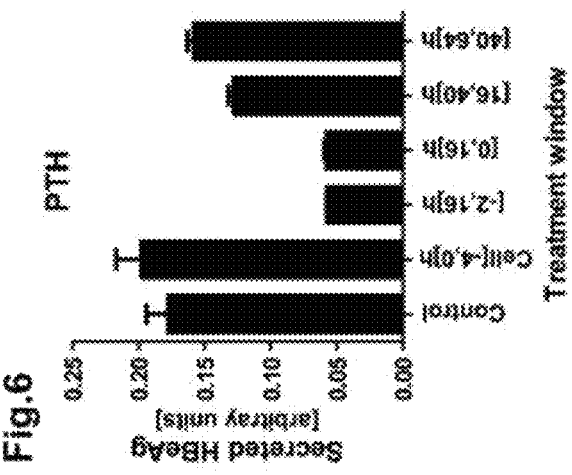

FIG. 5. CsA inhibits HepG2-NTCP cells uptake of [3H]-TC.

Figure 6:
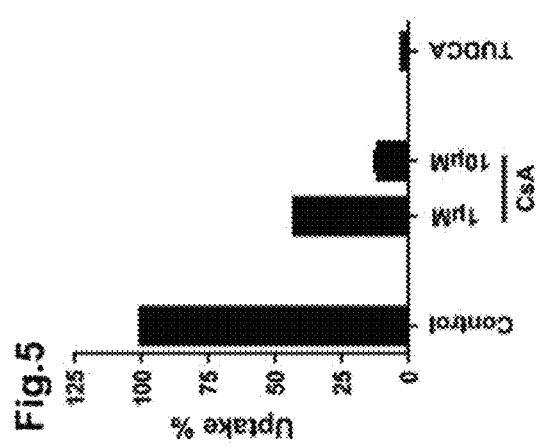

FIG. 6. Time course of CsA-1 inhibiting HBV infection.

Figure 7A:
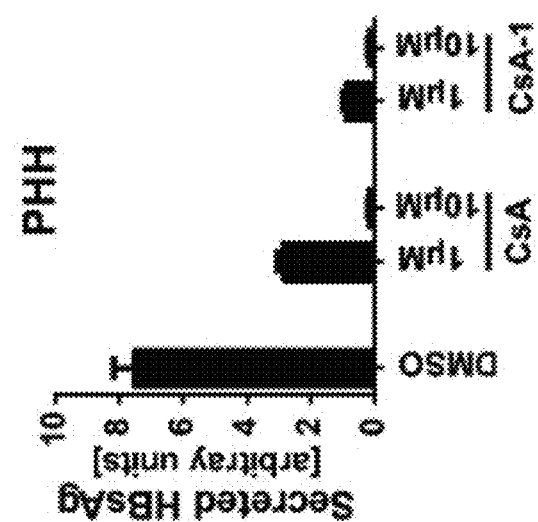
Figure 7B:
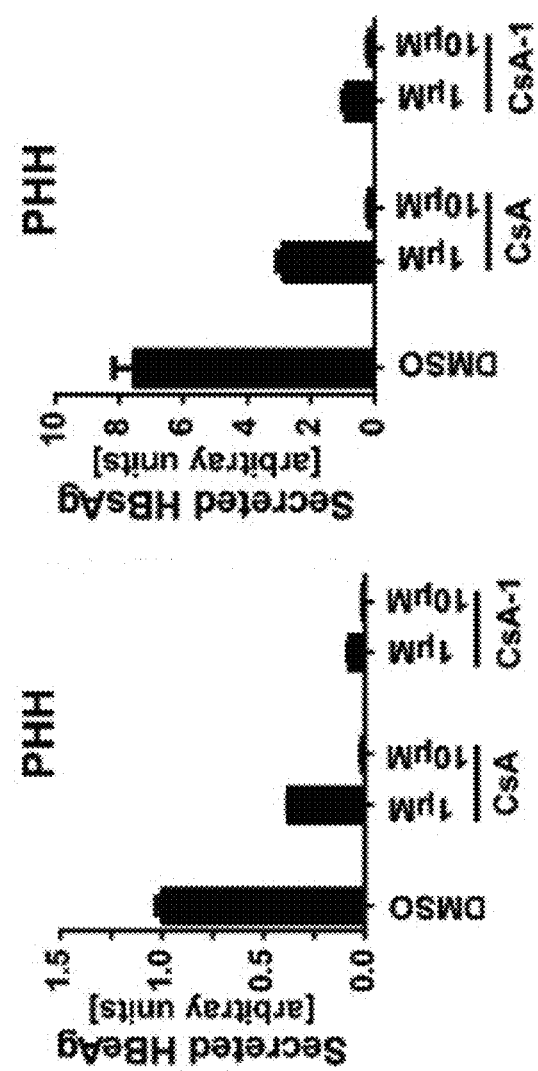
Figure 7C:
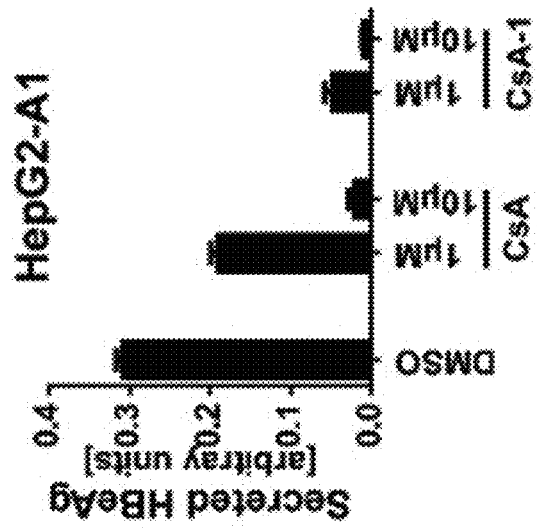

FIG. 7A. Comparison of anti-HBV activity of CsA and CsA-1, HepG2-NTCP cells; FIG. 7B. Primary human hepatocyte (PHH) at day 7; FIG. 1C. PHH infection level at day 11 post infection.

Figure 8:
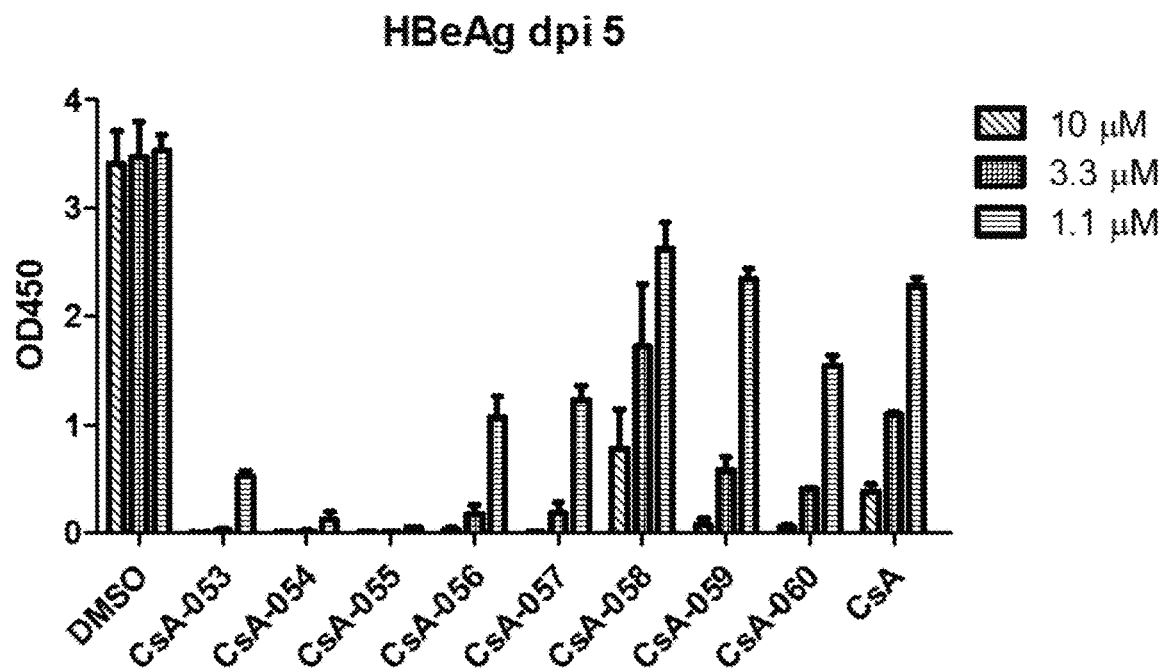

FIG. 8, CsA analogs inhibits HBV infection HBV infection of HepG2-NTCP cells.

Figure 9:
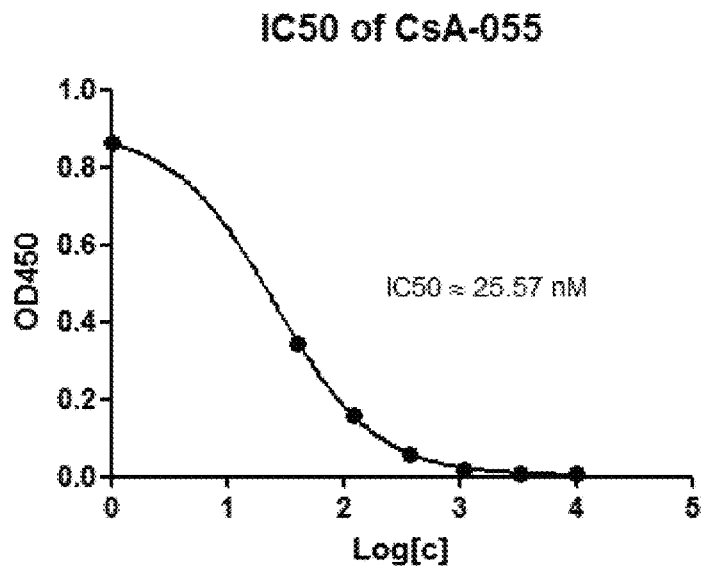

FIG. 9. IC50 determination of CsA-055 HBV infection of HepG2-NTCP cells.

Figure 10A:
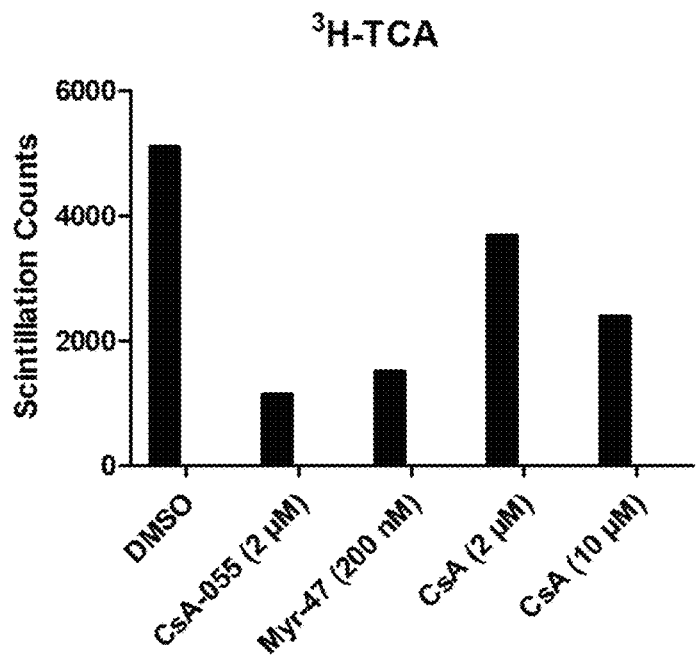
Figure 10B:
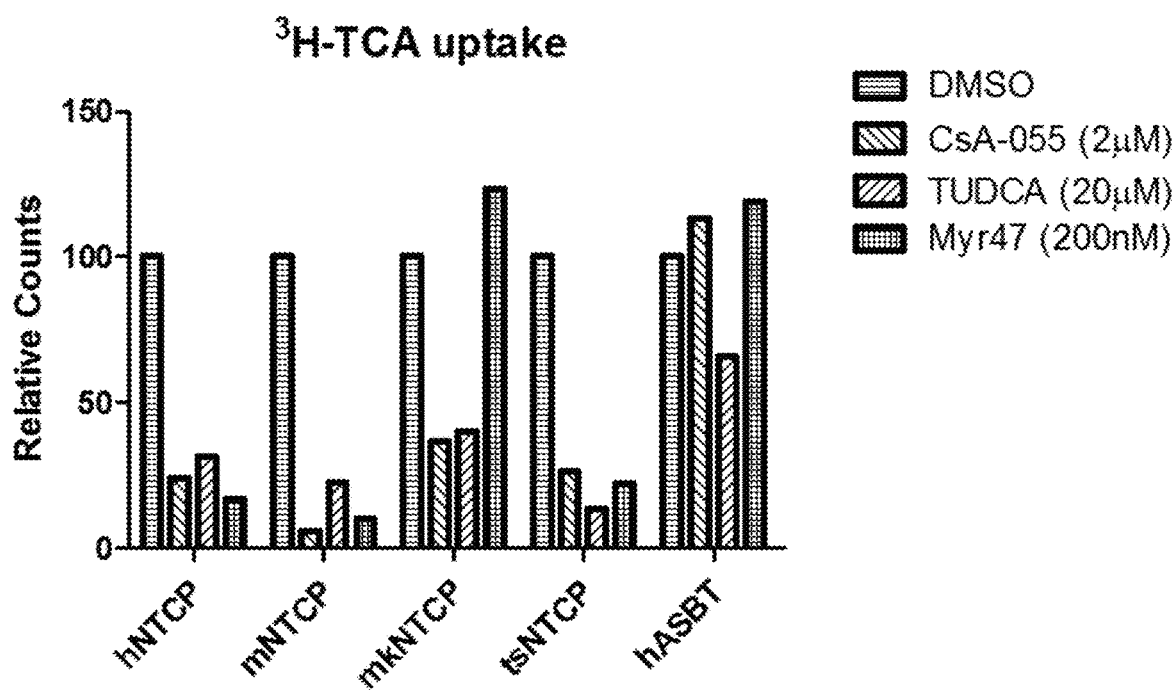

FIG. 10A. CsA-055 inhibits HepG2-NTCP uptake of [3H]-TC. FIG. 10B. Uptake of [3H]-TC.

Figure 11:
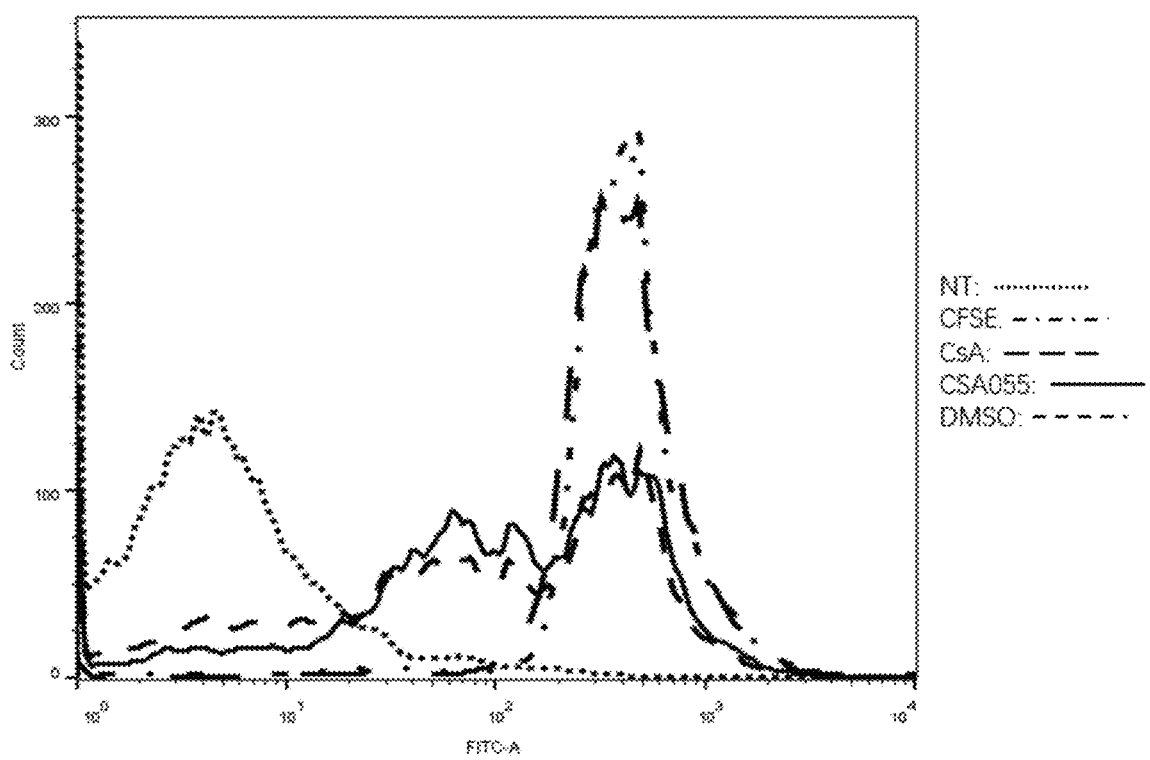

FIG. 11. Effect on T cell proliferation of CsA and Csa-055.

Figure 12:
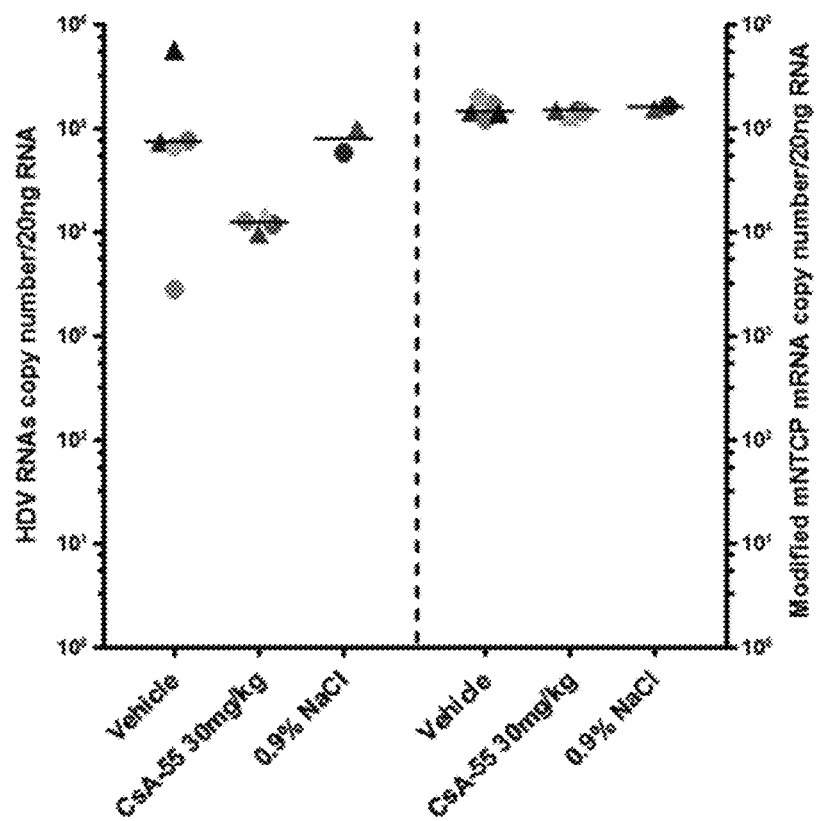

FIG. 12, CsA-055 blocks HDV infect hNTCP-mice.

Figure 13A:
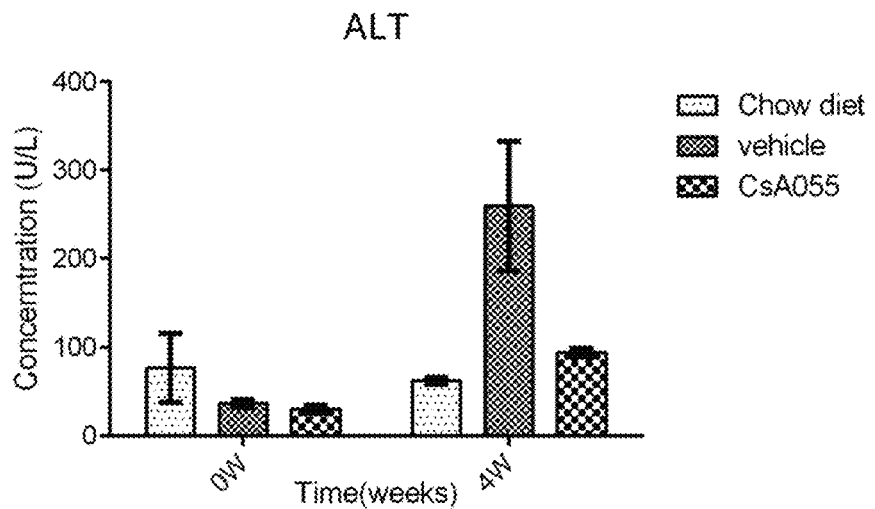
Figure 13B:
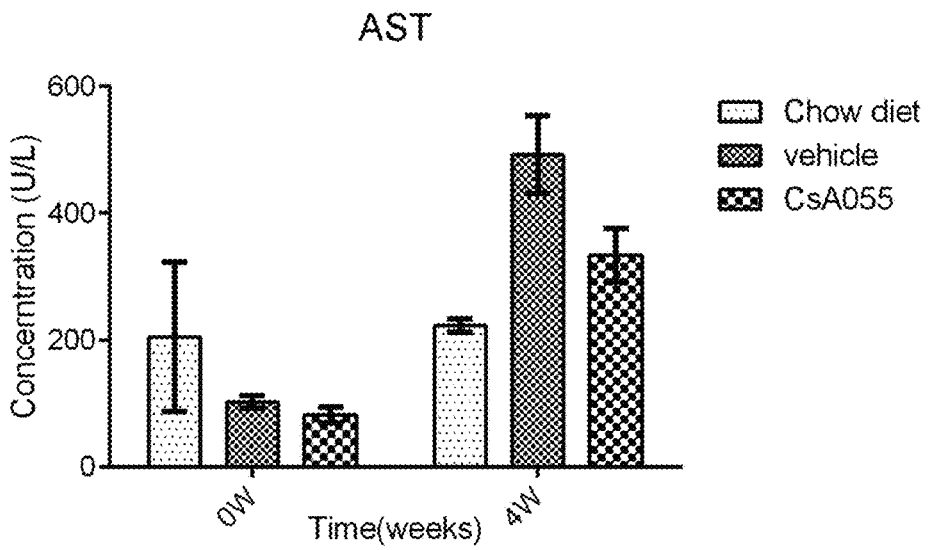
Figure 13C:
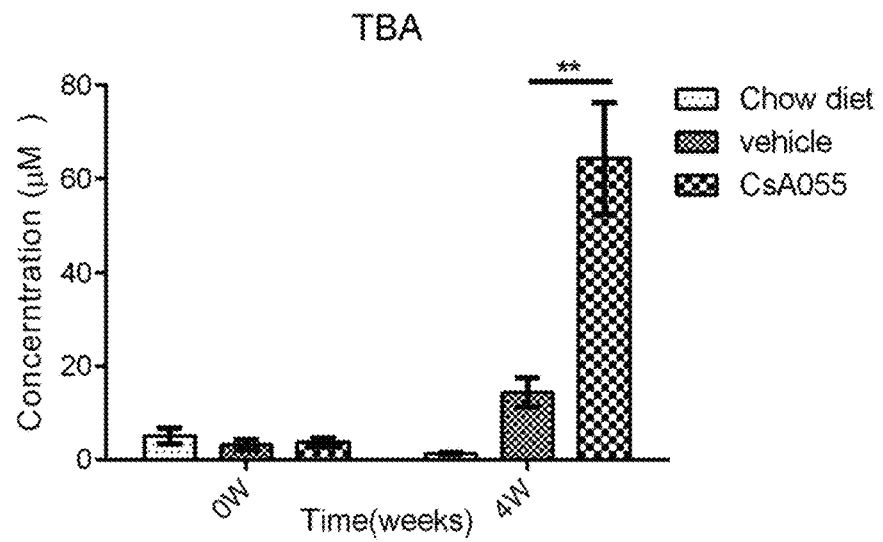
Figure 14:
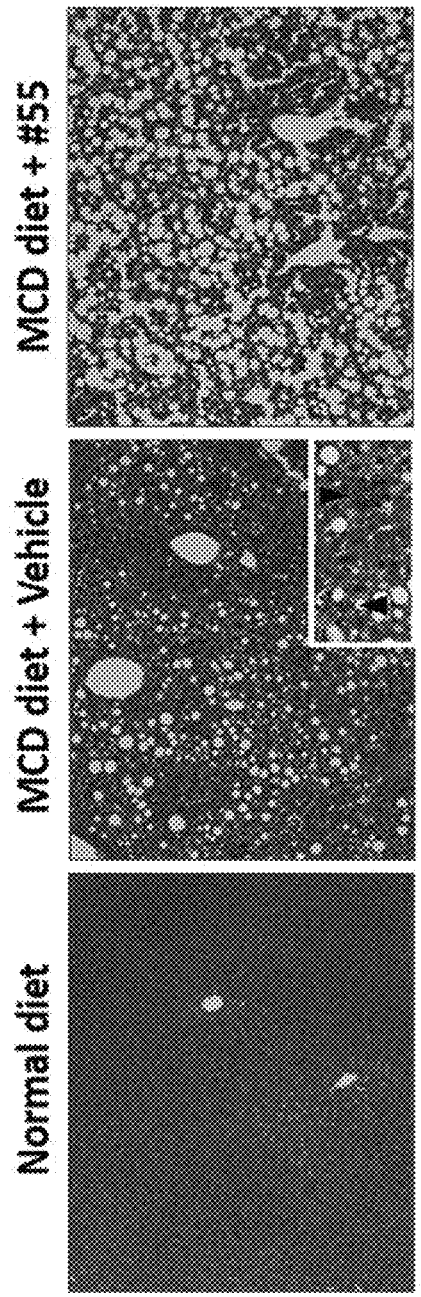

FIG. 13A. Serum parameters of C57BL/6 mice; ALT; FIG. 13B. Serum parameters of C57BL/6 mice; AST. FIG. 13C. Serum parameters of C57BL/6 mice; TBA FIG. 14. Representative images of hematoxylin and eosin staining, arrows indicate the infiltrating lymphocytes (10×).

Figure 15A:
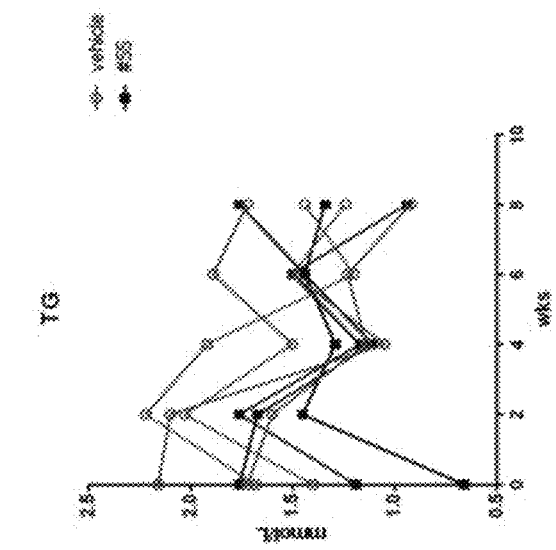
Figure 15B:
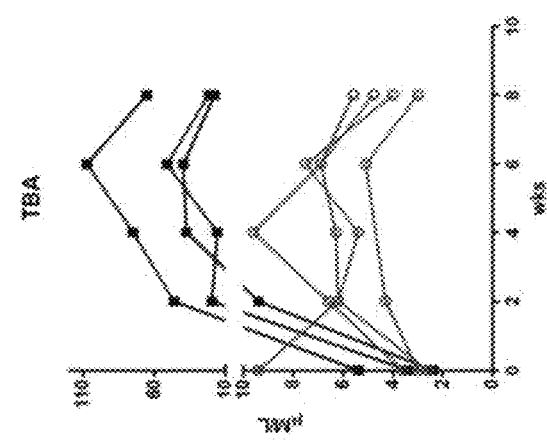
Figure 15C:
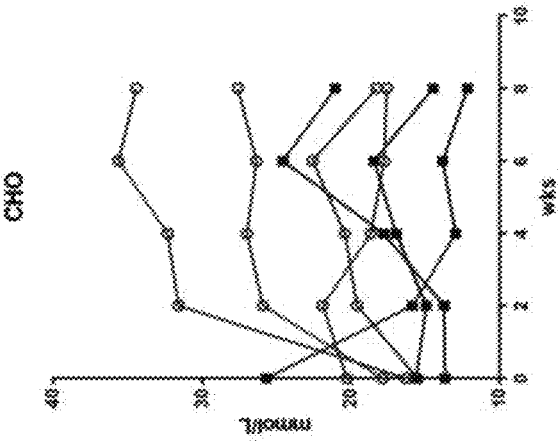

FIG. 15A. CsA-055 treatment (20 mg/kg, i.p.) lowered plasma total cholesterol levels and triglyceride levels in apoE−/− mice throughout the experiment; CHO: cholesterol; FIG. 15B. TBA: total bile acids; FIG. 15C. TG: triglyceride.

Figure 16A:
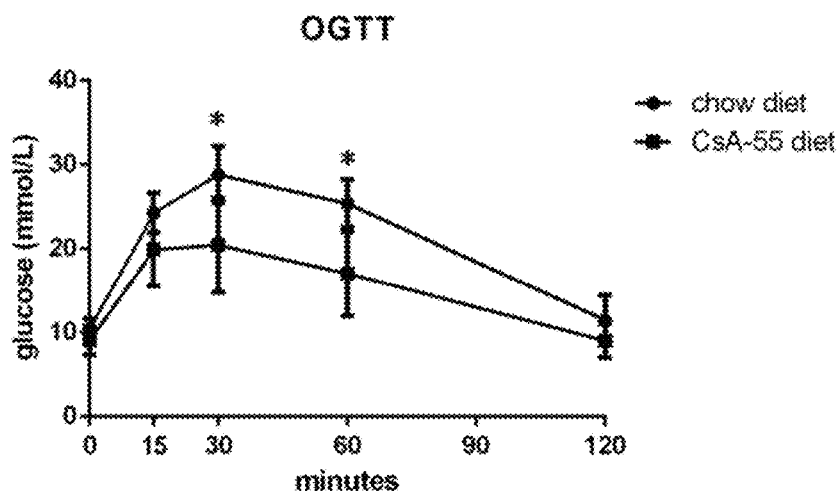
Figure 16B:
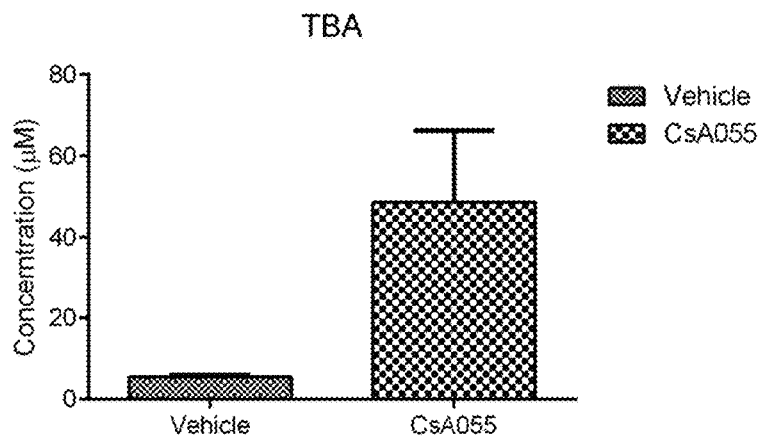

FIG. 16A. Glucose metabolism in fasted 2-week CsA-055 treated ob/ob mice; blood glucose was measured at indicated times after surcose administration. FIG. 16B Glucose metabolism in fasted 2-week CsA-055 treated ob/ob mice; bar graph.

Figure 17:
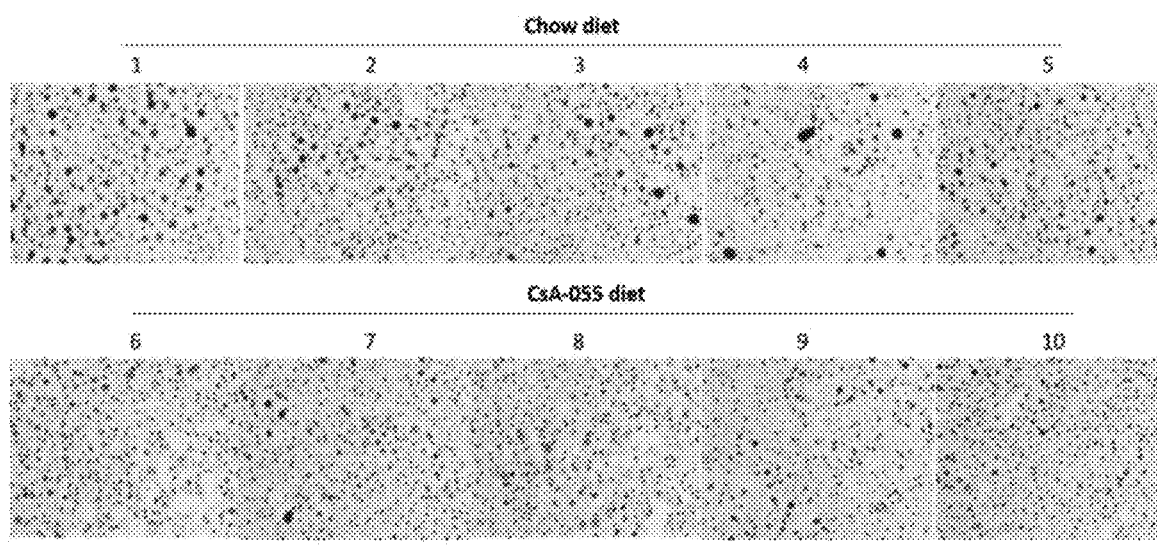

FIG. 17. Fat accumulation in liver after 2-week CsA-055 treatment in ob/ob mice; abundant large lipid droplets present in the chow diet group (mice: 1, 2, 3, 4, 5) compared with minimal lipid accumulation in CsA-055 treatment group (mice: 6, 7, 8, 9, 10).

DESCRIPTION OF PARTICULAR EMBODIMENTS OF THE INVENTION

The term "alkyl" refers to a hydrocarbon group selected from linear and branched saturated hydrocarbon groups of 1-18, or 1-12, or 1-6 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2'-butyl and 3,3-dimethyl-2-butyl groups.

Lower alkyl means 1-8, preferably 1-6, more preferably 1-4 carbon atoms; lower alkenyl or alkynyl means 2-8, 2-6 or 2-4 carbon atoms.

The term "alkenyl" refers to a hydrocarbon group selected from linear and branched hydrocarbon groups comprising at least one C=C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the and group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halogen" or "halo" refers to F, Cl, Br or I.

The term "heteroalkyl" refers to alkyl comprising at least one heteroatom.

The term "heteroaryl" refers to a group selected from:

5- to 7-membered aromatic, monocyclic rings comprising 1, 2, 3 or 4 heteroatoms selected from N, O, and S, with the remaining ring atoms being carbon;

8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring, and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1, 1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

In embodiments substituents are selected from optionally substituted heteroatom and optionally substituted, optionally hetero-, optionally cyclic C1-C18 hydrocarbyl, particularly wherein the optionally substituted, optionally hetero-, optionally cyclic C1-C18 hydrocarbyl is optionally-substituted, optionally hetero-, optionally cyclic alkyl, alkenyl or alkynyl, or optionally-substituted, optionally hetero-aryl; and/or the optionally substituted heteroatom is halogen, optionally substituted hydroxyl (such as alkoxy, aryloxy), optionally substituted acyl (such as formyl, alkanoyl, carbamoyl, carboxyl, amido), optionally substituted amino (such as amino, alkyiamino, dialkyiamino, amido, sulfamidyl), optionally substituted thiol (such as mercapto, alkylthioi, aryl thiol), optionally substituted sulfinyl or sulfonyl (such as alkylsulfinyl, arylsulfinyl, alkyl sulfonyl, aryl sulfonyl), nitro, or cyano.

In embodiments, substituents are selected from: halogen, —R', —OR', =O, =NR', =N—OR', —NR'R", —SR', —SiR'R"R''', —OC(O)R', —C(O)R', —CO2R', —CONR'R", —OC(O)NR'R", —NR"C(O)R', —NR'—C(O)NR"R", —NR'—SO2NR'", —NR"CO2R'. —NH—C(NH2)=NH, —NR'C(NH2)=NH, —NH—C(NH2)=NR', —S(O)R', —SO2R', —SO2NR'R", —NR"SO2R, —CN and —NO2, —N3, —CH(Ph)2, perfluoro(C1-C4)alkoxy and perfluoro(C1-C4)alkyl, in a number ranging from zero to three, with those groups having zero, one or two substituents being particularly preferred. R', R" and R'" each independently refer to hydrogen, unsubstituted (C1-C8)alkyl and heteroalkyl, (C1-C8)alkyl and heteroalkyl substituted with one to three halogens, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF3 and —CH2CF3), and when the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Preferred substituents are selected from: halogen, —R, —OR', =O, —NR'R", —SR', —SiR'R'R", —OC(O)R, —C(O)R', —CO2R', —CONR'R", —OC(O)NR'R", —NR"C(O)R', —NR"CO2R', —NR'—SO2NR"R'", —S(O) R', —SO2R', —SO2NR'R", —NR"SO2R, —CN and —NO2, perfluoro(C1-C4)alkoxy and perfluoro(C1-C4)alkyl, where R' and R" are as defined above.

Preferred substituents are disclosed herein and exemplified in the tables, structures, examples, and claims, and may be applied across different compounds of the invention, i.e. substituents of any given compound may be combi natorially used with other compounds.

In particular embodiments applicable substituents are independently substituted or unsubstituted heteroatom, substituted or unsubstituted, 0-3 heteroatom C1-C6 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamide, carboxyl, cyanyl, ester, halo, haloformyl, hydroperoxyl, hydroxyl, imine, isocyanide, iscyanide, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or triflurom-ethyl ether (OCF3).

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer/s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —CH2C(O)— groups (keto forms) may undergo tautomerism to form hydroxyl —CH=C(OH)— groups (end forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents. Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—(CH2)n-COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one pharmaceutically acceptable salt thereof to a subject in recognized need thereof.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of $R^{16}$ as described herein.

The subject compounds and stereoisomers thereof, and pharmaceutically acceptable salts thereof may be employed alone or in combination with at least one other therapeutic agent for treatment. In some embodiments, the compounds, stereoisomers thereof, and pharmaceutically acceptable salts thereof can be used in combination with at least one additional therapeutic agent. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

Also provided is a composition comprising a subject compound and stereoisomers thereof, and pharmaceutically acceptable salts thereof, and at least one pharmaceutically acceptable carrier.

The composition comprising a subject compound and stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The subject compounds and stereoisomers thereof, and pharmaceutically acceptable salts thereof can be administered orally in solid dosage forms, such as capsules, tablets, troches, dragdes, granules and powders, or in liquid dosage forms, such as elixirs, syrups, emulsions, dispersions, and suspensions. The subject compounds and stereoisomers thereof, and pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene gycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in *Remington's Pharmaceutical Sciences*, A. Osol, a standard reference text in the art.

For administration by inhalation, the subject compounds and stereoisomers thereof, and pharmaceutically acceptable salts thereof may be conveniently delivered in the form of an aerosol spray presentation from pressurized packs or nebulisers. The subject compounds and stereoisomers thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, and pharmaceutically acceptable salts thereof in an appropriate ophthalmic vehicle, such that the subject compound and stereoisomers thereof, and at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the compound, stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound, stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, and pharmaceutically acceptable salt thereof disclosed herein can be administered as the sole active ingredient or in combination with at least one second active ingredient.

The subject compounds are incorporated into pharmaceutical compositions or formulations. The compositions will contain pharmaceutically acceptable diluents and/or carriers, i. e. diluents or carriers that are physiologically compatible and substantially free from pathogenic impurities. Suitable excipients or carriers and methods for preparing administrable compositions are known or apparent to those skilled in the art and are described in more detail in such publications as Remington's Pharmaceutical Science, Mack Publishing Co, NJ (1991). The compositions may also be in the form of controlled release or sustained release compositions as known in the art. For many applications the subject compounds are administered for morning/daytime dosing, with off period at night.

The subject compounds may be used per se, or in the form of their pharmaceutically acceptable salts, such as hydrochlorides, hydrobromides, acetates, sulfates, citrates, carbonates, trifluoroacetates and the like. When compounds contain relatively acidic functionalities, salts can be obtained by addition of the desired base, either neat or in a suitable inert solvent. Examples of pharmaceutically acceptable base addition salts include sodium, potassium, calcium, ammonium, organic amino, or magnesium salts, or the like. When compounds contain relatively basic functionalities, salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al, "Pharmaceutical Salts", Journal of Pharmaceutical Science, 1977, 66, 1-19).

The neutral forms of the compounds may be regenerated by contacting the salt with a base or acid, and isolating the parent compound in the conventional manner. The parent form of the compound differs from the various salt forms in certain physical properties, such as solubility in polar solvents, but otherwise the salts are equivalent to the parent form of the compound for the purposes of this invention.

In addition to salt forms, this invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the present invention. Certain compounds of the invention may exist in multiple crystalline or amorphous forms. In general, all physical forms are equivalent for the uses contemplated by the present invention and are intended to be within the scope of the invention.

Some of the subject compounds possess asymmetric carbon atoms (optical centers) or double bonds; the racemates, diastereomers, geometric isomers and individual isomers are all intended to be encompassed within the scope of the present invention.

The compounds of the invention may also contain unnatural proportions of atomic isotopes at one or more of the atoms that constitute such compounds, such as deuterium, e.g. —$CD_3$, $CD_2H$ or $CDH_2$ in place of methyl. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

The compounds are generally administered in a "therapeutically effective amount", i.e. the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The contacting is generally effected by administering to the subject an effective amount of one or more compounds having the general formula I (supra), including the various embodiments described above. Generally administration is adjusted to achieve a therapeutic dosage of about 0.1 to 50, preferably 0.5 to 10, more preferably 1 to 10 mg/kg, though optimal dosages are compound specific, and generally empirically determined for each compound.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the mimetic is usually a minor component (from about 0.1 to about 50% by weight or preferably from about 1 to about 40% by weight) with the remainder being various vehicles or carriers and processing aids helpful for forming the desired dosing form. Unit dosage formulations are preferably about of 5, 10, 25, 50, 100, 250, 500, or 1,000 mg per unit. In a particular embodiment, unit dosage forms are packaged in a multipack adapted for sequential use, such as blisterpack comprising sheets of at least 6, 9 or 12 unit dosage forms.

The subject compositions may also be coformulated and/or coadministered with a different compound useful to treat HBV/HDV infection.

Tables of CsA analogs/NTCP inhibitors

CsA:

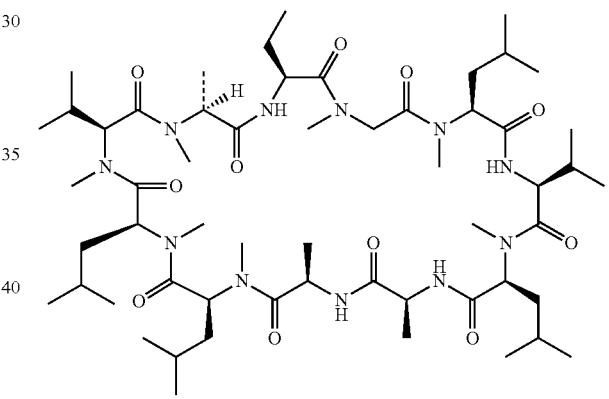

TABLE 1

| phenylthiol compounds |
|---|
| 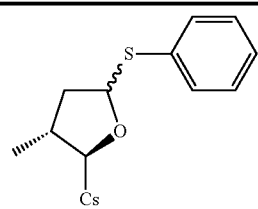 1B |
| 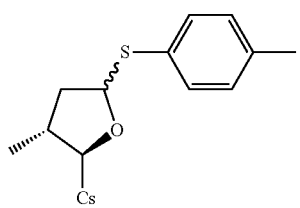 2A |

TABLE 1-continued
phenylthiol compounds
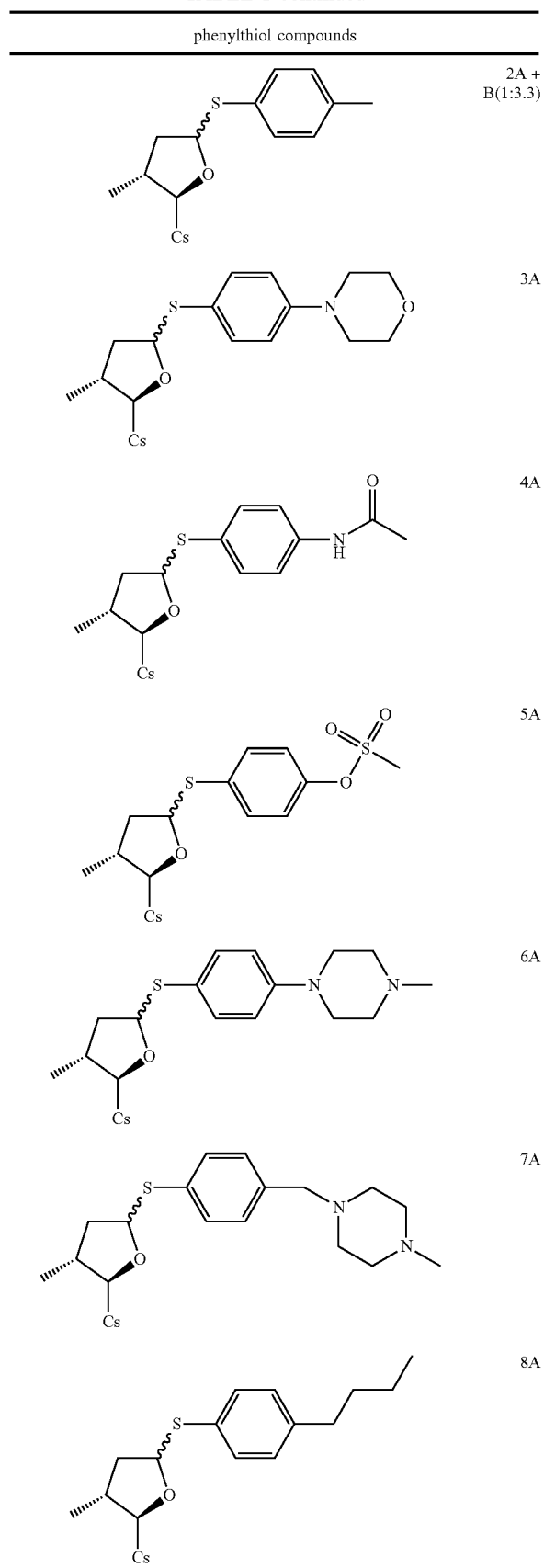
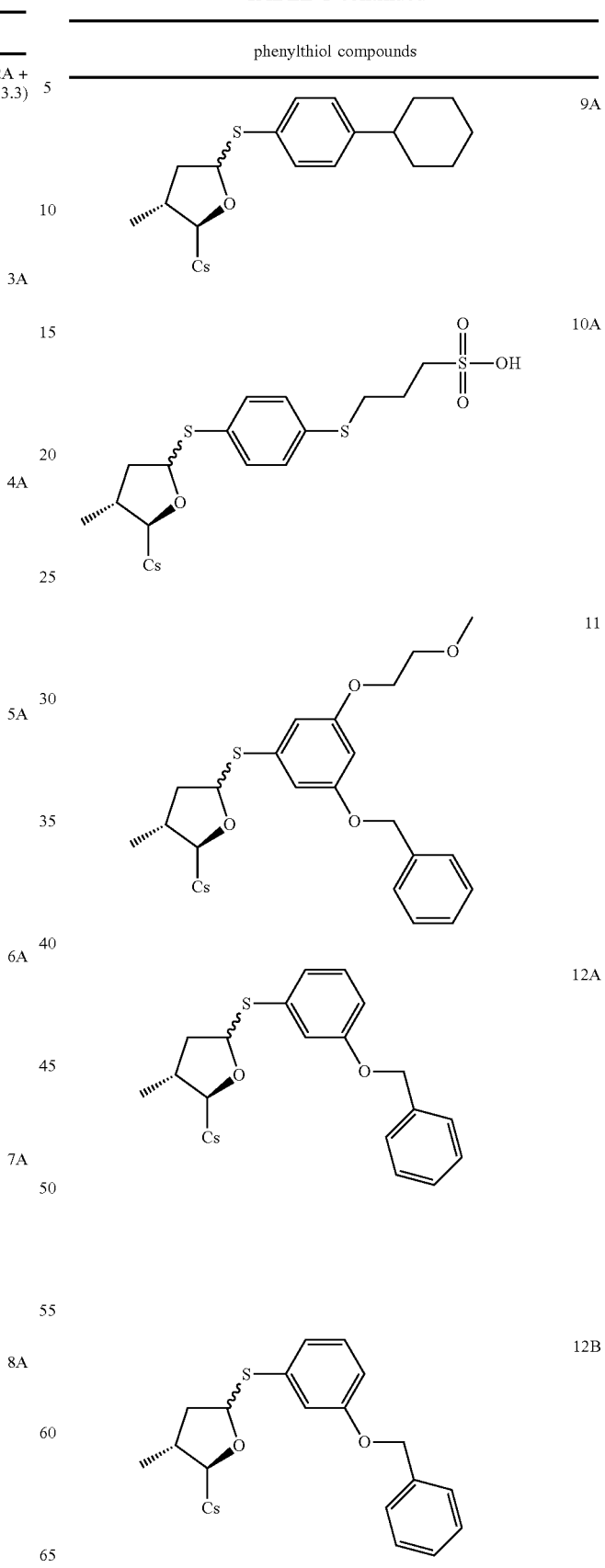

TABLE 1-continued
phenylthiol compounds
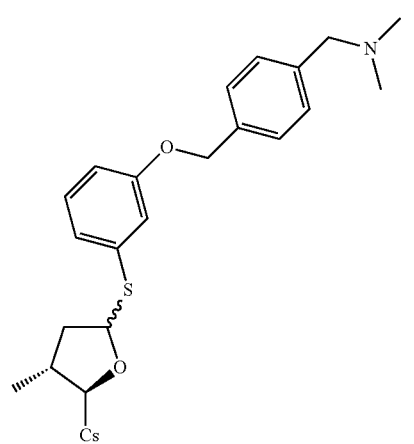 13A
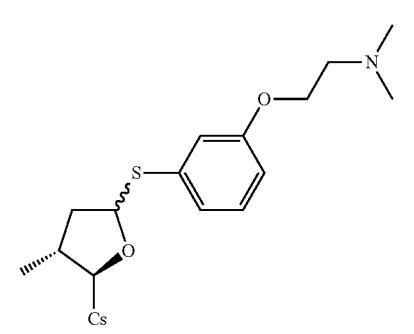 14A
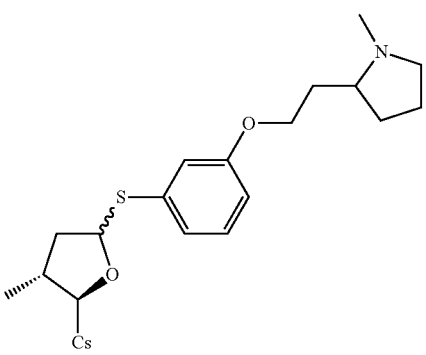 15A
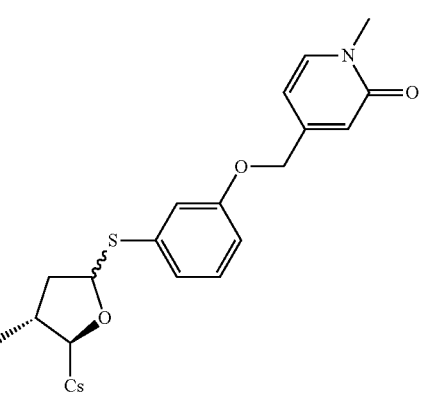 16A
TABLE 1-continued
phenylthiol compounds
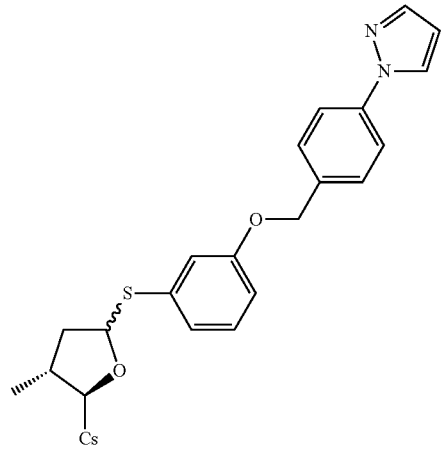 17A
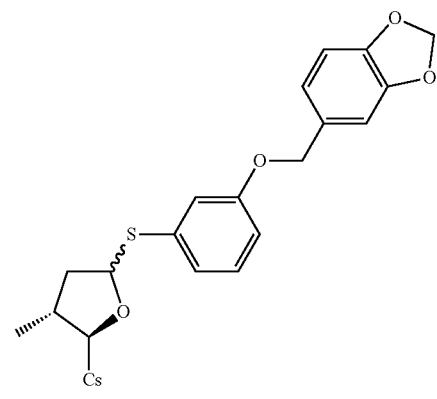 18A
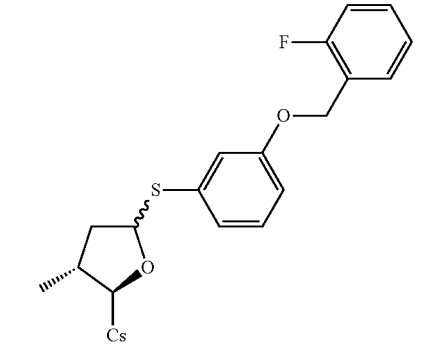 19A
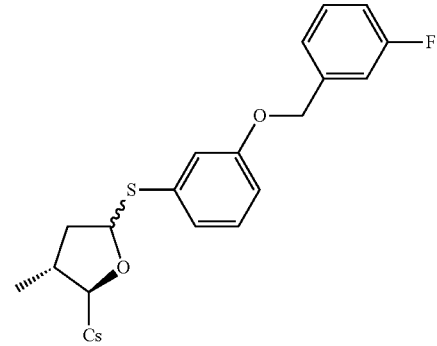 20A TABLE 1-continued
phenylthiol compounds
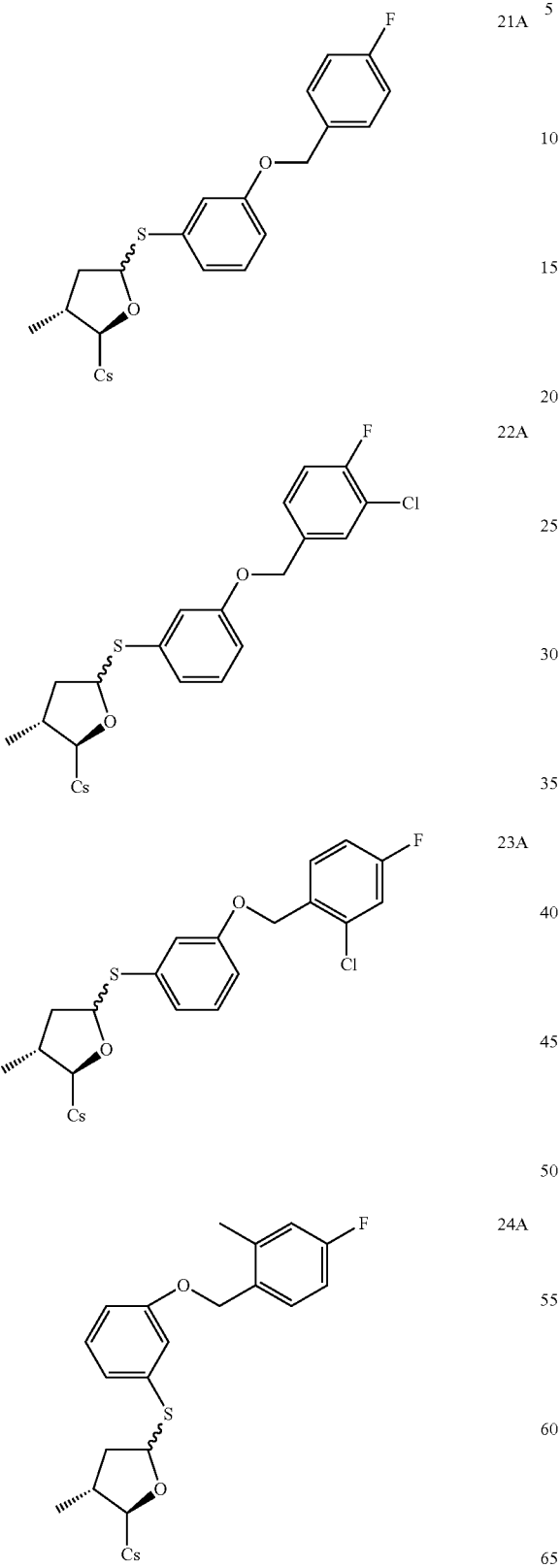
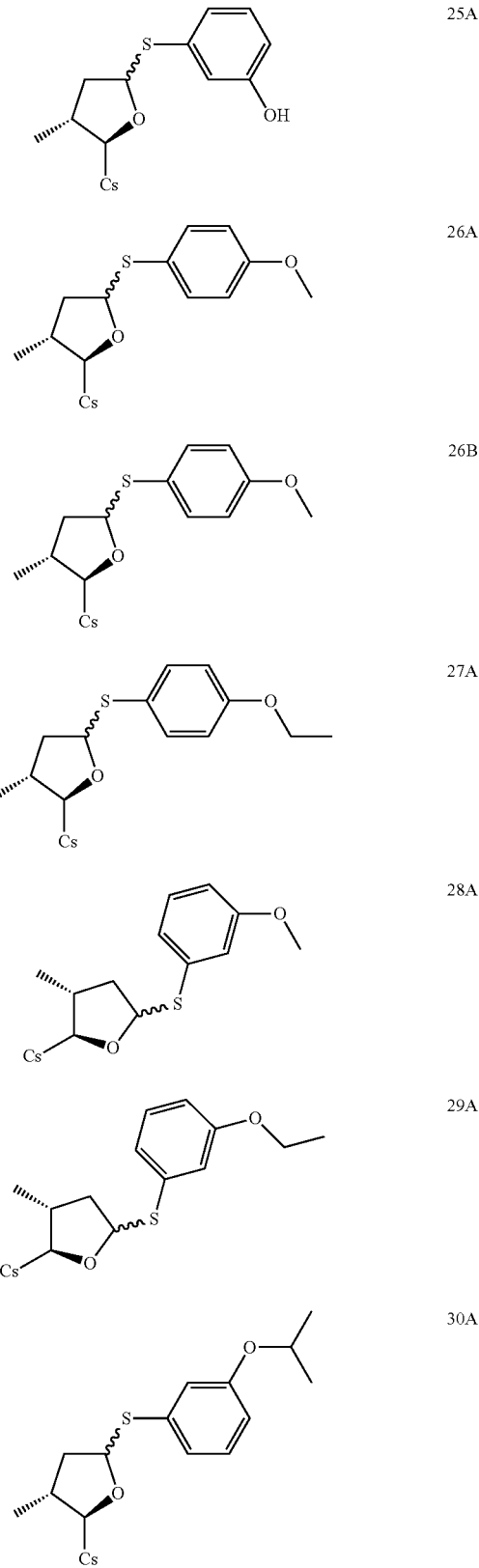

TABLE 1-continued
phenylthiol compounds
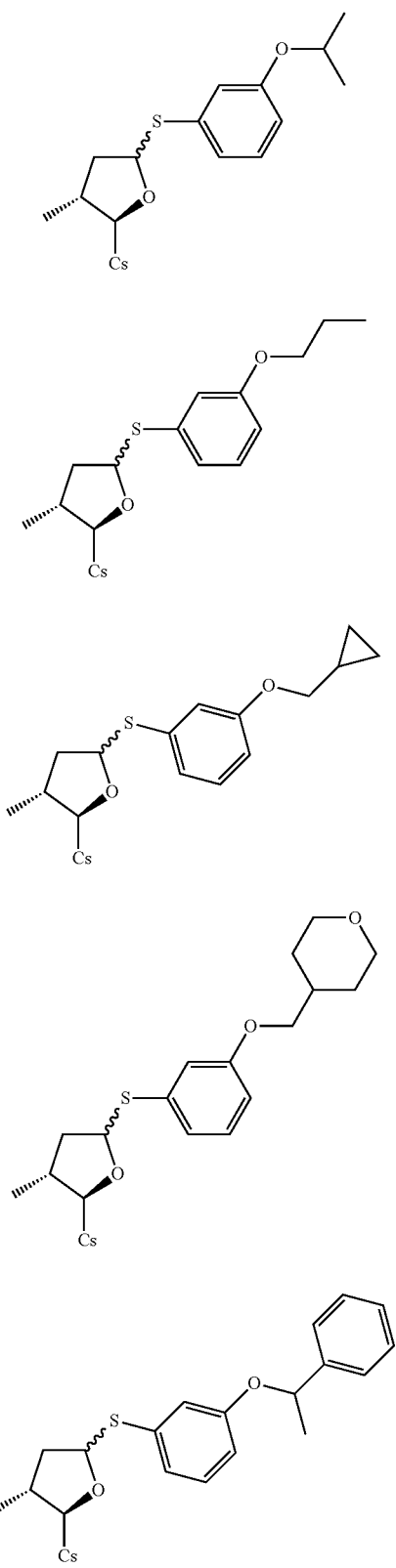
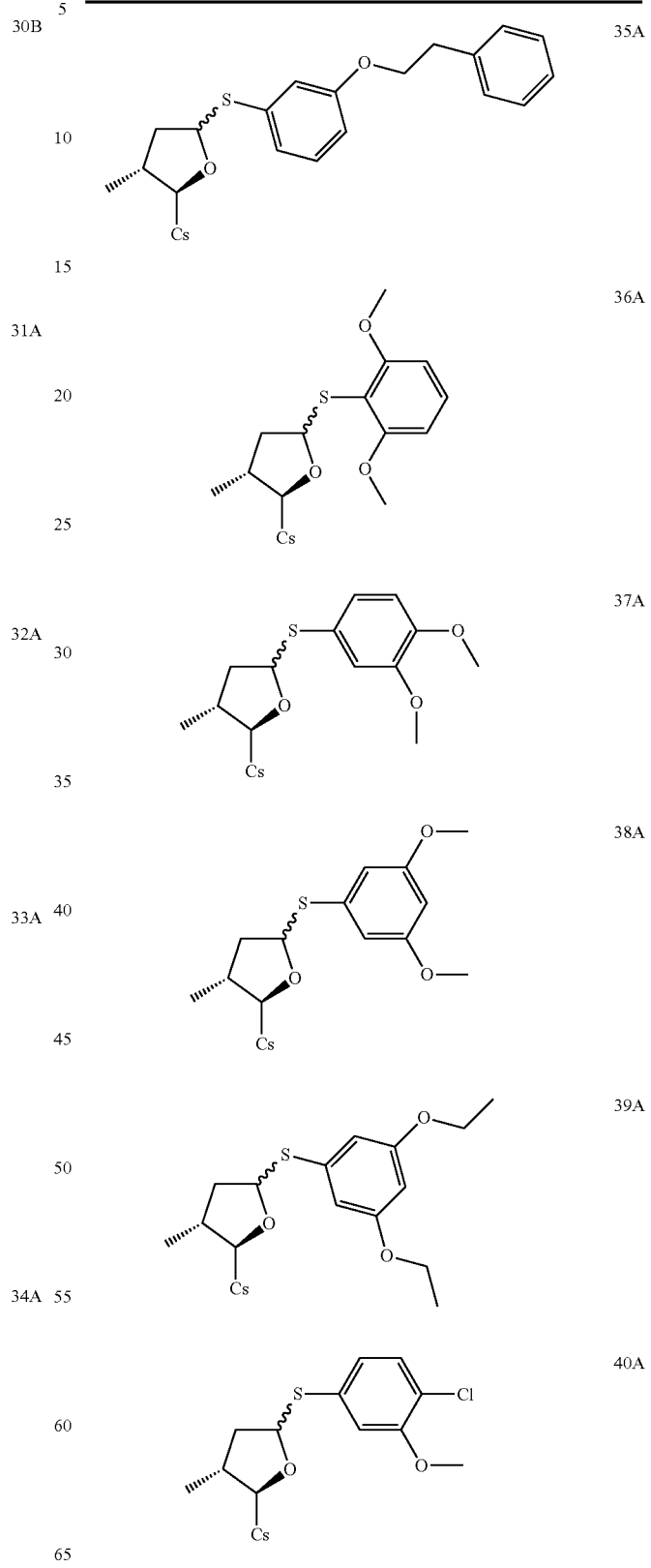

TABLE 1-continued
phenylthiol compounds
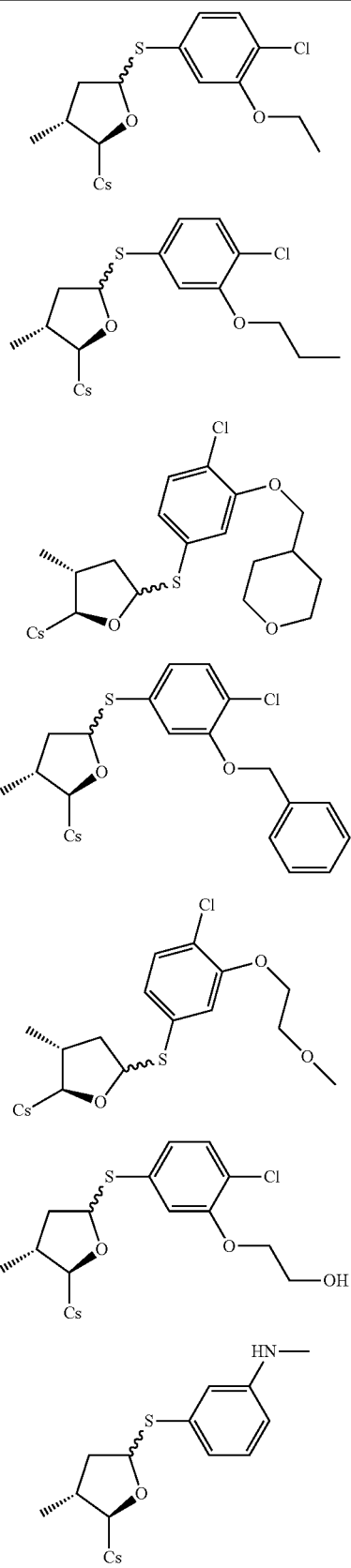
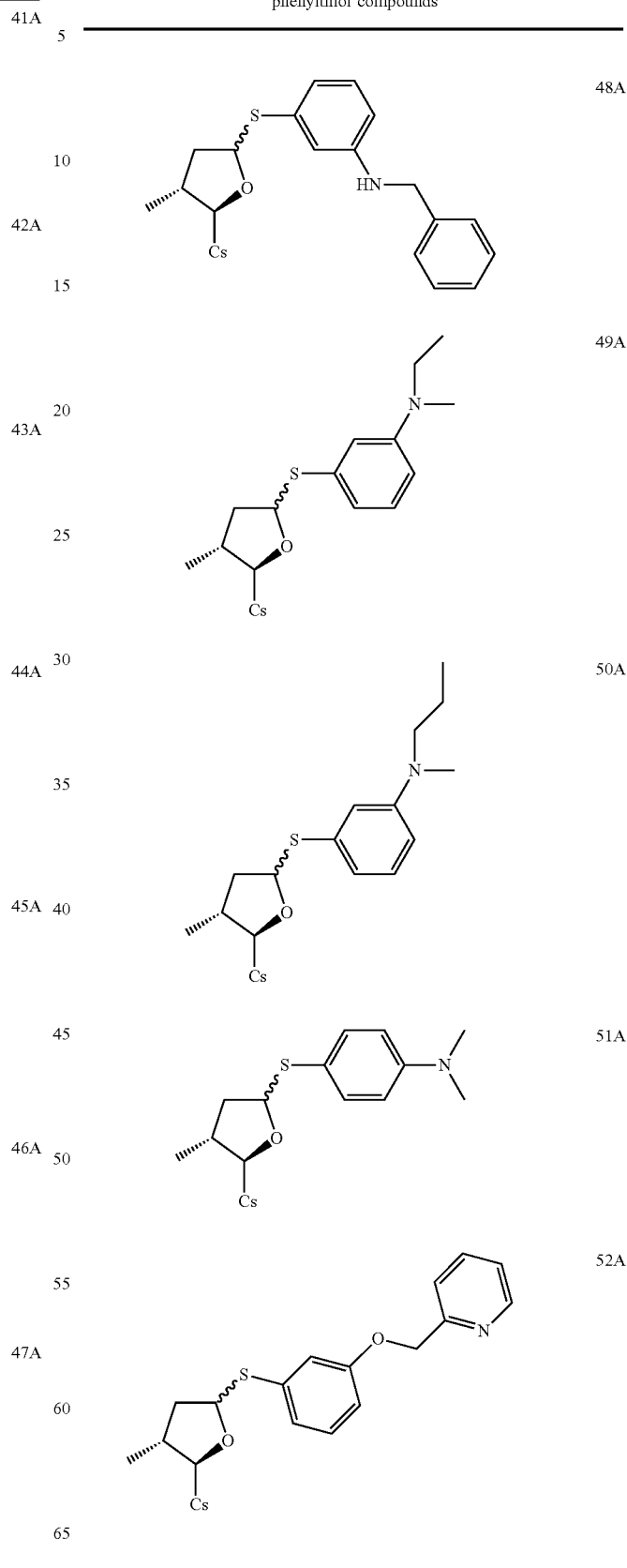

TABLE 1-continued
phenylthiol compounds
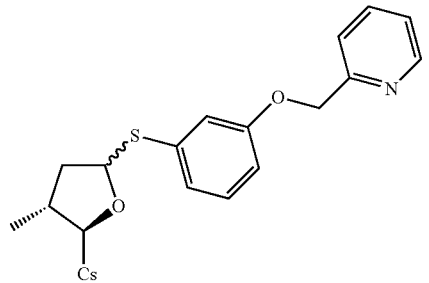 52A + B(1:1.1)
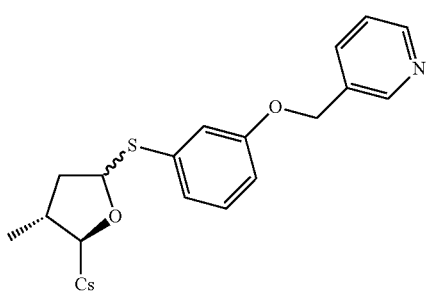 53A
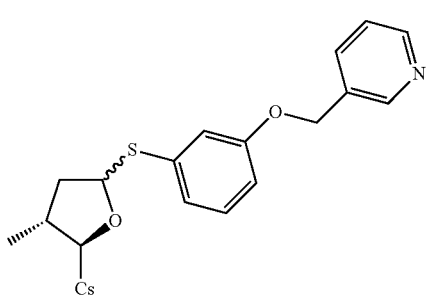 53A + B(1:1.5)
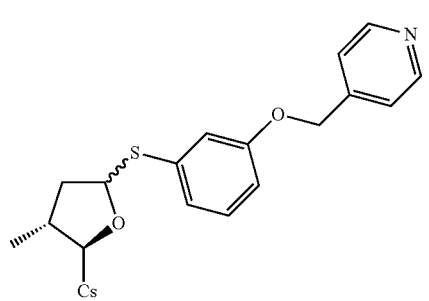 54A
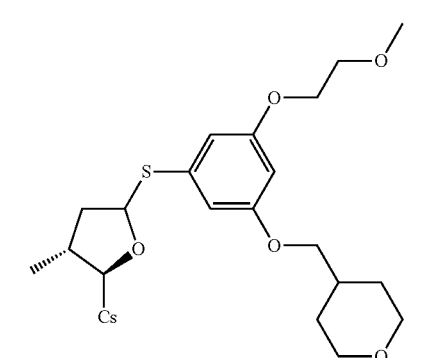 55
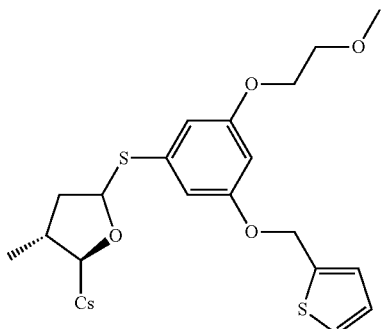 56
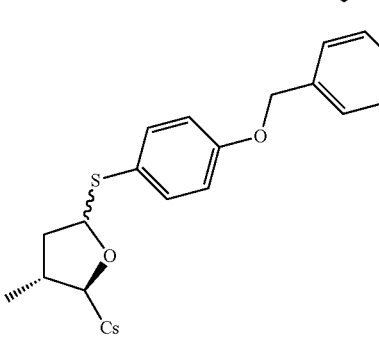 57A
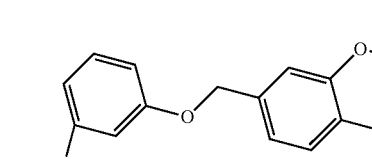 58A
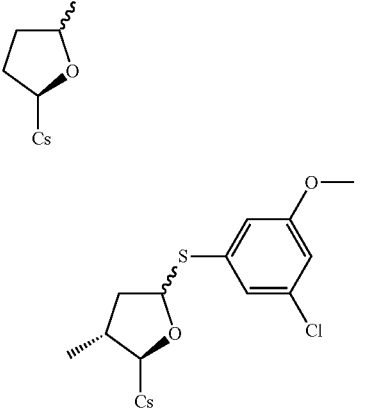 59A
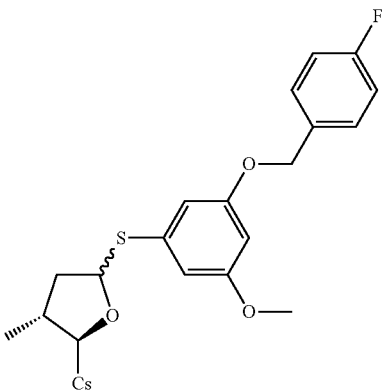 60A TABLE 1-continued
phenylthiol compounds
| | |
|---|---|
| 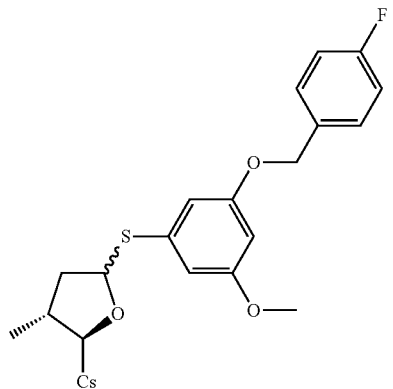 | 60A + B(1:1.4) |
| 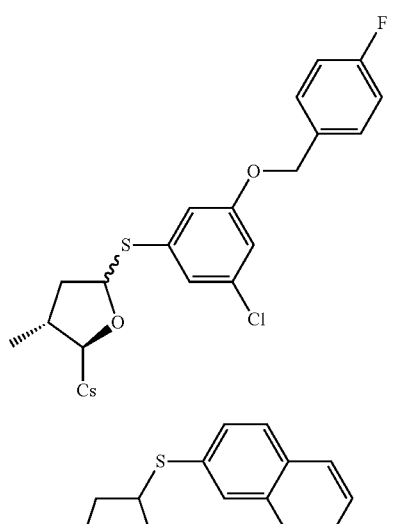 | 61A |
| 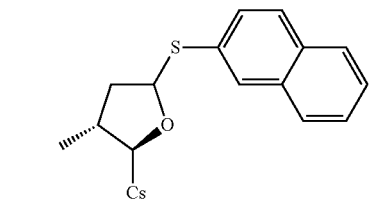 | 62 |
| 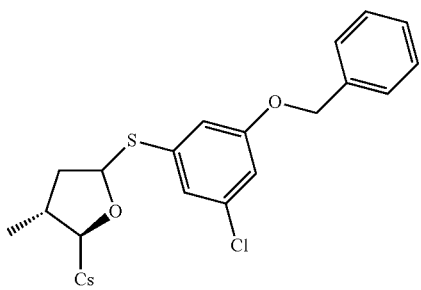 | 63 |
| 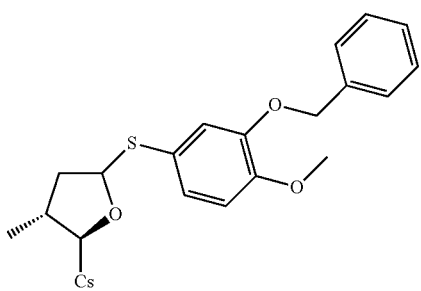 | 64 |
| 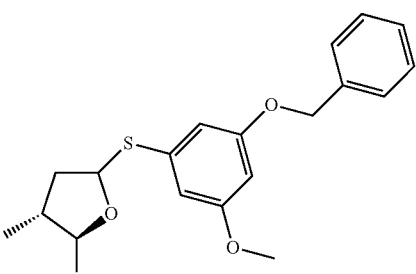 | 65 |
| 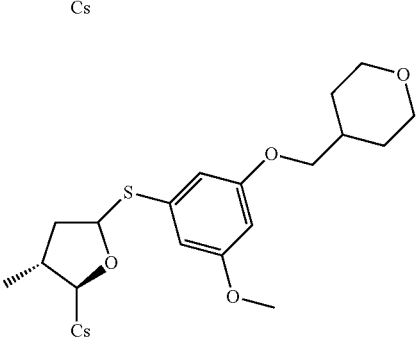 | 66 |
| 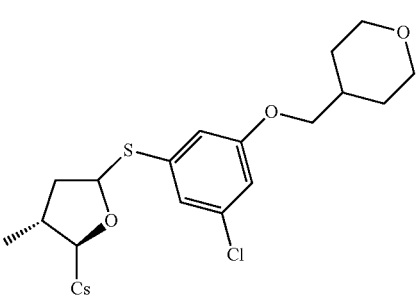 | 67 |
| 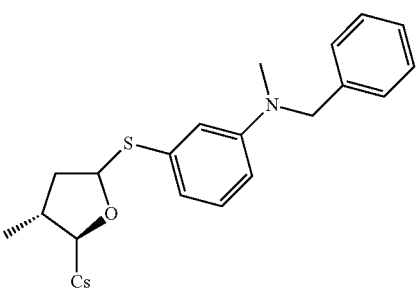 | 68 |
| 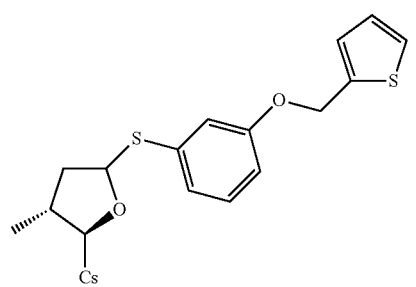 | 69 |

TABLE 1-continued
phenylthiol compounds
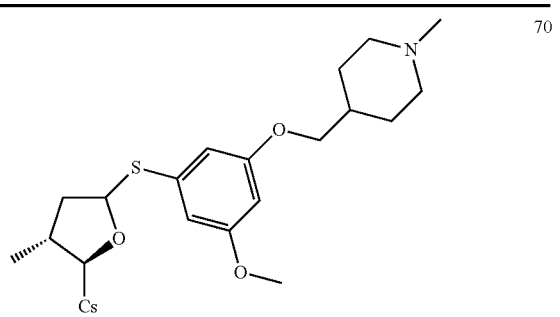
70
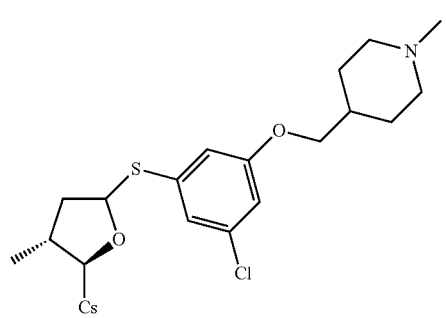
71
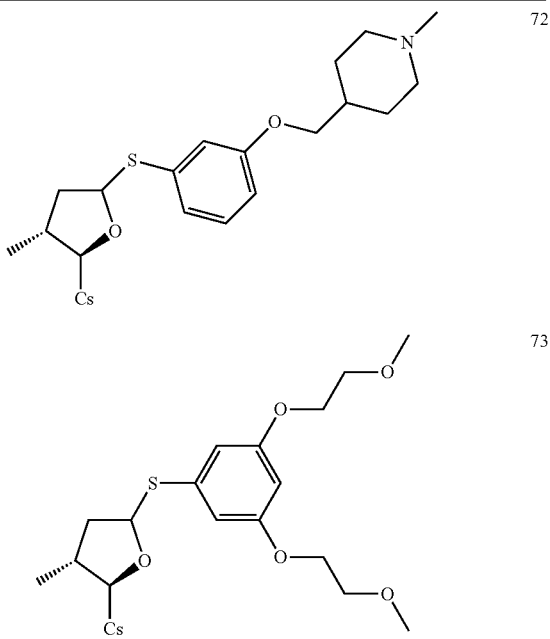
72
73
TABLE 2
phenyloxy compounds
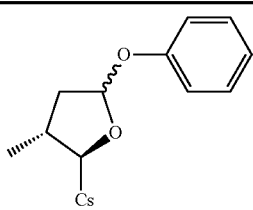
1B-o
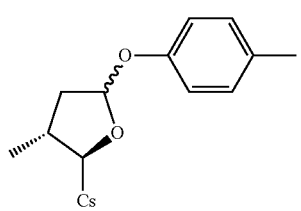
2A-o
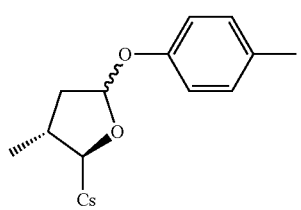
2A + B(1:3.3)-o
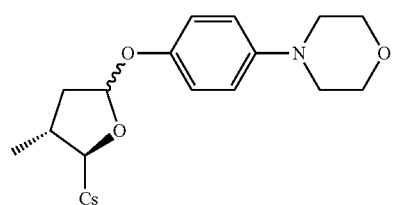
3A-o TABLE 2-continued
phenyloxy compounds
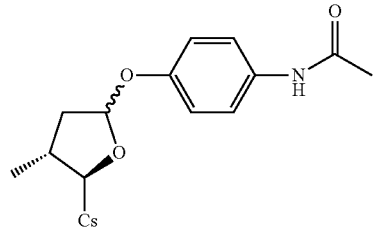
4A-o
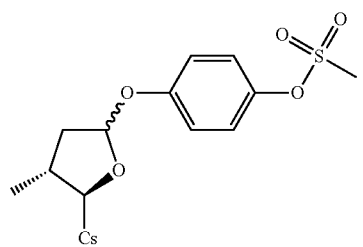
5A-o
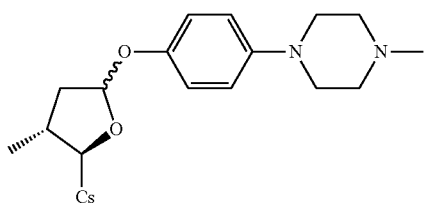
6A-o
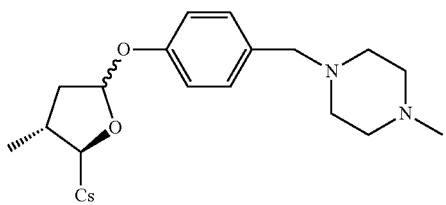
7A-o
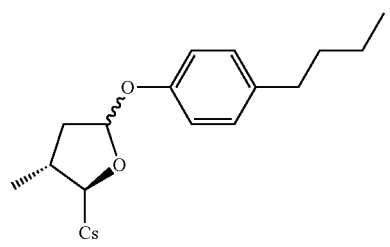
8A-o
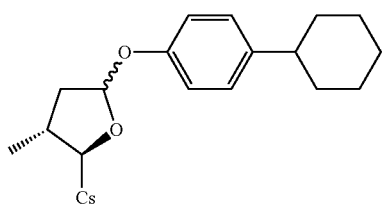
9A-o TABLE 2-continued phenyloxy compounds 10A-o 11-o 12A-o 12B-o 13A-o TABLE 2-continued
phenyloxy compounds
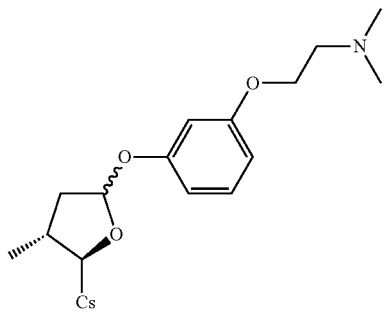
14A-o
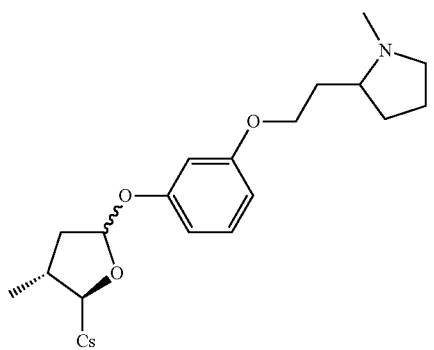
15A-o
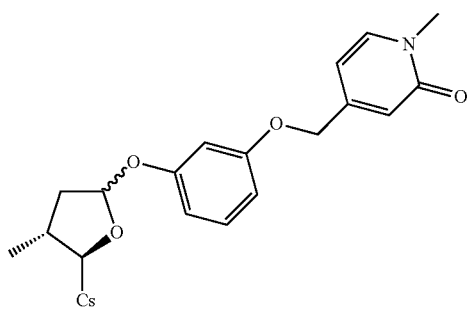
16A-o
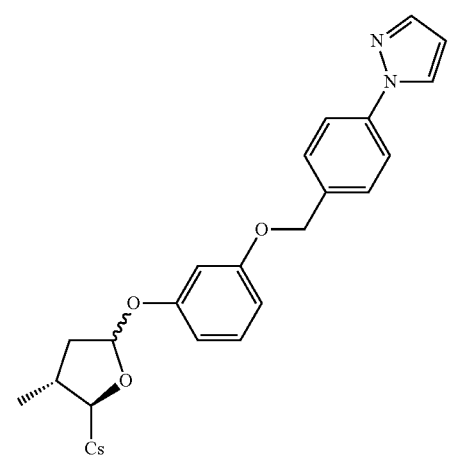
17A-o TABLE 2-continued
phenyloxy compounds
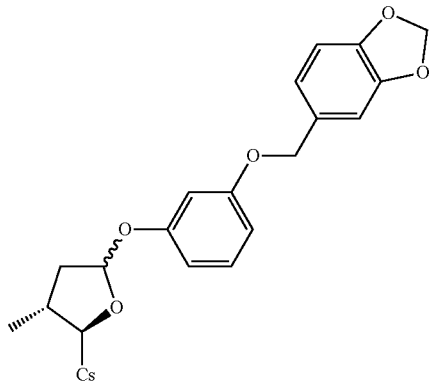
18A-o
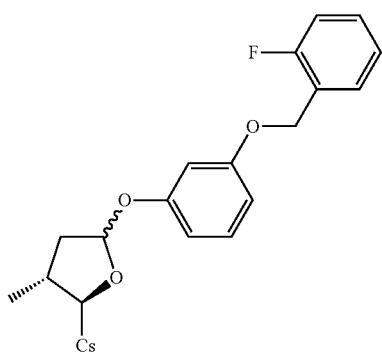
19A-o
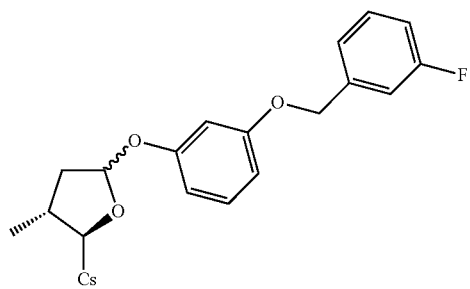
20A-o
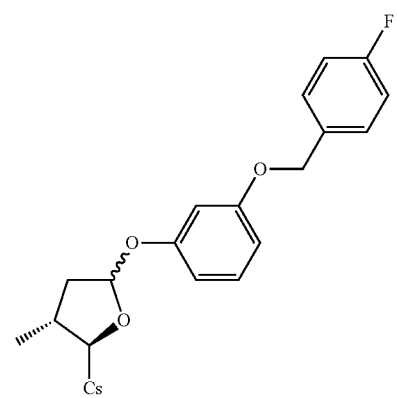
21A-o TABLE 2-continued
| phenyloxy compounds |
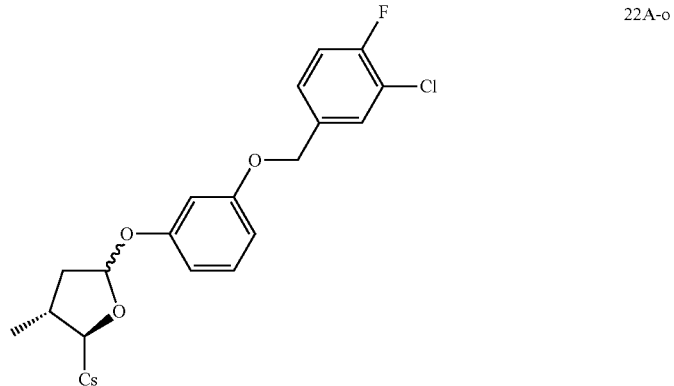
22A-o
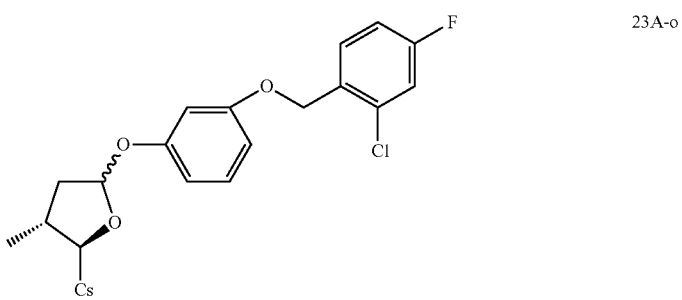
23A-o
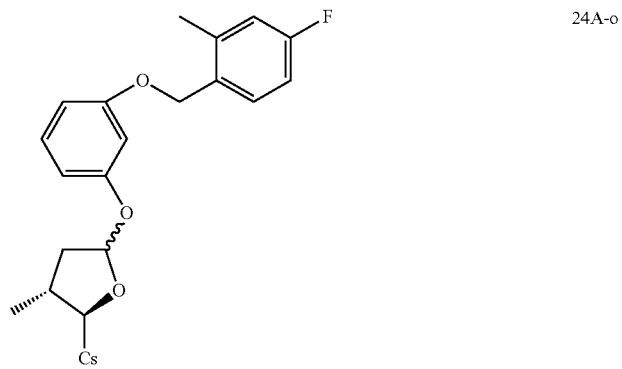
24A-o
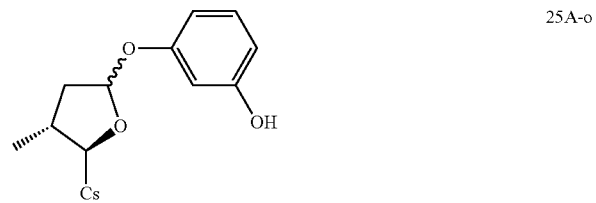
25A-o
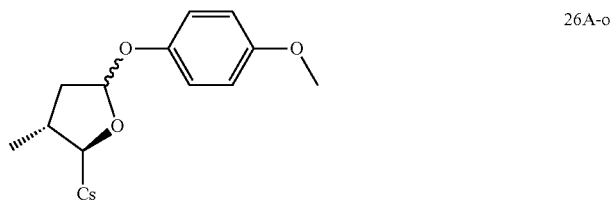
26A-o TABLE 2-continued
phenyloxy compounds
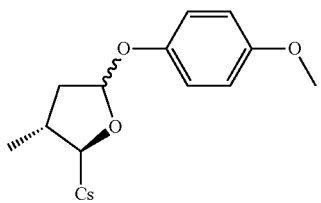
26B-o
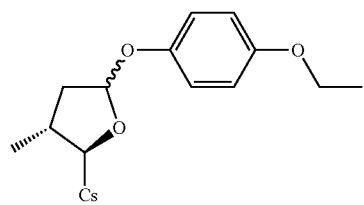
27A-o
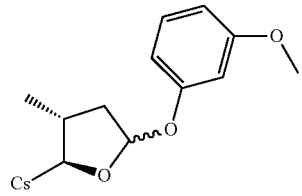
28A-o
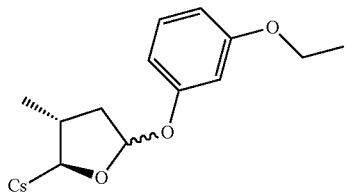
29A-o
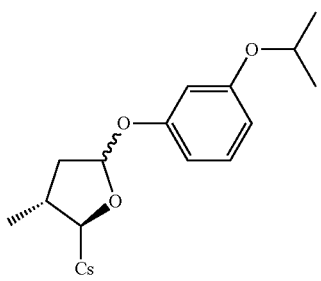
30A-o
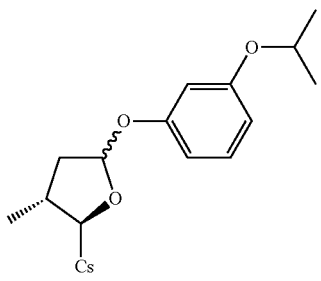
30B-o TABLE 2-continued
phenyloxy compounds
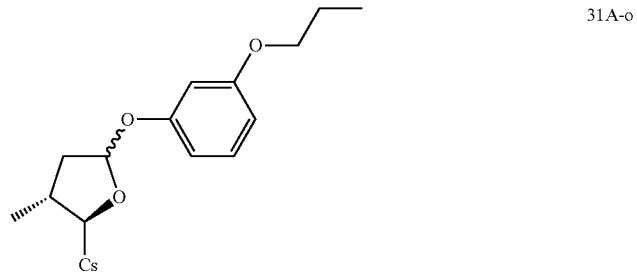
31A-o
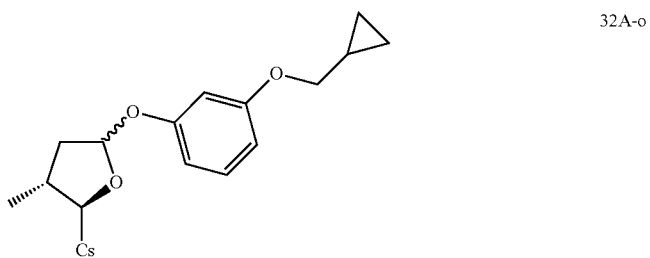
32A-o
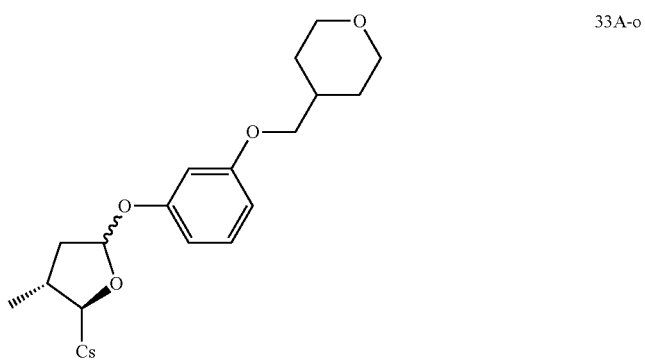
33A-o
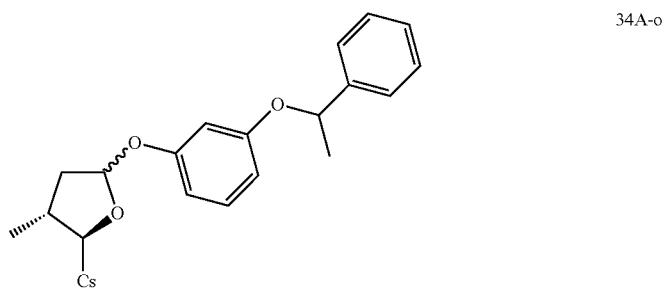
34A-o
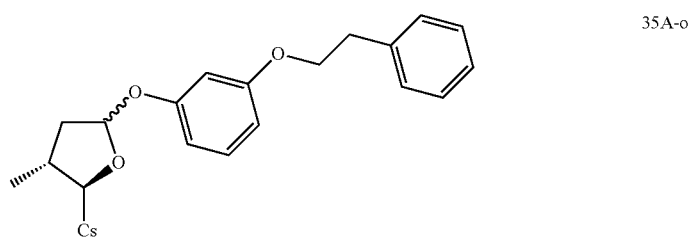
35A-o TABLE 2-continued
| phenyloxy compounds | |
|---|---|
| 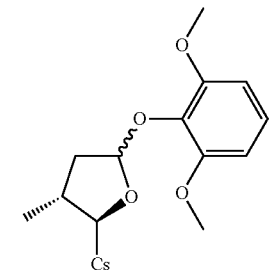 | 36A-o |
| 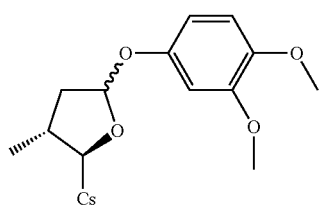 | 37A-o |
| 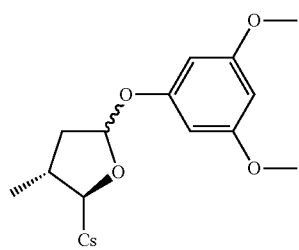 | 38A-o |
| 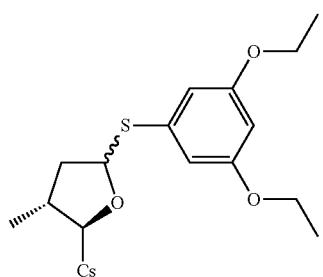 | 39A-o |
| 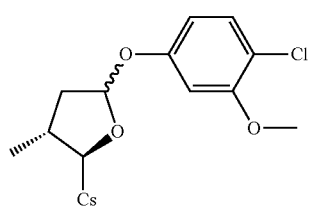 | 40A-o |
| 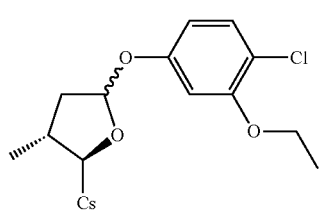 | 41A-o |

TABLE 2-continued
phenyloxy compounds
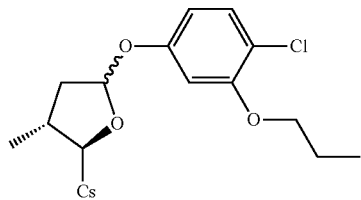
42A-o
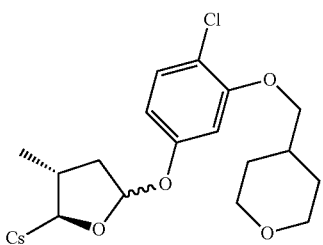
43A-o
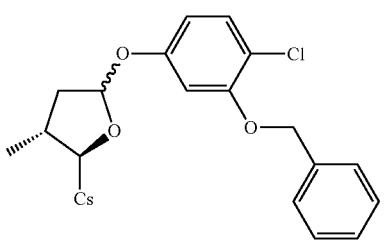
44A-o
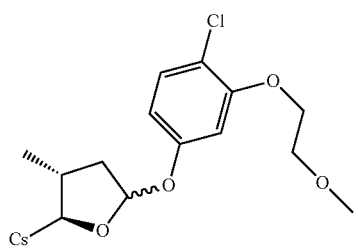
45A-o
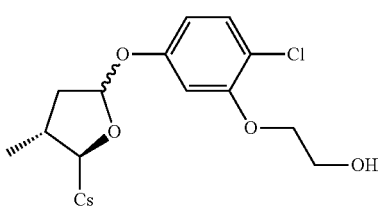
46A-o
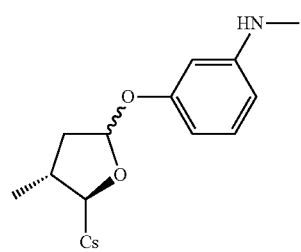
47A-o TABLE 2-continued
| phenyloxy compounds |
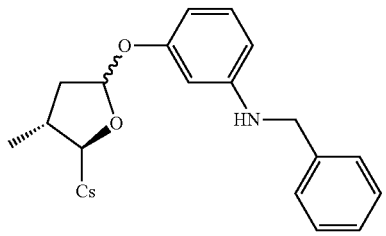
48A-o
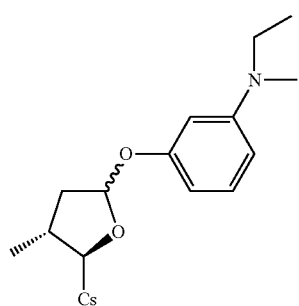
49A-o
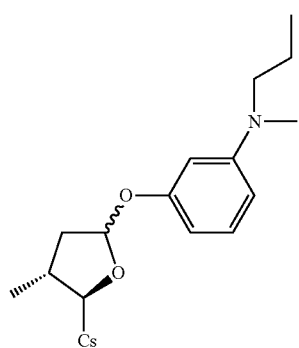
50A-o
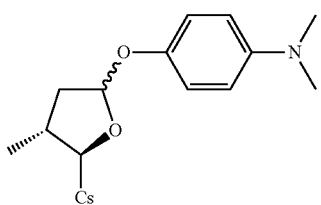
51A-o
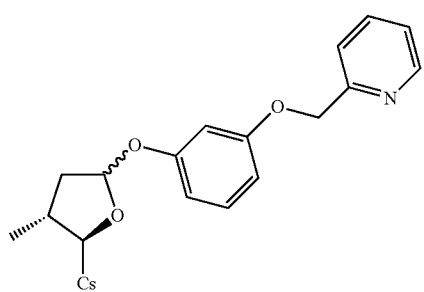
52A-o TABLE 2-continued
| phenyloxy compounds | |
|---|---|
| 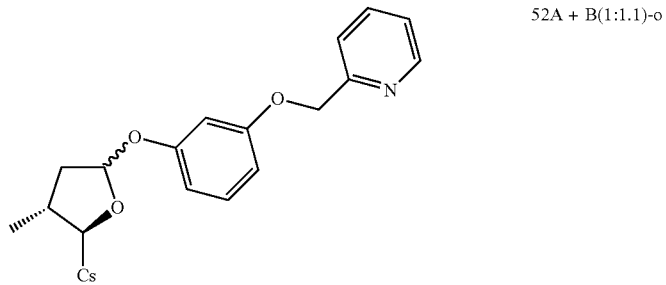 | 52A + B(1:1.1)-o |
| 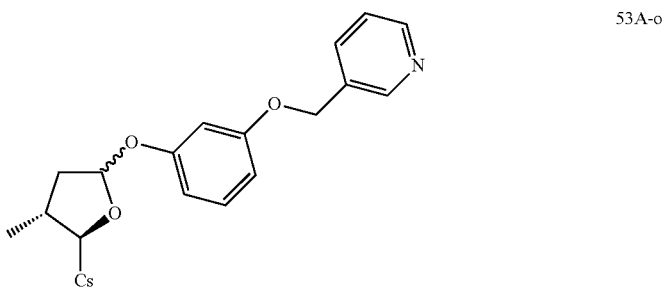 | 53A-o |
| 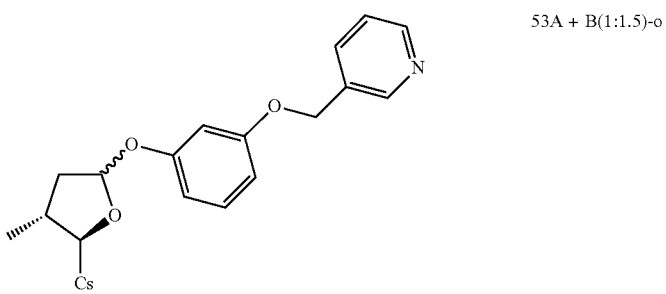 | 53A + B(1:1.5)-o |
| 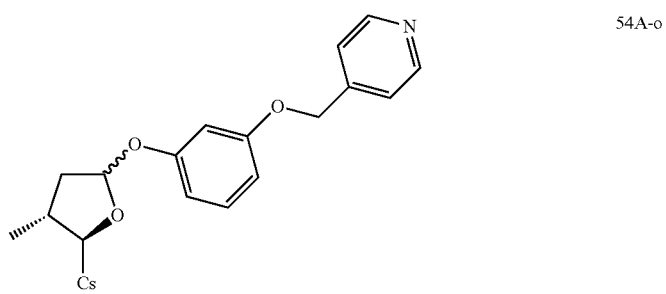 | 54A-o |
| 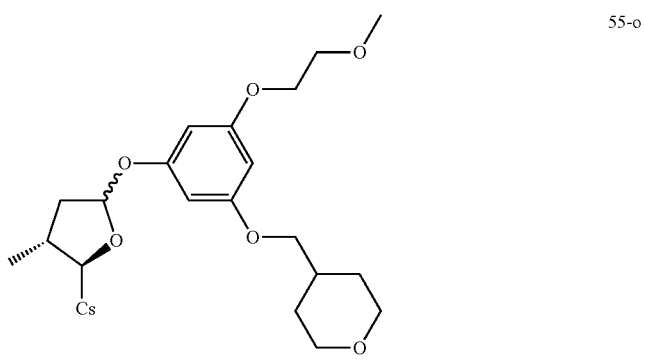 | 55-o |

TABLE 2-continued
phenyloxy compounds
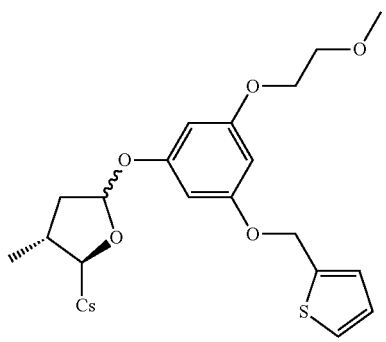
56-o
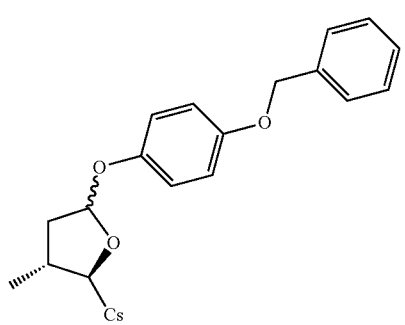
47A-o
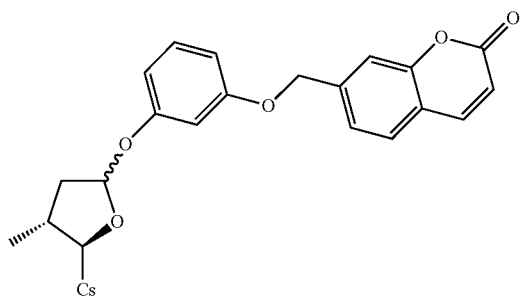
58A-o
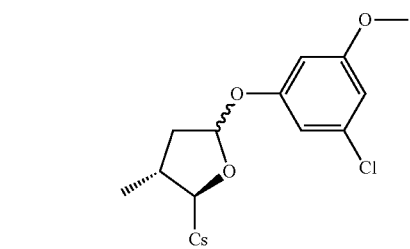
59A-o
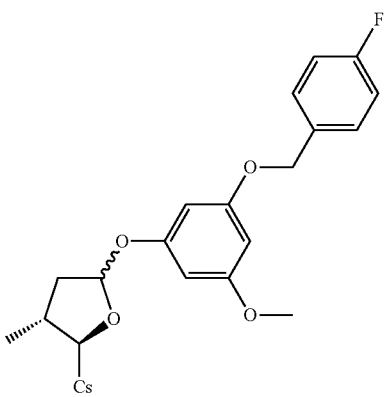
60A-o TABLE 2-continued
phenyloxy compounds
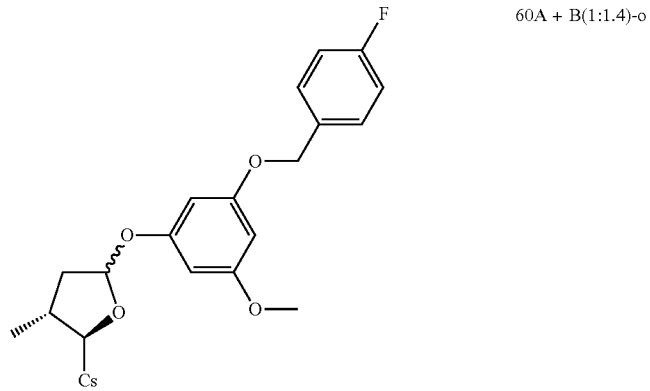 60A + B(1:1.4)-o
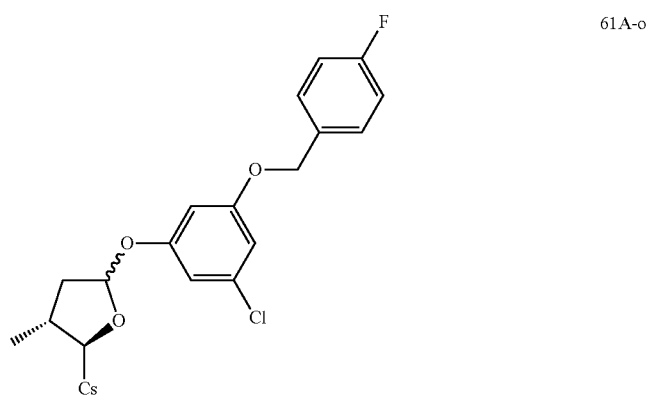 61A-o
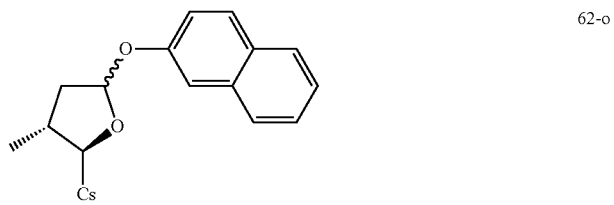 62-o
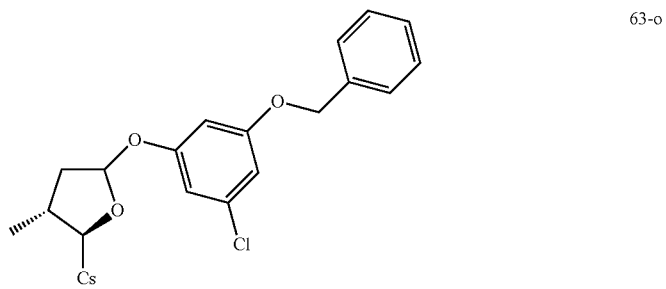 63-o
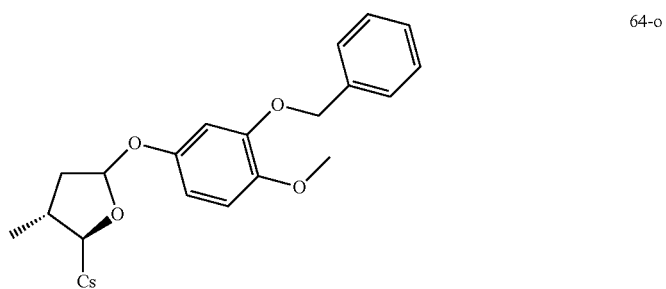 64-o TABLE 2-continued
phenyloxy compounds
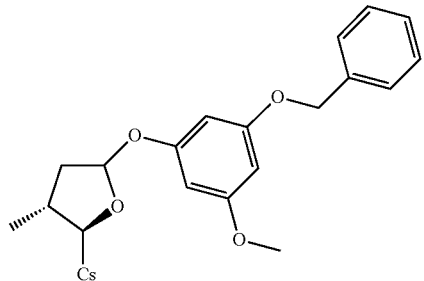
65-o
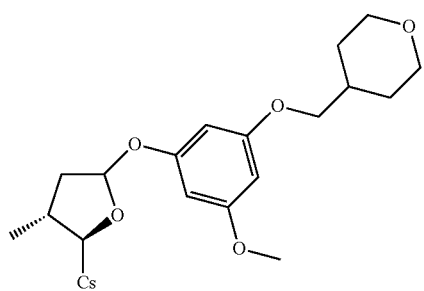
66-o
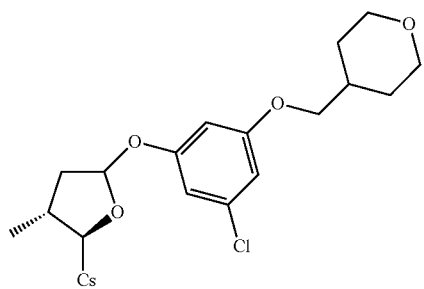
67-o
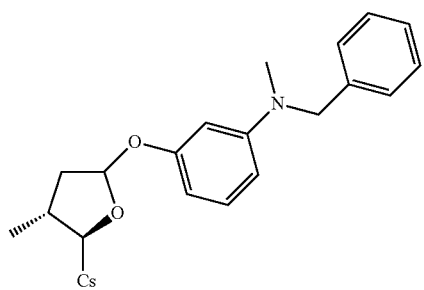
68-o
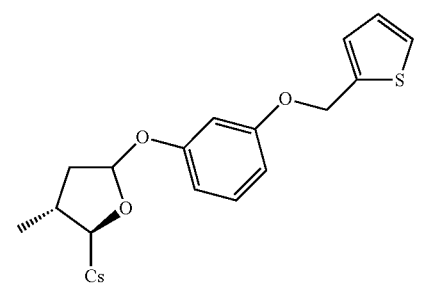
69-o TABLE 2-continued phenyloxy compounds 70-o, 71-o, 72-o, 73-o

TABLE 3 benzyloxy compounds

74A

TABLE 3-continued
benzyloxy compounds
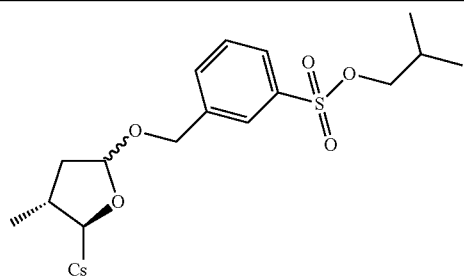 75A
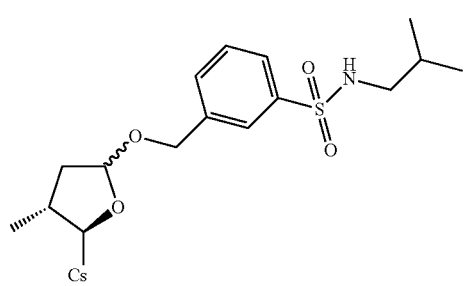 76A
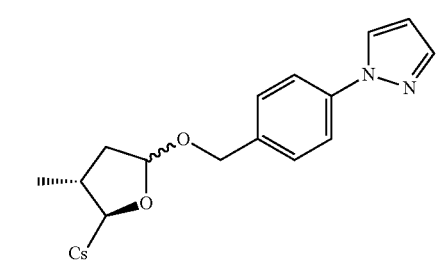 77A
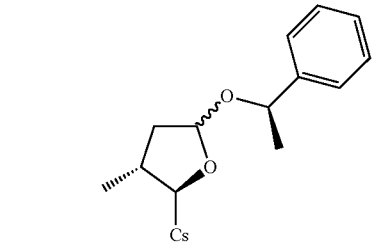 78A
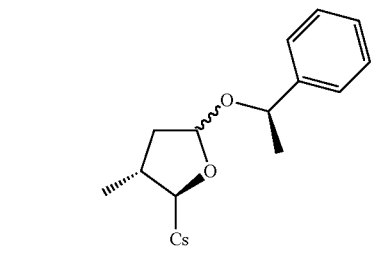 78B
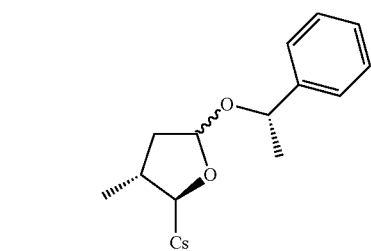 79A
TABLE 3-continued
benzyloxy compounds
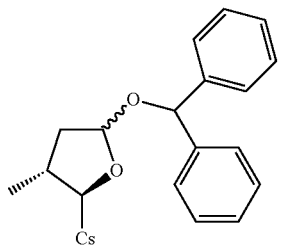 80A
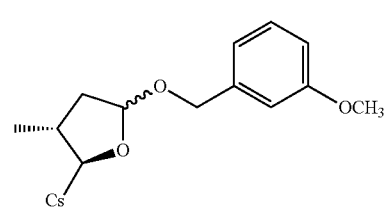 81A
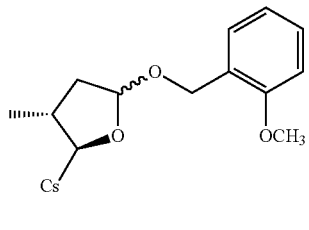 82A
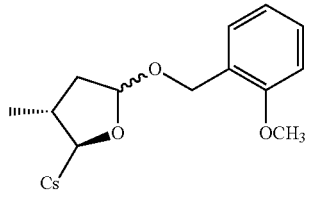 82B
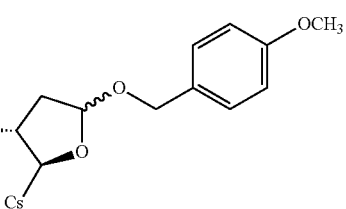 83A
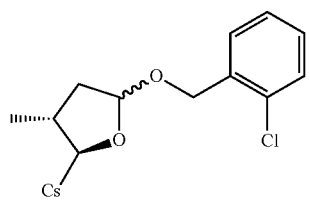 84A
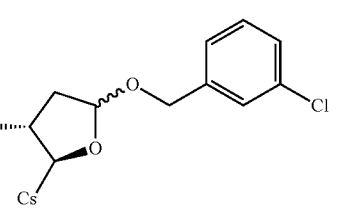 85A TABLE 3-continued benzyloxy compounds

| | |
|---|---|
| 86A | 90A |
| 86B | 90B |
| 87A | 91A |
| 88A | 91B |
| 88B | 92A |
| 89A | 93A |
| 89B | |

TABLE 3-continued
benzyloxy compounds
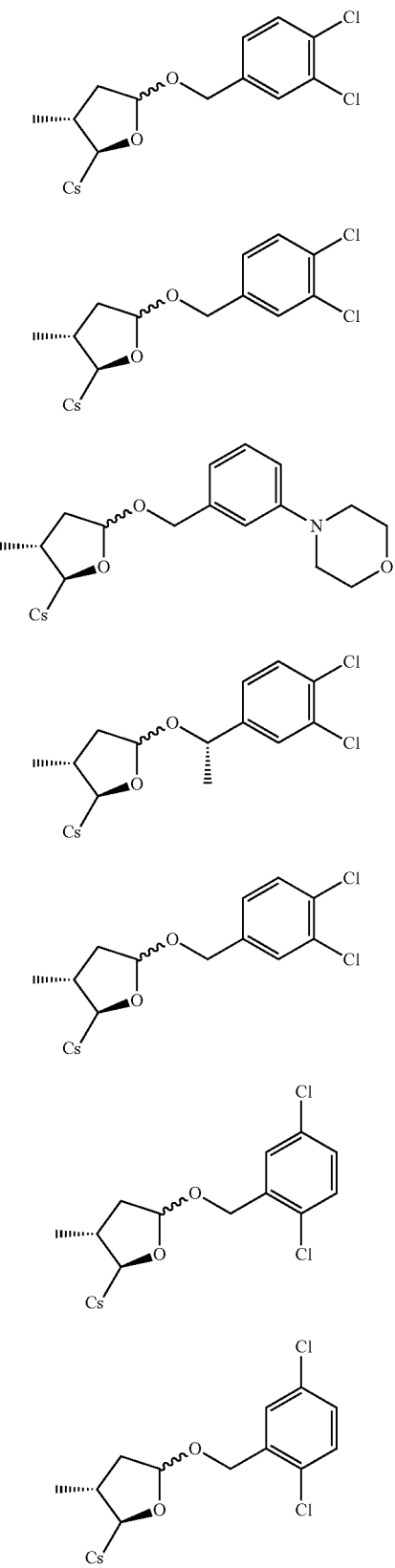
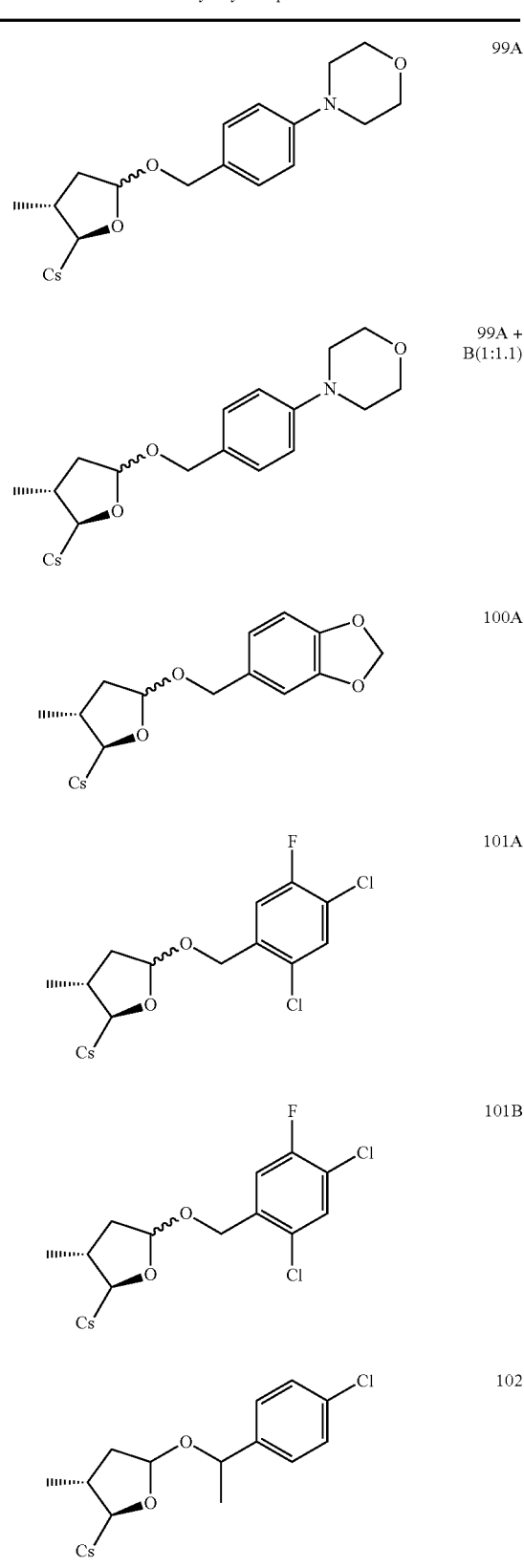

TABLE 3-continued benzyloxy compounds

| | |
|---|---|
| 103 | |
| 104 | |
| 105 | |

TABLE 4 benzylthiol compounds

| | |
|---|---|
| 74A-s | |
| 75A-s | |
| 76A-s | |

TABLE 4-continued benzylthiol compounds

| | |
|---|---|
| 77A-s | |
| 78A-s | |
| 78B-s | |
| 79A-s | |
| 80A-s | |
| 81A-s | |

TABLE 4-continued benzylthiol compounds

| Compound | ID |
|---|---|
| (structure) | 82A-s |
| (structure) | 82B-s |
| (structure) | 83A-s |
| (structure) | 84A-s |
| (structure) | 85A-s |
| (structure) | 86A-s |
| (structure) | 86B-s |
| (structure) | 87A-s |
| (structure) | 88A-s |
| (structure) | 88B-s |
| (structure) | 89A-s |
| (structure) | 89B-s |
| (structure) | 90A-s |
| (structure) | 90B-s |

TABLE 4-continued
benzylthiol compounds
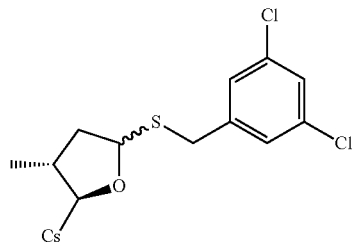
91A-s
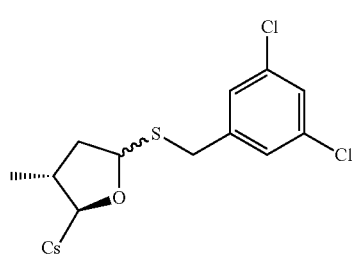
91B-s
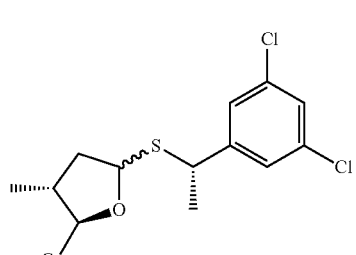
92A-s
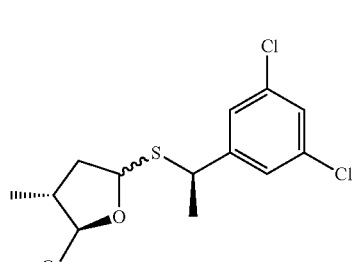
93A-s
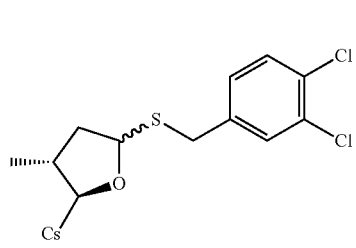
94A-s
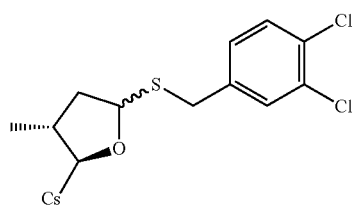
94B-s
TABLE 4-continued
benzylthiol compounds
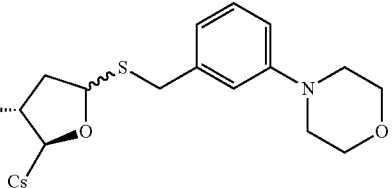
95-s
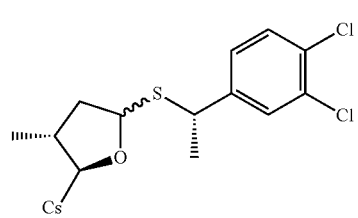
96A-s
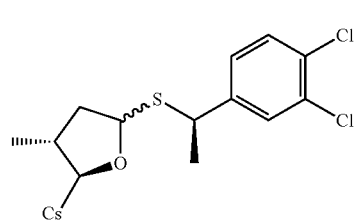
97A-s
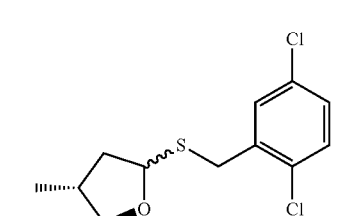
98A-s
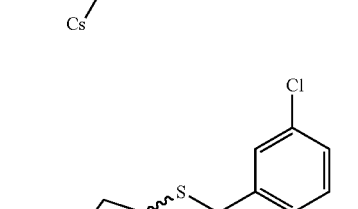
98A + B(1:1)-s
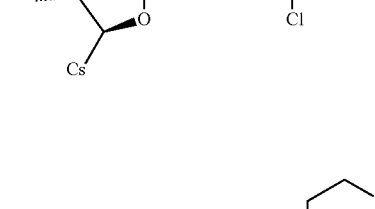
99A-s

TABLE 4-continued benzylthiol compounds

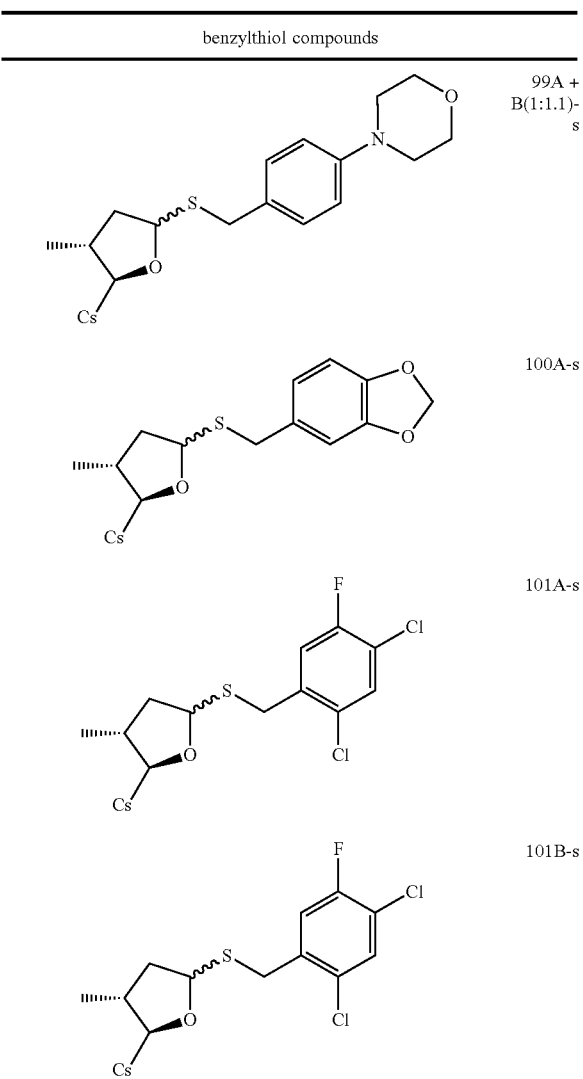

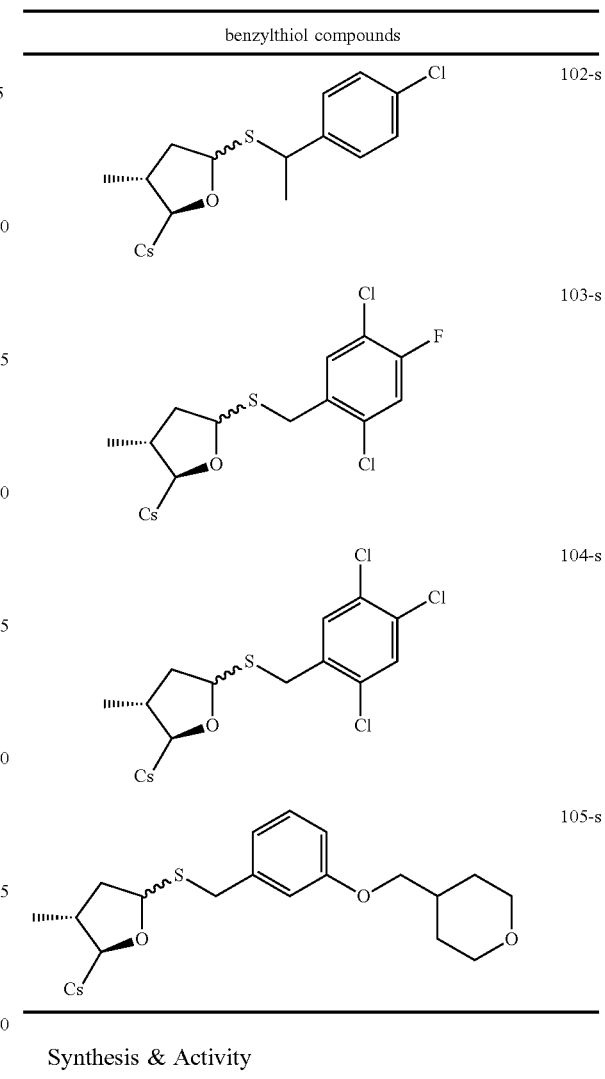

Synthesis & Activity

I. Abbreviations

| | | | |
|---|---|---|---|
| DMF | N,N-Dimethylformamide | MHz | Mega Hertz |
| THF | Tetrahydrofuran | s | singlet |
| DCM/CH$_2$Cl$_2$ | Dichloromethane | d | doublet |
| EA/EtOAc | Ethyl acetate | t | triplet |
| PE | Petroleum ether | q | quartet |
| TEA/Et$_3$N | Triethylamine | m | multiplet |
| MsCl | Methanesulfonyl chloride | dd | Doublet of doublets |
| ACN/CH$_3$CN | Acetonitrile | ddd | Doublet of doublet of doublets |
| EtOH | Ethanol | dt | Doublet of triplets |
| MeOH | Methanol | DIAD | Diisopropyl azodiformate |
| HCl | Hydrochloric acid | TLC | Thin Layer Chromatography |
| Sat. NH$_4$Cl | Saturated ammonium chloride solution | PPh$_3$ | Triphenylphosphine |
| NaHCO$_3$ | Sodium bicarbonate | AcOH | Acetic acid |
| Na$_2$SO$_4$ | Sodium sulfate | NIS | N-Iodosuccinimide |
| K$_2$CO$_3$ | Potassium carbonate | Sat. NaCl | Saturated sodium chloride solution |
| NaBH$_4$ | Sodium borohydride | r.t. | Room Temperature |
| NaOH | Sodium hydroxide | O$_3$ | Ozone |
| NaOMe | Sodium methanolate | iPrOH | Isopropanol |
| Pd(OH)$_2$ | Palladium hydroxide | LDA | Lithium diisopropylamide |
| Pd | Palladium | tBuOK | Potassium tert-butanolate |
| p-TsOH | p-Toluenesulfonic acid | NaNO$_2$ | Sodium nitrite |
| DHP | Dihydropyran | n-Bu$_3$P | Tributylphosphane |

| | | | |
|---|---|---|---|
| TfOH | Trifluoromethanesulfonic acid | NaH | Sodium hydride |
| $Na_2S_2O_3$ | Sodium thiosulfate | $H_2SO_4$ | Sulfuric acid |
| HATU | 2-(7-Aza-1H-benzotriazole-1-yl)-1,1,3,3-tetramethyluronium hexafluorophosphate | DIEA | N,N-Diisopropylethylamine |
| $NaBH_3CN$ | Sodium cyanoborohydride | HCOOH | Formic acid |
| $MgSO_4$ | Magnesium sulfate | DMAP | 4-Dimethylaminopyridine |
| $Ac_2O$ | Acetic anhydride | $LiAlH_4$ | Lithium aluminium hydride |
| $FeCl_3$ | Ferric chloride | $Ph_3P^+$—$CH_3Br^-$ | Methyltriphenylphosphonium bromide |
| Prep. TLC | Prepare Thin Layer Chromatography | Pre. HPLC | Prepare High Performance Liquid Chromatography |

II. Synthesis Schemes

Scheme I

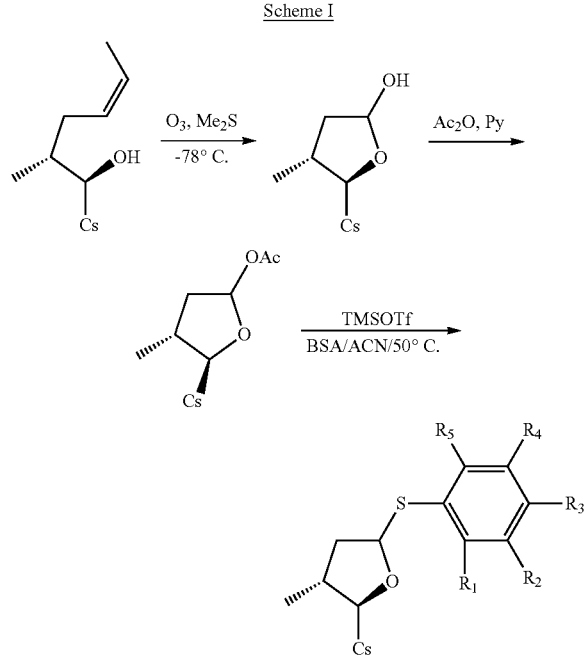

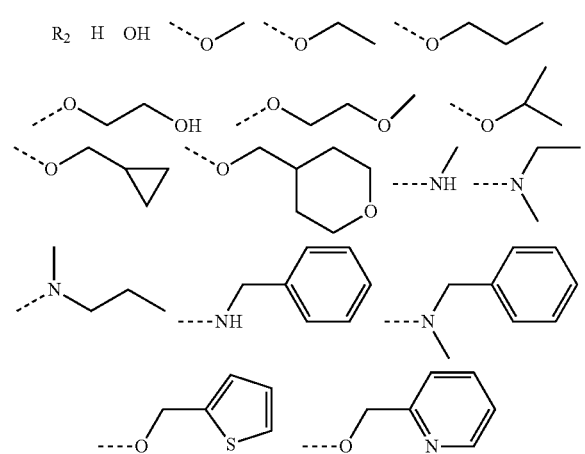

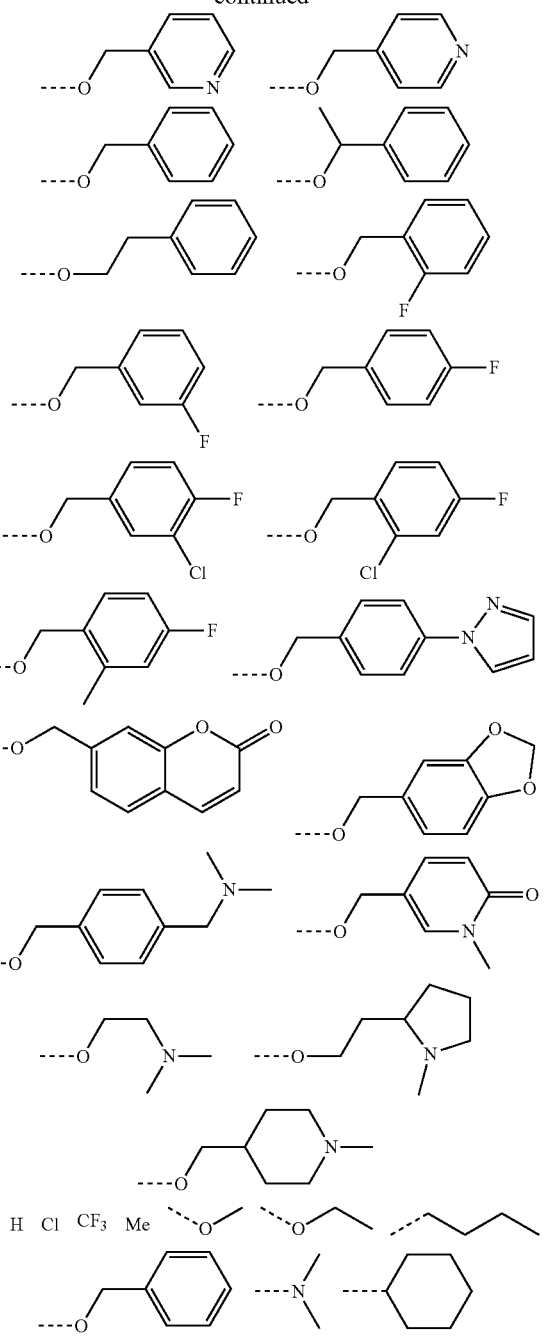

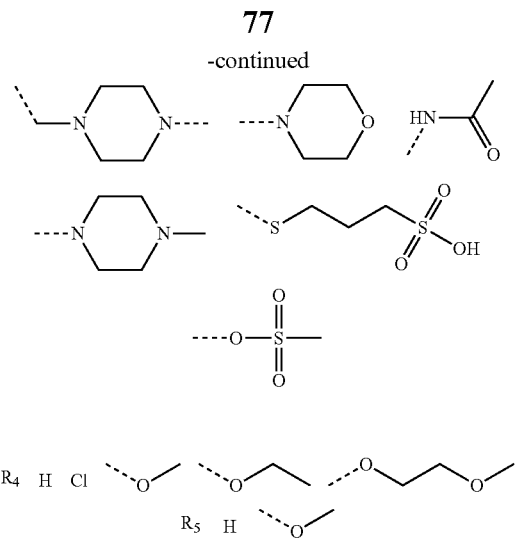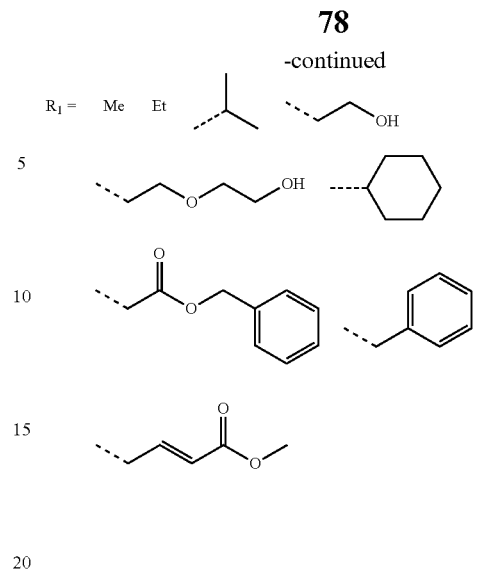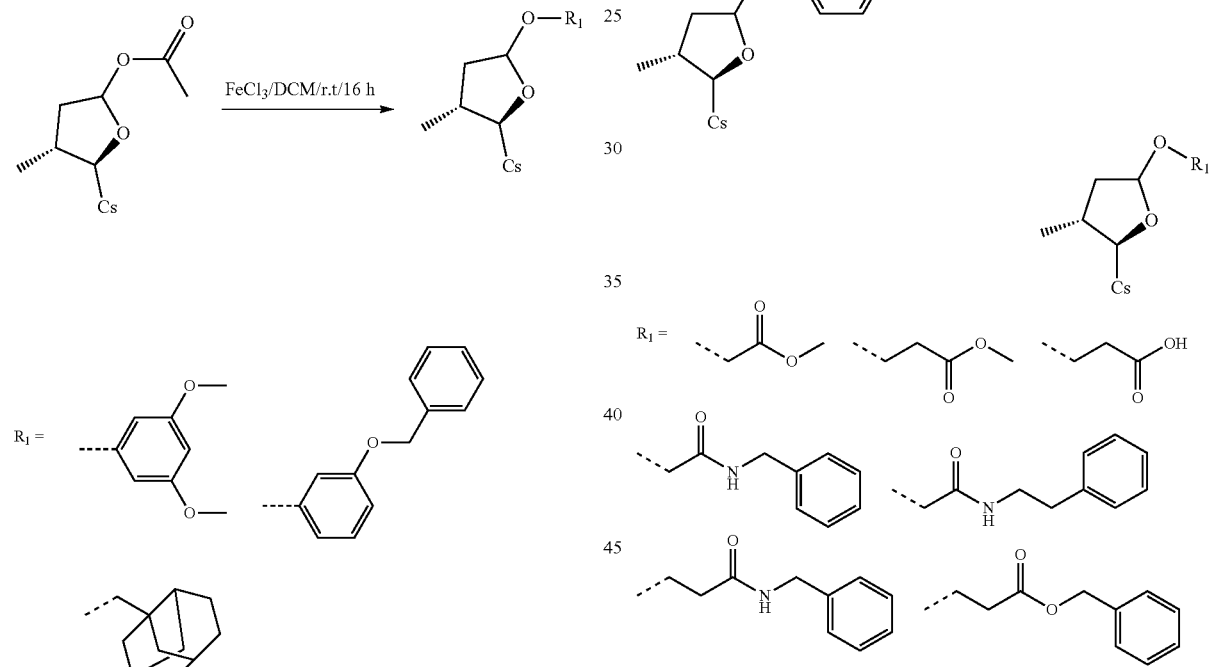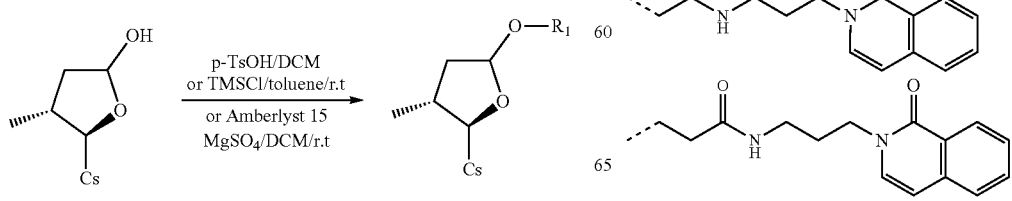

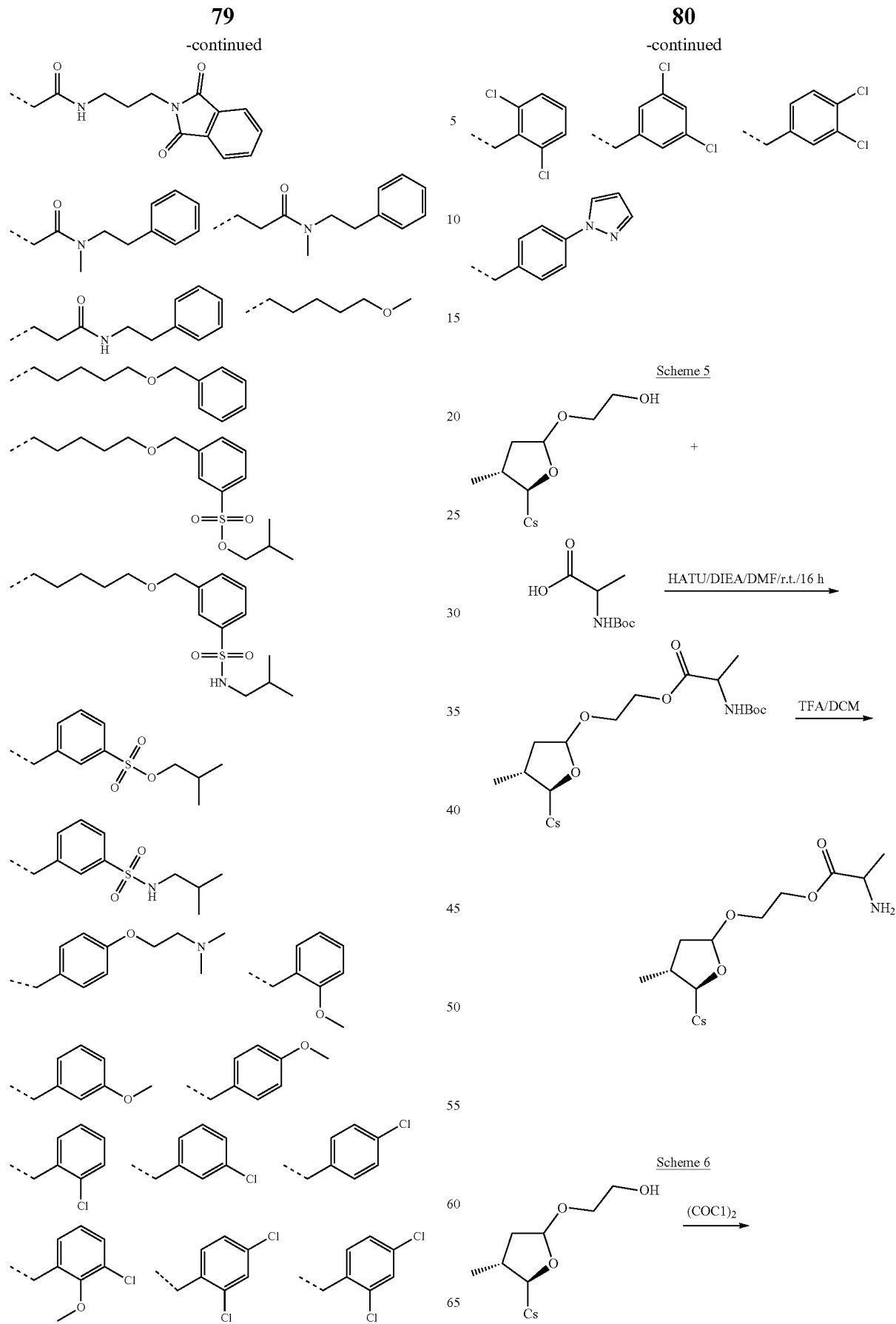

-continued

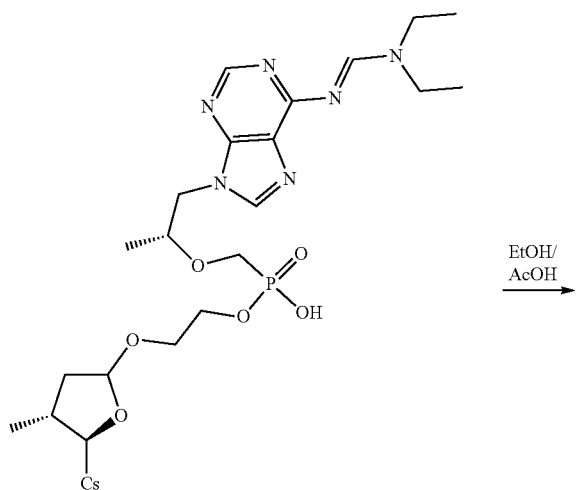

EtOH/
AcOH
→

III. Preparation

Compound 1B: Preparation of [2-((2R,3R)-3-methyl-5-(phenylthio)tetrahydrofuran-2-yl)-2-(methylamino)acetic acid]¹-cyclosporin A

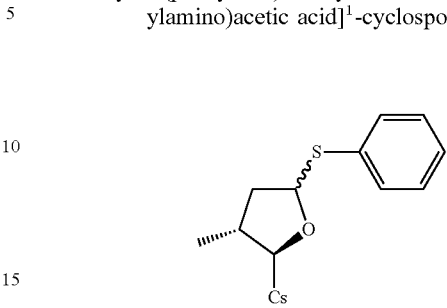

To the solution of [2-((2R,3R)-5-acetoxy-3-methyltetrahydrofuran-2-yl)-2-(methylamino)acetic acid]¹-cyclosporin A (100 mg, 0.081 mmol) and benzenethiol (17.8 mg, 0.162 mmol) in 6 mL acetonitrile was added N,O-Bis(trimethylsilyl)acetamide (0.08 mL, 0.327 mmol) and trimethylsilyl trifluoromethanesulfonate (0.044 mL, 0.24 mmol). Let it stir at 50° C. under nitrogen for 90 mins. The reaction mixture was evaporated to dryness and re-dissolved with DCM (10 mL). It was washed with sat. NaHCO₃ solution, brine and dried with Na₂SO₄. Filtered and evaporated to dryness. The brown residue was purified by prep. HPLC to give 5 mg colorless oil. Yield: 4.8%. Mass (ESI): m/z calcd for $C_{66}H_{111}N_{11}O_{12}S$ 1281.81, found 1283.30 [M+H]⁺.

Compound 2A: Preparation of [2-((2R,3R)-3-methyl-5-(p-tolylthio)tetrahydrofuran-2-yl)-2-(methylamino)acetic acid]¹-cyclosporin A

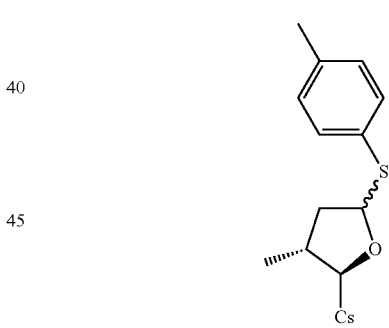

The compound was synthesized from [2-((2R,3R)-5-acetoxy-3-methyltetrahydrofuran-2-yl)-2-(methylamino)acetic acid]¹-cyclosporin A in a manner similar to that described for compound 1B. p-Toluenethiol was used instead of benzenethiol and 140 mg compound 2A and 42.2 mg compound 2A+B(1:3.3) were obtained as white solid. Total yield: 48.1%. ¹H NMR (400 MHz, CDCl₃) 8.43 (d, J=9.6 Hz, 1H), 8.07 (d, J=6.8 Hz, 1H), 7.67 (d, J=8.8 Hz, 1H), 7.53 (d, J=8.0 Hz, 1H), 7.35 (d, J=8.0 Hz, 2H), 7.10 (d, J=8.4 Hz, 2H), 5.67 (dd, J=4.0, 11.2 Hz, 1H), 5.42 (dd, J=3.6, 7.6 Hz, 1H), 5.33 (dd, J=4.0, 11.2 Hz, 1H), 5.22 (d, J=1.2 Hz, 1H), 5.08-5.14 (m, 3H), 4.97-5.01 (m, 1H), 4.90-4.95 (m, 1H), 4.81-4.88 (m, 2H), 4.65 (d, J=13.6 Hz, 1H), 4.35-4.40 (m, 1H), 4.29 (dd, J=6.4, 9.2 Hz, 1H), 3.46 (s, 3H), 3.39 (s, 3H), 3.22 (s, 3H), 3.18 (s, 3H), 3.07 (s, 3H), 2.71 (s, 3H), 2.66 (s, 3H), 2.39-2.47 (m, 1H), 2.31 (s, 3H), 2.22-2.27 (m, 1H), 2.05-2.12 (m, 3H), 1.93-2.01 (m, 3H), 1.60-1.70 (m, 5H), 1.41-

Scheme 7

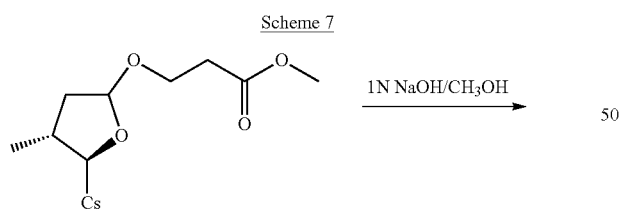

1N NaOH/CH₃OH
→

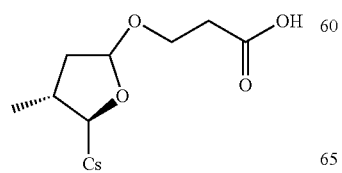

1.52 (m, 3H), 1.33 (d, J=7.2 Hz, 3H), 1.26 (d, J=6.8 Hz, 3H), 1.16 (d, J=6.8 Hz, 3H), 0.99-1.03 (m, 9H), 0.93-0.95 (m, 8H), 0.89-0.91 (m, 4H), 0.85-0.87 (m, 11H), 0.81 (d, J=6.4 Hz, 4H), 0.77 (d, J=6.8 Hz, 3H), 0.64 (d, J=6.8 Hz, 3H). Mass (ESI): m/z calcd for $C_{67}H_{113}N_{11}O_{12}S$ 1295.83, found 1296.79 $[M+H]^+$.

Compound 3A: Preparation of [2-((2R,3R)-3-methyl-5-(4-morpholinophenylthio)tetrahydrofuran-2-yl)-2-(methylamino)acetic acid][1]-cyclosporin A

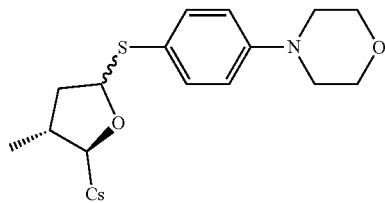

(I) Synthesis of 4-morpholin-4-yl-benzenethiol. The compound was synthesized from 4-morpholin-4-yl-phenylamine in a manner similar to that described for 4-Chloro-3-ethoxy-benzenethiol. 1.5 g 4-morpholin-4-yl-phenylamine was used and 0.1 g 4-morpholin-4-yl-benzenethiol was obtained as light-yellow solid through two reaction steps. Yield: 6.1%.

(II) Synthesis of [2-((2R,3R)-3-methyl-5-(4-morpholinophenylthio)tetrahydrofuran-2-yl)-2-(methylamino)acetic acid][1]-cyclosporin A. The compound was synthesized from [2-((2R,3R)-5-acetoxy-3-methyltetrahydrofuran-2-yl)-2-(methylamino)acetic acid][1]-cyclosporin A in a manner similar to that described for compound 1B. 4-morpholinobenzenethiol was used instead of benzenethiol, 100 mg of starting material was used and 32 mg white solid was obtained. Yield: 28.9%. $^1$H NMR (400 MHz, CDCl$_3$) 8.39 (d, J=9.6 Hz, 1H), 8.03 (d, J=6.8 Hz, 1H), 7.63 (d, J=9.2 Hz, 1H), 7.51 (d, J=7.6 Hz, 1H), 7.38 (d, J=8.8 Hz, 2H), 6.81-7.00 (m, 2H), 5.66 (dd, J=4.4, 10.8 Hz, 1H), 5.34 (d, J=4.0 Hz, 1H), 5.31 (d, J=4.4 Hz, 1H), 5.21 (d, J=8.8 Hz, 1H), 5.19 (d, J=6.0 Hz, 1H), 5.06-5.14 (m, 2H), 4.98-5.02 (m, 1H), 4.81-4.96 (m, 3H), 4.66 (d, J=13.6 Hz, 1H), 4.35-4.42 (m, 1H), 4.25 (dd, J=6.4, 8.8 Hz, 1H), 3.80-3.92 (m, 4H), 3.45 (s, 3H), 3.39 (s, 3H), 3.22 (s, 3H), 3.18 (s, 3H), 3.14-3.17 (m, 4H), 3.06 (s, 3H), 2.70 (s, 3H), 2.66 (s, 3H), 2.36-2.43 (m, 1H), 2.28-2.33 (m, 1H), 2.05-2.13 (m, 3H), 1.93-2.00 (m, 3H), 1.57-1.65 (m, 4H), 1.42-1.50 (m, 2H), 1.33 (d, J=7.2 Hz, 4H), 1.25 (d, J=6.8 Hz, 4H), 1.15 (d, J=6.8 Hz, 3H), 0.97-1.02 (m, 8H), 0.92-0.96 (m, 9H), 0.87-0.90 (m, 8H), 0.85-0.86 (m, 8H), 0.81 (d, J=6.4 Hz, 3H), 0.79 (d, J=6.4 Hz, 3H), 0.66 (d, J=6.4 Hz, 3H). Mass (ESI): m/z calcd for $C_{70}H_{118}ClN_{12}O_{13}S$ 1366.87, found 1368.24 $[M+H]^+$.

Compound 4A: Preparation of [2-((2R,3R)-5-(4-acetamidophenylthio)-3-methyltetrahydrofuran-2-yl)-2-(methylamino)acetic acid][1]-cyclosporin A

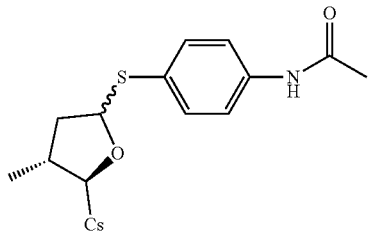

The compound was synthesized from [2-((2R,3R)-5-acetoxy-3-methyl tetrahydrofuran-2-yl)-2-(methylamino)acetic acid][1]-cyclosporin A in a manner similar to that described for compound 1B. N-(4-mercaptophenyl)acetamide was used instead of benzenethiol, 130 mg of starting material was used and 18 mg white solid was obtained. Yield: 12.8%. $^1$H NMR (400 MHz, CDCl$_3$) δ 8.35 (d, J=9.2 Hz, 1H), 8.02 (d, J=6.8 Hz, 1H), 7.64 (d, J=9.2 Hz, 1H), 7.51 (d, J=8.0 Hz, 1H), 7.35-7.45 (m, 5H), 5.66 (dd, J=4.0, 10.8 Hz, 1H), 5.46 (dd, J=4.0, 7.6 Hz, 1H), 5.27 (dd, J=4.0, 11.2 Hz, 1H), 5.23 (d, J=8.8 Hz, 1H), 5.18 (d, J=10.8 Hz, 1H), 5.07-5.15 (m, 2H), 4.95-5.05 (m, 2H), 4.83-4.92 (m, 2H), 4.65 (d, J=13.6 Hz, 1H), 4.36-4.45 (m, 1H), 4.25 (dd, J=6.4, 8.4 Hz, 1H), 3.40 (s, 3H), 3.36 (s, 3H), 3.21 (s, 3H), 3.17 (s, 3H), 3.05 (s, 3H), 2.71 (s, 3H), 2.67 (s, 3H), 2.42-2.49 (m, 1H), 2.26-2.35 (m, 1H), 2.16 (s, 3H), 2.04-2.14 (m, 4H), 1.90-1.99 (m, 2H), 1.57-1.69 (m, 5H), 1.38-1.50 (m, 3H), 1.32 (d, J=7.2 Hz, 3H), 1.26 (d, J=6.8 Hz, 3H), 1.15 (d, J=6.4 Hz, 3H), 0.97-1.01 (m, 7H), 0.91-0.95 (m, 12H), 0.84-0.90 (m, 13H), 0.79-0.82 (m, 7H), 0.69 (d, J=6.4 Hz, 3H). Mass (ESI): m/z calcd for $C_{69}H_{114}N_{12}O_3S$ 1338.83, found 1339.8 $[M+H]^+$.

Compound 5A: Preparation of [2-((2R,3R)-3-methyl-5-(4-(methylsulfonyloxy) phenylthio)tetrahydrofuran-2-yl)-2-(methylamino)acetic acid][1]-cyclosporin A

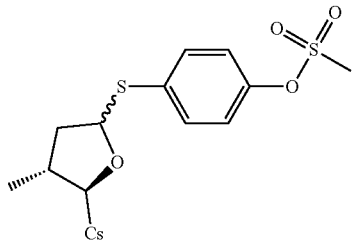

(I) Synthesis of 4-mercaptophenyl methanesulfonate. 4-Hydroxybenzenesulfonic acid (2.32 g, 0.01 mol) and NaOH (0.4 g, 0.011 mol) were dissolved in 10 mL water. Methanesulfonyl chloride (0.85 mL, 0.011 mol) was added slowly to the solution at 0° C. Let it stir at r.t. for 2 hrs. 4 mL of brine was added and the solution left to stand for 1 h. The solid was filtered to give 0.66 g 4-methanesulfonyloxy-benzenesulfonic acid as white solid. Yield: 23.7%.

4-methanesulfonyloxy-benzenesulfonic acid (660 mg, 2.37 mmol) was dissolved in 4 mL of thionyl chloride. 0.04 mL of N,N-Dimethylformamide was added to the solution at 0° C. Let it stir at 80° C. for 4 hrs. The solvent was evaporated to dryness. 30 mL of CH$_2$Cl$_2$ was added. Washed with water, brine. Dried with MgSO$_4$. Filtered ad evaporated to dryness to give 0.65 g methanesulfonic acid 4-chlorosulfonyl-phenyl ester as white solid. Yield: quantitative.

Methanesulfonic acid 4-chlorosulfonyl-phenyl ester (0.65 g, 2.4 mmol) was added slowly to the solution of red phosphorus (0.186 g, 6 mmol) and iodine (10.1 mg, 0.04 mmol) in 1.82 mL AcOH. Let it reflux for 2 hrs. 0.39 mL water was added and let it reflux for 1 h. It was cooled to room temperature and water was added. It was extracted with CH$_2$Cl$_2$ (20 mL×3), washed with water, brine. Dried with MgSO$_4$. Filtered and evaporated to dryness. The residue was purified by flash chromatography (PE/EA=3/1) to give 0.35 g 4-mercaptophenyl methanesulfonate as white solid. Yield: 71.5%.

(II) Synthesis of [2-((2R,3R)-3-methyl-5-(4-(methylsulfonyloxy)phenylthio) tetrahydrofuran-2-yl)-2-(methylamino)acetic acid]$^1$-cyclosporin A The compound was synthesized from [2-((2R,3R)-5-acetoxy-3-methyl tetrahydrofuran-2-yl)-2-(methylamino)acetic acid]$^1$-cyclosporin A in a manner similar to that described for compound 1B. 4-Mercaptophenyl methanesulfonate was used instead of benzenethiol, 100 mg of starting material was used and 32 mg white solid was obtained. Yield: 28.6%. $^1$H NMR (400 MHz, CDCl$_3$) 8.38 (d, J=9.6 Hz, 1H), 8.07 (d, J=6.8 Hz, 1H), 7.64 (d, J=8.8 Hz, 1H), 7.51 (d, J=8.0 Hz, 1H), 7.49 (d, J=8.8 Hz, 2H), 7.24 (d, J=8.8 Hz, 2H), 5.67 (dd, J=4.0, 11.6 Hz, 1H), 5.52 (dd, J=3.6, 8.0 Hz, 1H), 5.32 (dd, J=4.0, 11.2 Hz, 1H), 5.26 (d, J=9.2 Hz, 1H), 5.07-5.17 (m, 3H), 4.96-5.03 (m, 1H), 4.83-4.92 (m, 3H), 4.65 (d, J=13.6 Hz, 1H), 4.37-4.42 (m, 1H), 4.28-4.32 (m, 1H), 3.42 (s, 3H), 3.37 (s, 3H), 3.22 (s, 3H), 3.18 (s, 3H), 3.12 (s, 3H), 3.06 (s, 3H), 2.70 (s, 3H), 2.67 (s, 3H), 2.46-2.54 (m, 1H), 2.29-2.34 (m, 1H), 2.07-2.16 (m, 3H), 1.95-2.05 (m, 3H), 1.58-1.70 (m, 5H), 1.41-1.51 (m, 3H), 1.32 (d, J=7.2 Hz, 3H), 1.26 (d, J=6.8 Hz, 3H), 1.16 (d, J=6.8 Hz, 3H), 0.99-1.03 (m, 8H), 0.93-0.95 (m, 8H), 0.84-0.89 (m, 14H), 0.82-0.84 (m, 4H), 0.80 (d, J=6.4 Hz, 4H), 0.67 (d, J=6.4 Hz, 4H). Mass (ESI): m/z calcd for C$_{67}$H$_{113}$N$_{11}$O$_{15}$S$_2$ 1375.79, found 1376.80 [M+H]$^+$.

Compound 6A: Preparation of: [2-((2R,3R)-3-methyl-5-(4-(4-methylpiperazin-1-yl)phenylthio) tetrahydrofuran-2-yl)-2-(methylamino)acetic acid]$^1$-cyclosporin A

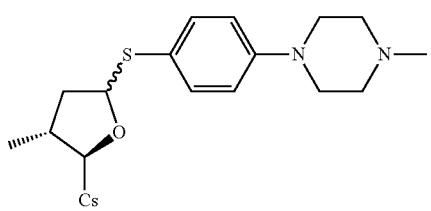

(I) Synthesis of 4-(4-methylpiperazin-1-yl)benzenethiol. The compound was synthesized from 4-(4-methylpiperazin-1-yl)aniline in a manner similar to that described for 4-Chloro-3-ethoxy-benzenethiol. 2 g of starting material was used and 680 mg white solid was obtained. Yield: 32.7%.

(II) Synthesis of [2-((2R,3R)-3-methyl-5-(4-(4-methylpiperazin-1-yl)phenylthio)tetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 4-(4-methylpiperazin-1-yl)benzenethiol was used instead of benzenethiol, 150 mg of starting material was used and 36 mg white solid was obtained which was purified by prep. TLC (CH$_2$Cl$_2$/MeOH=8/1). Yield: 21.7%. Mass (ESI): m/z calcd for C$_{71}$H$_{121}$N$_{13}$O$_{12}$S 1379.90, found 1381.55 [M+H]$^+$.

Compound 7A: Preparation of [2-((2R,3R)-3-methyl-5-(4-((4-methylpiperazin-1-yl)methyl)phenylthio)tetrahydrofuran-2-yl)-2-(methylamino)acetic acid]$^1$-cyclosporin A

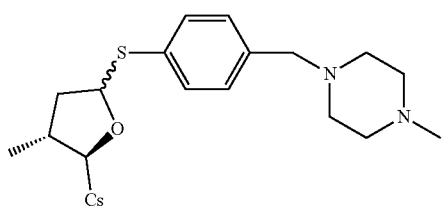

(I) Synthesis of 4-((4-methylpiperazin-1-yl)methyl)benzenethiol. The compound was synthesized from 4-(4-Methyl-piperazin-1-ylmethyl)-phenylamine in a manner similar to that described for 4-Chloro-3-ethoxy-benzenethiol. 1.5 g starting material was used and 0.52 g 4-((4-methyl piperazin-1-yl)methyl)benzenethiol was obtained as light-yellow oil through two reaction steps. Yield: 32.1%.

(II) Synthesis of [2-((2R,3R)-3-methyl-5-(4-((4-methylpiperazin-1-yl)methyl) phenylthio)tetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 4-((4-methylpiperazin-1-yl) methyl)benzenethiol was used instead of benzenethiol, 150 mg of starting material was used and 36 mg white solid was obtained. Yield: 21.1%. $^1$H NMR (400 MHz, CDCl$_3$) δ 8.41 (d, J=9.2 Hz, 1H), 8.05 (d, J=6.4 Hz, 1H), 7.65 (d, J=8.8 Hz, 1H), 7.52 (d, J=7.6 Hz, 1H), 7.39 (m, 2H), 7.16-7.23 (m, 2H), 5.64-5.68 (m, 1H), 5.51-5.53 (m, 1H), 5.30-5.34 (m, 1H), 5.10-5.23 (m, 4H), 4.96-5.02 (m, 1H), 4.81-4.92 (m, 3H), 4.65 (d, J=13.6 Hz, 1H), 4.37-4.42 (m, 11H), 4.29-4.31 (m, 1H), 3.54 (s, 2H), 3.42 (s, 3H), 3.38 (s, 3H), 3.22 (s, 3H), 3.18 (s, 3H), 3.06 (s, 3H), 2.94-2.99 (m, 2H), 2.82-2.92 (m, 6H), 2.77 (s, 3H), 2.70 (s, 3H), 2.67 (s, 3H), 2.41-2.49 (m, 1H), 2.27-2.34 (m, 1H), 2.09-2.18 (m, 3H), 1.92-2.06 (m, 3H), 1.57-1.74 (m, 6H), 1.45-1.55 (m, 2H), 1.33 (d, J=6.8 Hz, 3H), 1.26 (d, J=7.2 Hz, 3H), 1.17 (d, J=6.4 Hz, 3H), 0.99-1.04 (m, 8H), 0.93-0.95 (m, 10H), 0.84-0.90 (m, 14H), 0.79-0.83 (m, 7H), 0.69 (d, J=6.8 Hz, 3H). Mass (ESI): m/z calcd for C$_{72}$H$_{123}$N$_{13}$O$_{12}$S 1393.91, found 1395.04 [M+H]$^+$.

Compound 8A: Preparation of [2-((2R,3R)-5-(4-butylphenylthio)-3-methyltetrahydrofuran-2-yl)-2-(methylamino)acetic acid]¹-cyclosporin A

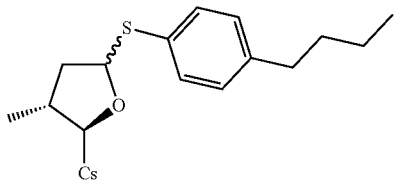

(I) Synthesis of 4-butylbenzenethiol. The solution of 4-butylbenzene-1-sulfonyl chloride (2.32 g, 0.01 mol) in 20 mL of THF was added slowly to the mixture of LiAlH$_4$ (0.945 g, 0.025 mol) in 10 mL of THF at 0° C. Let it reflux for 2 hrs. EtOAc was added. 40 mL of 2.5 M HCl solution was added. Filtered and extracted with EtOAc (50 mL×3). Dried with MgSO$_4$. Filtered and evaporated to dryness to give 1.45 g brown liquid. Yield: 87.3%. It was used for next step without further purification.

(II) Synthesis of [2-((2R,3R)-5-(4-butylphenylthio)-3-methyltetrahydrofuran-2-yl)-2-(methylamino)acetic acid]¹-cyclosporin A. The compound was synthesized from [2-((2R,3R)-5-acetoxy-3-methyltetrahydrofuran-2-yl)-2-(methylamino)acetic acid]¹-cyclosporin A in a manner similar to that described for compound 1B. 4-butylbenzenethiol was used instead of benzenethiol and 10 mg white solid was obtained. Yield: 9.2%. ¹H NMR (400 MHz, CDCl$_3$) δ 8.41 (d, J=9.6 Hz, 1H), 8.06 (d, J=6.8 Hz, 1H), 7.65 (d, J=8.8 Hz, 1H), 7.52 (d, J=8.0 Hz, 1H), 7.35 (d, J=8.0 Hz, 2H), 7.10 (d, J=8.0 Hz, 2H), 5.68 (dd, J=4.0, 11.2 Hz, 1H), 5.44 (dd, J=3.6, 8.0 Hz, 1H), 5.33 (dd, J=4.0, 11.2 Hz, 1H), 5.22 (d, J=6.4 Hz, 1H), 5.19 (d, J=5.2 Hz, 1H), 5.08-5.15 (m, 2H), 4.97-5.02 (m, 1H), 4.91-4.95 (m, 1H), 4.83-4.87 (m, 2H), 4.66 (d, J=13.6 Hz, 1H), 4.35-4.43 (m, 1H), 4.29 (dd, J=6.4, 9.6 Hz, 1H), 3.46 (s, 3H), 3.38 (s, 3H), 3.21 (s, 3H), 3.18 (s, 3H), 3.06 (s, 3H), 2.71 (s, 3H), 2.67 (s, 3H), 2.56 (t, J=8.0 Hz, 2H), 2.41-2.45 (m, 1H), 2.26-2.29 (m, 2H), 2.06-2.18 (m, 5H), 1.93-2.02 (m, 3H), 1.55-1.65 (m, 7H), 1.34 (d, J=6.8 Hz, 4H), 1.26 (d, J=6.8 Hz, 4H), 1.16 (d, J=6.8 Hz, 3H), 0.99-1.03 (m, 9H), 0.92-0.95 (m, 10H), 0.89-0.90 (m, 6H), 0.85-0.87 (m, 10H), 0.82 (d, J=6.4 Hz, 4H), 0.78 (d, J=6.4 Hz, 3H), 0.66 (d, J=6.4 Hz, 3H). Mass (ESI): m/z calcd for C$_{70}$H$_{119}$N$_{11}$O$_{12}$S 1337.88, found 1338.80 [M+H]⁺.

Compound 9A: Preparation of [2-((2R,3R)-5-(4-cyclohexylphenylthio)-3-methyltetrahydrofuran-2-yl)-2-(methylamino)acetic acid]¹-cyclosporin A

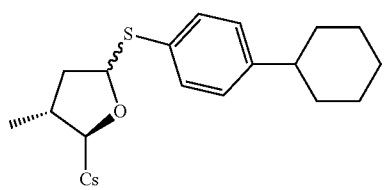

The compound was synthesized from [2-((2R,3R)-5-acetoxy-3-methyltetrahydrofuran-2-yl)-2-(methylamino)acetic acid]¹-cyclosporin A in a manner similar to that described for compound 1B. 4-cyclohexylbenzenethiol was used instead of benzenethiol and 12 mg white solid was obtained. Yield: 10.8%. ¹H NMR (400 MHz, CDCl$_3$) δ 8.40 (d, J=9.6 Hz, 1H), 8.06 (d, J=6.8 Hz, 1H), 7.64 (d, J=9.2 Hz, 1H), 7.52 (d, J=8.4 Hz, 1H), 7.36 (d, J=8.4 Hz, 2H), 7.13 (d, J=8.4 Hz, 2H), 5.67 (dd, J=4.4, 10.8 Hz, 1H), 5.45 (dd, J=3.6, 8.0 Hz, 1H), 5.33 (dd, J=4.0, 10.8 Hz, 1H), 5.21 (d, J=6.4 Hz, 1H), 5.19 (d, J=4.8 Hz, 1H), 5.08-5.14 (m, 2H), 4.96-5.02 (m, 2H), 4.90-4.94 (m, 1H), 4.83-4.87 (m, 1H), 4.66 (d, J=13.6 Hz, 1H), 4.35-4.42 (m, 1H), 4.29 (dd, J=6.0, 9.2 Hz, 1H), 3.46 (s, 3H), 3.38 (s, 3H), 3.21 (s, 3H), 3.18 (s, 3H), 3.06 (s, 3H), 2.71 (s, 3H), 2.67 (s, 3H), 2.41-2.47 (m, 2H), 2.29-2.33 (m, 3H), 2.06-2.16 (m, 5H), 1.93-2.01 (m, 3H), 1.59-1.74 (m, 8H), 1.38-1.42 (m, 3H), 1.33 (d, J=7.2 Hz, 5H), 1.26 (d, J=6.8 Hz, 4H), 1.16 (d, J=6.4 Hz, 3H), 0.99-1.03 (m, 8H), 0.93-0.95 (m, 9H), 0.89-0.90 (m, 5H), 0.85-0.87 (m, 10H), 0.82 (d, J=6.8 Hz, 4H), 0.78 (d, J=6.4 Hz, 3H), 0.66 (d, J=6.4 Hz, 3H). Mass (ESI): m/z calcd for C$_{72}$H$_{121}$N$_{11}$O$_{12}$S 1363.89, found 1365.20 [M+H]⁺.

Compound 10A: Preparation of [2-((2R,3R)-3-methyl-5-(4-(3-sulfopropylthio)phenylthio)tetrahydrofuran-2-yl)-2-(methylamino)acetic acid]¹-cyclosporin A

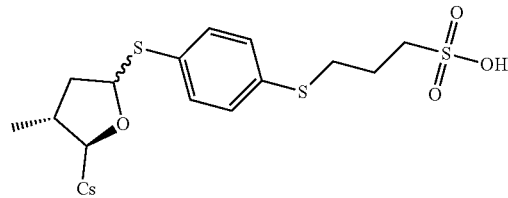

(I) Synthesis of 3-(4-mercaptophenylthio)propane-1-sulfonic acid. NaBr (1.685 g, 0.016 moL) was added to the solution of 1,3-propanesultone (2 g, 0.016 mol) in 25 mL H$_2$O. Let it stir at 60° C. for 1 h. The solvent was evaporated to dryness. It was recrystallized with EtOH/water (3/1) to give 2.27 g sodium 3-bromopropane-1-sulfonate as white solid. Yield: 63.3%.

Benzene-1,4-dithiol (500 mg, 3.515 mmol) was dissolved 1.5 mL of DMF. NaH (140.6 mg, 3.515 mmol) was added to the solution in portions at room temperature. Let it stir at room temperature for 1 h. The solution of sodium 3-bromopropane-1-sulfonate (0.74 g, 3.3 mmol) and tetrabutylammonium bromide (100 mg, 0.31 mmol) was added slowly to the mixture. Let it stir at 80° C. for 3 hrs. Ice-water was added. The white solid was filtered and the aqueous layer was acidified with con. HCl. It was evaporated to dryness and purified by C18 chromatography to give 150 mg of 3-(4-mercaptophenylthio)propane-1-sulfonic acid as colorless oil. Yield: 17.3° %.

(II) Synthesis of [2-((2R,3R)-3-methyl-5-(4-(3-sulfopropylthio)phenylthio) tetrahydrofuran-2-yl)-2-(methylamino) acetic acid]¹-cyclosporin A. The compound was synthesized from [2-((2R,3R)-5-acetoxy-3-methyltetrahydrofuran-2-yl)-2-(methylamino)acetic acid]¹-cyclosporin A in a manner similar to that described for compound 1B. 3-(4-mercaptophenylthio)propane-1-sulfonic acid was used instead of benzenethiol, 140 mg of starting material was used and 35 mg white solid was obtained which was purified by prep. TLC (CH$_2$Cl$_2$/MeOH=8/1). Yield: 21.4%. Mass (ESI): m/z calcd for C$_{69}$H$_{117}$N$_{11}$O$_5$S$_3$ 1435.79, found 1437.06 [M+H]⁺.

Compound 12A and Compound 12B: Preparation of [2-((2R,3R)-5-(3-(benzyloxy)phenylthio)-3-methyltetrahydrofuran-2-yl)-2-(methylamino)acetic acid]$^1$-cyclosporin A

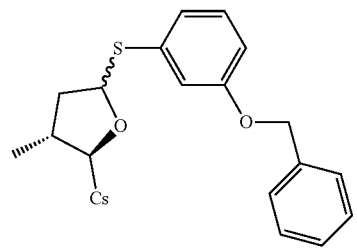

(I) Synthesis of 3-(benzyloxy)benzenethiol. The compound was synthesized from 3-benzyloxy-phenylamine in a manner similar to that described for 4-Chloro-3-ethoxy-benzenethiol. 1.5 g 3-benzyloxy-phenylamine was used and 0.33 g 3-(benzyloxy)benzenethiol was obtained as light-yellow solid through two reaction steps. Yield: 66.4%.

(I) Synthesis oft[2-((2R,3R)-5-(3-(benzyloxy)phenylthio)-3-methyltetrahydrofuran-2-yl)-2-(methylamino)acetic acid]$^1$-cyclosporin A. The compound was synthesized from [2-((2R,3R)-5-acetoxy-3-methyltetrahydro furan-2-yl)-2-(methylamino)acetic acid]$^1$-cyclosporin A in a manner similar to that described for compound 1B. 3-(benzyloxy)benzenethiol was used instead of benzenethiol, 5.2 g of starting material was used and 1 g compound 12A was obtained as white solid (yield: 17.1%) and 0.12 g compound 12B was obtained as white solid (yield: 2.05%).

Compound 12A: $^1$H NMR (400 MHz, CDCl$_3$) δ 8.40 (d, J=9.6 Hz, 1H), 8.06 (d, J=7.2 Hz, 1H), 7.63 (d, J=9.2 Hz, 1H), 7.51 (d, J=8.4 Hz, 1H), 7.43-7.44 (m, 2H), 7.35-7.39 (m, 2H), 7.29-7.33 (m, 1H), 7.23 (d, J=8.0 Hz, 1H), 7.14 (d, J=8.0 Hz, 1H), 7.01-7.04 (m, 1H), 6.82 (dd, J=2.4, 8.0 Hz, 1H), 5.66 (dd, J=4.0, 11.2 Hz, 1H), 5.49 (dd, J=3.6, 7.6 Hz, 1H), 5.33 (dd, J=4.0, 11.2 Hz, 1H), 5.21 (d, J=6.0 Hz, 1H), 5.19 (d, J=8.0 Hz, 1H), 5.07-5.14 (m, 2H), 5.05 (s, 2H), 4.98-5.02 (m, 1H), 4.83-4.97 (m, 3H), 4.65 (d, J=14.0 Hz, 1H), 4.37-4.44 (m, 1H), 4.32 (dd, J=6.0, 8.8 Hz, 1H), 3.46 (s, 3H), 3.37 (s, 3H), 3.25 (s, 3H), 3.17 (s, 3H), 3.06 (s, 3H), 2.69 (s, 3H), 2.65 (s, 3H), 2.39-2.47 (m, 1H), 2.26-2.33 (m, 1H), 2.07-2.15 (m, 3H), 1.93-2.05 (m, 3H), 1.55-1.70 (m, 5H), 1.42-1.49 (m, 3H), 1.33 (d, J=7.2 Hz, 3H), 1.25 (d, J=7.2 Hz, 3H), 1.17 (d, J=6.8 Hz, 3H), 0.97-1.04 (m, 8H), 0.93-0.95 (m, 8H), 0.84-0.90 (m, 16H), 0.81 (d, J=6.8 Hz, 4H), 0.79 (d, J=6.4 Hz, 3H), 0.62 (d, =6.4 Hz, 3H). Mass (ESI): m/z calcd for C$_{73}$H$_{117}$N$_{11}$O$_{13}$S 1387.86, found 1388.90 [M+H]$^+$.

Compound 12B: $^1$H NMR (400 MHz, CDCl$_3$) δ 8.32 (d, J=10.0 Hz, 1H), 7.97 (d, J=6.8 Hz, 1H), 7.31-7.45 (m, 7H), 7.15 (t, J=8.0 Hz, 1H), 7.13 (t, J=2.4 Hz, 1H), 7.00 (d, J=7.6 Hz, 1H), 6.79 (dd, J=2.4, 8.4 Hz, 1H), 5.67 (dd, J=4.0, 11.2 Hz, 1H), 5.40 (dd, J=6.0, 9.2 Hz, 1H), 5.31 (dd, J=4.0, 11.2 Hz, 1H), 5.27-5.29 (m, 2H), 5.20 (d, J=11.2 Hz, 1H), 5.04-5.09 (m, 2H), 5.03 (s, 2H), 4.89-4.95 (m, 1H), 4.79-4.86 (m, 2H), 4.55 (d, J=13.6 Hz, 1H), 4.40-4.47 (m, 1H), 4.08 (t, J=6.8 Hz, 1H), 3.56 (s, 3H), 3.24 (s, 6H), 3.15 (s, 3H), 3.02 (s, 3H), 2.67 (s, 6H), 2.28-2.36 (m, 1H), 2.18-2.24 (m, 1H), 2.05-2.14 (m, 3H), 1.90-1.99 (m, 3H), 1.76-1.87 (m, 2H), 1.54-1.68 (m, 3H), 1.35-1.46 (m, 3H), 1.33 (d, J=7.2 Hz, 3H), 1.23-1.25 (m, 6H), 1.02 (d, J=6.4 Hz, 3H), 0.97 (d, J=6.8 Hz, 3H), 0.91-0.95 (m, 14H), 0.82-0.87 (m, 15H), 0.80 (d, J=6.4 Hz, 4H), 0.67 (d, J=6.4 Hz, 3H). Mass (ESI): m/z calcd for C$_{73}$H$_{117}$N$_{11}$O$_{13}$S 1387.86, found 1389.05 [M+H]$^+$.

Compound 13A: Preparation of [2-((2R,3R)-5-(3-(4-((dimethylamino)methyl)benzyloxy)phenylthio)-3-methyltetrahydrofuran-2-yl)-2-(methylamino)acetic acid]$^1$-cyclosporin A

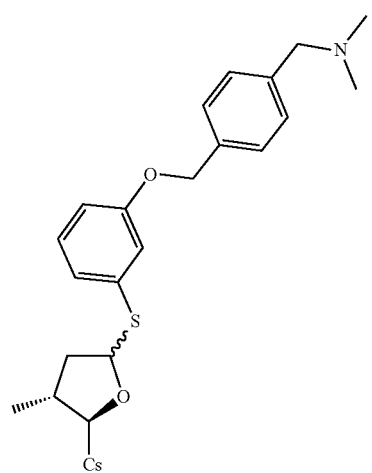

(I) Synthesis of 3-(4-((dimethylamino)methyl)benzyloxy)benzenethiol. 3,3'-Dihydroxydiphenyl disulfide (1 g, 4.05 mmol) was dissolved in 15 mL of N,N-dimethylformamide. NaH (320 mg, 8 mmol) was added slowly to the solution at 0° C. 4-Bromomethyl-N,N-dimethyl-benzamide (1.95 g, 3.34 mmol) in 3 mL of N,N-dimethylformamide was added slowly to the solution. Let it stir at room temperature for 16 hrs. It was poured into water and extracted with EtOAc (20 mL×3). The organic layers were combined and washed with brine. Dried with Na$_2$SO$_4$. Filtered and evaporated to dryness. The residue was purified by column chromatography (DCM/MeOH=10/1) to give 1.7 g 1,1'-(4,4'-(3,3'-disulfanediylbis (3,1-phenylene)bis(oxy))bis(methylene)bis(4,1-phenylene))bis(N,N-dimethylmethanamine) as light-brown oil. Yield: 73.2%.

1,1'-(4,4'-(3,3'-disulfanediylbis(3,1-phenylene)bis(oxy)) bis(methylene)bis(4,1-phenylene))bis(N,N-dimethylmethanamine) (1.2 g, 2.09 mmol) was suspended in 50 mL of THF. LiAlH$_4$ (0.348 g, 9.4 mmol) was added in portions to the mixture at 0° C. Then let it reflux for 5 hrs. Water was added slowly to quench the reaction. Filtered and the filtration was evaporated to dryness and purified by C18 chromatography (ACN/water=3/2) to give 120 mg 3-(4-((dimethylamino)methyl) benzyloxy)benzenethiol as light-yellow oil. Yield: 10.5%.

(II) Synthesis of [2-((2R,3R)-5-(3-(4-((dimethylamino) methyl) benzyloxy) phenylthio)-3-methyltetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(4-((dimethylamino)methyl) benzyloxy) benzenethiol was used instead of benzenethiol, 150 mg of starting material was used and 10 mg light-yellow solid was obtained. Yield: 10.0%. $^1$H NMR (400 MHz, CDCl$_3$) δ 8.39 (d, I=9.6 Hz, 1H), 8.05 (d, J=6.8 Hz, 1H), 7.64 (d, J=8.8 Hz, 2H), 7.53-7.60 (m, 3H), 7.50 (d, J=8.0 Hz, 1H), 7.15-7.17

(m, 1H), 7.05-7.11 (m, 1H), 6.98-7.00 (m, 1H), 6.78-6.84 (m, 1H), 5.66 (dd, J=4.0, 10.8 Hz, 1H), 5.50 (dd, J=4.0, 8.0 Hz, 1H), 5.33 (dd, J=4.0, 10.8 Hz, 1H), 5.17-5.26 (m, 3H), 5.12-5.14 (m, 1H), 5.08 (s, 2H), 4.96-5.02 (m, 1H), 4.89-4.93 (m, 1H), 4.83-4.88 (m, 2H), 4.66 (d, J=13.2 Hz, 1H), 4.37-4.42 (m, 1H), 4.29-4.33 (m, 1H), 4.16-4.21 (m, 2H), 3.45 (s, 3H), 3.38 (s, 3H), 3.22 (s, 3H), 3.17 (s, 3H), 3.06 (s, 3H), 2.79 (s, 3H), 2.76 (s, 3H), 2.68 (s, 3H), 2.66 (s, 3H), 2.42-2.47 (m, 1H), 2.30-2.34 (m, 1H), 2.09-2.15 (m, 3H), 1.98-2.05 (m, 3H), 1.59-1.67 (m, 5H), 1.46-1.52 (m, 3H), 1.33 (d, J=7.2 Hz, 3H), 1.25 (m, 3H), 1.17 (d, J=6.8 Hz, 3H), 0.97-1.02 (m, 8H), 0.90-0.95 (m, 14H), 0.86-0.89 (m, 10H), 0.81-0.82 (m, 4H), 0.79 (d, J=6.4 Hz, 3H), 0.63 (d, J=6.8 Hz, 3H). Mass (ESI): m/z calcd for $C_{76}H_{124}N_{12}O_{13}S$ 1444.91, found 1446.20 [M+H]$^+$.

Compound 14A: Preparation of [2-((2R,3R)-5-(3-(2-(dimethylamino)ethoxy)phenylthio)-3-methyltetrahydrofuran-2-yl)-2-(methylamino)acetic acid]$^1$-cyclosporin A

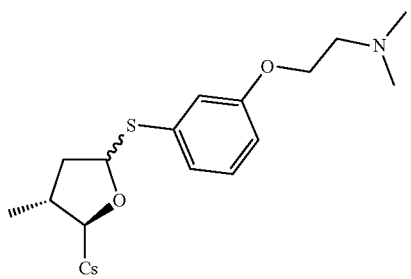

(I) Synthesis of 3-(2-(dimethylamino)ethoxy)benzenethiol. 4-(2-(dimethylamino)ethoxy)benzaldehyde (3.63 g, 18.8 mmol) was dissolved in 30 mL of MeOH. NaBH$_4$ (0.352 g, 9.51 mmol) was added in portions at 0° C. Let it stir at room temperature for 2.5 hrs. The solvent was evaporated to dryness and water was added. It was extracted with EtOAc (50 mL×3). Washed with water, dried with Na$_2$SO$_4$, filtered and evaporated to dryness to give 2.6 g (4-(2-(dimethylamino)ethoxy)phenyl)methanol as light-yellow oil. It was used for next step without further purification.

(4-(2-(dimethylamino)ethoxy)phenyl)methanol (1.8 g, 9.23 mmol), 3,3'-disulfanediyldiphenol (850 mg, 3.4 mmol) and PPh$_3$ (3.6 g, 13.74 mmol) were dissolved in 54 mL of THF. The solution of DIAD (2.79 g, 3.93 mmol) in 36 mL of THF was added slowly to the mixture at room temperature. Let it stir at room temperature for 16 hrs. The solvent was evaporated to dryness and purified by flash chromatography (DCM/MeOH=86/14) to give 861 mg 3-((3-(4-(((dimethylamino)methyl)benzyloxy)phenyl)disulfanyl)phenol as brown oil. Yield: 59.3%.

3-((3-(4-((dimethylamino)methyl)benzyloxy)phenyl)disulfanyl)phenol (639 mg, 1.99 mmol) was dissolved in 8 mL of THF. Bu$_3$P (0.474 mL, 1.894 mmol) was added to the solution. Let it stir at room temperature for 16 hrs. The solvent was evaporated to dryness and purified by C18 chromatography to give 60 mg 3-(2-(dimethylamino)ethoxy)benzenethiol as brown oil. Yield: 22%.

(II) Synthesis of [2-((2R,3R)-5-(3-(2-(dimethylamino)ethoxy)phenylthio)-3-methyltetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(2-(dimethylamino)ethoxy)benzenethiol was used instead of benzenethiol, 100 mg of starting material was used and 12 mg white solid was obtained. Yield: 10.8%. Mass (ESI): m/z calcd for $C_{70}H_{120}N_{12}O_{13}S$ 1368.88, found 1369.79 [M+H]$^+$.

Compound 15A: Preparation of [2-((2R,3R)-3-methyl-5-(3-(2-(1-methylpyrrolidin-2-yl)ethoxy)phenylthio)tetrahydrofuran-2-yl)-2-(methylamino)acetic acid]$^1$-cyclosporin A

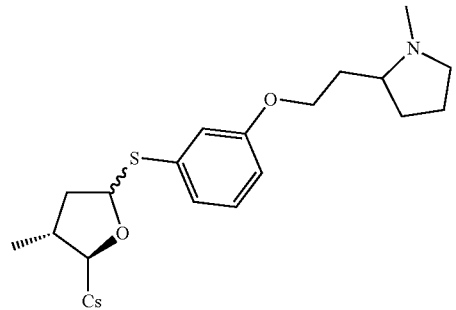

(I) Synthesis of 3-(2-(1-methylpyrrolidin-2-yl)ethoxy)benzenethiol

The compound was synthesized from 2-(2-chloroethyl)-1-methylpyrrolidine in a manner similar to that described for 3-(2-chloro-4-fluorobenzyloxy)benzenethiol. 340 mg of crude starting material was used and 68 mg 3-(2-(1-methylpyrrolidin-2-yl)ethoxy)benzenethiol was obtained as colorless oil.

(II) Synthesis of [2-((2R,3R)-3-methyl-5-(3-(2-(1-methylpyrrolidin-2-yl)ethoxy)phenylthio)tetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(2-(1-methylpyrrolidin-2-yl)ethoxy)benzenethiol was used instead of benzenethiol, 100 mg of starting material was used and 3.8 mg light-yellow solid was obtained. Yield: 3.3%. Mass (ESI): m/z calcd for $C_{73}H_{124}N_{12}O_{13}S$ 1408.91, found 1409.76 [M+H]$^+$.

Compound 16A: Preparation of [2-((2R,3R)-3-methyl-5-(3-((1-methyl-2-oxo-1,2-dihydropyridin-4-yl)methoxy)phenylthio)tetrahydrofuran-2-yl)-2-(methylamino)acetic acid]$^1$-cyclosporin A

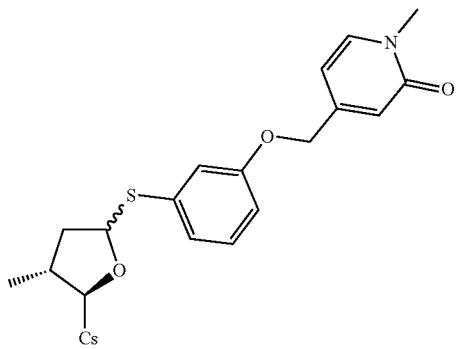

(I) Synthesis of 4-((3-mercaptophenoxy)methyl)-1-methylpyridin-2 (1H)-one. The compound was synthesized from 4-bromomethyl-1-methyl-1H-pyridin-2-one in a manner similar to that described for 3-(2-chloro-4-fluorobenzyloxy)benzenethiol. 146 mg starting material was used and 0.158 g 4-((3-mercaptophenoxy)methyl)-1-methylpyridin-2 (1H)-one was obtained as colorless oil. Yield: quantitative.

(II) Synthesis of [2-((2R,3R)-3-methyl-5-(3-((1-methyl-2-oxo-1,2-dihydropyridin-4-yl)methoxy)phenylthio)tetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino) acetic acid]$^1$-cyclosporin A in a manner similar to that described for compound 1B. 4-((3-mercaptophenoxy)methyl)-1-methylpyridin-2(1H)-one was used instead of benzenethiol, 150 mg of starting material was used and 22 mg white solid was obtained. Yield: 12.7%. $^1$H NMR (400 MHz, CDCl$_3$) δ 8.41 (d, J=9.2 Hz, 1H), 8.06 (d, J=6.8 Hz, 1H), 7.67 (d, J=8.8 Hz, 1H), 7.53 (d, J=8.0 Hz, 1H), 7.38-7.44 (m, 1H), 7.23-7.25 (m, 1H), 7.16-7.17 (m, 1H), 6.95-6.97 (m, 1H), 6.83-6.87 (m, J H), 6.76-6.80 (m, 1H), 6.44-6.49 (m, 1H), 5.65 (dd, J=4.0, 11.2 Hz, 1H), 5.49 (dd, J=3.2, 7.6 Hz, 1H), 5.34 (dd, J=4.0, 10.8 Hz, 1H), 5.22 (d, J=9.2 Hz, 1H), 5.18 (d, J=10.8 Hz, 1H), 5.05-5.14 (m, 2H), 4.92-5.02 (m, 4H), 4.81-4.91 (m, 2H), 4.66 (d, J=13.6 Hz, 1H), 4.37-4.44 (m, 1H), 4.32 (dd, J=6.4, 9.2 Hz, 1H), 3.64 (s, 3H), 3.46 (s, 3H), 3.38 (s, 3H), 3.22 (s, 3H), 3.17 (s, 3H), 3.07 (s, 3H), 2.68 (s, 3H), 2.66 (s, 3H), 2.40-2.48 (m, 1H), 2.28-2.34 (m, 1H), 2.09-2.17 (m, 3H), 1.95-2.05 (m, 3H), 1.60-1.72 (m, 5H), 1.40-1.51 (m, 3H), 1.33 (d, J=7.2 Hz, 3H), 1.25 (d, J=6.8 Hz, 3H), 1.17 (d, J=6.8 Hz, 3H), 0.97-1.02 (m, 9H), 0.92-0.95 (m, 10H), 0.85-0.89 (m, 13H), 0.81 (d, J=6.8 Hz, 4H), 0.78 (d, J=6.4 Hz, 3H), 0.62 (d, J=6.4 Hz, 3H). Mass (ESI): m/z calcd for C$_{73}$H$_{118}$N$_{12}$O$_{14}$S 1418.86, found 1419.85 [M+H]$^+$.

Compound 17A: Preparation of [2-((2R,3R)-5-(3-(4-(1H-pyrazol-1-yl)benzyloxy)phenylthio)-3-methyltetrahydrofuran-2-yl)-2-(methylamino)acetic acid]$^1$-cyclosporin A

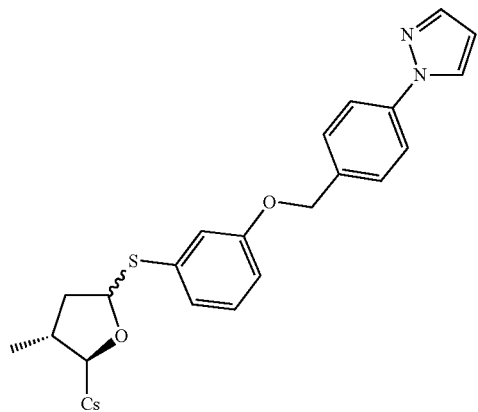

(I) Synthesis of 3-((4-(1H-pyrazol-1-yl)benzyl)oxy)benzenethiol. The compound was synthesized from 1-(4-(bromomethyl)phenyl)-1H-pyrazole in a manner similar to that described for 3-((3-chloro-4-fluorobenzyl)oxy)benzenethiol. 300 mg 1,2-bis(3-((4-(1H-pyrazol-1-yl) benzyl) oxy)phenyl)disulfane was obtained as white solid, yield: 33.4%. $^1$H-NMR (400 MHz, CDCl$_3$): δ 7.91 (d, J=2.4 Hz, 2H), 7.74 (d, J=1.6 Hz, 2H), 7.66 (dd, J=1.6 Hz, 4H), 7.46 (d, J=8.4 Hz, 4H), 7.20 (t, J=8.0 Hz, 2H), 7.13 (t, J=2.0 Hz, 2H), 7.05-7.08 (m, 2H), 6.80-6.83 (m, 2H), 6.47 (t, J=2.4 Hz, 2H), 5.03 (s, 4H). Then 300 mg 1,2-bis(3-((4-(1H-pyrazol-1-yl) benzyl) oxy)phenyl)disulfane was used and 260 mg yellow solid was obtained, yield: 86.3%. $^1$H-NMR (400 MHz, CDCl$_3$): δ 7.93-7.94 (m, 1H), 7.70-7.74 (m, 3H), 7.49 (d, J=8.8 Hz, 2H), 7.15 (t, J=8.0 Hz, 1H), 6.91 (t, J=1.6 Hz, 1H), 6.86-6.89 (m, 1H), 6.76-6.79 (m, 1H), 6.45-6.49 (m, 1H), 5.07 (s, 2H), 3.47 (s, 1H).

(II) Synthesis of [2-((2R,3R)-5-(3-(4-(1H-pyrazol-1-yl)benzyloxy)phenylthio)-3-methyltetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-((4-(1H-pyrazol-1-yl)benzyl)oxy)benzenethiol was used instead of benzenethiol and 40 mg white solid was obtained, yield: 22.6%. $^1$H NMR (400 MHz, CDCl$_3$) 8.39 (d, J=9.6 Hz, 1H), 8.05 (d, J=7.2 Hz, 1H), 7.94 (s, 1H), 7.73 (s, 1H), 7.71 (d, J=8.4 Hz, 2H), 7.63 (d, J=9.2 Hz, 1H), 7.53 (d, J=8.8 Hz, 3H), 7.51 (d, J=8.4 Hz, 1H), 7.15 (d, J=7.6 Hz, 1H), 7.02 (t, J=2.4 Hz, 1H), 6.83 (ddd, J=0.8, 2.4, 8.0 Hz, 1H), 6.48 (s, 1H), 5.66 (dd, J=4.0, 11.2 Hz, 1H), 5.50 (dd, J=3.6, 8.0 Hz, 1H), 5.33 (dd, J=4.0, 11.2 Hz, 1H), 5.22 (d, J=6.8 Hz, 1H), 5.19 (d, J=8.4 Hz, 1H), 5.12 (dd, J=5.6, 10.4 Hz, 1H), 5.08 (s, 2H), 5.06-5.07 (m, 2H), 4.96-5.02 (m, 1H), 4.92 (t, J=8.8 Hz, 1H), 4.85 (t, J=8.0 Hz, 1H), 4.66 (d, J=13.6 Hz, 1H), 4.37-4.42 (m, 1H), 4.33 (dd, J=6.0, 9.2 Hz, 1H), 3.47 (s, 3H), 3.38 (s, 3H), 3.22 (s, 3H), 3.17 (s, 3H), 3.06 (s, 3H), 2.69 (s, 3H), 2.66 (s, 3H), 2.42-2.45 (m, 1H), 2.30-2.35 (m, 1H), 2.09-2.16 (m, 3H), 1.94-2.02 (m, 3H), 1.61-1.70 (m, 5H), 1.42-1.49 (m, 3H), 1.33 (d, J=6.8 Hz, 3H), 1.25 (d, J=6.8 Hz, 3H), 1.18 (d, J=6.8 Hz, 3H), 1.01 (d, J=6.8 Hz, 3H), 0.97-0.99 (m, 7H), 0.93-0.95 (m, 8H), 0.89-0.91 (m, 4H), 0.85-0.88 (m, 10H), 0.81 (d, J=6.4 Hz, 4H), 0.77 (d, J=6.4 Hz, 3H), 0.63 (d, J=6.8 Hz, 3H). Mass (ESI) calcd for C$_{76}$H$_{119}$N$_{13}$O$_{13}$S 1453.88, found 1455.55 [M+H]$^+$.

Compound 18A: Preparation of [2-((2R,3R)-5-(3-(benzo[d][1,3]dioxol-5-ylmethoxy)phenylthio)-3-methyltetrahydrofuran-2-yl)-2-(methylamino)acetic acid]$^1$-cyclosporin A

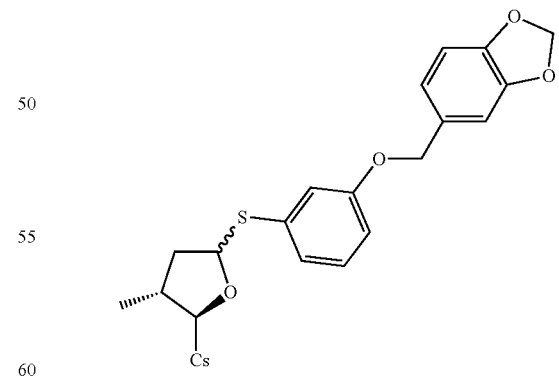

(I) Synthesis of 3-(benzo[d][1,3]dioxol-5-ylmethoxy)benzenethiol. The compound was synthesized from 5-(bromomethyl)benzo[d][1,3]dioxole in a manner similar to that described for 3-((3-chloro-4-fluorobenzyl)oxy)benzenethiol. 260 mg of 1,2-bis(3-(benzo[d][1,3]dioxol-5-ylmethoxy)phenyl)disulfane was obtained as colorless liquid, yield: 41.8%. ¹H-NMR (400 MHz, DMSO): δ 7.29 (t, J=8.0 Hz, 2H), 7.12 (t, J=2.4 Hz, 2H), 7.05-7.08 (m, 2H), 6.96 (s, 2H), 6.91-6.94 (m, 2H), 6.88 (m, 4H), 6.00 (s, 4H), 4.96 (s, 4H). 260 mg 1,2-bis(3-(benzo[d][1,3]dioxol-5-ylmethoxy)phenyl)disulfane was used, and 220 mg colorless liquid was obtained, yield: 84.3%. ¹H-NMR (400 MHz, CDCl₃): δ 7.14 (t, J=8.0 Hz, 1H), 6.90-6.91 (m, 1H), 6.84-6.89 (m, 3H), 6.82 (d, J=8.0 Hz, 1H), 6.73-6.76 (m, 1H), 5.97 (s, 2H), 4.92 (s, 2H), 3.45 (s, 1H).

(II) Synthesis of [2-((2R,3R)-5-(3-(benzo[d][1,3]dioxol-5-ylmethoxy)phenylthio)-3-methyltetrahydrofuran-2-yl)-2-(methylamino)acetic acid]¹-cyclosporin A. The compound was synthesized from [2-((2R,3R)-5-acetoxy-3-methyltetrahydrofuran-2-yl)-2-(methylamino)acetic acid]¹-cyclosporin A in a manner similar to that described for compound 1B. 3-(benzo[d][1,3]dioxol-5-ylmethoxy)benzenethiol was used instead of benzenethiol and 48 mg white solid was obtained, yield: 17%. ¹H NMR (400 MHz, CDCl₃) 8.39 (d, J=9.6 Hz, 1H), 8.06 (d, J=6.8 Hz, 1H), 7.62 (d, J=9.2 Hz, 1H), 7.51 (d, J=8.0 Hz, H), 7.13-7.15 (m, 1H), 6.98-6.99 (m, 1H), 6.95 (d, J=2.0 Hz, 1H), 6.90 (d, J=1.6 Hz, 1H), 6.88 (d, J=2.0 Hz, 1H), 6.80 (d, J=8.0 Hz, 2H), 5.96 (s, 2H), 5.66 (dd, J=4.0, 10.8 Hz, 1H), 5.49 (dd, J=3.6, 8.0 Hz, 1H), 5.33 (dd, J=4.4, 11.2 Hz, 1H), 5.22 (d, J=5.2 Hz, 1H), 5.19 (d, J=7.2 Hz, 1H), 5.10-5.14 (m, 1H), 5.06-5.08 (s, 1H), 4.97-5.02 (m, 2H), 4.94 (s, 2H), 4.83-4.86 (m, 2H), 4.66 (d, J=13.6 Hz, 1H), 4.37-4.41 (m, 1H), 4.32 (dd, J=6.4, 9.2 Hz, 1H), 3.47 (s, 3H), 3.38 (s, 3H), 3.22 (s, 3H), 3.18 (s, 3H), 3.06 (s, 3H), 2.69 (s, 3H), 2.66 (s, 3H), 2.42-2.45 (m, 1H), 2.29-2.34 (m, 1H), 2.12-2.17 (m, 3H), 1.94-1.99 (m, 3H), 1.58-1.64 (m, 5H), 1.45-1.50 (m, 3H), 1.33 (d, J=7.2 Hz, 3H), 1.25 (d, J=7.2 Hz, 3H), 1.18 (d, J=6.8 Hz, 3H), 1.01 (d, J=6.8 Hz, 3H), 0.97-1.00 (m, 8H), 0.94-0.95 (m, 7H), 0.89-0.91 (m, 4H), 0.87-0.88 (m, 10H), 0.81 (d, J=6.4 Hz, 4H), 0.79 (d, J=6.4 Hz, 3H), 0.62 (d, J=6.8 Hz, 3H). Mass (ESI) calcd for C₇₄H₁₁₇N₁₁O₁₅S 1431.85, found 1433.32 [M+H]⁺.

Compound 19A: Preparation of [2-((2R,3R)-5-(3-(2-fluorobenzyloxy)phenylthio)-3-methyltetrahydrofuran-2-yl)-2-(methylamino)acetic acid]¹-cyclosporin A

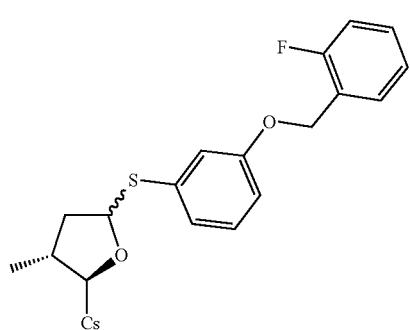

(I) Synthesis of 3-((2-fluorobenzyl)oxy)benzenethiol. The compound was synthesized from 5-(bromomethyl)benzo[d][1,3]dioxole in a manner similar to that described for 3-((3-chloro-4-fluorobenzyl)oxy)benzenethiol. 544 mg 1-(bromomethyl)-2-fluorobenzene was used and 400 mg 1,2-bis(3-((2-fluorobenzyl)oxy)phenyl)disulfane was obtained as colorless liquid, yield: 71.6%. ¹H-NMR (400 MHz, CDCl₃): δ 7.43-7.47 (m, 2H), 7.27-7.33 (m, 2H), 7.21 (t, J=8.0 Hz, 2H), 7.11-7.15 (m, 4H), 7.04-7.10 (m, 4H), 6.83-6.86 (m, 2H), 5.09 (s, 4H). Then 400 mg 1,2-bis(3-((2-fluorobenzyl)oxy)phenyl) disulfane was used and 335 mg 3-((2-fluorobenzyl)oxy)benzenethiol was obtained as colorless liquid, yield: 83.3%. ¹H-NMR (400 MHz, DMSO): δ 7.52-7.57 (m, 1H), 7.40-7.45 (m, 1H), 7.22-7.28 (m, 2H), 7.16 (t, J=8.0 Hz, 1H), 6.99-7.00 (m, 1H), 6.86-6.88 (m, 1H), 6.77-6.80 (m, 1H), 5.43 (s, 1H), 5.11 (s, 2H).

(II) Synthesis of [2-((2R,3R)-5-(3-(2-fluorobenzyloxy)phenylthio)-3-methyltetrahydrofuran-2-yl)-2-(methylamino)acetic acid]¹-cyclosporin A. The compound was synthesized from [2-((2R,3R)-5-acetoxy-3-methyltetrahydrofuran-2-yl)-2-(methylamino)acetic acid]¹-cyclosporin A in a manner similar to that described for compound 1B. 3-((2-fluoro benzyl)oxy)benzenethiol was used instead of benzenethiol and 26 mg white solid was obtained, yield: 22.8%. ¹H NMR (400 MHz, CDCl₃) δ 8.40 (d, J=9.6 Hz, 1H), 8.06 (d, J=6.8 Hz, 1H), 7.64 (d, J=8.8 Hz, 1H), 7.49-7.53 (m, 2H), 7.29-7.32 (m, 1H), 7.14-7.18 (m, 3H), 7.05-7.10 (m, 1H), 7.02 (t, J=2.0 Hz, 1H), 6.83 (dd, J=2.4, 8.0 Hz, 1H), 5.66 (dd, J=4.0, 11.2 Hz, 1H), 5.50 (dd, J=3.6, 7.6 Hz, 1H), 5.33 (dd, J=4.0, 11.2 Hz, 1H), 5.18-5.23 (m, 2H), 5.12 (s, 2H), 5.02-5.11 (m, 3H), 4.96-5.00 (m, 1H), 4.90-4.95 (m, 1H), 4.83-4.87 (m, 1H), 4.66 (d, J=13.6 Hz, 1H), 4.37-4.41 (m, 1H), 4.32 (dd, J=6.4, 9.6 Hz, 1H), 3.47 (s, 3H), 3.38 (s, 3H), 3.22 (s, 3H), 3.17 (s, 3H), 3.06 (s, 3H), 2.68 (s, 3H), 2.66 (s, 3H), 2.40-2.48 (m, 1H), 2.28-2.34 (m, 1H), 2.09-2.17 (m, 3H), 1.96-2.05 (m, 3H), 1.57-1.69 (m, 5H), 1.42-1.51 (m, 3H), 1.33 (d, J=7.2 Hz, 3H), 1.25 (d, J=6.8 Hz, 3H), 1.18 (d, J=6.8 Hz, 3H), 0.97-1.02 (m, 9H), 0.93-0.95 (m, 8H), 0.89-0.91 (m, 4H), 0.85-0.88 (m, 11H), 0.81 (d, J=6.4 Hz, 4H), 0.79 (d, J=6.4 Hz, 3H), 0.63 (d, J=6.4 Hz, 3H). Mass (ESI) calcd for C₇₃H₁₁₆FN₁₁O₁₃S 1405.85, found 1407.62 [M+H]⁺.

Compound 20A: Preparation of [2-((2R,3R)-5-(3-(3-fluorobenzyloxy)phenylthio)-3-methyltetrahydrofuran-2-yl)-2-(methylamino)acetic acid]¹-cyclosporin A(I) Synthesis of 3-((3-fluorobenzyl)oxy)benzenethiol

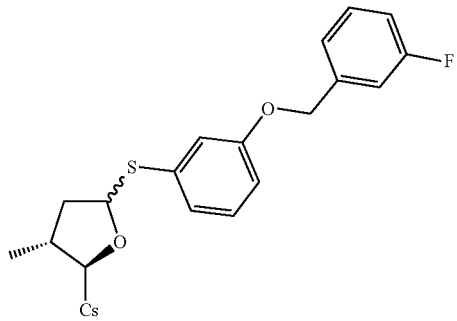

The compound was synthesized from 5-(bromomethyl)benzo[d][1,3]dioxole in a manner similar to that described for 3-((3-chloro-4-fluorobenzyl)oxy)benzenethiol. 544 mg 1-(bromomethyl)-3-fluorobenzene was used and 480 mg 1,2-bis(3-((3-fluorobenzyl) oxy) phenyl) disulfane was obtained as pale yellow liquid, yield: 85.9%. ¹H-NMR (400 MHz, CDCl₃): δ 7.28-7.34 (m, 2H), 7.21 (t, J=8.0 Hz, 2H), 7.06-7.15 (m, 8H), 6.94-7.02 (m, 2H), 6.81-6.84 (m, 2H), 5.01 (s, 4H). Then 480 mg 1,2-bis(3-((3-fluorobenzyl) oxy) phenyl) disulfane was used and 380 mg 3-((3-fluorobenzyl)oxy)benzenethiol was obtained as colorless liquid, yield:

78.8%. ¹H-NMR (400 MHz, DMSO): δ 7.41-7.47 (m, 1H), 7.25-7.28 (m, 2H), 7.16 (t, J=8.0 Hz, 2H), 6.97-6.98 (m, 1H), 6.87 (d, J=6.8 Hz, 1H), 6.76 (dd, J=2.4, 8.4 Hz, 1H), 5.43 (s, 1H), 5.10 (s, 2H).

(II) Synthesis of [2-((2R,3R)-5-(3-(3-fluorobenzyloxy)phenylthio)-3-methyltetrahydrofuran-2-yl)-2-(methylamino)acetic acid]¹-cyclosporin A. The compound was synthesized from [2-((2R,3R)-5-acetoxy-3-methyltetrahydrofuran-2-yl)-2-(methylamino)acetic acid]¹-cyclosporin A in a manner similar to that described for compound 1B. 3-((3-fluorobenzyl)oxy)benzenethiol was used instead of benzenethiol and 79 mg white solid was obtained, yield: 53.0%. ¹H NMR (400 MHz, CDCl₃) 8.40 (d, J=10.0 Hz, 1H), 8.05 (d, J=6.8 Hz, 1H), 7.63 (d, J=8.4 Hz, 1H), 7.51 (d, J=7.6 Hz, H), 7.31-7.35 (m, 1H), 7.19-7.21 (m, 2H), 7.14-7.17 (m, 2H), 6.98-7.02 (m, 2H), 6.80-6.82 (m, 1H), 5.66 (dd, J=4.0, 10.8 Hz, 1H), 5.49 (dd, J=3.6, 8.0 Hz, 1H), 5.33 (dd, J=4.0, 11.2 Hz, 1H), 5.18-5.23 (m, 2H), 5.07-5.14 (m, 3H), 5.05 (s, 2H), 4.98-5.02 (m, 1H), 4.92 (t, J=8.4 Hz, 1H), 4.85 (t, J=6.4 Hz, 1H), 4.66 (d, J=13.6 Hz, 1H), 4.37-4.42 (m, 1H), 4.32 (dd, J=6.4, 9.2 Hz, 1H), 3.47 (s, 3H), 3.38 (s, 3H), 3.22 (s, 3H), 3.18 (s, 3H), 3.06 (s, 3H), 2.68 (s, 3H), 2.66 (s, 3H), 2.40-2.48 (m, 1H), 2.28-2.34 (m, 1H), 2.08-2.17 (m, 3H), 1.96-2.03 (m, 3H), 1.58-1.70 (m, 5H), 1.40-1.50 (m, 3H), 1.33 (d, J=6.8 Hz, 3H), 1.25 (d, J=7.2 Hz, 3H), 1.18 (d, J=6.8 Hz, 3H), 1.01 (d, J=6.4 Hz, 3H), 0.96-0.99 (m, 7H), 0.93-0.95 (m, 8H), 0.89-0.91 (m, 4H), 0.85-0.88 (m, 10H), 0.82 (d, J=6.4 Hz, 4H), 0.78 (d, J=6.8 Hz, 3H), 0.62 (d, J=6.4 Hz, 3H). Mass (ESI) calcd for C₇₃H₁₁₆FN₁₁O₁₃S 1405.85, found 1407.55 [M+H]⁺.

Compound 21A: Preparation of [2-((2R,3R)-5-(3-(4-fluorobenzyloxy)phenylthio)-3-methyltetrahydrofuran-2-yl)-2-(methylamino)acetic acid]¹-cyclosporin A (I) Synthesis of 3-((4-fluorobenzyl)oxy)benzenethiol. The compound was synthesized from 5-(bromomethyl)benzo[d][1,3]dioxole in a manner similar to that described for 3-((3-chloro-4-fluorobenzyl)oxy)benzenethiol. 544 mg 1-(bromomethyl)-4-fluorobenzene was used and 400 mg 1,2-bis(3-((4-fluorobenzyl)oxy) phenyl) disulfane was obtained as pale yellow liquid, yield: 71.6%. ¹H-NMR (400 MHz, CDCl₃): δ 7.33-7.36 (m, 4H), 7.21 (t, J=8.0 Hz, 2H), 7.10-7.12 (m, 2H), 7.01-7.08 (m, 6H), 6.80-6.83 (m, 2H), 4.97 (s, 4H). Then 400 mg 1,2-bis(3-((4-fluorobenzyl)oxy) phenyl) disulfane was used and 280 mg 3-((4-fluorobenzyl)oxy)benzenethiol was obtained as colorless liquid, yield: 67.7%. ¹H-NMR (400 MHz, DMSO): δ 7.47-7.50 (m, 2H), 7.22 (t, J=8.8 Hz, 2H), 7.15 (t, J=8.0 Hz, 1H), 6.96-6.97 (m, 1H), 6.84-6.87 (m, 1H), 6.74-6.77 (m, 1H), 5.41 (s, 1H), 5.05 (s, 2H).

(II) Synthesis of [2-((2R,3R)-5-(3-(4-fluorobenzyloxy)phenylthio)-3-methyltetrahydrofuran-2-yl)-2-(methylamino)acetic acid]1-cyclosporin A. The compound was synthesized from [2-((2R,3R)-5-acetoxy-3-methyltetrahydrofuran-2-yl)-2-(methylamino)acetic acid]¹-cyclosporin A in a manner similar to that described for compound 1B. 3-((4-fluoro benzyl)oxy)benzenethiol was used instead of benzenethiol and 70 mg white solid was obtained, yield: 47.0%. ¹H NMR (400 MHz, CDCl₃) δ 8.39 (d, J=10.0 Hz, 1H), 8.05 (d, J=7.2 Hz, 1H), 7.63 (d, J=8.8 Hz, 1H), 7.51 (d, J=8.4 Hz, 1H), 7.41 (dd, J=5.6, 8.8 Hz, 2H), 7.23 (d, J=8.0 Hz, 1H), 7.15 (d, J=8.0 Hz, 1H), 7.06 (t, J=8.8 Hz, 2H), 7.00 (t, J=2.0 Hz, 1H), 6.80 (ddd, J=0.8, 2.4, 8.4 Hz, 1H), 5.66 (dd, J=4.0, 11.2 Hz, 1H), 5.49 (dd, J=3.6, 8.0 Hz, 1H), 5.33 (dd, J=4.0, 11.2 Hz, 1H), 5.21 (d, J=7.2 Hz, 1H), 5.19 (d, J=8.4 Hz, 1H), 5.06-0.14 (m, 3H), 5.01 (s, 2H), 4.96-4.98 (m, 1H), 4.92 (t, J=8.0 Hz, 1H), 4.85 (t, J=8.0 Hz, 1H), 4.66 (d, J=14.0 Hz, 1H), 4.37-4.42 (m, 1H), 4.32 (dd, J=6.4, 9.6 Hz, 1H), 3.46 (s, 3H), 3.38 (s, 3H), 3.22 (s, 3H), 3.17 (s, 3H), 3.06 (s, 3H), 2.69 (s, 3H), 2.66 (s, 3H), 2.39-2.47 (m, 1H), 2.28-2.33 (m, 1H), 2.08-2.16 (m, 3H), 1.93-2.04 (m, 3H), 1.58-1.70 (m, 5H), 1.39-1.50 (m, 3H), 1.33 (d, J=7.2 Hz, 3H), 1.25 (d, J=6.8 Hz, 3H), 1.17 (d, J=6.8 Hz, 3H), 1.01 (d, J=6.4 Hz, 3H), 0.96-0.99 (m, 6H), 0.93-0.95 (m, 7H), 0.89-0.91 (m, 4H), 0.85-0.88 (m, 12H), 0.81 (d, J=6.8 Hz, 4H), 0.78 (d, J=6.4 Hz, 3H), 0.62 (d, J=6.8 Hz, 3H). Mass (ESI) calcd for C₇₃H₁₁₆FN₁₁O₃S 1405.85, found 1407.55 [M+H]⁺.

Compound 22A: Preparation of [2-((2R,3R)-5-(3-(3-chloro-4-fluorobenzyloxy)phenylthio)-3-methyltetrahydrofuran-2-yl)-2-(methylamino)acetic acid]¹-cyclosporin A

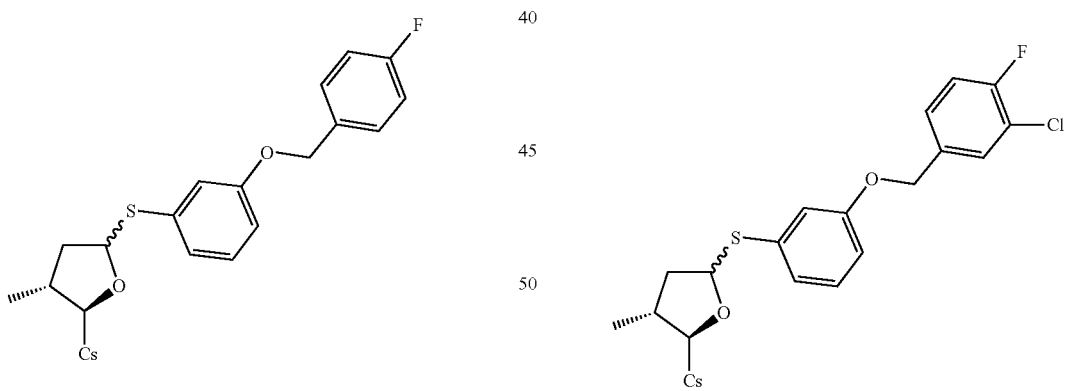

(I) Synthesis of 3-((3-chloro-4-fluorobenzyl)oxy)benzenethiol. A solution of 3,3'-(disulphanediyl)diphenol (500 mg, 2 mmol) was stirred in dry DMF (9 mL). NaH (168 mg, 4.2 mmol) was added at 0° C. Then 4-(bromomethyl)-2-chloro-1-fluorobenzene (939 mg, 4.2 mmol) was added after 10 minutes. The mixture was stirred at r.t. overnight. The reaction mixture was poured into water and extracted with EA (3×10 mL) and the organic layers were combined, dried over Na₂SO₄, filtered, concentrated and purified by column chromatography on silica gel (PE:EA=10:1) to obtain 320 mg 1,2-bis(3-((3-chloro-4-fluorobenzyl)oxy)phenyl)disulfane as colorless liquid. Yield: 30.0%. ¹H-NMR (400 MHz, CDCl₃): δ 7.45 (dd, J=2 Hz, 2H), 7.20-7.24 (m, 4H), 7.12 (d, J=8.8 Hz, 2H), 7.06-7.08 (m, 4H), 6.80-6.83 (m, 2H), 4.95 (s, 4H).

n-Bu₃P (121.2 mg, 0.6 mmol) was added to a solution of 1,2-bis(3-((3-chloro-4-fluorobenzyl)oxy)phenyl)disulfane (320 mg, 0.6 mmol) in dry THF (6 mL). The mixture was stirred at r.t. for 3 hrs. The reaction mixture was concentrated and purified by chromatography on silica gel (PE:EA=50:1) to obtain 243 mg colorless liquid. Yield: 75.6%. ¹H-NMR (400 MHz, DMSO): δ 7.60-7.68 (m, 1H), 7.44-7.46 (m, 2H), 7.16 (t, J=8.0 Hz, 1H), 7.96-7.97 (m, 1H), 6.85-6.88 (m, 1H), 6.75-6.78 (m, 1H), 5.44 (s, 1H), 5.06 (s, 2H).

(II) Synthesis of [2-((2R,3R)-5-(3-(3-chloro-4-fluorobenzyloxy)phenylthio)-3-methyltetrahydrofuran-2-yl)-2-(methylamino)acetic acid]¹-cyclosporin A. The compound was synthesized from [2-((2R,3R)-5-acetoxy-3-methyltetrahydrofuran-2-yl)-2-(methylamino)acetic acid]¹-cyclosporin A in a manner similar to that described for compound 1B. 3-((3-chloro-4-fluorobenzyl)oxy)benzenethiol was used instead of benzenethiol and 90 mg white solid was obtained, yield: 38.6%. ¹H NMR (400 MHz, CDCl₃) δ 8.39 (d, J=9.6 Hz, 1H), 8.05 (d, J=6.8 Hz, 1H), 7.63 (d, J=8.8 Hz, 1H), 7.55 (dd, J=2.0, 6.8 Hz, 1H), 7.51 (d, J=8.4 Hz, 1H), 7.30-7.33 (m, 1H), 7.24 (d, J=8.0 Hz, 1H), 7.14-7.16 (d, J=8.8 Hz, 2H), 7.10 (dd, J=1.6, 2.4 Hz, 1H), 6.80 (ddd, J=0.8, 2.8, 7.6 Hz, 1H), 5.65 (dd, J=4.0, 10.8 Hz, 1H), 5.48 (dd, J=3.6, 8.0 Hz, 1H), 5.33 (dd, J=4.0, 11.2 Hz, 1H), 5.21 (d, J=9.6 Hz, 1H), 5.19 (d, J=11.2 Hz, 1H), 5.02-5.14 (m, 3H), 5.00 (d, J=2.8 Hz, 2H), 4.96-4.98 (m, 1H), 4.91 (t, J=8.0 Hz, 1H), 4.85 (t, J=8.0 Hz, 1H), 4.66 (d, J=14.0 Hz, 1H), 4.37-4.42 (m, 1H), 4.33 (dd, J=6.0, 9.2 Hz, 1H), 3.47 (s, 3H), 3.38 (s, 3H), 3.22 (s, 3H), 3.17 (s, 3H), 3.06 (s, 3H), 2.69 (s, 3H), 2.66 (s, 3H), 2.39-2.47 (m, 1H), 2.27-2.35 (m, 1H), 2.11-2.17 (m, 3H), 1.96-2.04 (m, 3H), 1.59-1.69 (m, 5H), 1.42-1.49 (m, 3H), 1.33 (d, J=7.2 Hz, 3H), 1.25 (d, J=6.8 Hz, 3H), 1.18 (d, J=6.8 Hz, 3H), 1.01 (d, J=6.4 Hz, 3H), 0.97 (d, J=2.8 Hz, 3H), 0.96 (d, J=3.2 Hz, 3H), 0.93-0.95 (m, 7H), 0.89-0.91 (m, 4H), 0.85-0.88 (m, 12H), 0.81 (d, J=6.4 Hz, 4H), 0.77 (d, J=6.4 Hz, 3H), 0.60 (d, J=6.4 Hz, 3H). Mass (ESI) calcd for C₇₃H₁₁₅ClFN₁₁O₃S 1439.81, found 1441.25 [M+H]⁺.

Compound 23A: Preparation of [2-((2R,3R)-5-(3-(2-chloro-4-fluorobenzyloxy)phenylthio)-3-methyltetrahydrofuran-2-yl)-2-(methylamino)acetic acid]¹-cyclosporin A

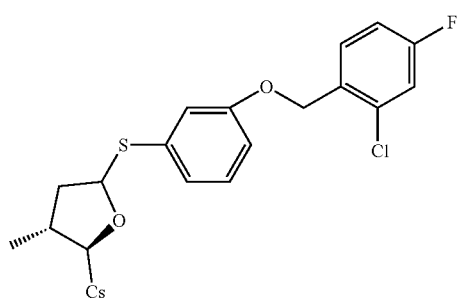

(I) Synthesis of 3-(2-chloro-4-fluorobenzyloxy)benzenethiol. 3,3'-Dihydroxydiphenyl disulfide (400 mg, 1.62 mmol) was dissolved in 7 mL of N,N-dimethylformamide. NaH (133 mg, 3.34 mmol) was added slowly to the solution at 0° C. 1-Bromomethyl-2-chloro-4-fluoro-benzene (754.7 mg, 3.34 mmol) in 2 mL of N,N-dimethylformamide was added slowly to the solution. Let it stir at room temperature for 16 hrs. It was poured into water and extracted with EtOAc (20 mL×3). The organic layer was combined and washed with 1N NaOH, brine. Dried with Na₂SO₄. Filtered and evaporated to dryness. The residue was purified by column chromatography (PE/EA=24/1) to give 530 mg 1,2-bis(3-(2-chloro-4-fluorobenzyloxy)phenyl)disulfane as light-brown oil. Yield: 62.1%.

1,2-bis(3-(2-chloro-4-fluorobenzyloxy)phenyl)disulfane (530 mg, 0.9 mmol) was dissolved in 11 mL of THF. n-Bu₃P (246 μL, 0.99 mmol) was added. Let it stir at room temperature for 1 h. Water was added. It was extracted with EtOAc (20 mL×3). Dried with Na₂SO₄. Filtered and evaporated to dryness. The residue was purified by column chromatography (PE/EA=93/7) to give 230 mg 3-(2-chloro-4-fluorobenzyloxy)benzenethiol as light-yellow solid. Yield: 43.3%.

(II) Synthesis of [2-((2R,3R)-5-(3-(2-chloro-4-fluorobenzyloxy)phenylthio)-3-methyltetrahydrofuran-2-yl)-2-(methylamino)acetic acid]¹-cyclosporin A. The compound was synthesized from [2-((2R,3R)-5-acetoxy-3-methyltetrahydrofuran-2-yl)-2-(methylamino)acetic acid]¹-cyclosporin A in a manner similar to that described for compound 1B. 3-(2-chloro-4-fluorobenzyloxy)benzenethiol was used instead of benzenethiol, 150 mg of starting material was used and 25 mg light-yellow solid was obtained. Yield: 14.3%. ¹H NMR (400 MHz, CDCl₃) δ 8.38 (d, J=9.6 Hz, 1H), 8.05 (d, J=6.8 Hz, 1H), 7.63 (d, J=9.2 Hz, 1H), 7.55 (d, J=6.4 Hz, 1H), 7.49-7.54 (m, 2H), 7.13-7.18 (m, 2H), 7.01-7.03 (m, 2H), 6.81 (dd, J=2.0, 8.0 Hz, 1H), 5.66 (dd, J=4.0, 11.2 Hz, 1H), 5.50 (dd, J=3.6, 8.0 Hz, 1H), 5.33 (dd, J=4.0, 11.2 Hz, 1H), 5.17-5.22 (m, 2H), 5.12-5.14 (m, 1H), 5.10 (s, 2H), 5.05-5.08 (m, 2H), 4.96-5.02 (m, 1H), 4.92 (t, J=8.4 Hz, 1H), 4.84 (t, J=7.6 Hz, 1H), 4.65 (d, J=13.6 Hz, 1H), 4.37-4.42 (m, 1H), 4.32 (dd, J=6.4, 9.2 Hz, 1H), 3.46 (s, 3H), 3.37 (s, 3H), 3.22 (s, 3H), 3.17 (s, 3H), 3.06 (s, 3H), 2.67 (s, 3H), 2.65 (s, 3H), 2.42-2.48 (m, 1H), 2.28-2.33 (m, 1H), 2.08-2.14 (m, 3H), 1.93-2.03 (m, 3H), 1.54-1.69 (m, 6H), 1.43-1.49 (m, 2H), 1.33 (d, J=7.2 Hz, 3H), 1.25 (d, J=7.2 Hz, 3H), 1.17 (d, J=6.4 Hz, 3H), 0.97-1.02 (m, 8H), 0.93-0.96 (m, 8H), 0.89-0.90 (m, 4H), 0.84-0.87 (m, 12H), 0.81 (d, J=6.4 Hz, 4H), 0.78 (d, J=6.8 Hz, 3H), 0.63 (d, J=6.4 Hz, 3H). Mass (ESI): m/z calcd for C₇₃H₁₁₅ClFN₁₁O₁₃S 1439.81, found 1441.49 [M+H]⁺.

Compound 24A: Preparation of [2-((2R,3R)-5-(3-(4-fluoro-2-methylbenzyloxy)phenylthio)-3-methyltetrahydrofuran-2-yl)-2-(methylamino)acetic acid]¹-cyclosporin A

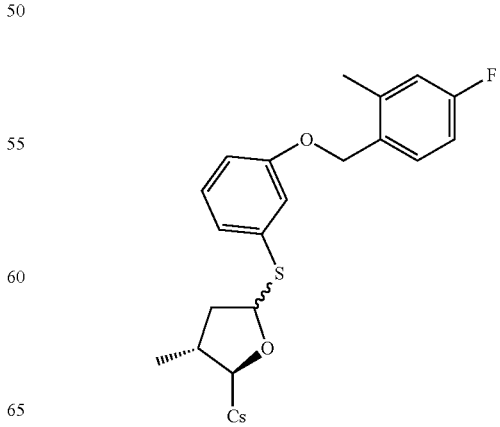

(I) Synthesis of 3-(4-fluoro-2-methylbenzyloxy)benzenethiol. The compound was synthesized from 1-bromomethyl-4-fluoro-2-methyl-benzene in a manner similar to that described for 3-(2-chloro-4-fluorobenzyloxy)benzenethiol. 677 mg starting material was used and 0.33 g 3-(4-fluoro-2-methylbenzyloxy)benzenethiol was obtained as light-pale oil. Yield: 65.9%.

(II) Synthesis of [2-((2R,3R)-5-(3-(4-fluoro-2-methylbenzyloxy)phenylthio)-3-methyltetrahydrofuran-2-yl)-2-(methylamino)acetic acid][1]-cyclosporin A. The compound was synthesized from [2-((2R,3R)-5-acetoxy-3-methyltetrahydrofuran-2-yl)-2-(methylamino)acetic acid][1]-cyclosporin A in a manner similar to that described for compound 1B. 3-(4-fluoro-2-methylbenzyloxy)benzenethiol was used instead of benzenethiol, 100 mg of starting material was used and 56 mg white solid was obtained. Yield: 49.3%. $^1$H NMR (400 MHz, CDCl$_3$) δ 8.39 (d, J=10.0 Hz, 1H), 8.04 (d, J=6.0 Hz, 1H), 7.63 (d, J=9.2 Hz, 1H), 7.50 (d, J=7.2 Hz, 1H), 7.35-7.38 (m, 1H), 7.23-7.26 (m, 1H), 7.14-7.20 (m, 1H), 7.00-7.02 (m, 1H), 6.79-6.97 (m, 3H), 5.63-5.68 (m, 1H), 5.48-5.53 (m, 1H), 5.30-5.34 (m, 1H), 5.18-5.23 (m, 2H), 5.05-5.14 (m, 2H), 4.99-5.01 (m, 1H), 4.96 (s, 2H), 4.82-4.93 (m, 3H), 4.65 (d, J=13.6 Hz, 1H), 4.36-4.42 (m, 1H), 4.30-4.34 (m, 1H), 3.46 (s, 3H), 3.38 (s, 3H), 3.22 (s, 3H), 3.17 (s, 3H), 3.06 (s, 3H), 2.69 (s, 3H), 2.66 (s, 3H), 2.39-2.49 (m, 1H), 2.35 (s, 3H), 2.23-2.33 (m, 1H), 2.07-2.18 (m, 3H), 1.90-2.05 (m, 3H), 1.54-1.73 (m, 5H), 1.38-1.52 (m, 3H), 1.33 (d, J=6.8 Hz, 3H), 1.25 (d, J=6.8 Hz, 3H), 1.17 (d, J=6.8 Hz, 3H), 0.96-1.02 (m, 9H), 0.90-0.94 (m, 10H), 0.84-0.88 (m, 13H), 0.77-0.82 (m, 7H), 0.63 (d, J=6.0 Hz, 3H). Mass (ESI): m/z calcd for C$_{74}$H$_{118}$FN$_{11}$O$_{13}$S 1419.86, found 1420.70 [M+H]$^+$.

Compound 25A: Preparation of [2-((2R,3R)-5-(3-hydroxyphenylthio)-3-methyltetrahydrofuran-2-yl)-2-(methylamino)acetic acid][1]-cyclosporine A

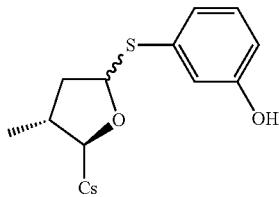

The compound was synthesized from [2-((2R,3R)-5-acetoxy-3-methyltetrahydrofuran-2-yl)-2-(methylamino)acetic acid][1]-cyclosporin A in a manner similar to that described for compound 1B. 3-Mercaptophenol was used instead of benzenethiol and 6 mg brown solid was obtained. Yield: 2.3%. $^1$H NMR (400 MHz, CDCl$_3$) δ 8.97 (brs, 1H), 8.44 (d, J=9.2 Hz, 1H), 8.12 (d, J=7.2 Hz, 1H), 7.74 (d, J=9.2 Hz, 1H), 7.60 (d, J=8.4 Hz, 1H), 7.29 (t, J=2.0 Hz, 1H), 7.08 (t, J=8.0 Hz, 1H), 6.74 (d, J=8.0 Hz, 1H), 6.67-6.70 (m, 1H), 5.64 (dd, J=4.0, 11.2 Hz, 1H), 5.58 (dd, J=3.6, 8.0 Hz, 1H), 5.34-5.38 (m, 3H), 5.24 (dd, J=6.8, 9.2 Hz, 1H), 5.18 (t, J=6.8 Hz, 1H), 4.99-5.05 (m, 2H), 4.86-4.91 (m, 2H), 4.65 (d, J=13.2 Hz, 1H), 4.38-4.45 (m, 1H), 4.28 (dd, J=8.0, 9.6 Hz, 1H), 3.44 (s, 3H), 3.43 (s, 3H), 3.24 (s, 3H), 3.18 (s, 3H), 3.09 (s, 3H), 2.73 (s, 3H), 2.69 (s, 3H), 2.32-2.42 (m, 1H), 2.14-2.21 (m, 2H), 1.98-2.11 (m, 3H), 1.88-1.97 (m, 2H), 1.62-1.70 (m, 5H), 1.41-1.49 (m, 3H), 1.31 (d, J=7.2 Hz, 3H), 1.27 (d, J=7.2 Hz, 3H), 1.26 (d, J=4.8 Hz, 3H), 1.12 (d, J=6.8 Hz, 3H), 1.00-1.04 (m, 6H), 0.91-0.95 (m, 14H), 0.86-0.89 (m, 12H), 0.84 (d, J=2.8 Hz, 4H), 0.76 (d, J=6.4 Hz, 3H). Mass (ESI) calcd for C$_{66}$H$_{111}$N$_{11}$O$_{13}$S 1297.81, found 1299.28 [M+H]$^+$.

Compound 26A and Compound 26B: Preparation of [2-((2R,3R)-5-(4-methoxyphenylthio)-3-methyltetrahydrofuran-2-yl)-2-(methylamino)acetic acid][1]-cyclosporin A

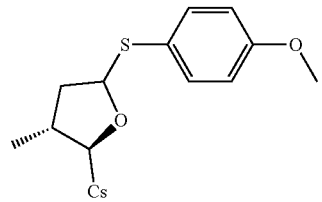

The compound was synthesized from [2-((2R,3R)-5-acetoxy-3-methyl tetrahydrofuran-2-yl)-2-(methylamino)acetic acid][1]-cyclosporin A in a manner similar to that described for compound 1B. 4-methoxybenzenethiol was used instead of benzenethiol, 100 mg of starting material was used and 50 mg of compound 26A was obtained as white solid. Yield: 47.1%. 8 mg of compound 26B was obtained as white solid. Yield: 7.5%.

Compound 26A: $^1$H NMR (400 MHz, CDCl$_3$) δ 8.38 (d, J=9.6 Hz, 1H), 8.05 (d, J=6.8 Hz, 1H), 7.64 (d, J=9.2 Hz, 1H), 7.49 (d, J=8.0 Hz, 1H), 7.39 (d, J=8.8 Hz, 2H), 6.84 (d, J=9.2 Hz, 2H), 5.65 (dd, J=4.0, 10.8 Hz, 1H), 5.32 (dd, J=4.0, 11.2 Hz, 1H), 5.27-5.31 (m, 1H), 5.19 (t, J=9.2 Hz, 2H), 5.04-5.12 (m, 3H), 4.95-5.01 (m, 1H), 4.89-4.93 (m, 1H), 4.82-4.86 (m, 1H), 4.65 (d, J=14.0 Hz, 1H), 4.34-4.41 (m, 1H), 4.26 (dd, J=6.4, 9.2 Hz, 1H), 3.78 (s, 3H), 3.46 (s, 3H), 3.38 (s, 3H), 3.21 (s, 3H), 3.17 (s, 3H), 3.05 (s, 3H), 2.70 (s, 3H), 2.65 (s, 3H), 2.34-2.41 (m, 1H), 2.25-2.31 (m, 1H), 2.07-2.15 (m, 3H), 1.93-1.98 (m, 3H), 1.59-1.68 (m, 5H), 1.41-1.47 (m, 3H), 1.32 (d, J=6.8 Hz, 3H), 1.24 (d, J=6.8 Hz, 3H), 1.14 (d, J=6.8 Hz, 3H), 0.99-1.01 (m, 4H), 0.97-0.98 (m, 4H), 0.93-0.95 (m, 10H), 0.89-0.90 (m, 6H), 0.85-0.86 (m, 8H), 0.81 (d, J=6.4 Hz, 4H), 0.74 (d, J=6.4 Hz, 3H), 0.59 (d, J=6.8 Hz, 3H). Mass (ESI): m/z calcd for C$_{67}$H$_{113}$N$_{11}$O$_{13}$S 1311.82, found 1313.52 [M+H]$^+$.

Compound 26B: $^1$H NMR (400 MHz, CDCl$_3$) δ 8.35 (d, J=9.6 Hz, 1H), 7.99 (d, J=6.8 Hz, 1H), 7.45 (d, J=8.8 Hz, 1H), 7.41 (d, J=8.8 Hz, 2H), 7.38 (d, J=8.4 Hz, 1H), 6.83 (d, J=8.8 Hz, 2H), 5.68 (dd, J=4.0, 11.2 Hz, 1H), 5.31 (dd, J=4.0, 11.2 Hz, 1H), 5.18-5.24 (m, 3H), 5.07-5.16 (m, 3H), 4.92-4.98 (m, 1H), 4.83-4.88 (m, 2H), 4.67 (d, J=14.0 Hz, 1H), 4.40-4.48 (m, 1H), 4.03 (dd, J=5.6, 8.0 Hz, 1H), 3.79 (s, 3H), 3.54 (s, 3H), 3.27 (s, 3H), 3.25 (s, 3H), 3.17 (s, 3H), 3.07 (s, 3H), 2.70 (s, 6H), 2.30-2.39 (m, 1H), 2.20-2.27 (m, 1H), 2.10-2.16 (m, 3H), 1.93-2.01 (m, 3H), 1.78-1.90 (m, 4H), 1.58-1.70 (m, 4H), 1.40-1.49 (m, 3H), 1.34 (d, J=7.2 Hz, 3H), 1.25 (d, J=6.8 Hz, 3H), 1.03 (d, J=6.8 Hz, 3H), 0.99 (d, J=6.8 Hz, 3H), 0.95-0.97 (m, 5H), 0.92-0.95 (m, 13H), 0.87-0.89 (m, 8H), 0.82-0.85 (m, 7H), 0.74 (d, J=6.8 Hz, 3H). Mass (ESI): m/z calcd for C$_{67}$H$_{113}$N$_{11}$O$_3$S 1311.82, found 1313.12 [M+H]$^+$.

Compound 27A: Preparation of [2-((2R,3R)-5-(4-ethoxyphenylthio)-3-methyltetrahydrofuran-2-yl)-2-(methylamino)acetic acid]$^1$-cyclosporin A

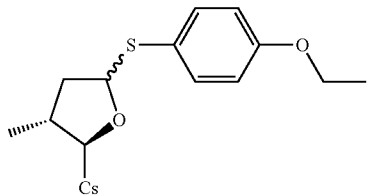

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 4-ethoxybenzenethiol was used instead of benzenethiol and 40 mg light-yellow foam was obtained. Yield: 31°%. $^1$H NMR (400 MHz, CDCl$_3$) δ 8.39 (d, J=9.6 Hz, 1H), 8.03 (d, J=7.2 Hz, 1H), 7.65 (d, J=8.8 Hz, 1H), 7.49 (d, J=8.0 Hz, 1H), 7.38 (d, J=8.8 Hz, 2H), 6.83 (d, J=9.2 Hz, 2H), 5.66 (dd, J=4.4, 10.8 Hz, 1H), 5.34 (dd, J=4.0, 11.2 Hz, 1H), 5.29 (dd, J=3.6, 7.6 Hz, 1H), 5.22 (d, J=11.2 Hz, 1H), 5.19 (d, J=9.2 Hz, 1H), 5.05-5.12 (m, 2H), 4.96-5.02 (m, 1H), 4.90-4.94 (m, 1H), 4.81-4.88 (m, 2H), 4.65 (d, J=13.6 Hz, 1H), 4.34-4.41 (m, 1H), 4.27 (dd, J=6.0, 9.2 Hz, 1H), 4.00 (q, J=7.2 Hz, 2H), 3.47 (s, 3H), 3.39 (s, 3H), 3.21 (s, 3H), 3.17 (s, 3H), 3.06 (s, 3H), 2.70 (s, 3H), 2.65 (s, 3H), 2.33-2.41 (m, 1H), 2.25-2.32 (m, 1H), 2.07-2.15 (m, 3H), 1.94-2.01 (m, 3H), 1.57-1.69 (m, 6H), 1.43-1.48 (m, 2H), 1.38 (t, J=7.2 Hz, 3H), 1.33 (d, J=7.2 Hz, 3H), 1.25 (d, J=7.2 Hz, 3H), 1.15 (d, J=6.4 Hz, 3H), 0.98-1.01 (m, 8H), 0.93-0.95 (m, 8H), 0.89-0.91 (m, 4H), 0.84-0.87 (m, 12H), 0.81 (d, J=6.4 Hz, 4H), 0.75 (d, J=6.4 Hz, 3H), 0.59 (d, J=6.8 Hz, 3H). Mass (ESI): m/z calcd for C$_{68}$H$_{115}$N$_{11}$O$_{13}$S 1325.84, found 1326.72 [M+H]$^+$.

Compound 28A: Preparation of [2-((2R,3R)-5-(3-methoxyphenylthio)-3-methyltetrahydrofuran-2-yl)-2-(methylamino)acetic acid]$^1$-cyclosporin A

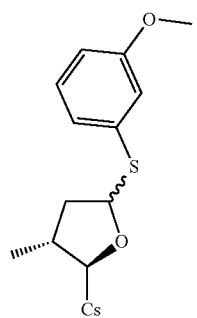

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-methoxybenzenethiol was used instead of benzenethiol and 30 mg pale yellow solid was obtained, yield: 28.3%. $^1$H NMR (400 MHz, CDCl$_3$) δ 8.39 (d, J=9.6 Hz, 1H), 8.04 (d, J=6.8 Hz, 1H), 7.63 (d, J=8.8 Hz, 1H), 7.52 (d, J=8.4 Hz, 1H), 7.21 (t, J=8.0 Hz, 1H), 7.07 (d, J=8.0 Hz, 1H), 6.96 (t, J=2.0 Hz, 1H), 6.74 (dd, J=2.4, 8.0 Hz, 1H), 5.67 (dd, J=4.0, 10.8 Hz, 1H), 5.48 (dd, J=3.6, 8.0 Hz, 1H), 5.32 (dd, J=3.6, 11.2 Hz, 1H), 5.16-5.20 (m, 2H), 5.06-5.12 (m, 3H), 4.95-5.01 (m, 1H), 4.92 (t, J=8.0 Hz, 1H), 4.82-4.87 (m, 1H), 4.65 (d, J=14.0 Hz, 1H), 4.36-4.43 (m, 1H), 4.32 (dd, J=6.0, 9.2 Hz, 1H), 3.78 (s, 3H), 3.45 (s, 3H), 3.37 (s, 3H), 3.21 (s, 3H), 3.17 (s, 3H), 3.05 (s, 3H), 2.69 (s, 3H), 2.65 (s, 3H), 2.37-2.44 (m, 1H), 2.24-2.33 (m, 1H), 2.07-2.15 (m, 3H), 1.92-2.01 (m, 3H), 1.58-1.70 (m, 5H), 1.43-1.50 (m, 3H), 1.32 (d, J=7.2 Hz, 3H), 1.25 (d, J=5.6 Hz, 3H), 1.18 (d, J=6.8 Hz, 3H), 0.99-1.01 (m, 8H), 0.93-0.94 (m, 9H), 0.88-0.90 (m, 4H), 0.84-0.86 (m, 11H), 0.80 (d, J=6.4 Hz, 4H), 0.76 (d, J=6.8 Hz, 3H), 0.60 (d, J=6.4 Hz, 3H). Mass (ESI) calcd for C$_{67}$H$_{113}$N$_{13}$S 1311.82, found 1313.32 [M+H]$^+$.

Compound 29A: Preparation of [2-((2R,3R)-5-(3-ethoxyphenylthio)-3-methyltetrahydrofuran-2-yl)-2-(methylamino)acetic acid]$^1$-cyclosporin A

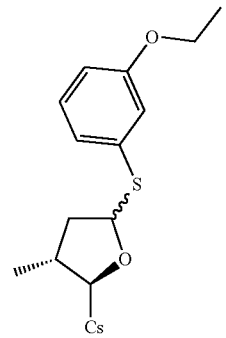

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-ethoxybenzenethiol was used instead of benzenethiol and 22 mg light-yellow solid was obtained. Yield: 17.1%. $^1$H NMR (400 MHz, CDCl$_3$) δ 8.38 (d, J=9.6 Hz, 1H), 8.04 (d, J=6.8 Hz, 1H), 7.61 (d, J=8.8 Hz, 1H), 7.50 (d, J=8.0 Hz, 1H), 7.21 (t, J=8.0 Hz, 1H), 7.09 (d, J=8.0 Hz, 1H), 6.91 (t, J=1.6 Hz, 1H), 6.73 (dd, J=1.6, 7.6 Hz, 1H), 5.66 (dd, J=4.0, 10.8 Hz, 1H), 5.48 (dd, J=3.6, 8.0 Hz, 1H), 5.33 (dd, J=4.0, 11.2 Hz, 1H), 5.21 (d, J=6.4 Hz, 1H), 5.18 (d, J=4.4 Hz, 1H), 5.06-5.13 (m, 2H), 4.92-5.02 (m, 2H), 4.81-4.87 (m, 2H), 4.65 (d, J=13.6 Hz, 1H), 4.36-4.43 (m, 1H), 4.31 (dd, J=6.0, 9.2 Hz, 1H), 4.00 (q, J=6.8 Hz, 2H), 3.45 (s, 3H), 3.37 (s, 3H), 3.22 (s, 3H), 3.17 (s, 3H), 3.06 (s, 3H), 2.69 (s, 3H), 2.65 (s, 3H), 2.37-2.45 (m, 1H), 2.26-2.34 (m, 1H), 2.08-2.16 (m, 3H), 1.94-2.04 (m, 3H), 1.53-1.70 (m, 6H), 1.44-1.51 (m, 2H), 1.40 (t, J=6.8 Hz, 3H), 1.33 (d, J=7.2 Hz, 3H), 1.25 (d, J=6.8 Hz, 3H), 1.18 (d, J=6.8 Hz, 3H), 0.97-1.01 (m, 8H), 0.93-0.95 (m, 9H), 0.89-0.91 (m, 4H), 0.84-0.88 (m, 11H), 0.81 (d, J=6.4 Hz, 4H), 0.78 (d, J=6.8 Hz, 3H), 0.61 (d, J=6.4 Hz, 3H). Mass (ESI): m/z calcd for C$_{68}$H$_{115}$N$_{11}$O$_{13}$S 1325.84, found 1326.87 [M+H]$^+$.

105

Compound 30A and Compound 30B: Preparation of [2-((2R,3R)-5-(3-isopropoxyphenylthio)-3-methyltetrahydrofuran-2-yl)-2-(methylamino)acetic acid]$^1$-cyclosporin

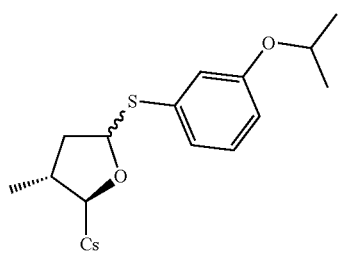

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-propoxy benzenethiol was used instead of benzenethiol and 12 mg compound 30A was obtained as white solid. Yield: 7.4%. 9 mg compound 30B was obtained as white solid. Yield: 5.5%.

Compound 30A: $^1$H NMR (400 MHz, CDCl$_3$) 8.38 (d, J=9.6 Hz, 1H), 8.04 (d, J=6.8 Hz, 1H), 7.62 (d, J=9.2 Hz, 1H), 7.50 (d, J=8.0 Hz, 1H), 7.21 (t, J=8.0 Hz, 1H), 7.09 (d, J=8.0 Hz, 1H), 6.89 (t, J=2.0 Hz, 1H), 6.72 (dd, J=2.4, 8.0 Hz, 1H), 5.67 (dd, J=4.0, 11.2 Hz, 1H), 5.48 (dd, J=3.6, 8.0 Hz, 1H), 5.33 (dd, J=4.0, 11.2 Hz, 1H), 5.21 (d, J=6.4 Hz, 1H), 5.19 (d, J=4.4 Hz, 1H), 5.06-5.14 (m, 2H), 4.90-5.00 (m, 3H), 4.81-4.88 (m, 1H), 4.66 (d, J=14.0 Hz, 1H), 4.48-4.54 (m, 1H), 4.35-4.42 (m, 1H), 4.31 (dd, J=6.0, 9.2 Hz, 1H), 3.45 (s, 3H), 3.37 (s, 3H), 3.22 (s, 3H), 3.18 (s, 3H), 3.06 (s, 3H), 2.70 (s, 3H), 2.66 (s, 3H), 2.38-2.45 (m, 1H), 2.27-2.34 (m, 1H), 2.06-2.14 (m, 3H), 1.95-2.01 (m, 3H), 1.59-1.68 (m, 5H), 1.44-1.52 (m, 3H), 1.32-1.34 (m, 3H), 1.30-1.31 (m, 3H), 1.25-1.26 (m, 3H), 1.17 (d, J=6.8 Hz, 6H), 0.99-1.02 (m, 9H), 0.93-0.95 (m, 6H), 0.89-0.91 (m, 4H), 0.85-0.88 (m, 13H), 0.78-0.82 (m, 7H), 0.63 (d, J=6.4 Hz, 3H). Mass (ESI) calcd for C$_{69}$H$_{117}$N$_{11}$O$_{13}$S, 1339.86 found 1340.91 [M+H]$^+$.

Compound 30B: $^1$H NMR (400 MHz, CDCl$_3$) δ 8.35 (d, J=9.6 Hz, 1H), 7.96 (d, J=6.8 Hz, 1H), 7.44 (d, J=8.8 Hz, 1H), 7.36 (d, J=8.0 Hz, 1H), 7.14 (t, J=8.0 Hz, 1H), 6.99-7.00 (m, 2H), 6.69-6.72 (m, 1H), 5.68 (dd, J=4.0, 10.8 Hz, 1H), 5.40 (dd, J=6.0, 8.8 Hz, 1H), 5.33 (dd, J=4.0, 11.2 Hz, 1H), 5.22 (d, J=5.2 Hz, 1H), 5.06-5.12 (m, 2H), 4.91-4.98 (m, 2H), 4.83-4.89 (m, 2H), 4.68 (d, J=14.0 Hz, 1H), 4.48-4.56 (m, 2H), 4.40-4.47 (m, 1H), 4.07-4.10 (m, 1H), 3.56 (s, 3H), 3.28 (s, 3H), 3.26 (s, 3H), 3.16 (s, 3H), 3.08 (s, 3H), 2.69 (s, 3H), 2.68 (s, 3H), 2.30-2.35 (m, 1H), 2.20-2.24 (m, 1H), 2.08-2.14 (m, 3H), 1.90-1.97 (m, 3H), 1.60-1.69 (m, 5H), 1.44-1.48 (m, 3H), 1.34-1.35 (m, 3H), 1.29-1.30 (m, 3H), 1.22-1.24 (m, 3H), 1.04 (d, J=6.8 Hz, 6H), 1.01 (d, J=6.8 Hz, 3H), 0.99 (d, J=6.4 Hz, 3H), 0.93-0.95 (m, 12H), 0.87-0.90 (m, 14H), 0.80-0.83 (m, 7H), 0.68 (d, J=6.8 Hz, 3H). Mass (ESI) calcd for C$_{69}$H$_{117}$N$_{11}$O$_{13}$S 1339.86, found 1340.78 [M+H]$^+$.

106

Compound 31A: Preparation of [2-((2R,3R)-3-methyl-5-(3-propoxyphenylthio)tetrahydrofuran-2-yl)-2-(methylamino)acetic acid]$^1$-cyclosporin A

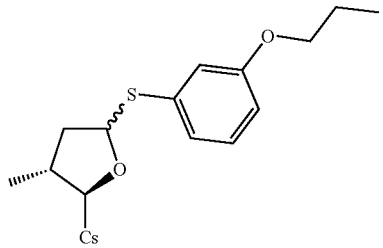

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-propoxybenzenethiol was used instead of benzenethiol and 35 mg white solid was obtained. Yield: 21.5%. $^1$H NMR (400 MHz, CDCl$_3$) δ 8.37 (d, J=9.6 Hz, 1H), 8.03 (d, J=6.8 Hz, 1H), 7.61 (d, J=8.8 Hz, 1H), 7.49 (d, J=8.0 Hz, 1H), 7.20 (t, J=8.0 Hz, 1H), 7.08 (d, J=8.0 Hz, 1H), 6.90 (t, J=1.6 Hz, 1H), 6.73 (dd, J=1.6, 8.0 Hz, 1H), 5.65 (dd, J=4.0, 10.8 Hz, 1H), 5.46 (dd, J=3.2, 7.6 Hz, 1H), 5.32 (dd, J=3.2, 10.8 Hz, 1H), 5.17-5.20 (m, 2H), 5.04-5.12 (m, 3H), 4.94-5.00 (m, 1H), 4.91 (t, J=8.0 Hz, 1H), 4.83 (t, J=7.2 Hz, 1H), 4.64 (d, J=13.6 Hz, 1H), 4.35-4.42 (m, 1H), 4.30 (dd, J=6.4, 9.2 Hz, 1H), 3.88 (t, J=6.4 Hz, 2H), 3.44 (s, 3H), 3.36 (s, 3H), 3.21 (s, 3H), 3.16 (s, 3H), 3.05 (s, 3H), 2.68 (s, 3H), 2.64 (s, 3H), 2.37-2.44 (m, 1H), 2.25-2.33 (m, 1H), 2.06-2.15 (m, 3H), 1.93-2.02 (m, 3H), 1.73-1.82 (m, 2H), 1.57-1.66 (m, 5H), 1.41-1.50 (m, 3H), 1.32 (d, J=7.2 Hz, 3H), 1.24 (d, J=6.0 Hz, 3H), 1.16 (d, J=6.8 Hz, 3H), 0.97-1.02 (m, 12H), 0.92-0.94 (m, 8H), 0.88-0.89 (m, 4H), 0.83-0.86 (m, 11H), 0.79 (d, J=6.8 Hz, 4H), 0.77 (d, J=6.8 Hz, 3H), 0.61 (d, J=6.4 Hz, 3H). Mass (ESI) calcd for C$_{69}$H$_{117}$N$_{11}$O$_{13}$S 1339.86, found 1341.37 [M+H]$^+$.

Compound 32A: Preparation of [2-((2R,3R)-5-(3-(cyclopropylmethoxy)phenylthio)-3-methyltetrahydrofuran-2-yl)-2-(methylamino)acetic acid]$^1$-cyclosporin A

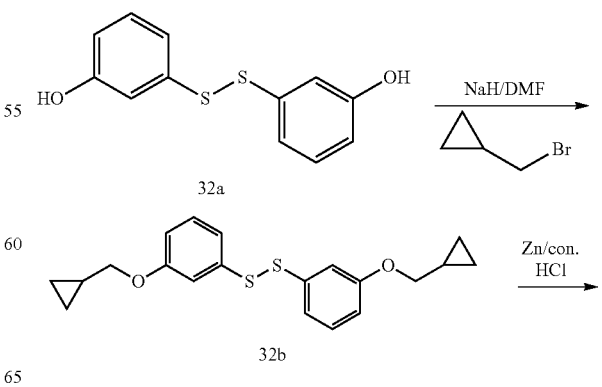

-continued

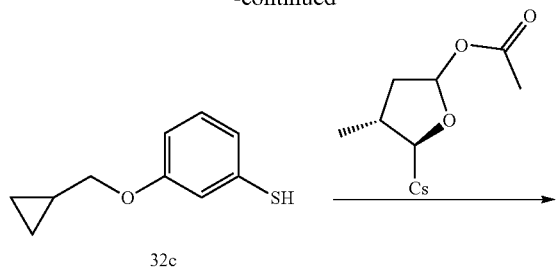

(I) Synthesis of 3-(cyclopropylmethoxy)benzenethiol (32c). NaH (119.2 mg, 2.98 mmol, 60% in oil) was added to the solution of 3,3'-disulfanediyldiphenol (350 mg, 1.417 mmol) in dry DMF (7 mL) at 0° C. (bromomethyl)cyclopropane (415.8 mg, 3.08 mmol) was added to the mixture after 30 mins. The mixture was stirred at r.t. overnight and diluted with EA (100 mL). The organic layer were washed with $H_2O$ (20 mL) and saturated aqueous NaCl (20 mL), dried over $Na_2SO_4$, filtered and concentrated. The residue was purified by column chromatography (PE/EA=4/1) to give 470 mg 1,2-bis(3-(cyclopropylmethoxy)phenyl)disulfane(32b) as yellow solid, yield: 92.6%.

Con. HCl (1 mL) was added to the solution of 1,2-bis(3-(cyclopropylmethoxy)phenyl) disulfane (470 mg, 1.31 mmol) in methanol (5 mL) and THF (7 mL). Then zinc powder (8.58 g, 131 mmol) was added slowly at 0° C. for 3 hrs. The mixture was filtered, and diluted with EA (100 mL). The organic layer were washed with saturated aqueous $NaHCO_3$ (20 mL) and NaCl (20 mL), dried over $Na_2SO_4$, filtered and concentrated. The residue was purified by column chromatography (PE/EA=5/1) to give 170 mg (32c) as light yellow oil. Yield: 36%.

(I) Synthesis of[2-((2R,3R)-5-(3-(cyclopropylmethoxy) phenylthio)-3-methyltetrahydrofuran-2-yl)-2-(methylamino)acetic acid]1-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(cyclopropylmethoxy)benzenethiol was used instead of benzenethiol and 40 mg white solid was obtained. Yield: 18.3% $^1$H NMR (400 MHz, CDCl$_3$): δ 8.36 (d, J=9.2 Hz, 1H), 8.05 (d, J=6.4 Hz, 1H), 7.63 (d, J=9.2 Hz, 1H), 7.49 (d, J=7.6 Hz, 1H), 7.20 (t, J=8.0 Hz, 1H), 7.08-7.11 (m, 1H), 6.89 (s, 1H), 6.74 (dd, J=0.8, 8.0 Hz, 1H), 5.65 (dd, J=3.2, 10.4 Hz, 1H), 5.46 (dd, J=3.6, 7.6 Hz, 1H), 5.31 (dd, J=3.2, 10.8 Hz, 1H), 5.16-5.19 (m, 2H), 5.05-5.12 (m, 2H), 4.93-4.99 (m, 2H), 4.89 (t, J=8.4 Hz, 1H), 4.83 (t, J=7.6 Hz, 1H), 4.64 (d, J=14.0 Hz, 1H), 4.34-4.41 (m, 1H), 4.29 (dd, J=6.4, 8.4 Hz, 1H), 3.76 (d, J=6.8 Hz, 2H), 3.43 (s, 3H), 3.35 (s, 3H), 3.20 (s, 3H), 3.16 (s, 3H), 3.04 (s, 3H), 2.68 (s, 3H), 2.65 (s, 3H), 2.38-2.45 (m, 1H), 2.24-2.30 (m, 1H), 2.03-2.17 (m, 4H), 1.91-2.01 (m, 2H), 1.53-1.67 (m, 5H), 1.40-1.48 (m, 3H), 1.31 (d, J=7.2 Hz, 3H), 1.24 (d, J=6.4 Hz, 3H), 1.15 (d, J=6.4 Hz, 3H), 0.96-1.00 (m, 8H), 0.92-0.93 (m, 8H), 0.87-0.89 (m, 4H), 0.83-0.86 (m, 11H), 0.80 (d, J=6.4 Hz, 4H), 0.76 (d, J=6.8 Hz, 4H), 0.67-0.68 (m, 1H), 0.60-0.62 (m, 4H), 0.32 (q, J=4.8 Hz, 3H). Mass (ESI): m/z calcd for $C_{70}H_{117}N_{11}O_{13}S$ 1351.86, found 1352.88 [M+H]$^+$.

Compound 33A: Preparation of [2-((2R,3R)-3-methyl-5-(3-((tetrahydro-2H-pyran-4-yl)methoxy) phenylthio)tetrahydrofuran-2-yl)-2-(methylamino) acetic acid]$^1$-cyclosporin A

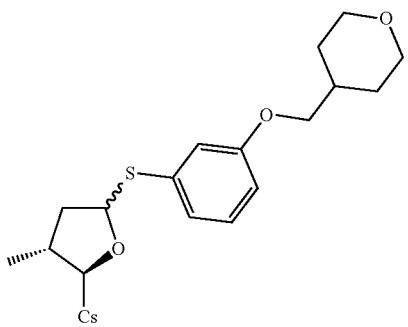

(I) Synthesis of 3-((tetrahydro-2H-pyran-4-yl)methoxy) benzenethiol. 3,3'-disulfanediyldiphenol (170 mg, 0.68 mmol) and 4-(bromomethyl)tetrahydro-2H-pyran (730 mg, 4.077 mmol) and $K_2CO_3$ (566.9 mg, 4.078 mmol) were mixed in 27 mL of DMF. Let it stir at 80° C. for 3 hrs. When the stating material was consumed, the solvent was removed under vacuum and water was added. It was extracted with EtOAc (30 mL×3). The organic layer was evaporated to dryness and purified by prep. TLC (PE/EA=3/2) to give 200 mg 1,2-bis(3-((tetrahydro-2H-pyran-4-yl)methoxy)phenyl) disulfane as colorless oil. Yield: 65.9%.

1,2-bis(3-((tetrahydro-2H-pyran-4-yl)methoxy)phenyl) disulfane (140 mg, 0.314 mmol) was dissolved in 5 mL of THF/MeOH (5/1). 6 mL 10% $H_2SO_4$ was added. Then zinc powder (200 mg, 3.076 mmol) was added slowly to the mixture at 0° C. Let it stir at room temperature for 16 hrs. The organic solvent was evaporated to dryness and extracted with DCM (30 mL×3). The solvent was evaporated to dryness and purified with column chromatography (PE/EA=79/21) to give 70 mg 3-((tetrahydro-2H-pyran-4-yl) methoxy)benzenethiol as white solid. Yield: 49.8%.

(II) Synthesis of [2-((2R,3R)-3-methyl-5-(3-((tetrahydro-2H-pyran-4-yl)methoxy)phenylthio)tetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-((tetrahydro-2H-pyran-4-yl)methoxy)benzenethiol was used instead of benzenethiol, 100 mg of starting material was used and 16 mg light-yellow solid was obtained. Yield: 14.2%. $^1$H NMR (400 MHz, CDCl$_3$) δ 8.40 (d, J=9.6 Hz, 1H), 8.05 (d, J=6.8 Hz, 1H), 7.65 (d, J=9.2 Hz, 1H), 7.51 (d, J=8.0 Hz, 1H), 7.22 (t, J=8.0 Hz, 1H), 7.12 (d, J=7.6 Hz, 1H), 6.89 (s, 1H), 6.73 (dd, J=1.6, 7.6 Hz, 1H), 5.66 (dd, J=4.0, 11.2 Hz, 1H), 5.47 (dd, J=3.6, 7.6 Hz, 1H), 5.33 (dd, J=3.6, 11.2 Hz, 1H), 5.21 (d, J=5.2 Hz, 1H), 5.18 (d, J=7.2 Hz, 1H), 5.06-5.13 (m, 2H), 4.96-5.01 (m, 1H), 4.89-4.93 (m, 1H), 4.78-4.89 (m, 2H), 4.66 (d, J=13.6 Hz, 1H), 4.37-4.45 (m, 1H), 4.30 (dd, J=6.4, 9.2 Hz, 1H), 4.01 (dd, J=3.2, 11.2 Hz, 3H), 3.78 (d, J=6.8 Hz, 3H), 3.44 (s, 3H), 3.37 (s, 3H), 3.22 (s, 3H), 3.17 (s, 3H), 3.06 (s, 3H), 2.69 (s, 3H), 2.65 (s, 3H), 2.38-2.46 (m, 1H), 2.26-2.33 (m, 1H), 2.02-2.16 (m, 6H), 1.93-2.00 (m, 2H), 1.74-1.77 (m, 3H), 1.58-1.69 (m, 5H), 1.40-1.49 (m, 3H), 1.33 (d, J=6.8 Hz, 3H), 1.25 (d, J=6.8 Hz, 3H), 1.17 (d, J=6.8 Hz, 3H), 0.98-1.01 (m, 8H), 0.90-0.95 (m, 10H), 0.84-0.88 (m, 14H), 0.81 (d, J=6.4 Hz, 4H), 0.77 (d, J=6.4 Hz, 3H), 0.61 (d, J=6.4 Hz, 3H). Mass (ESI): m/z calcd for $C_{72}H_{121}N_{11}O_{14}S$ 1395.88, found 1396.95 $[M+H]^+$.

Compound 34A: Preparation of [2-((2R,3R)-3-methyl-5-(3-(1-phenylethoxy)phenylthio)tetrahydro-furan-2-yl)-2-(methylamino)acetic acid]$^1$-cyclosporin A

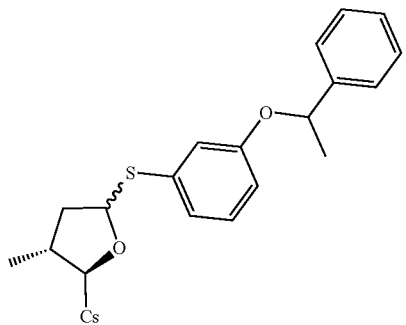

(I) Synthesis of 3-(1-phenylethoxy)benzenethiol. NaH (119.2 mg, 2.98 mmol, 60% in oil) was added to the solution of 3,3'-disulfanediyldiphenol (350 mg, 1.417 mmol) in dry DMF (7 mL) at 0° C. (1-bromoethyl)benzene (548 mg, 2.98 mmol) was added to the mixture after 30 min. The mixture was stirred at r.t. overnight and diluted with EA (100 mL). The organic layer were washed with $H_2O$ (20 mL) and saturated aqueous NaCl (20 mL), dried over $Na_2SO_4$, filtered and concentrated. The residue was purified by column chromatography (PE/EA=4/1) to give 576 mg 1,2-bis(3-(1-phenylethoxy)phenyl) disulfane as yellow solid, yield: 88.6%.

Con. HCl (5 mL) was added to the solution of 1,2-bis(3-(1-phenylethoxy)phenyl) disulfane (560 mg, 1.22 mmol) in methanol (5 mL) and THF (7 mL). Then zinc powder (7.98 g, 122 mmol) was added slowly at 0° C. for 3 hrs. The mixture was filtered, and diluted with EA (100 mL). The organic layer were washed with saturated aqueous $NaHCO_3$ (20 mL) and NaCl (20 mL), dried over $Na_2SO_4$, filtered and concentrated. The residue was purified by prep. TLC (PE/EA=4/1) to give 320 mg colorless liquid. Yield: 57.0%. $^1$H-NMR (400 MHz, $CDCl_3$): δ 7.31-7.36 (m, 4H), 7.23-7.28 (m, 1H), 7.04 (t, J=8.0 Hz, 1H), 6.77-6.81 (m, 2H), 6.30 (dd, J=2.4, 8.0 Hz, 1H), 5.27 (q, J=6.4 Hz, 1H), 3.38 (s, 1H), 1.62 (d, J=6.4 Hz, 3H).

(II) Synthesis of [2-((2R,3R)-3-methyl-5-(3-(1-phenylethoxy)phenylthio)tetrahydrofuran-2-yl)-2-(methylamino) acetic acid]1-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(1-phenylethoxy)benzenethiol was used instead of benzenethiol and 41 mg white solid was obtained. Yield: 18.1%. $^1$H NMR (400 MHz, $CDCl_3$): δ 8.36 (d, J=9.6 Hz, 1H), 8.05 (d, J=6.4 Hz, 1H), 7.62 (d, J=8.8 Hz, 1H), 7.49 (d, J=7.6 Hz, 1H), 7.28-7.35 (m, 5H), 7.20-7.24 (m, 1H), 7.03-7.05 (m, 1H), 6.85-6.90 (m, 1H), 6.66-6.68 (m, 1H), 5.65 (d, J=9.2 Hz, 1H), 5.41-5.44 (m, 1H), 5.29-5.32 (m, 1H), 5.25-5.26 (m, 1H), 5.19 (s, 1H), 5.16 (s, 1H), 5.02-5.12 (m, 2H), 4.93-4.99 (m, 2H), 4.89 (t, J=8.4 Hz, 1H), 4.83 (t, J=6.8 Hz, 1H), 4.63 (d, J=14.0 Hz, 1H), 4.34-4.39 (m, 1H), 4.24-4.28 (m, 1H), 3.42 (s, 3H), 3.34 (s, 3H), 3.20 (s, 3H), 3.16 (s, 3H), 3.04 (s, 3H), 2.68 (s, 3H), 2.65 (s, 3H), 2.35-2.43 (m, 1H), 2.24-2.30 (m, 1H), 2.03-2.13 (m, 4H), 1.92-2.00 (m, 2H), 1.60-1.67 (m, 5H), 1.59 (d, J=6.0 Hz, 3H), 1.39-1.52 (m, 3H), 1.31 (d, J=7.2 Hz, 3H), 1.24 (d, J=6.0 Hz, 3H), 1.12 (d, J=6.4 Hz, 3H), 0.95-1.00 (m, 8H), 0.92-0.94 (m, 11H), 0.84-0.88 (m, 13H), 0.75-0.80 (m, 7H), 0.62 (d, J=6.4 Hz, 3H). Mass (ESI): m/z calcd for $C_{74}H_{119}N_{11}O_{13}S$ 1401.87, found 1402.87 $[M+H]^+$.

Compound 35A: Preparation of [2-((2R,3R)-3-methyl-5-(3-phenethoxyphenylthio)tetrahydrofuran-2-yl)-2-(methylamino)acetic acid]$^1$-cyclosporin A

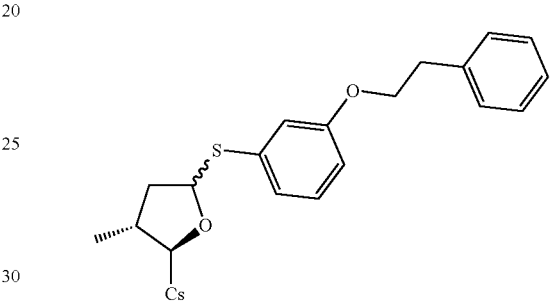

(I) Synthesis of 3-phenethoxybenzenethiol. NaH (100 mg, 2.5 mmol) was added to the solution of 3,3'-disulfanediyl-diphenol (250 mg, 1.0 mmol) in dry DMF (5 mL) at 0° C. (2-bromoethyl)benzene (460 mg, 2.5 mmol) was added to the mixture after 30 mins. The mixture was stirred at r.t. overnight and diluted with EA (100 mL). The organic layer were washed with $H_2O$ (20 mL) and saturated aqueous NaCl (20 mL), dried over $Na_2SO_4$, filtered and concentrated. The residue was purified by column chromatography (PE/EA=4/1) to give 100 mg 1,2-bis(3-phenethoxyphenyl)disulfane as light yellow oil, yield: 21.8%. $^1$H-NMR (400 MHz, $CDCl_3$): δ 7.13-7.25 (m, 10H), 7.04-7.05 (m, 2H), 6.98-6.99 (m, 2H), 6.74-6.77 (m, 2H), 6.66-6.69 (m, 2H), 4.13 (t, J=7.2 Hz, 4H), 3.07 (t, J=7.2 Hz, 4H).

Con. HCl (1 mL) was added to the solution of 1,2-bis(3-phenethoxyphenyl)disulfane (100 mg, 0.218 mmol) in methanol (1 mL) and THF (5 mL). Then zinc powder (1.43 g, 21.8 mmol) was added slowly at 0° C. for 3 hrs. The mixture was filtered, and diluted with EA (50 mL). The organic layer were washed with saturated aqueous $NaHCO_3$ (20 mL) and NaCl (20 mL), dried over $Na_2SO_4$, filtered and concentrated. The residue was purified by column chromatography (PE/EA=5/1) to give 90 mg light yellow oil. Yield: 89.7%.

(II) Synthesis of [2-((2R,3R)-3-methyl-5-(3-phenethoxy-phenylthio)tetrahydrofuran-2-yl)-2-(methylamino)acetic acid]1-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-phenethoxyben-zenethiol was used instead of benzenethiol and 5 mg white solid was obtained. Yield: 2.0% $^1$H NMR (400 MHz, $CDCl_3$): δ 8.38 (d, J=9.6 Hz, 1H), 8.06 (d, J=6.8 Hz, 1H), 7.63 (d, J=8.8 Hz, 1H), 7.50 (d, J=8.8 Hz, 1H), 7.29-7.33 (m, 5H), 7.20-7.24 (m, 1H), 7.12 (d, J=7.6 Hz, 1H), 6.92 (s, 1H), 6.73-6.75 (m, 1H), 5.67 (dd, J=3.2, 10.8 Hz, 1H), 5.47 (dd, J=3.6, 7.6 Hz, 1H), 5.31-5.37 (m, 2H), 5.20-5.22 (m, 1H), 5.18 (d, J=3.6 Hz, 1H), 5.11-5.13 (m, 1H), 5.08 (t, J=6.8 Hz, 2H), 4.96-5.01 (m, 2H), 4.91 (t, J=8.4 Hz, 1H), 4.85 (t, J=6.8 Hz, 1H), 4.66 (d, J=13.6 Hz, 1H), 4.39 (t, J=6.8 Hz, 1H), 4.31 (dd, J=6.4, 8.8 Hz, 1H), 4.16 (dt, J=2.4, 7.2 Hz, 2H), 3.43 (s, 3H), 3.37 (s, 3H), 3.22 (s, 3H), 3.18 (s, 3H), 3.06 (s, 3H), 2.70 (s, 3H), 2.66 (s, 3H), 2.39-2.44 (m, 1H), 2.28-2.31 (m, 1H), 2.09-2.15 (m, 3H), 1.93-2.00 (m, 3H), 1.57-1.63 (m, 5H), 1.44-1.51 (m, 3H), 1.33 (d, J=7.2 Hz, 3H), 1.26 (d, J=6.8 Hz, 3H), 1.17 (d, J=6.8 Hz, 3H), 0.98-1.02 (m, 8H), 0.93-0.95 (m, 8H), 0.89-0.91 (m, 5H), 0.85-0.88 (m, 11H), 0.81 (d, J=6.4 Hz, 4H), 0.78 (d, J=6.8 Hz, 3H), 0.61 (d, J=6.8 Hz, 3H). Mass (ESI): m/z calcd for $C_{74}H_{119}N_{11}O_{13}S$ 1401.87, found 1403.00 $[M+H]^+$.

Compound 36A: Preparation of [2-((2R,3R)-5-(2,6-dimethoxyphenylthio)-3-methyltetrahydrofuran-2-yl)-2-(methylamino)acetic acid]$^1$-cyclosporin A

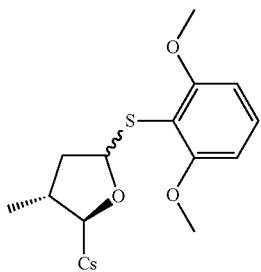

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 2,6-dimethoxybenzenethiol was used instead of benzenethiol and 4 mg white solid was obtained. Yield: 3.7%. Mass (ESI): m/z calcd for $C_{68}H_{115}N_{11}O_{14}S$ 1341.83, found 1342.71 $[M+H]^+$.

Compound 37A: Preparation of [2-((2R,3R)-5-(3,4-dimethoxyphenylthio)-3-methyltetrahydrofuran-2-yl)-2-(methylamino)acetic acid]$^1$-cyclosporin A

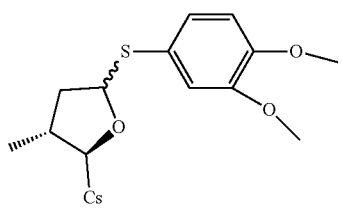

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3,4-dimethoxybenzenethiol was used instead of benzenethiol, 120 mg of starting material was used and 25 mg white foam was obtained. Yield: 19.1%. $^1$H NMR (400 MHz, CDCl$_3$) 8.36 (d, J=9.6 Hz, 1H), 8.01 (d, J=6.4 Hz, 1H), 7.61 (d, J=8.8 Hz, 1H), 7.50 (d, J=7.6 Hz, 1H), 7.04 (d, J=7.6 Hz, 1H), 6.99 (s, 1H), 6.81 (d, J=8.0 Hz, 1H), 5.62-5.65 (m, 1H), 5.30-5.32 (m, 2H), 5.12-5.20 (m, 2H), 5.04-5.10 (m, 2H), 4.90-5.00 (m, 3H), 4.81-4.84 (m, 1H), 4.64 (d, J=13.2 Hz, 1H), 4.33-4.38 (m, 1H), 4.28-4.30 (m, 1H), 3.86 (s, 3H), 3.84 (s, 3H), 3.47 (s, 3H), 3.37 (s, 3H), 3.20 (s, 3H), 3.15 (s, 3H), 3.04 (s, 3H), 2.67 (s, 3H), 2.64 (s, 3H), 2.27-2.35 (m, 2H), 2.06-2.12 (m, 3H), 1.89-2.03 (m, 3H), 1.54-1.66 (m, 5H), 1.37-1.49 (m, 3H), 1.31 (d, J=6.4 Hz, 3H), 1.23 (d, J=6.0 Hz, 3H), 1.16 (d, J=6.0 Hz, 3H), 0.95-0.99 (m, 9H), 0.89-0.93 (m, 10H), 0.82-0.87 (m, 13H), 0.79-0.80 (m, 4H), 0.73 (d, J=6.0 Hz, 3H), 0.57 (d, J=6.0 Hz, 3H). Mass (ESI): m/z calcd for $C_{68}H_{115}N_{11}O_{14}S$ 1341.83, found 1343.64 $[M+H]^+$.

Compound 38A: Preparation of [2-((2R,3R)-5-(3,5-dimethoxyphenylthio)-3-methyltetrahydrofuran-2-yl)-2-(methylamino)acetic acid]$^1$-cyclosporin A

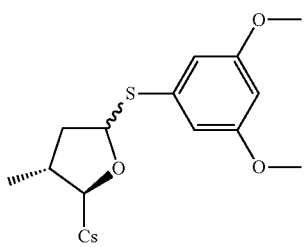

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3,5-dimethoxybenzenethiol was used instead of benzenethiol and 37 mg white solid was obtained. Yield: 28.4%. $^1$H NMR (400 MHz, CDCl$_3$) δ 8.37 (d, J=10.0 Hz, 1H), 8.03 (d, J=7.2 Hz, 1H), 7.57 (d, J=9.2 Hz, 1H), 7.53 (d, J=8.0 Hz, 1H), 6.62-6.65 (m, 2H), 6.31-6.32 (m, 1H), 5.65 (dd, J=3.2, 10.8 Hz, 1H), 5.46 (dd, J=2.4, 7.6 Hz, 1H), 5.33 (dd, J=3.6, 10.8 Hz, 1H), 5.20 (d, J=11.2 Hz, 1H), 5.05-5.12 (m, 3H), 4.93-5.01 (m, 2H), 4.81-4.88 (m, 2H), 4.66 (d, J=13.6 Hz, 1H), 4.34-4.43 (m, 2H), 3.78 (s, 3H), 3.77 (s, 3H), 3.49 (s, 3H), 3.37 (s, 3H), 3.21 (s, 3H), 3.17 (s, 3H), 3.06 (s, 3H), 2.69 (s, 3H), 2.65 (s, 3H), 2.25-2.35 (m, 2H), 2.10-2.20 (m, 3H), 1.92-2.00 (m, 3H), 1.54-1.67 (m, 5H), 1.39-1.47 (m, 3H), 1.33 (d, J=7.2 Hz, 3H), 1.22-1.26 (m, 6H), 0.97-1.01 (m, 8H), 0.91-0.95 (m, 10H), 0.83-0.89 (m, 14H), 0.80 (d, J=6.4 Hz, 4H), 0.76 (d, J=6.4 Hz, 3H), 0.58 (d, J=6.8 Hz, 3H). Mass (ESI): m/z calcd for $C_{68}H_{115}N_{11}O_{14}S$ 1341.83, found 1342.91 $[M+H]^+$.

Compound 39A: Preparation of [2-((2R,3R)-5-(3,5-diethoxyphenylthio)-3-methyltetrahydrofuran-2-yl)-2-(methylamino)acetic acid]$^1$-cyclosporin A

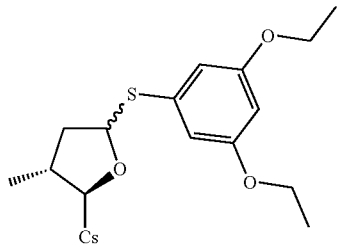

The compound was synthesized from [2-((2R,3R)-5-acetoxy-3-methyltetrahydrofuran-2-yl)-2-(methylamino)acetic acid]¹-cyclosporin A in a manner similar to that described for compound 1B. 3,5-diethoxybenzenethiol was used instead of benzenethiol and 25 mg light-yellow solid was obtained. Yield: 18.8%. ¹H NMR (400 MHz, CDCl₃) δ 8.32 (d, J=9.6 Hz, 1H), 8.04 (d, J=6.8 Hz, 1H), 7.55 (d, J=9.2 Hz, 1H), 7.48 (d, J=8.0 Hz, 1H), 6.60 (d, J=2.4 Hz, 2H), 6.31 (t, J=2.0 Hz, 1H), 5.65 (dd, J=4.0, 11.2 Hz, 1H), 5.42 (dd, J=3.6, 7.6 Hz, 1H), 5.32 (dd, J=4.0, 11.2 Hz, 1H), 5.19 (d, J=11.2 Hz, 1H), 5.11 (d, J=8.8 Hz, 1H), 5.03-5.08 (m, 2H), 4.90-4.98 (m, 3H), 4.82-4.88 (m, 1H), 4.66 (d, J=14.0 Hz, 1H), 4.38-4.43 (m, 1H), 4.33-4.37 (m, 1H), 3.99 (q, J=7.2 Hz, 4H), 3.47 (s, 3H), 3.34 (s, 3H), 3.21 (s, 3H), 3.16 (s, 3H), 3.05 (s, 3H), 2.68 (s, 3H), 2.65 (s, 3H), 2.23-2.39 (m, 2H), 2.14-2.17 (m, 3H), 1.92-2.00 (m, 3H), 1.57-1.67 (m, 6H), 1.43-1.49 (m, 2H), 1.39 (t, J=7.2 Hz, 6H), 1.32 (d, J=6.8 Hz, 3H), 1.25 (d, J=6.8 Hz, 3H), 1.18 (d, J=6.8 Hz, 3H), 0.97-1.01 (m, 9H), 0.91-0.94 (m, 12H), 0.85-0.89 (m, 11H), 0.77-0.81 (m, 7H), 0.60 (d, J=6.4 Hz, 3H). Mass (ESI): m/z calcd for $C_{70}H_{119}N_{11}O_{14}S$ 1369.87, found 1370.29 [M+H]⁺.

Compound 40A: Preparation of [2-((2R,3R)-5-(4-chloro-3-methoxyphenylthio)-3-methyltetrahydrofuran-2-yl)-2-(methylamino)acetic acid]¹-cyclosporin A

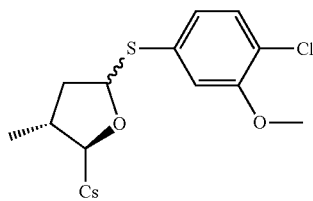

(I) Synthesis of 4-chloro-3-methoxybenzenethiol. The compound was synthesized from 4-chloro-3-methoxyaniline in a manner similar to that described for 4-Chloro-3-ethoxy-benzenethiol. 500 mg of starting material was used and 170 mg light-yellow oil was obtained. Yield: 41.3%.

(II) Synthesis of [2-((2R,3R)-5-(4-chloro-3-methoxyphenylthio)-3-methyltetrahydrofuran-2-yl)-2-(methylamino) acetic acid]¹-cyclosporin A. The compound was synthesized from [2-((2R,3R)-5-acetoxy-3-methyltetrahydrofuran-2-yl)-2-(methylamino)acetic acid]¹-cyclosporin A in a manner similar to that described for compound 1B. 4-chloro-3-methoxybenzenethiol was used instead of benzenethiol and 25 mg light-yellow foam was obtained. Yield: 19.1%. ¹H NMR (400 MHz, CDCl₃) δ 8.40 (d, J=10.0 Hz, 1H), 8.06 (d, J=6.8 Hz, 1H), 7.63 (d, J=9.2 Hz, 1H), 7.53 (d, J=8.4 Hz, 1H), 7.33 (d, J=8.4 Hz, 1H), 7.06 (dd, J=2.0, 8.4 Hz, 1H), 7.02 (d, J=2.0 Hz, 1H), 5.66 (dd, J=4.0, 11.2 Hz, 1H), 5.44 (dd, J=3.6, 8.0 Hz, 1H), 5.33 (dd, J=4.0, 11.6 Hz, 1H), 5.19 (d, J=8.0 Hz, 1H), 5.17 (d, J=9.6 Hz, 1H), 5.07-5.13 (m, 3H), 4.96-5.02 (m, 1H), 4.91-4.95 (m, 1H), 4.83-4.89 (m, 1H), 4.66 (d, J=14.0 Hz, 1H), 4.33-4.42 (m, 2H), 3.90 (s, 3H), 3.48 (s, 3H), 3.39 (s, 3H), 3.22 (s, 3H), 3.18 (s, 3H), 3.07 (s, 3H), 2.70 (s, 3H), 2.66 (s, 3H), 2.38-2.46 (m, 1H), 2.26-2.35 (m, 1H), 2.11-2.17 (m, 3H), 1.96-2.04 (m, 3H), 1.59-1.69 (m, 5H), 1.44-1.48 (m, 3H), 1.33 (d, J=6.8 Hz, 3H), 1.25 (d, J=6.8 Hz, 3H), 1.20 (d, J=6.8 Hz, 3H), 1.00-1.04 (m, 9H), 0.94-0.95 (m, 8H), 0.89-0.91 (m, 5H), 0.85-0.88 (m, 10H), 0.82 (d, J=6.8 Hz, 4H), 0.75 (d, J=6.8 Hz, 3H), 0.59 (d, J=6.4 Hz, 3H). Mass (ESI): m/z calcd for $C_{67}H_{112}ClN_{11}O_{13}S$ 1345.79, found 1346.86 [M+H]⁺.

Compound 41A: Preparation of [2-((2R,3R)-5-(4-chloro-3-ethoxyphenylthio)-3-methyltetrahydrofuran-2-yl)-2-(methylamino)acetic acid]¹-cyclosporin A

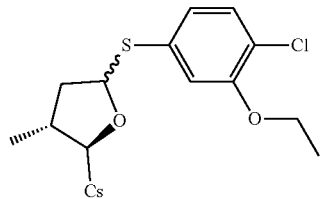

(I) Synthesis of 4-Chloro-3-ethoxy-benzenethiol. 1-Chloro-2-ethoxy-4-nitro-benzene (3.065 g, 2.6 mmol) was dissolved in 18.9 mL AcOH. The solution was added to the mixture of iron (4.25 g, 75.9 mmol) and 47.32 mL of H₂O. Let it stir at 110° C. for 2.5 hrs. The starting material was consumed completely after monitored by TLC. Let it cool to room temperature. Filtered by celite, washed with EtOAc (100 mL) and water (100 mL). The organic layer was washed with water (150 mL), sat. K₂CO₃ (50 mL), brine. Dried with Na₂SO₄. Filtered and evaporated to dryness to give 3.2 g 4-Chloro-3-ethoxy-phenylamine as dark liquid, quantitative yield.

4-Chloro-3-ethoxy-phenylamine (1.5 g, 8.772 mmoL) was mixed with con. HCl (1.57 mL) and ice (2.15 g). The solution of NaNO₂ (0.602 g, 8.72 mmol) in 3.2 mL H₂O was added to the mixture at 0° C. Let it stir at 0° C. for 30 min. The reaction solution was added to the solution of potassium ethylxanthate (2.8 g, 17.5 mmol) in 8.28 mL water at 65° C. Let it stir at 65° C. for 2 hrs. It was cooled to room temperature. The mixture was evaporated with EtOAc (50 mL×3). The organic layers were combined and evaporated to dryness and the residue was purified by flash chromatography (PE/EA=10/1) to give 1.5 g dithiocarbonic acid S-(4-chloro-3-ethoxy-phenyl) ester O-ethyl ester crude product.

Dithiocarbonic acid S-(4-chloro-3-ethoxy-phenyl) ester O-ethyl ester (1.5 g) was dissolved in 39.3 mL of EtOH. 23.6 mL of 3M NaOH was added. Let it stir at 65° C. for 2 hrs. The organic layer was evaporated and the aq. solution was acidified by con. HCl to PH=3 and extracted with EtOAc (20 mL×3). The organic layer was evaporated to dryness and purified by flash chromatography (PE) to give 0.6 g 4-Chloro-3-ethoxy-benzenethiol as light-yellow liquid. Yield 58.8%.

(II) Synthesis of [2-((2R,3R)-5-(4-chloro-3-ethoxyphenylthio)-3-methyltetrahydro furan-2-yl)-2-(methylamino) acetic acid]¹-cyclosporin A. The compound was synthesized from [2-((2R,3R)-5-acetoxy-3-methyltetrahydrofuran-2-yl)-2-(methylamino)acetic acid]¹-cyclosporin A in a manner similar to that described for compound 1B. 4-chloro-3-ethoxybenzenethiol was used instead of benzenethiol, 120 mg of starting material was used and 52 mg light-yellow solid was obtained. Yield: 39.4%. ¹H NMR (400 MHz, CDCl₃) δ 8.39 (d, J=9.6 Hz, 1H), 8.06 (d, J=7.2 Hz, 1H), 7.65 (d, J=9.2 Hz, 1H), 7.53 (d, J=8.4 Hz, 1H), 7.33 (d, J=8.0 Hz, 1H), 7.08 (dd, J=1.6, 8.0 Hz, 1H), 6.95 (d, J=1.6 Hz, 1H), 5.67 (dd, J=4.0, 10.8 Hz, 1H), 5.43 (dd, J=3.2, 7.6 Hz, 1H), 5.33 (dd, J=4.0, 11.2 Hz, 1H), 5.20 (d, J=9.6 Hz, 1H), 5.17 (d, J=11.2 Hz, 1H), 5.06-5.13 (m, 2H), 4.98-5.02 (m, 1H), 4.90-4.96 (m, 1H), 4.82-4.89 (m, 1H), 4.66 (d, J=14.0 Hz, 1H), 4.39 (t, J=7.2 Hz, 1H), 4.32 (dd, J=6.0, 9.2 Hz, 1H), 4.05-4.13 (m, 3H), 3.47 (s, 3H), 3.38 (s, 3H), 3.22 (s, 3H), 3.18 (s, 3H), 3.06 (s, 3H), 2.70 (s, 3H), 2.66 (s, 3H), 2.39-2.46 (m, 1H), 2.26-2.35 (m, 1H), 2.10-2.17 (m, 3H), 1.94-2.04 (m, 3H), 1.58-1.70 (m, 4H), 1.44-1.48 (m, 4H), 1.33 (d, J=7.2 Hz, 4H), 1.25 (d, J=7.2 Hz, 4H), 1.17 (d, J=6.8 Hz, 4H), 1.02 (t, J=6.0 Hz, 9H), 0.94 (d, J=6.4 Hz, 8H), 0.90 (d, J=6.4 Hz, 4H), 0.84-0.87 (m, 12H), 0.82 (d, J=6.4 Hz, 3H), 0.76 (d, J=6.4 Hz, 3H), 0.60 (d, J=6.4 Hz, 3H). Mass (ESI): m/z calcd for $C_{68}H_{114}ClN_{11}O_{13}S$ 1359.80, found 1361.2 $[M+H]^+$.

Compound 42A: Preparation of [2-((2R,3R)-5-(4-chloro-3-propoxyphenylthio)-3-methyltetrahydrofuran-2-yl)-2-(methylamino)acetic acid]$^1$-cyclosporin A

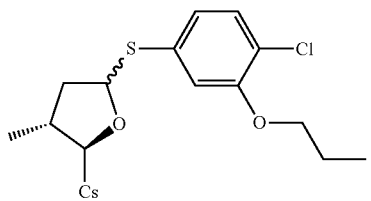

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 4-chloro-3-propoxybenzenethiol was used instead of benzenethiol and 20 mg white solid was obtained. Yield: 9.0%. $^1$H NMR (400 MHz, CDCl$_3$) δ 8.37 (d, J=9.6 Hz, 1H), 8.06 (d, J=6.8 Hz, 1H), 7.63 (d, J=9.2 Hz, 1H), 7.50 (d, J=8.0 Hz, 1H), 7.31 (d, J=8.0 Hz, 1H), 7.07 (dd, J=2.0, 8.0 Hz, 1H), 6.92 (d, J=2.0 Hz, 1H), 5.65 (dd, J=4.0, 11.2 Hz, 1H), 5.41 (dd, J=3.6, 7.6 Hz, 1H), 5.31 (dd, J=4.0, 11.2 Hz, 1H), 5.19 (d, J=9.2 Hz, 1H), 5.15 (d, J=11.2 Hz, 1H), 5.05-5.12 (m, 2H), 4.94-5.00 (m, 2H), 4.90 (t, J=8.8 Hz, 1H), 4.83 (t, J=7.6 Hz, 1H), 4.65 (d, J=13.6 Hz, 1H), 4.33-4.41 (m, 1H), 4.30 (dd, J=6.0, 9.2 Hz, 1H), 3.93-3.98 (m, 2H), 3.45 (s, 3H), 3.37 (s, 3H), 3.21 (s, 3H), 3.16 (s, 3H), 3.05 (s, 3H), 2.68 (s, 3H), 2.65 (s, 3H), 2.38-2.46 (m, 1H), 2.25-2.33 (m, 1H), 2.07-2.15 (m, 3H), 1.92-2.03 (m, 3H), 1.80-1.88 (m, 2H), 1.57-1.69 (m, 5H), 1.40-1.48 (m, 3H), 1.31 (d, J=7.2 Hz, 3H), 1.24 (d, J=6.4 Hz, 3H), 1.15 (d, J=6.4 Hz, 3H), 1.04 (t, J=7.2 Hz, 3H), 0.98-1.01 (m, 8H), 0.90-0.93 (m, 8H), 0.87-0.89 (m, 4H), 0.80-0.86 (m, 16H), 0.75 (d, J=6.4 Hz, 3H), 0.60 (d, J=6.4 Hz, 3H). Mass (ESI) calcd for $C_{69}H_{116}ClN_{11}O_{13}S$ 1373.82, found 1374.98 $[M+H]^+$.

Compound 43A: Preparation of [2-((2R,3R)-5-(4-chloro-3-((tetrahydro-2H-pyran-4-yl)methoxy)phenylthio)-3-methyltetrahydrofuran-2-yl)-2-(methylamino)acetic acid]$^1$-cyclosporin A

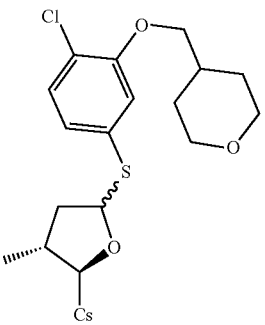

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 4-chloro-3-((tetrahydro-2H-pyran-4-yl)methoxy)benzenethiol was used instead of benzenethiol and 50 mg white solid was obtained. Yield: 21.6%. 1H NMR (400 MHz, CDCl$_3$) δ 8.36 (d, J=9.6 Hz, 1H), 8.06 (d, J=6.8 Hz, 1H), 7.64 (d, J=9.2 Hz, 1H), 7.49 (d, J=8.0 Hz, 1H), 7.32 (d, J=8.4 Hz, 1H), 7.09 (dd, J=1.2, 8.0 Hz, 1H), 6.91 (d, J=1.2 Hz, 1H), 5.65 (dd, J=4.0, 11.2 Hz, 1H), 5.42 (dd, J=3.6, 7.6 Hz, 1H), 5.31 (dd, J=4.0, 11.6 Hz, 1H), 5.20 (d, J=9.2 Hz, 1H), 5.14 (d, J=11.2 Hz, 1H), 5.05-5.11 (m, 2H), 4.94-5.00 (m, 1H), 4.82-4.91 (m, 3H), 4.65 (d, J=14.0 Hz, 1H), 4.34-4.41 (m, 1H), 4.30 (dd, J=6.4, 9.2 Hz, 1H), 4.01 (dd, J=2.8, 11.2 Hz, 3H), 3.79-3.88 (m, 3H), 3.44 (s, 3H), 3.36 (s, 3H), 3.21 (s, 3H), 3.16 (s, 3H), 3.05 (s, 3H), 2.68 (s, 3H), 2.65 (s, 3H), 2.40-2.47 (m, 1H), 2.25-2.33 (m, 1H), 2.08-2.14 (m, 3H), 1.95-2.03 (m, 3H), 1.79 (d, J=12.0 Hz, 3H), 1.55-1.67 (m, 6H), 1.40-1.49 (m, 4H), 1.31 (d, J=7.2 Hz, 3H), 1.24 (d, J=6.8 Hz, 3H), 1.14 (d, J=6.4 Hz, 3H), 0.97-1.00 (m, 9H), 0.92-0.93 (m, 8H), 0.87-0.89 (m, 4H), 0.82-0.86 (m, 14H), 0.75 (d, J=6.4 Hz, 4H), 0.60 (d, J=6.4 Hz, 3H). Mass (ESI) calcd for $C_{72}H_{120}ClN_{11}O_{14}S$ 1429.84, found 1431.15 $[M+H]^+$.

Compound 44A: Preparation of [2-((2R,3R)-5-(3-(benzyloxy)-4-chlorophenylthio)-3-methyltetrahydrofuran-2-yl)-2-(methylamino)acetic acid]$^1$-cyclosporin A

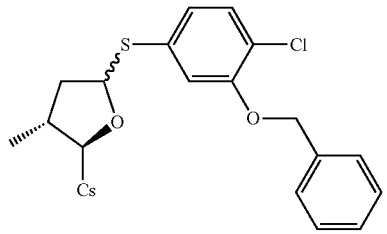

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(benzyloxy)-4-chlorobenzenethiol was used instead of benzenethiol and 70 mg white solid was obtained. Yield: 24.2%. $^1$H NMR (400 MHz, CDCl$_3$) δ 8.39 (d, J=9.6 Hz, 1H), 8.08 (d, J=6.8 Hz, 1H), 7.66 (d, J=9.2 Hz, 1H), 7.53 (d, J=8.0 Hz, 1H), 7.49 (d, J=7.2 Hz, 2H), 7.36-7.40 (m, 3H), 7.29-7.33 (m, 1H), 7.13 (dd, J=1.6, 8.0 Hz, 1H), 7.02 (d, J=1.6 Hz, 1H), 5.66 (dd, J=4.0, 11.2 Hz, 1H), 5.42 (dd, J=4.0, 8.0 Hz, 1H), 5.33 (dd, J=4.0, 11.2 Hz, 1H), 5.23 (d, J=9.2 Hz, 1H), 5.15-5.18 (m, 2H), 5.14 (s, 2H), 5.06-5.11 (m, 2H), 4.96-5.02 (m, 1H), 4.83-4.93 (m, 2H), 4.65 (d, J=14.0 Hz, 1H), 4.36-4.43 (m, 1H), 4.31 (dd, J=6.4, 9.2 Hz, 1H), 3.48 (s, 3H), 3.38 (s, 3H), 3.22 (s, 3H), 3.17 (s, 3H), 3.06 (s, 3H), 2.68 (s, 3H), 2.66 (s, 3H), 2.41-2.48 (m, 1H), 2.27-2.35 (m, 1H), 2.07-2.17 (m, 3H), 1.97-2.03 (m, 3H), 1.56-1.69 (m, 5H), 1.41-1.49 (m, 3H), 1.31 (d, J=7.2 Hz, 3H), 1.25 (d, J=6.8 Hz, 3H), 1.15 (d, J=6.8 Hz, 3H), 0.98-1.02 (m, 9H), 0.93-0.95 (m, 8H), 0.89-0.90 (m, 4H), 0.82-0.86 (m, 14H), 0.77 (d, J=6.4 Hz, 4H), 0.62 (d, J=6.8 Hz, 3H). Mass (ESI) calcd for C$_{73}$H$_{116}$ClN$_{11}$O$_{13}$S 1421.82, found 1423.03 [M+H]$^+$.

Compound 45A: Preparation of [2-((2R,3R)-5-(4-chloro-3-(2-methoxyethoxy)phenylthio)-3-methyltetrahydrofuran-2-yl)-2-(methylamino)acetic acid]$^1$-cyclosporin A

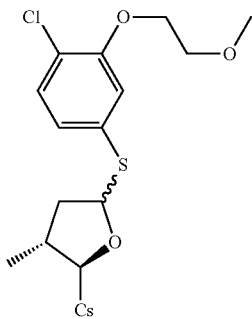

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 4-chloro-3-(2-methoxyethoxy) benzenethiol was used instead of benzenethiol and 18 mg white solid was obtained. Yield: 8.0%. $^1$H NMR (400 MHz, CDCl$_3$) δ 8.39 (d, J=9.2 Hz, 1H), 8.07 (d, J=6.4 Hz, 1H), 7.71 (d, J=8.4 Hz, 1H), 7.55 (d, J=7.6 Hz, 1H), 7.33 (d, J=8.4 Hz, 1H), 7.11 (dd, J=1.6, 8.4 Hz, 1H), 6.97 (d, J=1.6 Hz, 1H), 5.66 (dd, J=3.6, 11.2 Hz, 1H), 5.43 (dd, J=3.6, 7.6 Hz, 1H), 5.33 (dd, J=3.6, 11.2 Hz, 1H), 5.22 (d, J=9.2 Hz, 1H), 5.15 (d, J=10.8 Hz, 1H), 5.07-5.12 (m, 2H), 4.96-5.02 (m, 2H), 4.92 (t, J=8.0 Hz, 1H), 4.85 (t, J=7.2 Hz, 1H), 4.66 (d, J=14.0 Hz, 1H), 4.38-4.43 (m, 1H), 4.30-4.33 (m, 1H), 4.17 (t, J=4.4 Hz, 2H), 3.82 (t, J=4.4 Hz, 2H), 3.48 (s, 3H), 3.46 (s, 3H), 3.37 (s, 3H), 3.21 (s, 3H), 3.17 (s, 3H), 3.06 (s, 3H), 2.70 (s, 3H), 2.67 (s, 3H), 2.41-2.49 (m, 1H), 2.27-2.35 (m, 1H), 2.07-2.17 (m, 3H), 1.93-2.04 (m, 3H), 1.58-1.69 (m, 5H), 1.40-1.47 (m, 3H), 1.32 (d, J=6.8 Hz, 3H), 1.26 (d, J=6.4 Hz, 3H), 1.15 (d, J=6.4 Hz, 3H), 0.99-1.02 (m, 8H), 0.93-0.95 (m, 8H), 0.83-0.90 (m, 20H), 0.76 (d, J=6.4 Hz, 3H), 0.62 (d, J=6.4 Hz, 3H). Mass (ESI) calcd for C$_{69}$H$_{116}$ClN$_{11}$O$_{14}$S 1389.81, found 1390.97 [M+H]$^+$.

Compound 46A: Preparation of [2-((2R,3R)-5-(4-chloro-3-(2-hydroxyethoxy)phenylthio)-3-methyltetrahydrofuran-2-yl)-2-(methylamino)acetic acid]$^1$-cyclosporin A

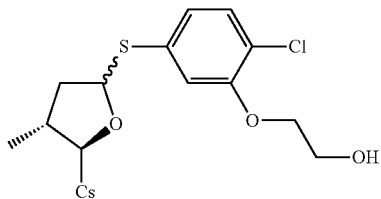

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 2-(2-chloro-5-mercaptophenoxy) ethanol was used instead of benzenethiol and 30 mg white solid was obtained. Yield: 13.5%. $^1$H NMR (400 MHz, CDCl$_3$) δ 8.37 (d, J=9.6 Hz, 1H), 8.05 (d, J=6.4 Hz, 1H), 7.61 (d, J=8.8 Hz, 1H), 7.52 (d, J=8.0 Hz, 1H), 7.28 (s, 1H), 7.15 (s, 1H), 7.02 (d, J=8.0 Hz, 1H), 5.62 (dd, J=3.2, 11.2 Hz, 1H), 5.38 (dd, J=3.2, 7.6 Hz, 1H), 5.31 (dd, J=2.8, 11.2 Hz, 1H), 5.15 (d, J=9.6 Hz, 1H), 5.04-5.11 (m, 2H), 4.92-4.98 (m, 1H), 4.81-4.90 (m, 2H), 4.65 (d, J=14.0 Hz, 1H), 4.34-4.38 (m, 2H), 4.10-4.16 (m, 2H), 3.97-4.04 (m, 4H), 3.48 (s, 3H), 3.35 (s, 3H), 3.19 (s, 3H), 3.16 (s, 3H), 3.04 (s, 3H), 2.66 (s, 6H), 2.36-2.43 (m, 1H), 2.24-2.30 (m, 1H), 2.10-2.16 (m, 3H), 1.91-1.98 (m, 3H), 1.55-1.66 (m, 5H), 1.36-1.44 (m, 3H), 1.30 (d, J=6.8 Hz, 3H), 1.24 (d, J=5.6 Hz, 3H), 1.17 (d, J=6.8 Hz, 3H), 0.96-0.99 (m, 9H), 0.89-0.93 (m, 11H), 0.81-0.88 (m, 16H), 0.71 (d, J=6.4 Hz, 3H), 0.55 (d, J=6.8 Hz, 3H). Mass (ESI) calcd for C$_{68}$H$_{114}$ClN$_{11}$O$_{14}$S 1375.80, found 1377.06 [M+H]$^+$.

Compound 47A: Preparation of [2-((2R,3R)-3-methyl-5-(3-(methylamino)phenylthio)tetrahydrofuran-2-yl)-2-(methylamino)acetic acid]$^1$-cyclosporin A

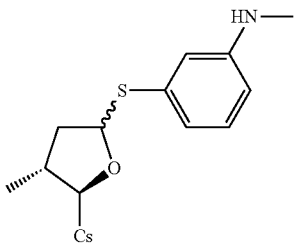

(I) Synthesis of 3-(methylamino)benzenethiol. 3-Aminobenzenethiol (4 g, 0.032 mol) was dissolved in 12 mL of HCOOH. 12 mL of formyl acetate was added. Let it stir at room temperature for 16 hrs. The reaction mixture was washed with water and extracted with EtOAc (50 mL×3). Dried with Na$_2$SO$_4$, filtered and evaporated to dryness. The residue was purified by flash chromatography (DCM/MeOH=25/1) to give 3.77 g N-(3-mercaptophenyl)formamide as light-brown oil. Yield: 77.5%.

The solution of N-(3-mercaptophenyl)formamide (1.1 g, 7.2 mmol) in 12.5 mL of THF was added to the mixture of LiAlH$_4$ (1.25 g, 33.8 mmol) in 50 mL of THF. Let it stir at 70° C. for 16 hrs. It was quenched with sat. NH$_4$Cl. Extracted with EtOAc (50 mL×3). Dried with Na$_2$SO$_4$, filtered and evaporated to dryness. The residue was purified by flash chromatography (PE/EA=94/6) to give 330 mg 3-(methylamino)benzenethiol as light-brown liquid. Yield: 33.0%.

(II) Synthesis of [2-((2R,3R)-3-methyl-5-(3-(methylamino)phenylthio)tetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(methylamino)benzenethiol was used instead of benzenethiol and 21 mg light-yellow solid was obtained. Yield: 13.1%. $^1$H NMR (400 MHz, CDCl$_3$) δ 8.39 (d, I=9.6 Hz, 1H), 8.09 (d, J=6.4 Hz, 1H), 7.67 (d, J=8.8 Hz, 1H), 7.55 (d, J=8.4 Hz, 1H), 7.15 (t, J=7.6 Hz, 1H), 7.09 (s, 1H), 6.83 (d, J=7.6 Hz, 1H), 6.66 (d, J=7.6 Hz, 1H), 5.64 (dd, J=3.2, 10.8 Hz, 1H), 5.53 (dd, J=2.8, 8.0 Hz, 1H), 5.34 (dd, J=3.2, 10.8 Hz, 1H), 5.25 (d, J=9.6 Hz, 1H), 5.15 (dd, J=6.4, 9.2 Hz, 1H), 5.08-5.11 (m, 2H), 4.97-5.03 (m, 1H), 4.84-4.93 (m, 2H), 4.66 (d, J=14.0 Hz, 1H), 4.40 (t, J=7.2 Hz, 1H), 4.29-4.33 (m, 2H), 3.45 (s, 3H), 3.40 (s, 3H), 3.22 (s, 3H), 3.17 (s, 3H), 3.07 (s, 3H), 2.89 (s, 3H), 2.70 (s, 3H), 2.69 (s, 3H), 2.47-2.54 (m, 1H), 2.29-2.37 (m, 1H), 2.11-2.17 (m, 2H), 2.03-2.07 (m, 1H), 1.93-2.01 (m, 2H), 1.83-1.88 (m, 1H), 1.55-1.70 (m, 5H), 1.40-1.50 (m, 3H), 1.31 (d, J=7.2 Hz, 3H), 1.26 (d, J=6.8 Hz, 3H), 1.16 (d, J=6.8 z, 3H), 1.01 (d, J=6.8 Hz, 3H), 0.93-0.98 (m, 14H), 0.87-0.91 (m, 11H), 0.77-0.85 (m, 11H), 0.68 (d, J=6.4 Hz, 3H). Mass (ESI): m/z calcd for C$_{67}$H$_{114}$N$_{12}$O$_{12}$S 1310.84, found 1311.68 [M+H]$^+$.

Compound 48A: Preparation of [2-((2R,3R)-5-(3-(benzylamino)phenylthio)-3-methyltetrahydrofuran-2-yl)-2-(methylamino)acetic acid]$^1$-cyclosporin A

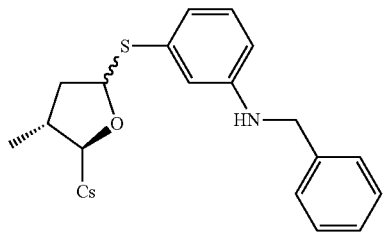

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(benzylamino)benzenethiol was used instead of benzenethiol and 140 mg white solid was obtained. Yield: 49.3%. $^1$H NMR (400 MHz, CDCl$_3$) δ 8.40 (d, J=9.6 Hz, 1H), 8.09 (d, J=6.8 Hz, 1H), 7.65 (d, J=9.2 Hz, 1H), 7.54 (d, J=8.0 Hz, 1H), 7.35 (d, J=7.2 Hz, 2H), 7.29 (t, J=7.6 Hz, 2H), 7.22 (t, J=7.6 Hz, 1H), 7.03 (t, J=8.0 Hz, 1H), 6.92 (s, 1H), 6.70 (d, J=7.6 Hz, 1H), 6.39 (dd, J=1.6, 8.0 Hz, 1H), 5.64 (dd, J=4.0, 10.8 Hz, 1H), 5.55 (dd, J=3.2, 7.6 Hz, 1H), 5.34 (dd, J=3.6, 11.2 Hz, 1H), 5.24 (d, J=9.2 Hz, 1H), 5.16 (dd, J=6.4, 9.2 Hz, 1H), 5.09 (d, J=11.2 Hz, 1H), 5.05 (d, J=7.2 Hz, 1H), 4.97-5.01 (m, 1H), 4.92 (t, J=8.0 Hz, 1H), 4.86 (t, J=7.2 Hz, 1H), 4.65 (d, J=13.6 Hz, 1H), 4.40 (d, J=6.4 Hz, 1H), 4.36 (d, J=12.4 Hz, 2H), 4.28-4.32 (m, 2H), 3.45 (s, 3H), 3.40 (s, 3H), 3.22 (s, 3H), 3.16 (s, 3H), 3.07 (s, 3H), 2.66 (s, 3H), 2.53 (s, 3H), 2.28-2.37 (m, 1H), 2.08-2.17 (m, 2H), 1.92-2.05 (m, 5H), 1.57-1.69 (m, 5H), 1.40-1.49 (m, 3H), 1.32 (d, J=7.2 Hz, 3H), 1.25 (d, J=6.8 Hz, 3H), 1.16 (d, J=6.8 Hz, 3H), 1.01 (d, J=6.4 Hz, 3H), 0.92-0.97 (m, 13H), 0.87-0.91 (m, 10H), 0.81-0.86 (m, 13H), 0.70 (d, J=6.4 Hz, 3H). Mass (ESI) calcd for C$_{73}$H$_{118}$N$_{12}$O$_{12}$S 1386.87, found 1388.37 [M+H]$^+$.

Compound 49A: Preparation of [2-((2R,3R)-5-(3-(ethyl(methyl)amino)phenylthio)-3-methyltetrahydrofuran-2-yl)-2-(methylamino)acetic acid]$^1$-cyclosporin A

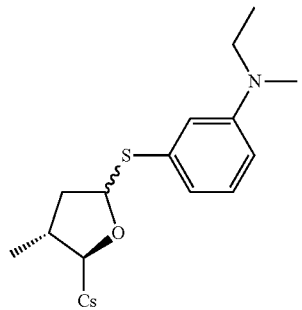

(I) Synthesis of 3-(ethyl(methyl)amino)benzenethiol. 3,3'-disulfanediylbis(N-methylaniline) (155 mg, 0.56 mmol) was dissolved in 5 mL of DCM. 3.15 mL of TEA was added. Ac$_2$O (3.15 mL) was added at room temperature. Let it stir at r.t. for 16 hrs. Water was added. The organic layer was evaporated to dryness and the residue was purified by flash chromatography (DCM/MeOH=85/15) to give 220 mg N,N'-(3,3'-disulfanediylbis(3,1-phenylene))bis(N-methylacetamide) as light-yellow oil. Yield: quantitative.

N,N'-(3,3'-disulfanediylbis(3,1-phenylene))bis(N-methylacetamide) (220 mg, 0.61 mmol) in 5 mL of THF was added slowly to the mixture of LiAlH$_4$ (132 mg, 3.568 mmol) in 30 mL of THF at 0° C. Then let it reflux for 2 hrs. Sat. NH$_4$Cl was added to quench the reaction. It was extracted with EtOAc (30 mL×3). Dried with Na$_2$SO$_4$, filtered and evaporated to dryness. The residue was purified by flash chromatography (PE/EA=85/15) to give 110 mg 3-(ethyl(methyl)amino)benzenethiol as light-yellow oil. Yield: 54%.

(II) Synthesis of [2-((2R,3R)-5-(3-(ethyl(methyl)amino)phenylthio)-3-methyltetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(ethyl(methyl)amino)benzenethiol was used instead of benzenethiol and 10 mg light-yellow solid was obtained. Yield: 6.8%. $^1$H NMR (400 MHz, CDCl$_3$) δ 8.38 (d, J=9.6 Hz, 1H), 8.07 (d, J=7.2 Hz, 1H), 7.63 (d, J=9.2 Hz, 1H), 7.53 (d, J=8.0 Hz, 1H), 7.40-7.44 (m, 2H), 7.29-7.35 (m, 1H), 7.19-7.23 (m, 1H), 5.66 (dd, J=4.0, 11.6 Hz, 1H), 5.55 (dd, J=3.2, 7.6 Hz, 1H), 5.33 (dd, J=4.0, 11.6 Hz, 1H), 5.23 (d, J=9.2 Hz, 1H), 5.09-5.16 (m, 3H), 4.97-5.01 (m, 1H), 4.89-4.95 (m, 2H), 4.82-4.87 (m, 1H), 4.66 (d, J=13.6 Hz, 1H), 4.37-4.43 (m, 1H), 4.34 (dd, J=6.4, 9.2 Hz, 1H), 3.48 (q, J=6.8 Hz, 2H), 3.43 (s, 3H), 3.38 (s, 3H), 3.22 (s, 3H), 3.18 (s, 3H), 3.09 (s, 3H), 3.06 (s, 3H), 2.69 (s, 3H), 2.67 (s, 3H), 2.43-2.50 (m, 1H), 2.26-2.35 (m, 1H), 2.11-2.17 (m, 3H), 1.93-2.03 (m, 3H), 1.59-1.71 (m, 5H), 1.41-1.51 (m, 3H), 1.32 (d, J=6.8 Hz, 3H), 1.26 (d, J=7.2 Hz, 3H), 1.18 (d, J=6.8 Hz, 3H), 1.15 (t, J=6.8 Hz, 3H), 0.97-1.02 (m, 9H), 0.93-0.95 (m, 8H), 0.84-0.90 (m, 15H), 0.79-0.83 (m, 7H), 0.67 (d, J=6.4 Hz, 3H). Mass (ESI): m/z calcd for $C_{69}H_{118}N_{12}O_{12}S$ 1338.87, found 1340.01 $[M+H]^+$.

Compound 50A: Preparation of [2-((2R,3R)-3-methyl-5-(3-(methyl(propyl)amino)phenylthio)tetrahydrofuran-2-yl)-2-(methylamino)acetic acid]$^1$-cyclosporin A

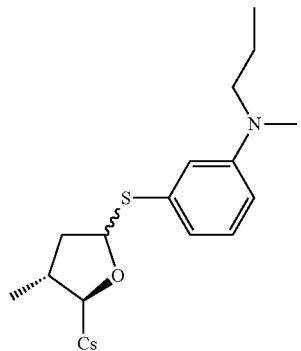

(I) Synthesis of 3-(methyl(propyl)amino)benzenethiol. The compound was synthesized from propionic anhydride in a manner similar to that described for 3-(ethyl(methyl)amino)benzenethiol. 2.52 mL of propionic anhydride was used and 100 mg 3-(methyl(propyl)amino)benzenethiol was obtained as light-yellow oil. Yield: 66.1%.

(II) Synthesis of [2-((2R,3R)-3-methyl-5-(3-(methyl(propyl)amino)phenylthio)tetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(methyl(propyl)amino)benzenethiol was used instead of benzenethiol and 45 mg light-yellow solid was obtained. Yield: 34.3%. $^1$H NMR (400 MHz, CDCl$_3$) δ 8.37 (d, J=9.6 Hz, 1H), 8.05 (d, J=6.8 Hz, 1H), 7.61 (d, J=8.8 Hz, 1H), 7.51 (d, J=8.0 Hz, 1H), 7.23 (t, J=8.0 Hz, 1H), 7.03 (d, J=7.6 Hz, 1H), 6.90 (s, 1H), 6.78 (d, J=8.0 Hz, 1H), 5.65 (dd, J=4.0, 11.2 Hz, 1H), 5.50 (dd, J=3.2, 8.0 Hz, 1H), 5.32 (dd, J=4.0, 11.2 Hz, 1H), 5.16-5.19 (m, 2H), 5.07-5.14 (m, 2H), 4.96-5.00 (m, 1H), 4.82-4.94 (m, 3H), 4.65 (d, J=13.6 Hz, 1H), 4.36-4.43 (m, 1H), 4.31 (dd, J=6.4, 8.8 Hz, 1H), 3.44 (s, 3H), 3.36 (s, 3H), 3.27 (t, J=7.2 Hz, 2H), 3.21 (s, 3H), 3.17 (s, 3H), 3.05 (s, 3H), 2.97 (s, 3H), 2.69 (s, 3H), 2.66 (s, 3H), 2.37-2.45 (m, 1H), 2.24-2.33 (m, 1H), 2.08-2.14 (m, 3H), 1.93-2.03 (m, 3H), 1.61-1.68 (m, 5H), 1.54-1.58 (m, 2H), 1.41-1.50 (m, 3H), 1.32 (d, J=6.8 Hz, 3H), 1.25 (d, J=6.8 Hz, 3H), 1.17 (d, J=6.8 Hz, 3H), 0.99-1.01 (m, 9H), 0.91-0.94 (m, 10H), 0.83-0.89 (m, 16H), 0.77-0.81 (m, 7H), 0.64 (d, J=6.4 Hz, 3H). Mass (ESI): m/z calcd for $C_{70}H_{120}N_{12}O_{12}S$ 1352.89, found 1353.90 $[M+H]^+$.

Compound 51A: Preparation of [2-((2R,3R)-5-(4-(dimethylamino)phenylthio)-3-methyltetrahydrofuran-2-yl)-2-(methylamino)acetic acid]$^1$-cyclosporin A

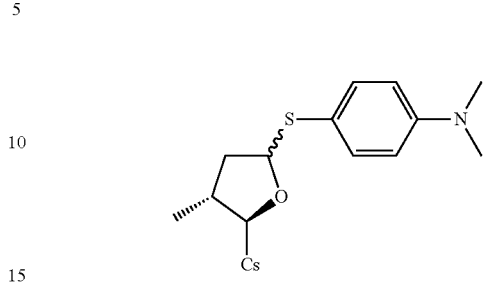

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 4-(dimethylamino)benzenethiol was used instead of benzenethiol and 22 mg white solid was obtained. Yield: 10.3%. $^1$H NMR (400 MHz, CDCl$_3$) δ 8.37 (d, J=9.6 Hz, 1H), 8.02 (d, J=6.8 Hz, 1H), 7.62 (d, J=8.8 Hz, 1H), 7.48 (d, J=8.0 Hz, 1H), 7.33 (d, J=8.4 Hz, 2H), 6.67 (d, J=7.2 Hz, 2H), 5.65 (dd, J=4.0, 10.8 Hz, 1H), 5.32 (dd, J=4.0, 10.8 Hz, 1H), 5.22 (d, J=10.8 Hz, 2H), 5.14 (d, J=9.2 Hz, 1H), 5.08 (dd, J=4.0, 10.0 Hz, 1H), 5.03-5.05 (m, 1H), 4.97-5.01 (m, 1H), 4.92 (t, J=8.4 Hz, 1H), 4.80-4.87 (m, 2H), 4.65 (d, J=14.0 Hz, 1H), 4.34-4.42 (m, 1H), 4.22 (dd, J=6.4, 9.2 Hz, 1H), 3.46 (s, 3H), 3.37 (s, 3H), 3.20 (s, 3H), 3.16 (s, 3H), 3.05 (s, 3H), 2.93 (s, 6H), 2.70 (s, 3H), 2.65 (s, 3H), 2.27-2.37 (m, 2H), 2.07-2.21 (m, 3H), 1.91-1.99 (m, 3H), 1.57-1.64 (m, 5H), 1.41-1.48 (m, 3H), 1.33 (d, J=6.8 Hz, 3H), 1.24-1.25 (m, 3H), 1.12 (d, J=6.4 Hz, 3H), 0.97-1.00 (m, 6H), 0.90-0.95 (m, 12H), 0.84-0.88 (m, 14H), 0.80 (d, J=6.4 Hz, 4H), 0.77 (d, J=6.8 Hz, 3H), 0.64 (d, J=6.8 Hz, 3H). Mass (ESI) calcd for $C_{68}H_{16}N_{12}O_{12}S$ 1324.86, found 1326.02 $[M+H]^+$.

Compound 52A: Preparation of [2-((2R,3R)-3-methyl-5-(3-(pyridin-2-ylmethoxy)phenylthio)tetrahydrofuran-2-yl)-2-(methylamino)acetic acid]$^1$-cyclosporin A

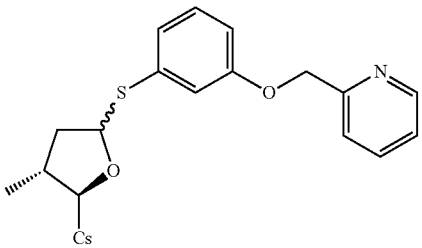

(I) Synthesis of 1,2-bis(3-(pyridin-2-ylmethoxy)phenyl)disulfane. A solution of 3,3'-disulfanediyldiphenol (250 mg, 1 mmol), pyridin-2-ylmethanol (240 mg, 2.2 mmol) and PPh$_3$ (656 mg, 2.5 mmol) was stirred in dry THF (25 mL) at 0° C. under a nitrogen atmosphere. To this mixture was added DIAD (0.49 mL, 2.5 mmol) in dropwise over a period of 5 min. The mixture was stirred at r.t. for 15 hrs. The solvent was evaporated under reduced pressure and resulting oil purified by column chromatography (PE/EA=2/1) to give 100 mg yellow oil. Yield: 23.1%. $^1$H-NMR (400 MHz, CDCl$_3$): δ 8.57 (d, J=4.4 Hz, 2H), 7.68-7.72 (m, 2H), 7.48 (d, J=8.0 Hz, 2H), 7.21-7.23 (m, 2H), 7.19 (d, J=8.0 Hz, 2H), 7.15 (d, J=6.0 Hz, 2H), 7.06-7.08 (m, 2H), 6.83-6.85 (m, 2H), 5.18 (s, 4H).

(II) Synthesis of 3-(pyridin-2-ylmethoxy)benzenethiol. 1,2-bis(3-(pyridin-2-ylmethoxy)phenyl)disulfane (100 mg, 0.23 mmol) was dissolved in dry THF (2 mL). Then n-Bu$_3$P (63 μL, 0.25 mmol) was added. The mixture was stirred at r.t. for 3 hrs. The solvent was evaporated to dryness and purified by column chromatography (PE/EA=4/1) to give 90 mg colorless oil, yield: 90.2%. $^1$H-NMR (400 MHz, CDCl$_3$): δ 8.62 (s, 1H), 7.70-7.74 (m, 1H), 7.51-7.53 (m, 1H), 7.22-7.23 (m, 1H), 7.14 (t, J=8.0 Hz, 1H), 6.92 (t, J=2.0 Hz, 1H), 6.87 (d, J=7.6 Hz, 1H), 6.77 (dd, J=2.4, 8.4 Hz, 1H), 5.19 (s, 2H), 3.45 (s, 1H).

(III) Synthesis of [2-((2R,3R)-3-methyl-5-(3-(pyridin-2-ylmethoxy)phenylthio)tetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(pyridin-2-ylmethoxy)benzenethiol was used instead of benzenethiol and 30 mg compound 52A and 10 mg compound 52A+B(1:1.1) were obtained as white solid. Total yield: 17.8%. $^1$H NMR (400 MHz, CDCl$_3$) δ 8.77 (brs, 1H), 8.39 (d, J=9.6 Hz, 1H), 8.06 (d, J=6.8 Hz, 1H), 8.03 (s, 1H), 7.81 (s, 1H), 7.64 (d, J=9.2 Hz, 1H), 7.51 (d, J=8.4 Hz, 2H), 7.27 (t, J=8.0 Hz, 1H), 7.18 (d, J=7.6 Hz, 1H), 7.03 (s, 1H), 6.83 (d, J=7.2 Hz, 1H), 5.64 (dd, J=4.0, 10.8 Hz, 1H), 5.49 (dd, J=3.2, 7.6 Hz, 1H), 5.29-5.36 (m, 4H), 5.20 (d, J=9.2 Hz, 1H), 5.17 (d, J=11.2 Hz, 1H), 5.11 (dd, J=5.6, 10.0 Hz, 1H), 5.06 (t, J=6.8 Hz, 1H), 4.98 (dd, =8.4, 14.8 Hz, 1H), 4.90 (t, J=8.4 Hz, 1H), 4.80-4.85 (m, 1H), 4.65 (d, J=14.0 Hz, 1H), 4.36-4.43 (m, 1H), 4.32 (dd, J=6.4, 9.2 Hz, 1H), 3.45 (s, 3H), 3.37 (s, 3H), 3.21 (s, 3H), 3.16 (s, 3H), 3.05 (s, 3H), 2.65 (s, 3H), 2.64 (s, 3H), 2.40-2.48 (m, 1H), 2.25-2.34 (m, 1H), 2.07-2.14 (m, 3H), 1.93-2.03 (m, 3H), 1.54-1.70 (m, 6H), 1.41-1.48 (m, 2H), 1.31 (d, J=7.2 Hz, 3H), 1.24 (d, J=6.4 Hz, 3H), 1.16 (d, J=6.8 Hz, 3H), 1.00 (d, J=6.8 Hz, 3H), 0.96-0.98 (m, 4H), 0.92-0.95 (m, 9H), 0.88-0.89 (m, 4H), 0.83-0.86 (m, 12H), 0.80 (d, J=6.4 Hz, 4H), 0.77 (d, J=6.4 Hz, 3H), 0.62 (d, J=6.4 Hz, 3H). Mass (ESI) calcd for C$_{72}$H$_{116}$N$_{12}$O$_{13}$S 1388.85, found 1390.04 [M+H]$^+$.

Compound 53A: Preparation of [2-((2R,3R)-3-methyl-5-(3-(pyridin-3-ylmethoxy)phenylthio)tetrahydrofuran-2-yl)-2-(methylamino)acetic acid]$^1$-cyclosporin A

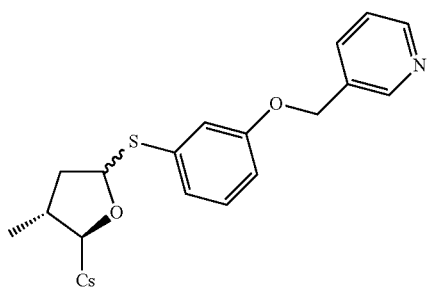

(I) Synthesis of 1,2-bis(3-(pyridin-3-ylmethoxy)phenyl)disulfane. A solution of 3,3'-disulfanediyldiphenol (250 mg, 1 mmol), pyridin-3-ylmethanol (240 mg, 2.2 mmol) and PPh$_3$ (656 mg, 2.5 mmol) was stirred in dry THF (25 mL) at 0° C. under a nitrogen atmosphere. To this mixture was added DIAD (0.49 mmL, 2.5 mmol) in dropwise over a period of 5 mins. The mixture was stirred at r.t. for 15 hrs. The solvent was evaporated under reduced pressure and resulting oil purified by column chromatography (PE/EA=2/1) to give 240 mg yellow oil. Yield: 55.6%. $^1$H-NMR (400 MHz, CDCl$_3$): δ 8.67 (d, J=6.8 Hz, 4H), 7.83 (d, J=6.8 Hz, 2H), 7.40 (t, J=5.2 Hz, 2H), 7.23 (d, J=8.0 Hz, 2H), 7.08 (d, J=8.4 Hz, 4H), 6.83 (d, J=8.4 Hz, 2H), 5.07 (s, 4H).

(II) Synthesis of 3-(pyridin-3-ylmethoxy)benzenethiol. 1,2-bis(3-(pyridin-3-ylmethoxy)phenyl)disulfane (120 mg, 0.28 mmol) was dissolved in dry THF (3 mL). Then n-Bu$_3$P (76 μL, 0.31 mmol) was added. The mixture was stirred at r.t. for 3 hrs. The solvent was evaporated to dryness and purified by column chromatography (PEEA=4/1) to give 200 mg colorless oil, yield: >100%. $^1$H-NMR (400 MHz, CDCl$_3$): δ 8.72 (s, 1H), 8.63 (s, 1H), 7.85 (d, J=8.0 Hz, 1H), 7.42 (t, J=6.4 Hz, 1H), 7.16 (t, J=8.0 Hz, 1H), 6.91 (s, 2H), 6.76 (d, J=8.4 Hz, 1H), 5.08 (s, 2H), 3.48 (s, 1H).

(III) Synthesis of [2-((2R,3R)-3-methyl-5-(3-(pyridin-3-ylmethoxy)phenylthio)tetrahydrofuran-2-yl)-2-(methylamino)acetic acid]$^1$-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-(pyridin-3-ylmethoxy)benzenethiol was used instead of benzenethiol and 40 mg.

Compound 53A and 10 mg compound 53A+B(1:1.5) were obtained as white solid was obtained. Total yield: 23.1%. $^1$H NMR (400 MHz, CDCl$_3$) δ 8.90 (brs, 2H), 8.40 (d, J=9.6 Hz, 1H), 8.21 (d, J=4.0 Hz, 1H), 8.06 (d, J=6.8 Hz, 1H), 7.80 (brs, 1H), 7.63 (d, J=8.8 Hz, 1H), 7.51 (d, J=8.0 Hz, 1H), 7.27 (t, J=8.0 Hz, 1H), 7.18 (d, J=7.6 Hz, 1H), 7.07 (s, 1H), 6.83 (d, J=8.0 Hz, 1H), 5.63 (dd, J=4.0, 11.2 Hz, 1H), 5.48 (dd, J=3.6, 7.6 Hz, 1H), 5.33 (dd, J=3.6, 11.2 Hz, 1H), 5.21 (d, J=9.2 Hz, 2H), 5.17 (d, J=11.2 Hz, 2H), 5.11 (dd, J=5.6, 10.4 Hz, 1H), 5.06 (t, J=6.8 Hz, 1H), 4.95-5.01 (m, 1H), 4.89 (t, J=8.4 Hz, 1H), 4.80-4.86 (m, 1H), 4.66 (d, J=13.6 Hz, 1H), 4.41-4.49 (m, 1H), 4.33-4.40 (m, 2H), 3.48 (s, 3H), 3.38 (s, 3H), 3.22 (s, 3H), 3.17 (s, 3H), 3.06 (s, 3H), 2.65 (s, 3H), 2.64 (s, 3H), 2.39-2.47 (m, 1H), 2.27-2.35 (m, 1H), 2.09-2.15 (m, 3H), 1.90-2.04 (m, 3H), 1.55-1.71 (m, 5H), 1.38-1.49 (m, 3H), 1.32 (d, J=7.2 Hz, 3H), 1.24 (d, J=7.2 Hz, 3H), 1.18 (d, J=6.4 Hz, 3H), 1.01 (d, J=6.8 Hz, 3H), 0.93-0.95 (m, 10H), 0.90-0.92 (m, 5H), 0.88-0.89 (m, 4H), 0.83-0.87 (m, 9H), 0.79-0.82 (m, 5H), 0.76 (d, J=6.4 Hz, 3H), 0.58 (d, J=6.4 Hz, 3H). Mass (ESI) calcd for C$_{72}$H$_{116}$N$_{12}$O$_{13}$S 1388.85, found 1390.43 [M+H]$^+$.

Compound 54A: Preparation of [2-((2,3R)-3-methyl-5-(3-(pyridin-4-ylmethoxy)phenylthio)tetrahydrofuran-2-yl)-2-(methylamino)acetic acid]$^1$-cyclosporin A

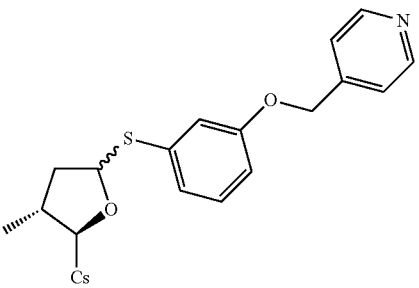

(I) Synthesis of 1,2-bis(3-(pyridin-4-ylmethoxy)phenyl) disulfane. A solution of 3,3'-disulfanediyldiphenol (250 mg, 1 mmol), pyridin-4-ylmethanol (240 mg, 2.2 mmol) and PPh$_3$ (656 mg, 2.5 mmol) was stirred in dry THF (25 mL) at 0° C. under a nitrogen atmosphere. To this mixture was added DIAD (0.49 mmL, 2.5 mmol) in dropwise over a period of 5 min. The mixture was stirred at r.t. for 15 hrs. The solvent was evaporated under reduced pressure and resulting oil purified by column chromatography (PEEA=2/1) to give 200 mg yellow oil. Yield: 46.3%. $^1$H-NMR (400 MHz, CDCl$_6$) δ 8.59 (d, J=5.6 Hz, 4H), 7.31 (d, J=5.6 Hz, 4H), 7.22 (t, J=8.0 Hz, 2H), 7.07-7.08 (m, 4H), 6.81 (dd, J=2.0, 8.0 Hz, 2H), 5.06 (s, 4H).

(II) Synthesis of 3-(pyridin-4-ylmethoxy)benzenethiol. 1,2-bis(3-(pyridin-4-ylmethoxy)phenyl)disulfane (210 mg, 0.49 mmol) was dissolved in dry THF (3 mL). Then n-Bu$_3$P (108 μL, 0.54 mmol) was added. The mixture was stirred at r.t. for 3 hrs. The solvent was evaporated to dryness and purified by column chromatography (PEEA=4/1) to give 200 mg colorless oil, yield: 95.2%.

(III) Synthesis of [2-((2R,3R)-3-methyl-5-(3-(pyridin-4-ylmethoxy)phenylthio)tetrahydrofuran-2-yl)-2-(methylamino)acetic acid]-cyclosporin A. The compound was synthesized from [2-((2R,3R)-5-acetoxy-3-methyltetrahydrofuran-2-yl)-2-(methylamino)acetic acid]t-cyclosporin A in a manner similar to that described for compound 1B. 3-(pyridin-3-ylmethoxy)benzenethiol was used instead of benzenethiol and 30 mg white solid was obtained. Yield: 13.3%. $^1$H NMR (400 MHz, CDCl$_3$) δ 8.90 (brs, 2H), 8.40 (d, J=9.6 Hz, 1H), 8.04 (d, J=7.2 Hz, 1H), 7.83 (brs, 2H), 7.62 (d, J=9.2 Hz, 1H), 7.51 (d, J=8.0 Hz, 1H), 7.27 (t, J=8.0 Hz, 1H), 7.18 (d, J=8.0 Hz, 1H), 7.02-7.04 (m, 1H), 6.82 (dd, J=2.0, 8.0 Hz, 1H), 5.63 (dd, J=4.0, 11.2 Hz, 1H), 5.47 (dd, J=3.6, 7.6 Hz, 1H), 5.31 (dd, J=4.0, 11.6 Hz, 1H), 5.29 (s, 2H), 5.19-5.24 (m, 2H), 5.16 (d, J=10.8 Hz, 1H), 5.10 (dd, J=5.6, 10.4 Hz, 1H), 5.06 (t, J=6.8 Hz, 1H), 4.94-5.00 (m, 1H), 4.88 (t, J=8.4 Hz, 1H), 4.83 (t, J=7.2 Hz, 1H), 4.65 (d, J=13.6 Hz, 1H), 4.31-4.39 (m, 2H), 3.46 (s, 3H), 3.37 (s, 3H), 3.22 (s, 3H), 3.16 (s, 3H), 3.06 (s, 3H), 2.65 (s, 3H), 2.64 (s, 3H), 2.39-2.46 (m, 1H), 2.26-2.35 (m, 1H), 2.09-2.16 (m, 3H), 1.92-2.04 (m, 3H), 1.54-1.72 (m, 6H), 1.39-1.46 (m, 2H), 1.31 (d, J=7.2 Hz, 3H), 1.24 (d, J=6.8 Hz, 3H), 1.16 (d, J=6.8 Hz, 3H), 1.01 (d, J=6.4 Hz, 3H), 0.92-0.96 (m, 13H), 0.87-0.89 (m, 7H), 0.83-0.86 (m, 9H), 0.80-0.82 (m, 4H), 0.76 (d, J=6.4 Hz, 3H), 0.58 (d, J=6.4 Hz, 3H). Mass (ESI) calcd for C$_{72}$H$_{116}$N$_{12}$O$_{13}$S 1388.85, found 1390.43 [M+H]$^+$.

Compound 57A: Preparation of [2-((2R,3R)-5-(4-(benzyloxy)phenylthio)-3-methyltetrahydrofuran-2-yl)-2-(methylamino)acetic acid]$^1$-cyclosporin A

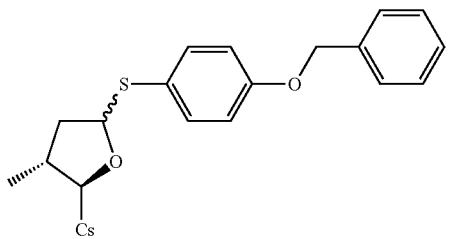

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 4-(benzyloxy)benzenethiol was used instead of benzenethiol, 120 mg of starting material was used and 20 mg white solid was obtained. Yield: 14.8%. $^1$H NMR (400 MHz, CDCl$_3$): δ 8.38 (d, J=9.2 Hz, 1H), 8.03 (d, J=6.8 Hz, 1H), 7.65 (d, J=8.8 Hz, 1H), 7.50 (d, J=7.6 Hz, 1H), 7.36-7.41 (m, 7H), 6.92 (d, J=8.8 Hz, 2H), 5.66 (dd, J=3.6, 10.8 Hz, 1H), 5.30-5.36 (m, 2H), 5.21 (d, J=8.8 Hz, 1H), 5.19 (d, J=7.2 Hz, 1H), 5.05-5.13 (m, 3H), 5.04 (s, 2H), 4.99 (t, J=7.2 Hz, 1H), 4.92 (t, J=8.0 Hz, 1H), 4.85 (t, J=7.2 Hz, 1H), 4.66 (d, J=13.2 Hz, 1H), 4.36-4.42 (m, 1H), 4.27 (dd, J=6.4, 8.8 Hz, 1H), 3.47 (s, 3H), 3.38 (s, 3H), 3.21 (s, 3H), 3.17 (s, 3H), 3.06 (s, 3H), 2.70 (s, 3H), 2.66 (s, 3H), 2.36-2.43 (m, 1H), 2.26-2.32 (m, 1H), 2.07-2.16 (m, 3H), 1.94-2.01 (m, 3H), 1.58-1.71 (m, 5H), 1.42-1.50 (m, 3H), 1.33 (d, J=7.2 Hz, 3H), 1.25-1.28 (m, 3H), 1.14 (d, J=6.4 Hz, 3H), 1.01 (d, J=6.4 Hz, 3H), 0.93-0.97 (m, 13H), 0.89-0.90 (m, 4H), 0.84-0.87 (m, 12H), 0.81 (d, J=6.0 Hz, 4H), 0.77 (d, J=6.4 Hz, 3H), 0.63 (d, J=6.4 Hz, 3H). Mass (ESI): m/z calcd for C$_{73}$H$_{117}$N$_{11}$O$_{13}$S 1387.86, found 1389.54 [M+H]$^+$.

Compound 58A: Preparation of [2-((2R,3R)-3-methyl-5-(3-((2-oxo-2H-chromen-7-yl)methoxy)phenylthio)tetrahydrofuran-2-yl)-2-(methylamino) acetic acid]$^1$-cyclosporin A

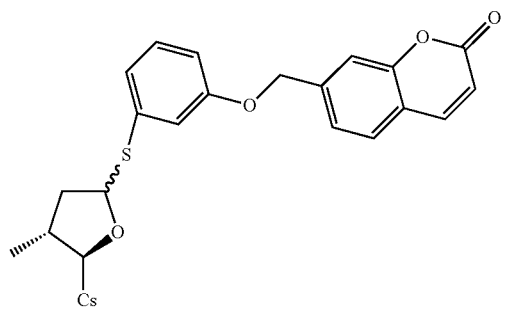

(I) Synthesis of 7-((3-mercaptophenoxy)methyl)-2H-chromen-2-one. NaH (88 mg, 2.2 mmol) was added to the solution of 3,3'-disulfanediyldiphenol (250 mg, 1.0 mmol) in dry DMF (5 mL) at 0° C. 7-(bromomethyl)-2H-chromen-2-one (523 mg, 2.2 mmol) was added to the mixture after 30 mins. The mixture was stirred at r.t. overnight and diluted with EA (100 mL). The organic layer were washed with H$_2$O (20 mL) and saturated aqueous NaCl (20 mL), dried over Na$_2$SO$_4$, filtered and concentrated. The residue was purified by column chromatography (PE/EA=3/1) to give 420 mg 7-((3-((3-(1-(2-oxo-2H-chromen-6-yl)ethoxy)phenyl)disulfanyl)phenoxy)methyl)-2H-chromen-2-one as white solid, yield: 74.5%. $^1$H-NMR (400 MHz, CDCl$_3$): δ 7.66 (d, J=9.2 Hz, 2H), 7.49-7.52 (m, 4H), 7.29 (d, J=9.2 Hz, 2H), 7.20 (t, J=8.0 Hz, 2H), 7.06 (t, J=1.6 Hz, 2H), 7.02-7.05 (m, 2H), 6.81-6.83 (m, 2H), 6.42 (d, J=9.2 Hz, 2H), 5.06 (s, 4H).

7-((3-((3-(1-(2-oxo-2H-chromen-6-yl)ethoxy)phenyl)disulfanyl)phenoxy)methyl)-2H-chromen-2-one (220 mg, 0.39 mmol) was dissolved in dry THF (4 mL). Then n-Bu$_3$P (107 μL, 0.43 mmol) was added. The mixture was stirred at r.t. for 3 hrs. The solvent was evaporated to dryness and purified by column chromatography (PEJEA=5/1) to give 92 mg colorless oil, yield: 41.7°. $^1$H-NMR (400 MHz, CDCl$_3$): δ 7.72 (d, J=9.6 Hz, 1H), 7.56-7.58 (m, 2H), 7.26 (d, J=8.4 Hz, 1H), 7.16 (t, J=8.0 Hz, 1H), 6.88-6.91 (m, 2H), 6.75-6.77 (m, 1H), 6.45 (d, J=9.6 Hz, 1H), 5.08 (s, 2H), 3.47 (s, 1H).

(II) Synthesis of [2-((2R,3R)-3-methyl-5-(3-((2-oxo-2H-chromen-7-yl)methoxy)phenylthio)tetrahydrofuran-2-yl)-2-(methylamino)acetic acid]1-cyclosporin A. The compound was synthesized from [2-((2R,3R)-5-acetoxy-3-methyltetrahydrofuran-2-yl)-2-(methylamino)acetic acid][1]-cyclosporin A in a manner similar to that described for compound 1B. 7-((3-mercaptophenoxy)methyl)-2H-chromen-2-one was used instead of benzenethiol and 45 mg yellow solid was obtained. Yield: 19.1%. $^1$H NMR (400 MHz, CDCl$_3$): δ 8.38 (d, J=9.6 Hz, 1H), 8.03 (d, J=6.4 Hz, 1H), 7.71 (d, J=9.2 Hz, 1H), 7.67 (d, J=8.8 Hz, 1H), 7.59-7.62 (m, 2H), 7.51 (d, J=8.0 Hz, 1H), 7.34 (d, J=8.8 Hz, 1H), 7.23 (d, J=8.0 Hz, 1H), 7.15 (d, J=7.6 Hz, 1H), 7.01 (s, 1H), 6.80 (d, J=8.0 Hz, 1H), 6.43 (d, J=9.6 Hz, 1H), 5.64 (dd, J=4.0, 10.8 Hz, 1H), 5.48 (dd, J=3.6, 8.0 Hz, 1H), 5.32 (dd, J=2.4, 10.4 Hz, 1H), 5.21 (d, J=9.6 Hz, 1H), 5.18 (d, J=12.0 Hz, 1H), 5.11-5.13 (m, 1H), 5.08 (s, 2H), 5.05-5.07 (m, 2H), 4.95-5.01 (m, 1H), 4.90 (t, J=8.0 Hz, 1H), 4.83 (t, J=8.0 Hz, 1H), 4.65 (d, J=12.8 Hz, 1H), 4.37-4.43 (m, 1H), 4.30 (dd, J=6.0, 8.4 Hz, 1H), 3.44 (s, 3H), 3.36 (s, 3H), 3.21 (s, 3H), 3.16 (s, 3H), 3.05 (s, 3H), 2.68 (s, 3H), 2.65 (s, 3H), 2.39-2.46 (m, 1H), 2.25-2.32 (m, 1H), 2.06-2.15 (m, 3H), 1.93-2.03 (m, 3H), 1.58-1.68 (m, 5H), 1.40-1.47 (m, 3H), 1.32 (d, J=6.8 Hz, 3H), 1.24 (d, J=6.4 Hz, 3H), 1.15 (d, J=6.4 Hz, 3H), 1.00 (d, J=6.4 Hz, 3H), 0.95-0.96 (m, 5H), 0.92-0.94 (m, 8H), 0.87-0.89 (m, 5H), 0.83-0.86 (m, 11H), 0.80 (d, J=6.4 Hz, 4H), 0.77 (d, J=6.4 Hz, 3H), 0.62 (d, J=6.4 Hz, 3H). Mass (ESI): m/z calcd for C$_{76}$H$_{117}$N$_{11}$O$_{15}$S 1455.85, found 1457.15 [M+H]$^+$.

Compound 59A: Preparation of [2-((2R,3R)-5-(3-chloro-5-methoxyphenylthio)-3-methyltetrahydrofuran-2-yl)-2-(methylamino)acetic acid]$^1$-cyclosporin A

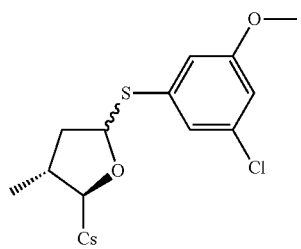

The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-chloro-5-methoxybenzenethiol was used instead of benzenethiol and 35 mg white solid was obtained. Yield: 16.1%. $^1$H NMR (400 MHz, CDCl$_3$) δ 8.39 (d, J=9.6 Hz, 1H), 8.05 (d, J=6.8 Hz, 1H), 7.59 (d, J=9.2 Hz, 1H), 7.54 (d, J=8.4 Hz, 1H), 7.03 (dd, J=1.6, 3.2 Hz, 1H), 6.89 (dd, J=1.2, 2.0 Hz, 1H), 6.74 (t, J=2.0 Hz, 1H), 5.66 (dd, J=4.0, 11.2 Hz, 1H), 5.49 (dd, J=2.4, 7.6 Hz, 1H), 5.32 (dd, J=4.0, 10.8 Hz, 1H), 5.21 (d, J=11.2 Hz, 1H), 5.13 (d, J=9.2 Hz, 1H), 5.06-5.11 (m, 2H), 4.92-5.01 (m, 2H), 4.81-4.88 (m, 2H), 4.67 (d, J=14.0 Hz, 1H), 4.35-4.4 (m, 2H), 3.79 (s, 3H), 3.47 (s, 3H), 3.36 (s, 3H), 3.22 (s, 3H), 3.18 (s, 3H), 3.06 (s, 3H), 2.69 (s, 3H), 2.66 (s, 3H), 2.31-2.39 (m, 1H), 2.23-2.29 (m, 1H), 2.11-2.18 (m, 2H), 1.93-2.04 (m, 4H), 1.55-1.66 (m, 5H), 1.41-1.49 (m, 3H), 1.33 (d, J=7.2 Hz, 3H), 1.25 (d, J=6.4 Hz, 3H), 1.22 (d, J=6.8 Hz, 3H), 0.99-1.01 (m, 8H), 0.94-0.95 (m, 8H), 0.89-0.91 (m, 5H), 0.84-0.87 (m, 12H), 0.80 (d, J=6.4 Hz, 6H), 0.62 (d, J=6.8 Hz, 3H). Mass (ESI) calcd for C$_{67}$H$_{112}$ClN$_{11}$O$_{13}$S 1345.79, found 1346.67 [M+H]$^+$.

Compound 60A: Preparation of [2-((2R,3R)-5-(3-(4-fluorobenzyloxy)-5-methoxyphenylthio)-3-methyltetrahydrofuran-2-yl)-2-(methylamino)acetic acid]$^1$-cyclosporin A

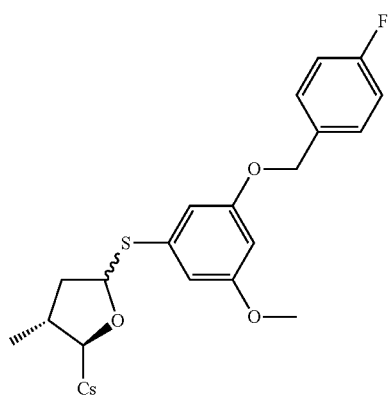

(I) Synthesis of 1-((4-fluorobenzyl)oxy)-3-methoxy-5-nitrobenzene. NaH (121.6 mg, 3.04 mmol) was added to the solution of 3-methoxy-5-nitrophenol (420 mg, 2.49 mmol) in dry DMF (5 mL) at 0° C. 1-(bromomethyl)-4-fluorobenzene (429 mg, 2.98 mmol) was added to the mixture after 30 min. The mixture was stirred at r.t. for 15 hrs and diluted with EA (100 mL). The organic layer were washed with H$_2$O (20 mL) and saturated aqueous NaCl (20 mL), dried over Na$_2$SO$_4$, filtered and concentrated. The residue was purified by column chromatography (PE/EA=4/1) to give 570 mg light yellow solid, yield: 82.6%. $^1$H-NMR (400 MHz, CDCl$_3$): δ 7.38-7.44 (m, 4H), 7.10 (t, J=8.8 Hz, 2H), 6.80 (t, J=2.4 Hz, 1H), 5.07 (s, 2H), 3.86 (s, 3H).

(I) Synthesis of 3-((4-fluorobenzyl)oxy)-5-methoxyaniline. 1-((4-fluorobenzyl)oxy)-3-methoxy-5-nitrobenzene (570 mg, 2.06 mmol) was dissolved in H$_2$O (8 mL) and CH$_3$COOH (3 mL). Then Fe (691 mg, 12.3 mmol) was added. The mixture was refluxing for 2 hrs and filtered. The filtrate was diluted with EA (100 mL). The organic layer were washed with saturated aqueous NaHCO$_3$ (30 mL), H$_2$O (30 mL) and saturated aqueous NaCl (20 mL), dried over Na$_2$SO$_4$, filtered and concentrated. The residue was purified by column chromatography (PE/EA=3/1) to give 505 mg brown oil, yield: 99.2%. $^1$H-NMR (400 MHz, DMSO-D-d$_6$): δ 7.45 (dd, J=5.6, 8.8 Hz, 2H), 7.20 (t, J=8.8 Hz, 2H), 5.81 (t, J=2.0 Hz, 1H), 5.75 (d, J=1.6 Hz, 2H), 5.08 (s, 2H), 4.94 (s, 2H), 3.62 (s, 3H).

(II) Synthesis of O-ethyl S-(3-((4-fluorobenzyl)oxy)-5-methoxyphenyl)carbonodithioate. 3-((4-fluorobenzyl)oxy)-5-methoxyaniline (505 mg, 2.04 mmol) was dissolved in ice (508 mg) and con. HCl (400 L) at 0° C. Then NaNO$_2$ (141 mg, 2.04 mmol) in H$_2$O (1 mL) was added. The mixture was stirred at r.t. for 30 min and added to the solution of potassium O-ethyl carbonodithioate (490 mg, 3.06 mmol) in H$_2$O (3 mL). Then the mixture was stirred at 65° C. for 2.5 hrs and diluted with EA(100 mL). The organic layer were washed with H$_2$O (20 mL) and saturated aqueous NaCl (20 mL), dried over Na$_2$SO$_4$, filtered and concentrated. The residue was purified by column chromatography (PE/EA=4/1) to give 100 mg yellow liquid, yield: 14.0%. $^1$H-NMR (400 MHz, CDCl₃): δ 7.39 (dd, J=5.2, 8.8 Hz, 2H), 7.08 (t, J=8.8 Hz, 2H), 6.73 (dd, J=1.6, 2.4 Hz, 1H), 6.69 (dd, J=1.6, 2.4 Hz, 1H), 6.59 (t, J=2.4 Hz, 1H), 5.00 (s, 2H), 4.61 (q, J=7.2 Hz, 2H), 3.79 (s, 3H), 1.34 (t, J=7.2 Hz, 3H).

(IV) Synthesis of 3-((4-fluorobenzyl)oxy)-5-methoxybenzenethiol. 2N NaOH (2 mL) was added to a solution of O-ethyl S-(3-((4-fluorobenzyl)oxy)-5-methoxyphenyl) carbonodithioate in CH₃H (6 mL) at 0° C. 3 hrs later the solvent was evaporated and the pH was adjusted to 3.0 with 1N HCl. The mixture was extracted with EA (100 mL), dried over Na₂SO₄, filtered and concentrated to give 130 mg light yellow oil, yield: 37.6%.

(V) Synthesis of [2-((2R,3R)-5-(3-(4-fluorobenzyloxy)-5-methoxyphenylthio)-3-methyltetrahydrofuran-2-yl)-2-(methylamino)acetic acid]¹-cyclosporin A. The compound was synthesized from [2-((2R,3R)-5-acetoxy-3-methyltetrahydro furan-2-yl)-2-(methylamino)acetic acid]¹-cyclosporin A in a manner similar to that described for compound 1B. 3-((4-fluorobenzyl)oxy)-5-methoxybenzenethiol was used instead of benzenethiol. 50 mg of pure compound 60A was obtained as white solid and 50 mg of compound 60A+B(1: 1.4) mixture isomers was obtained as white solid. Total yield: 42.9%. ¹H NMR (400 MHz, CDCl₃) δ 8.37 (d, J=10.0 Hz, 1H), 8.05 (d, J=6.8 Hz, 1H), 7.57 (d, J=9.2 Hz, 1H), 7.52 (d, J=8.4 Hz, 1H), 7.41 (dd, J=5.2, 8.4 Hz, 2H), 7.05 (t, J=8.8 Hz, 2H), 6.71 (dd, J=1.2, 2.0 Hz, 1H), 6.66 (dd, J=1.2, 2.0 Hz, 1H), 6.37 (t, J=2.4 Hz, 1H), 5.63 (dd, J=4.0, 11.2 Hz, 1H), 5.44 (dd, J=3.2, 8.0 Hz, 1H), 5.32 (dd, J=4.0, 11.6 Hz, 1H), 5.18 (d, J=10.8 Hz, 1H), 5.12 (d, J=9.2 Hz, 1H), 5.06-5.10 (m, 1H), 5.00-5.06 (m, 2H), 4.99 (s, 2H), 4.90-4.96 (m, 2H), 4.80-4.87 (m, 1H), 4.66 (d, J=14.0 Hz, 1H), 4.36-4.40 (m, 2H), 3.77 (s, 3H), 3.50 (s, 3H), 3.36 (s, 3H), 3.21 (s, 3H), 3.17 (s, 3H), 3.05 (s, 3H), 2.67 (s, 3H), 2.64 (s, 3H), 2.27-2.38 (m, 2H), 2.08-2.17 (m, 3H), 1.92-1.99 (m, 3H), 1.58-1.68 (m, 5H), 1.39-1.49 (m, 3H), 1.32 (d, J=7.2 Hz, 3H), 1.25 (d, J=6.8 Hz, 3H), 1.20 (d, J=7.2 Hz, 3H), 1.00 (d, J=6.8 Hz, 3H), 0.94-0.97 (m, 8H), 0.92-0.94 (m, 4H), 0.88-0.91 (m, 5H), 0.85-0.87 (m, 8H), 0.83-0.84 (m, 4H), 0.80 (d, J=6.8 Hz, 4H), 0.76 (d, J=6.4 Hz, 3H), 0.57 (d, J=6.4 Hz, 3H). Mass (ESI) calcd for C₇₄H₁₁₈FN₁₁O₁₄S 1435.86, found 1437.45 [M+H]⁺.

Compound 61A: Preparation of [2-((2R,3R)-5-(3-chloro-5-(4-fluorobenzyloxy)phenylthio)-3-methyl-tetrahydrofuran-2-yl)-2-(methylamino)acetic acid]¹-cyclosporin A

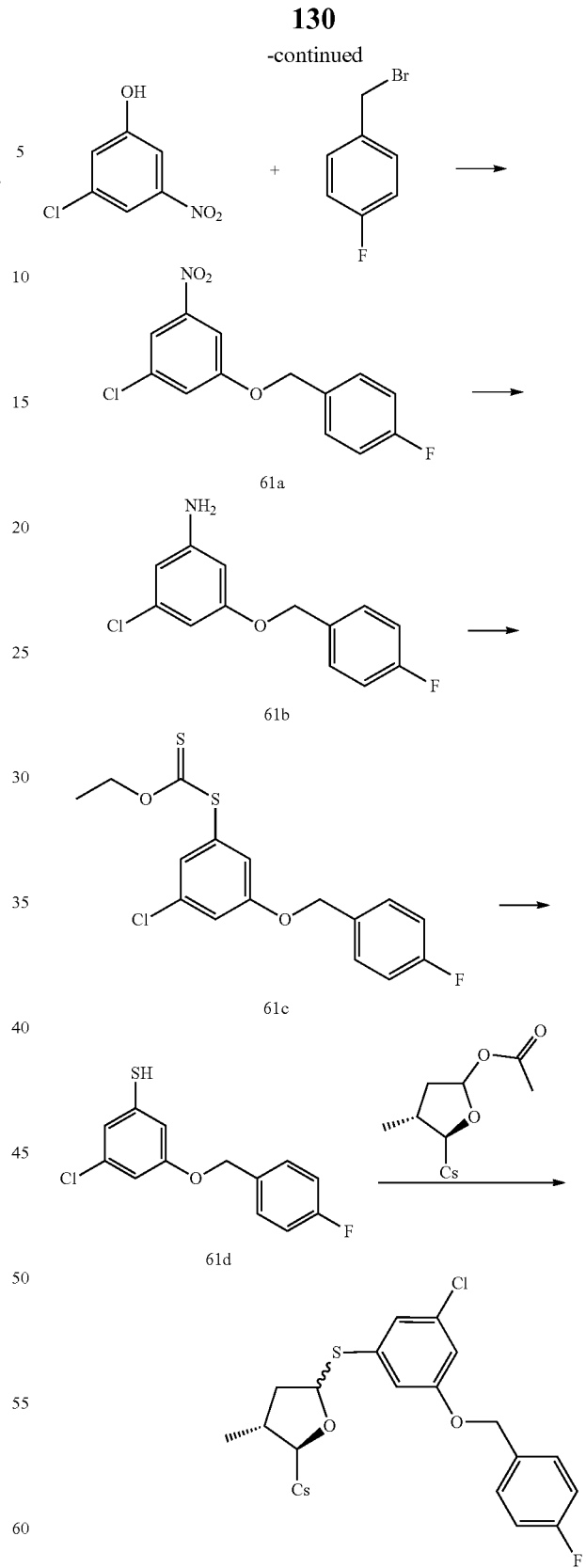

(I) Synthesis of 1-chloro-3-((4-fluorobenzyl)oxy)-5-nitrobenzene (61a). NaH (104 mg, 2.6 mmol) was added to the solution of 3-chloro-5-nitrophenol (300 mg, 1.73 mmol) in dry DMF (5 mL) at 0° C. 1-(bromomethyl)-4-fluorobenzene (488 mg, 2.6 mmol) was added to the mixture after 30 min. The mixture was stirred at 50° C. for 15 hrs and diluted with EA (100 mL). The organic layer were washed with H$_2$O (20 mL) and saturated aqueous NaCl (20 mL), dried over Na$_2$SO$_4$, filtered and concentrated. The residue was purified by column chromatography (PE/EA=4/1) to give 486 mg brown solid, yield: 100%. $^1$H-NMR (400 MHz, CDCl$_3$): δ 7.84 (t, J=2.0 Hz, 1H), 7.71 (t, J=2.0 Hz, 1H), 7.40 (dd, J=5.2, 8.4 Hz, 2H), 7.28 (t, J=2.0 Hz, 1H), 7.11 (t, J=8.8 Hz, 2H), 5.10 (s, 2H).

(I) Synthesis of 3-chloro-5-((4-fluorobenzyl)oxy)aniline (61b). 1-chloro-3-((4-fluorobenzyl)oxy)-5-nitrobenzene (486 mg, 1.73 mmol) was dissolved in H$_2$O (6 mL) and CH$_3$COOH (2 mL). Then Fe (513 mg, 9.2 mmol) was added. The mixture was refluxing for 2 hrs and filtered. The filtrate diluted with EA (100 mL). The organic layer were washed with saturated aqueous NaHCO$_3$ (30 mL), H$_2$O (30 mL) and saturated aqueous NaCl (20 mL), dried over Na$_2$SO$_4$, filtered and concentrated. The residue was purified by column chromatography (PE/EA=3/1) to give 420 mg yellow oil, yield: 96.8%. $^1$H-NMR (400 MHz, CDCl$_3$): δ 7.37 (t, J=6.0 Hz, 2H), 7.07 (t, J=8.0 Hz, 2H), 6.43 (s, 1H), 6.38 (s, 1H), 6.23 (s, 1H), 4.95 (s, 2H).

(III) Synthesis of S-(3-chloro-5-((4-fluorobenzyl)oxy) phenyl) O-ethyl carbonodithioate (61c). 3-chloro-5-((4-fluorobenzyl)oxy)aniline (420 mg, 1.67 mmol) was dissolved in ice (416 mg) and con. HCl (300 sL) at 0° C. Then NaNO$_2$ (115 mg, 1.67 mmol) in H$_2$O (615 μL) was added. The mixture was stirred at r.t. for 30 min and added to the solution of potassium O-ethyl carbonodithioate (535 mg, 3.34 mmol) in H$_2$O (2 mL). Then the mixture was stirred at 65° C. for 2.5 hrs and diluted with EA(100 mL). The organic layer were washed with H$_2$O (20 mL) and saturated aqueous NaCl (20 mL), dried over Na$_2$SO$_4$, filtered and concentrated. The residue was purified by column chromatography (PE/EA=5/1) to give 100 mg yellow liquid, yield: 17.7%. $^1$H-NMR (400 MHz, CDCl$_3$): 7.38 (dd, J=5.6, 8.8 Hz, 2H), 7.13 (t, J=1.6 Hz, 1H), 7.09 (t, J=8.8 Hz, 2H), 7.04 (t, J=2.0 Hz, 1H), 7.01 (q, J=1.2 Hz, 1H), 5.02 (s, 2H), 4.61 (q, J=7.2 Hz, 2H), 1.35 (t, J=7.2 Hz, 3H)

(IV) Synthesis of 3-chloro-5-((4-fluorobenzyl)oxy)benzenethiol (61d). 2N NaOH (2 mL) was added to a solution of S-(3-chloro-5-((4-fluorobenzyl) oxy) phenyl) O-ethyl carbonodithioate in CH$_3$H (4 mL) at 0° C. After 3 hrs the solvent was evaporated and the pH was adjusted to 3.0 with 1N HCl. The mixture was extracted with EA(100 mL), dried over Na$_2$SO$_4$, filtered and concentrated to give 60 mg colorless oil, yield: 80%.

(V) Synthesis of [2-((2R,3R)-5-(3-chloro-5-(4-fluorobenzyloxy)phenylthio)-3-methyltetrahydrofuran-2-yl)-2-(methylamino)acetic acid] 1-cyclosporin A. The compound was synthesized from [2-((2R,3R)-5-acetoxy-3-methyltetrahydrofuran-2-yl)-2-(methylamino)acetic acid]$^1$-cyclosporin A in a manner similar to that described for compound 1B. 3-chloro-5-((4-fluorobenzyl)oxy)benzenethiol was used instead of benzenethiol. 12 mg of pure compound 61A was obtained as white solid and 15 mg of compound 61A+B(3:1) mixture isomers was obtained as white solid. Total yield: 11.6%. $^1$H NMR (400 MHz, CDCl$_3$) δ 8.37 (d, J=9.6 Hz, 1H), 8.04 (d, J=6.8 Hz, 1H), 7.60 (d, J=8.8 Hz, 1H), 7.53 (d, J=8.0 Hz, 1H), 7.42 (dd, J=5.6 Hz, 1H), 7.40 (d, J=5.6 Hz, 1H), 7.04-7.09 (m, 3H), 6.88-6.92 (m, 1H), 6.78-6.81 (m, 1H), 5.65 (dd, J=4.0, 11.2 Hz, 1H), 5.48 (dd, J=2.8, 7.6 Hz, 1H), 5.32 (dd, J=3.6, 11.2 Hz, 1H), 5.20 (d, J=10.8 Hz, 1H), 5.16 (d, J=8.8 Hz, 1H), 5.04-5.11 (m, 2H), 5.00 (s, 2H), 4.94-4.98 (m, 2H), 4.90-4.92 (m, 1H), 4.81-4.88 (m, 1H), 4.66 (d, J=13.6 Hz, 1H), 4.34-4.44 (m, 2H), 3.47 (s, 3H), 3.35 (s, 3H), 3.22 (s, 3H), 3.17 (s, 3H), 3.06 (s, 3H), 2.67 (s, 3H), 2.65 (s, 3H), 2.33-2.41 (m, 1H), 2.24-2.31 (m, 1H), 2.10-2.18 (m, 3H), 1.94-2.04 (m, 3H), 1.55-1.68 (m, 5H), 1.39-1.46 (m, 3H), 1.33 (d, J=7.2 Hz, 3H), 1.25 (d, J=6.8 Hz, 3H), 1.19 (d, J=6.8 Hz, 3H), 1.00 (d, J=6.4 Hz, 3H), 0.93-0.97 (m, 12H), 0.89-0.91 (m, 6H), 0.85-0.86 (m, 11H), 0.83 (d, J=3.2 Hz, 3H), 0.79-0.81 (m, 4H), 0.64 (d, J=6.8 Hz, 3H). Mass (ESI) calcd for C$_{73}$H$_{115}$ClFN$_{11}$O$_{13}$S 143981, found 1441.42 [M+H]$^+$.

Compounds 11, 55, 56, 62-73: Compounds 11, 55, 56, 62-73 are prepared according to the procedure outlined in scheme 1:

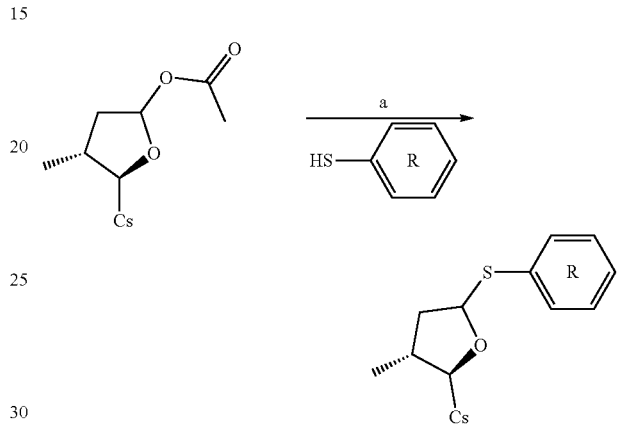

scheme 1: reagent and conditions: (a) BSA, TMSOTf, CH$_3$CN

Compound 38A-o: Preparation of [2-((2R,3R)-5-(3,5-dimethoxphenoxy)-3-methyltetrahydrofuran-2-yl)-2-(methylamino)acetic acid]$^1$-cyclosporin A.

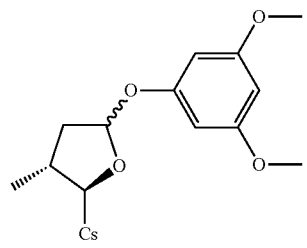

[2-((2R,3R)-5-acetoxy-3-methyltetrahydrofuran-2-yl)-2-(methylamino)acetic acid]$^1$-cyclosporin A (120 mg, 0.097 mmol) was dissolved in 4 mL of CH$_2$C2. FeCl$_3$ (8 mg, 0.049 mmol) and 4 A molecular sieves (10 mg) were added to the solution. Let it stir at room temperature for 16 hrs. Filtered and the filtrate was evaporated to dryness and the residue was purified by prep. HPLC to give 13 mg white solid. Yield: 10.1%. $^1$H NMR (400 MHz, CDCl$_3$) δ 8.34 (d, J=9.2 Hz, 1H), 8.04 (d, J=6.0 Hz, 1H), 7.63 (d, J=9.2 Hz, 1H), 7.49 (d, J=8.0 Hz, 1H), 6.08-6.17 (m, 1H), 6.01 (s, 1H), 5.95 (s, 1H), 5.64-5.69 (m, 1H), 5.33-5.39 (m, 2H), 5.20-5.29 (m, 2H), 4.98-5.14 (m, 5H), 4.83-4.88 (m, 1H), 4.67-4.74 (m, 1H), 4.36-4.42 (m, 2H), 3.74 (s, 3H), 3.71 (s, 3H), 3.51 (s, 3H), 3.37 (s, 3H), 3.22 (s, 3H), 3.17 (s, 3H), 3.06 (s, 3H), 2.69 (s, 3H), 2.67 (s, 3H), 2.28-2.41 (m, 3H), 2.06-2.20 (m, 5H), 1.91-2.00 (m, 3H), 1.56-1.72 (m, 4H), 1.41-1.49 (m, 2H), 1.34 (d, J=6.8 Hz, 3H), 1.24-1.27 (m, 3H), 1.12 (d, J=6.0 Hz, 2H), 0.97-1.03 (m, 5H), 0.90-0.95 (m, 13H), 0.80-0.86 (m, 15H), 0.65-0.69 (m, 2H), 0.63 (d, J=6.4 Hz, 4H), 0.52 (d, J=6.4 Hz, 3H). Mass (ESI): m/z calcd for $C_{68}H_{115}N_{11}O_{15}$ 1325.86, found 1326.47 $[M+H]^+$.

Compound 12A-o and 12B-o: Preparation of [2-((2R,3R)-5-(3-(benzyloxy)phenoxy)-3-methyltetrahydrofuran-2-yl)-2-(methylamino)acetic acid]$^1$-cyclosporin A

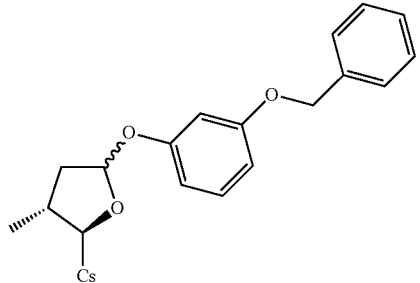

The compound was synthesized from [2-((2R,3R)-5-acetoxy-3-methyltetrahydrofuran-2-yl)-2-(methylamino)acetic acid]$^1$-cyclosporin A in a manner similar to that described for compound 38A-o. 3-(benzyloxy)phenol was used instead of 3,5-dimethoxyphenol, 150 mg of starting material was used and 2 mg of compound 12A-o and 2 mg of compound 12B-o were obtained as white solid. Total yield: 2.4%.

Compound 12A-o: $^1$H NMR (400 MHz, CDCl$_3$) 8.39 (d, J=9.6 Hz, 1H), 8.06 (d, J=7.2 Hz, 1H), 7.62 (d, J=8.8 Hz, 1H), 7.51 (d, J=8.4 Hz, 1H), 7.43 (d, J=7.6 Hz, 2H), 7.37 (t, J=8.0 Hz, 3H), 7.32 (d, J=7.2 Hz, 1H), 7.14 (t, J=8.0 Hz, 1H), 6.59 (s, 2H), 5.69 (dd, J=4.0, 10.8 Hz, 1H), 5.62 (d, J=5.2 Hz, 1H), 5.33 (dd, J=3.6, 11.6 Hz, 1H), 5.22 (d, J=9.2 Hz, 1H), 5.14 (d, J=9.2 Hz, 1H), 5.09-5.10 (m, 1H), 5.03 (s, 2H), 4.95-5.00 (m, 2H), 4.83-4.89 (m, 3H), 4.66 (d, J=14.0 Hz, 1H), 4.39-4.44 (m, 1H), 4.33 (dd, J=4.0, 9.6 Hz, 1H), 3.44 (s, 3H), 3.35 (s, 3H), 3.24 (s, 3H), 3.18 (s, 3H), 3.06 (s, 3H), 2.69 (s, 3H), 2.68 (s, 3H), 2.32-2.38 (m, 1H), 2.22-2.29 (m, 1H), 2.06-2.16 (m, 6H), 1.56-1.67 (m, 5H), 1.44-1.52 (m, 3H), 1.34 (d, I=7.2 Hz, 3H), 1.28 (d, J=7.2 Hz, 3H), 1.25 (d, J=1.2 Hz, 3H), 0.98-1.03 (m, 12H), 0.93-0.95 (m, 9H), 0.86-0.91 (m, 14H), 0.82 (d, J=6.4 Hz, 4H), 0.76 (d, J=6.8 Hz, 3H). Mass (ESI): m/z calcd for $C_{73}H_{117}N_{11}O_{14}$ 1371.88, found 1373.04 $[M+H]^+$.

Compound 12B-o: $^1$H NMR (400 MHz, CDCl$_3$) δ 8.33 (d, J=10.0 Hz, 1H), 7.93 (d, J=6.8 Hz, 1H), 7.51 (d, J=9.2 Hz, 1H), 7.44 (d, J=7.6 Hz, 1H), 7.34-7.39 (m, 3H), 7.27-7.33 (m, 2H), 7.09-7.14 (m, 1H), 6.62-6.63 (m, 1H), 6.55-6.59 (m, 2H), 5.66-5.69 (m, 1H), 5.60-5.62 (m, 1H), 5.31-5.35 (m, 1H), 5.28-5.29 (m, 1H), 5.18-5.22 (m, 1H), 5.03-5.07 (m, 2H), 5.02 (s, 2H), 4.93-4.98 (m, 1H), 4.82-4.87 (m, 2H), 4.69 (d, J=7.6 Hz, 1H), 4.42-4.46 (m, 1H), 4.12-4.16 (m, 1H), 4.07-4.09 (m, 1H), 3.49 (s, 3H), 3.38 (s, 3H), 3.20 (s, 3H), 3.16 (s, 3H), 3.08 (s, 3H), 2.69 (s, 3H), 2.68 (s, 3H), 2.27-2.37 (m, 2H), 2.09-2.17 (m, 3H), 1.95-2.04 (m, 3H), 1.57-1.65 (m, 5H), 1.39-1.47 (m, 3H), 1.33 (d, J=7.2 Hz, 5H), 1.23-1.24 (m, 2H), 1.16-1.20 (m, 2H), 1.02-1.04 (m, 4H), 0.98-0.99 (m, 7H), 0.92-0.95 (m, 9H), 0.87-0.90 (m, 8H), 0.84 (d, J=7.2 Hz, 4H), 0.79 (d, J=6.8 Hz, 4H), 0.76 (d, J=6.0 Hz, 3H), 0.59 (d, J=6.0 Hz, 3H). Mass (ESI): m/z calcd for $C_{73}H_{117}N_{11}O_{14}$ 1371.88, found 1373.24 $[M+H]^+$.

Compound 1B-o to 11-o, 13 A-o to 37 A-o, 39 A-o to 73-o: Compound 1B-o to 11-o, 13 A-o to 37 A-o, 39 A-o to 73-o are Prepared According to the Procedure Outlined in Scheme 2

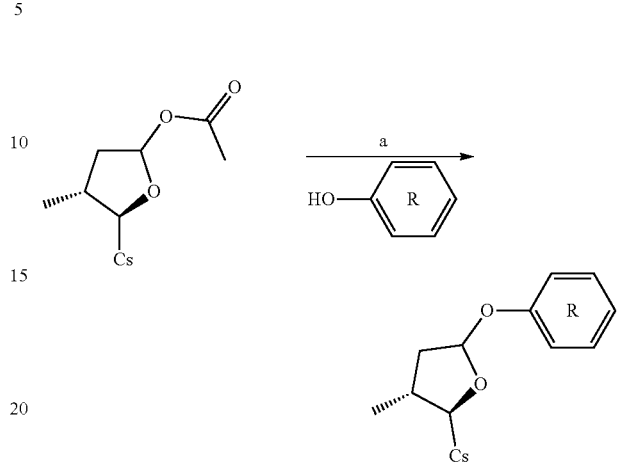

scheme 2: reagent and conditions: (a) FeCl$_3$, 4 A molecular sieves, CH$_2$Cl$_2$.

Compound 74A: Preparation of [2-((2R,3R)-5-(benzyloxy)-3-methyltetrahydrofuran-2-yl)-2-(methylamino)acetic acid]$^1$-cyclosporin A

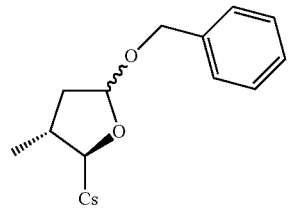

To the solution of [2-((2R,3R)-5-hydroxy-3-methyltetrahydrofuran-2-yl)-2-(methylamino)acetic acid]$^1$-cyclosporin A (500 mg, 042 mmol) in 9 mL of DCM was added benzyl alcohol (90 mg, 0.83 mmol), Amberlyst 15 (20 mg) and MgSO$_4$ (125 mg). Let it stir at room temperature for 16 hrs. Then another part of Amberlyst (20 mg) and MgSO$_4$ (125 mg) were added. Let it stir at room temperature for another 16 hrs. The mixture was filtered and the filtrate was evaporated to dryness and the brown residue was purified by prep. HPLC to give 130 mg white solid. Yield: 24.2%. $^1$H NMR (400 MHz, CDCl$_3$) δ 8.39 (d, J=9.6 Hz, 1H), 8.05 (d, J=6.8 Hz, 1H), 7.63 (d, J=9.2 Hz, 1H), 7.50 (d, J=8.0 Hz, 1H), 7.29-7.34 (m, 5H), 5.69 (dd, J=4.0, 11.2 Hz, 1H), 5.33 (dd, J=4.0, 11.2 Hz, 1H), 5.23 (d, J=10.8 Hz, 1H), 5.10-5.14 (m, 3H), 4.96-5.02 (m, 2H), 4.84-4.88 (m, 2H), 4.67 (d, J=12.0 Hz, 2H), 4.36-4.44 (m, 3H), 4.19 (dd, J=4.8, 9.6 Hz, 1H), 3.45 (s, 3H), 3.40 (s, 3H), 3.23 (s, 3H), 3.18 (s, 3H), 3.06 (s, 3H), 2.71 (s, 3H), 2.67 (s, 3H), 2.29-2.38 (m, 1H), 2.04-2.16 (m, 4H), 1.85-2.01 (m, 3H), 1.64-1.73 (m, 2H), 1.57-1.62 (m, 3H), 1.42-1.54 (m, 3H), 1.34 (d, J=7.2 Hz, 3H), 1.26 (d, J=6.8 Hz, 3H), 1.21 (d, J=6.8 Hz, 3H), 1.01-1.05 (m, 8H), 0.94-0.97 (m, 8H), 0.85-0.89 (m, 16H), 0.81-0.83 (m, 7H), 0.68 (d, J=6.4 Hz, 3H). Mass (ESI): m/z calcd for $C_{67}H_{113}N_{11}O_{13}$ 1279.85, found 1281.17 $[M+H]^+$.

Compound 75A: Preparation of [2-((2R,3R)-5-(3-(isobutoxysulfonyl)benzyloxy)-3-methyltetrahydrofuran-2-yl)-2-(methylamino)acetic acid]¹-cyclosporin A

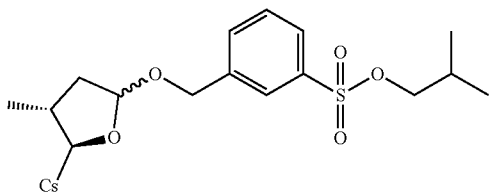

[2-((2R,3R)-3-methyl-5-(p-tolylthio)tetrahydrofuran-2-yl)-2-(methylamino)acetic acid]¹-cyclosporin A (80 mg, 0.062 mmol), isobutyl-3-(hydroxymethyl)benzenesulfonate (30 mg, 0.123 mmol), silver trifluoromethanesulfonate (15.8 mg, 0.123 mmol) and activated 3 Å molecular sieves (160 mg) were stirred in dry $CH_2Cl_2$ (3 mL) for 2 hrs under a nitrogen atmosphere in a three-neck flask (10 mL). N-iodosuccinimide (27.8 mg, 0.123 mmol) and activated 3 Å molecular sieves (160 mg) in dry ACN (1 mL) in another three-neck flask (10 mL) were stirred at r.t. for 2 hrs too. Then the mixture in the second flask was added to the first one, stirred at r.t. for another 1 hour to complete the reaction. The mixture was filtered, and diluted with $CH_2Cl_2$. The organic layer was washed with saturated aqueous $Na_2S_2O_3$, dried over $Na_2SO_4$, filtered and concentrated. The residue was purified by prep. HPLC to give 13 mg pale yellow solid, yield: 14.8%. ¹H NMR (CDCl₃, 400 MHz): δ 8.33 (d, J=9.6 Hz, 1H), 8.06 (d, J=6.8 Hz, 1H), 7.85 (s, 1H), 7.80 (d, J=7.6 Hz, 1H), 7.59 (d, J=7.2 Hz, 2H), 7.50 (dd, J=8.0, 16.0 Hz, 2H), 5.67 (dd, J=4.4, 11.2 Hz, 1H), 5.32 (dd, J=4.4, 11.6 Hz, 1H), 5.29 (s, 2H), 5.20 (d, J=10.8 Hz, 1H), 5.17-5.11 (m, 3H), 5.04 (d, J=4.8 Hz, 1H), 5.01-4.95 (m, 1H), 4.87-4.82 (m, 2H), 4.78 (d, J=12.8 Hz, 1H), 4.67 (d, J=14.0 Hz, 1H), 4.44-4.41 (m, 1H), 4.22 (dd, J=4.8, 9.2 Hz, 1H), 3.80 (d, J=6.4 Hz, 2H), 3.47 (s, 3H), 3.39 (s, 3H), 3.23 (s, 3H), 3.18 (s, 3H), 3.05 (s, 3H), 2.69 (s, 3H), 2.68 (s, 3H), 2.35-2.30 (m, 2H), 2.14-2.08 (m, 3H), 2.06-2.03 (m, 3H), 2.00-1.93 (m, 5H), 1.66-1.57 (m, 4H), 1.33 (d, J=7.2 Hz, 3H), 1.26 (d, J=7.2 Hz, 3H), 1.19 (d, J=6.8 Hz, 3H), 1.02-1.00 (m, 8H), 0.95-0.91 (m, 9H), 0.90-0.88 (m, 4H), 0.88-0.84 (m, 20H), 0.82 (d, J=6.4 Hz, 4H), 0.72 (d, J=6.4 Hz, 3H). Mass (ESI): m/z calcd for $C_{71}H_{121}N_{11}O_{16}S$ 1415.87, found 1417.75 [M+H]⁺.

Compound 76A: Preparation of [2-((2R,3R)-5-(3-(N-isobutylsulfamoyl)benzyloxy)-3-methyltetrahydrofuran-2-yl)-2-(methylamino)acetic acid]¹-cyclosporin A

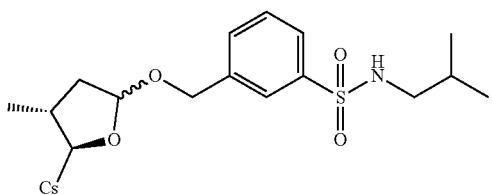

The compound was synthesized from [2-((2R,3R)-5-(3-methoxy-3-oxopropoxy)-3-methyltetrahydrofuran-2-yl)-2-(methylamino)acetic acid]¹-cyclosporin A in a manner similar to that described for compound 75A. 50 mg starting material and 19 mg 3-(hydroxymethyl)-N-isobutylbenzenesulfonamide were used, and 7 mg white solid was obtained. Yield: 12.8%. ¹H NMR (CDCl₃, 400 MHz): δ 8.36 (d, J=9.6 Hz, 1H), 8.03 (d, J=6.8 Hz, 1H), 7.79 (s, 1H), 7.74 (d, J=7.6 Hz, 1H), 7.61 (d, J=8.8 Hz, 1H), 7.58 (d, J=8.0 Hz, 1H), 7.50 (d, J=7.6 Hz, 2H), 5.67 (dd, J=4.0, 10.8 Hz, 1H), 5.32 (dd, J=3.6, 11.2 Hz, 1H), 5.16-5.09 (m, 4H), 5.03 (d, J=5.2 Hz, 1H), 5.01-4.95 (m, 1H), 4.90-4.82 (m, 3H), 4.67 (d, J=4.8 Hz, 1H), 4.64 (d, J=3.6 Hz, 1H), 4.51 (d, J=12.8 Hz, 1H), 4.40 (t, J=7.2 Hz, 1H), 4.11 (dd, J=5.2, 9.6 Hz, 1H), 3.40 (s, 3H), 3.27 (s, 3H), 3.20 (s, 3H), 3.18 (s, 3H), 3.06 (s, 3H), 2.79-2.76 (m, 2H), 2.69 (s, 3H), 2.67 (s, 3H), 2.39-2.28 (m, 2H), 2.13-2.07 (m, 3H), 2.02-1.94 (m, 3H), 1.75-1.71 (m, 3H), 1.67-1.58 (m, 6H), 1.33 (d, J=7.2 Hz, 3H), 1.28 (d, J=8.4 Hz, 3H), 1.20 (d, J=6.8 Hz, 3H), 1.05-1.01 (m, 8H), 0.96-0.92 (m, 9H), 0.90-0.85 (m, 24H), 0.81 (d, J=6.4 Hz, 4H), 0.72 (d, J=6.8 Hz, 3H). Mass (ESI): m/z calcd for $C_{71}H_{122}N_{12}O_{15}S$ 1414.89, found 1415.83 [M+H]⁺.

Compound 77A: Preparation of [2-((2R,3R)-5-(4-(1H-pyrazol-1-yl)benzyloxy)-3-methyltetrahydrofuran-2-yl)-2-(methylamino)acetic acid]¹-cyclosporin A

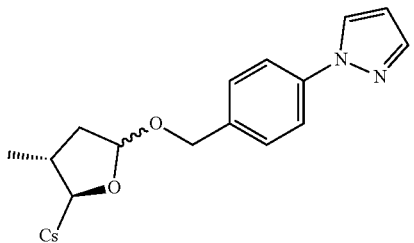

The compound was synthesized from [2-((2R,3R)-5-(3-methoxy-3-oxopropoxy)-3-methyltetrahydrofuran-2-yl)-2-(methylamino)acetic acid]¹-cyclosporin A in a manner similar to that described for compound 75A. 40 mg starting material and 11 mg (4-(1H-pyrazol-1-yl)phenyl)methanol were used, and 7 mg white solid was obtained. Yield: 17.1%. ¹H NMR (CDCl₃, 400 MHz): δ 8.38 (d, J=9.6 Hz, 1H), 8.06 (d, J=6.8 Hz, 1H), 7.93 (s, 1H), 7.72 (s, 1H), 7.66 (d, J=8.0 Hz, 2H), 7.61 (d, J=9.2 Hz, 1H), 7.50 (d, J=8.0 Hz, 1H), 7.39 (d, J=8.0 Hz, 2H), 6.46 (s, 1H), 5.67 (dd, J=4.0, 10.8 Hz, 1H), 5.33 (dd, J=4.0, 11.6 Hz, 1H), 5.22 (d, J=11.2 Hz, 1H), 5.16-5.11 (m, 4H), 5.02-4.98 (m, 2H), 4.88-4.83 (m, 2H), 4.72-4.63 (m, 2H), 4.44-4.41 (m, 2H), 4.21 (dd, J=4.8, 9.6 Hz, 1H), 3.48 (s, 3H), 3.40 (s, 3H), 3.23 (s, 3H), 3.18 (s, 3H), 3.06 (s, 3H), 2.70 (s, 3H), 2.67 (s, 3H), 2.38-2.29 (m, 2H), 2.16-2.09 (m, 3H), 2.01-1.89 (m, 3H), 1.71-1.58 (m, 5H), 1.55-1.42 (m, 3H), 1.33 (d, J=6.8 Hz, 3H), 1.25 (d, J=7.6 Hz, 3H), 1.21 (d, J=6.8 Hz, 3H), 1.04-1.01 (m, 8H), 0.95-0.92 (m, 9H), 0.88-0.83 (m, 18H), 0.83-0.81 (d, J=6.8 Hz, 4H), 0.71-0.70 (d, J=6.4 Hz, 3H). Mass (ESI): m/z calcd for $C_{70}H_{115}N_{13}O_{13}$ 1345.87, found 1346.79 [M+H]⁺.

Compound 78A and Compound 78B: Preparation of [2-((2R,3R)-3-methyl-5-((R)-1-phenylethoxy)tetrahydrofuran-2-yl)-2-(methylamino)acetic acid]$^1$-cyclosporin A

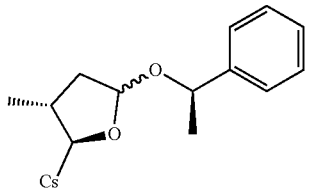

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for Compound 75A. 70 mg starting material and 13 mg (R)-(+)-1-Phenylethanol were used, 30 mg white solid compound 78A and 8 mg compound 78B were obtained. Total yield: 54.3%. $^1$H NMR (CDCl$_3$, 400 MHz):

compound 78A: δ 8.30 (d, J=10.0 Hz, 1H), 8.01 (d, J=6.8 Hz, 1H), 7.58 (d, J=8.8 Hz, 1H), 7.45 (d, J=7.6 Hz, 1H), 7.28-7.32 (m, 4H), 7.18-7.22 (m, 1H), 5.67 (dd, J=4.0, 10.8 Hz, 1H), 5.31 (dd, J=4.0, 11.2 Hz, 1H), 5.15 (d, J=11.2 Hz, 1H), 5.10 (d, J=11.2 Hz, 2H), 5.07 (d, J=5.2 Hz, 1H), 4.97 (d, J=5.2 Hz, 1H), 4.80-4.93 (m, 4H), 4.63 (d, J=14.0 Hz, 1H), 4.53 (q, J=6.4 Hz, 1H), 4.36 (d, J=7.2 Hz, 1H), 3.84 (q, J=4.8 Hz, 1H), 3.36 (s, 3H), 3.22 (s, 3H), 3.17 (s, 3H), 3.04 (s, 3H), 2.93 (s, 3H), 2.69 (s, 3H), 2.63 (s, 3H), 2.28-2.33 (m, 1H), 2.17-2.23 (m, 1H), 2.05-2.11 (m, 3H), 1.95-2.04 (m, 3H), 1.68-1.82 (m, 3H), 1.52-1.63 (m, 5H), 1.38 (d, J=6.4 Hz, 3H), 1.31 (d, J=7.2 Hz, 3H), 1.24 (d, J=6.8 Hz, 3H), 1.19 (d, J=6.8 Hz, 3H), 1.04-1.06 (m, 6H), 0.99 (d, J=6.4 Hz, 3H), 0.92-0.94 (m, 7H), 0.82-0.89 (m, 19H), 0.75-0.71 (m, 4H), 0.69 (d, J=6.4 Hz, 3H). Mass (ESI): m/z calcd for C$_{68}$H$_{115}$N$_{11}$O$_{13}$ 1293.87, found 1294.90 [M+H]$^+$.

Compound 78B: δ 8.14 (d, J=9.6 Hz, 1H), 7.95 (d, J=7.2 Hz, 1H), 7.29-7.33 (m, 4H), 7.23-7.24 (m, 1H), 5.71 (dd, J=4.0, 11.2 Hz, 1H), 5.33 (d, J=5.2 Hz, 1H), 5.28 (d, J=10.8 Hz, 1H), 5.22 (dd, J=4.0, 11.6 Hz, 1H), 5.06-5.15 (m, 3H), 4.85-4.91 (m, 3H), 4.76 (q, J=6.4 Hz, 1H), 4.65-4.72 (m, 2H), 4.43 (t, J=7.2 Hz, 1H), 4.01 (dd, J=5.2, 8.0 Hz, 1H), 3.67 (s, 3H), 3.31 (s, 3H), 3.25 (s, 3H), 3.17 (s, 3H), 3.07 (s, 3H), 2.72 (s, 3H), 2.71 (s, 3H), 2.32-2.41 (m, 2H), 2.16-2.24 (m, 3H), 2.06-2.15 (m, 3H), 1.90-2.01 (m, 5H), 1.59-1.64 (m, 3H), 1.32-1.35 (m, 6H), 1.25-1.27 (m, 6H), 1.03-1.05 (m, 4H), 0.98-0.99 (m, 5H), 0.92-0.95 (m, 11H), 0.86-0.87 (m, 6H), 0.84-0.85 (m, 6H), 0.81-0.83 (m, 7H), 0.75 (d, J=6.4 Hz, 3H). Mass (ESI): m/z calcd for C$_{68}$H$_{115}$N$_{11}$O$_{13}$ 1293.87, found 1294.77 [M+H]$^+$.

Compound 79A: Preparation of [2-((2R,3R)-3-methyl-5-((S)-1-phenylethoxy)tetrahydrofuran-2-yl)-2-(methylamino)acetic acid]$^1$-cyclosporin A

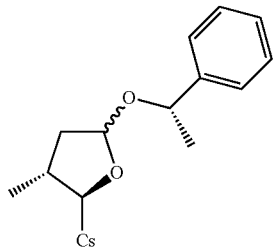

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 70 mg starting material and 13 mg (s)-(+)-1-Phenylethanol were used, 46 mg white solid was obtained. Yield: 65.7%. $^1$H NMR (CDCl$_3$, 400 MHz): δ 8.37 (d, J=9.6 Hz, 1H), 8.04 (d, J=6.8 Hz, 1H), 7.56 (d, J=9.2 Hz, 1H), 7.45 (d, J=8.0 Hz, 1H), 7.28-7.32 (m, 2H), 7.22-7.25 (m, 3H), 5.65 (dd, J=4.4, 11.2 Hz, 1H), 5.31 (dd, J=4.0, 11.6 Hz, 1H), 5.22 (d, J=10.8 Hz, 1H), 5.08 (d, J=7.2 Hz, 1H), 5.04 (d, J=10.0 Hz, 1H), 4.95-5.02 (m, 2H), 4.80-4.84 (m, 3H), 4.71-4.74 (m, 2H), 4.66 (q, J=14.0 Hz, 1H), 4.35 (d, J=7.2 Hz, 1H), 4.23 (dd, J=4.4, 10.0 Hz, 1H), 3.53 (s, 3H), 3.41 (s, 3H), 3.17 (s, 6H), 3.04 (s, 3H), 2.69 (s, 3H), 2.64 (s, 3H), 2.27-2.32 (m, 1H), 2.05-2.14 (m, 4H), 1.91-1.99 (m, 3H), 1.51-1.70 (m, 8H), 1.40 (d, J=6.8 Hz, 3H), 1.31 (d, J=7.2 Hz, 3H), 1.25 (d, J=6.8 Hz, 3H), 1.22 (d, J=7.2 Hz, 3H), 1.04-1.06 (m, 6H), 0.99 (d, J=6.4 Hz, 3H), 0.92-0.94 (m, 7H), 0.88-0.90 (m, 4H), 0.83-0.86 (m, 11H), 0.80-0.82 (m, 4H), 0.60 (d, J=6.4 Hz, 4H), 0.44 (d, J=6.4 Hz, 3H). Mass (ESI): m/z calcd for C$_{68}$H$_{115}$N$_{11}$O$_{13}$ 1293.87, found 1294.90 [M+H]$^+$.

Compound 80A: Preparation of [2-((2R,3R)-3-methyl-5-(benzhydryloxy)tetrahydrofuran-2-yl)-2-(methylamino)acetic acid]$^1$-cyclosporin A

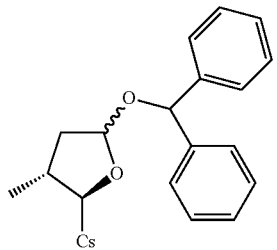

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 70 mg starting material and 20 mg diphenylmethanol were used, 47 mg white solid was obtained. Yield: 67.1%. $^1$H NMR (CDCl$_3$, 400 MHz): δ 8.37 (d, J=9.6 Hz, 1H), 8.06 (d, J=6.8 Hz, 1H), 7.59 (d, J=8.8 Hz, 1H), 7.47 (d, J=8.0 Hz, 1H), 7.28-7.34 (m, 10H), 5.67-5.71 (m, 2H), 5.33 (dd, J=4.0, 11.2 Hz, 1H), 5.23 (d, J=10.8 Hz, 1H), 5.04-5.14 (m, 4H), 4.96-5.00 (m, 2H), 4.82-4.87 (m, 2H), 4.66 (d, J=14.0 Hz, 1H), 4.37 (t, J=6.8 Hz, 1H), 4.18 (dd, J=4.4, 10.0 Hz, 1H), 3.47 (s, 3H), 3.36 (s, 3H), 3.20 (s, 3H), 3.19 (s, 3H), 3.06 (s, 3H), 2.72 (s, 3H), 2.66 (s, 3H), 2.29-2.35 (m, 1H), 2.10-2.19 (m, 4H), 1.93-2.01 (m, 3H), 1.62-1.78 (m, 5H), 1.54-1.60 (m, 3H), 1.33 (d, J=6.8 Hz, 3H), 1.29 (d, J=7.2 Hz, 3H), 1.25 (d, J=6.8 Hz, 3H), 1.08-1.10 (m, 6H), 1.01 (d, J=6.8 Hz, 3H), 0.95-0.97 (m, 6H), 0.92 (d, J=6.4 Hz, 4H), 0.84-0.88 (m, 10H), 0.81-0.83 (m, 6H), 0.68 (d, J=6.4 Hz, 4H), 0.53 (d, J=6.8 Hz, 3H). Mass (ESI): m/z calcd for $C_{73}H_{117}N_{11}O_{13}$ 1355.88, found 1356.67.

Compound 81A: Preparation of [2-((2R,3R)-5-(3-methoxybenzyloxy)-3-methyltetrahydrofuran-2-yl)-2-(methylamino)acetic acid]$^1$-cyclosporin A

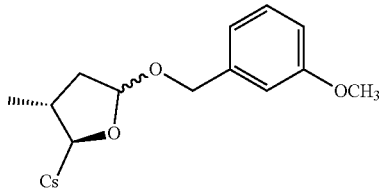

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material and 11 mg (3-methoxyphenyl)methanol were used, and 22 mg white solid was obtained. Yield: 43.5%. $^1$H NMR (CDCl$_3$, 400 MHz): δ 8.36 (d, J=9.6 Hz, 1H), 8.04 (d, J=6.8 Hz, 1H), 7.59 (d, J=8.8 Hz, 1H), 7.48 (d, J=8.0 Hz, 1H), 7.22 (t, J=8.0 Hz, 1H), 6.87-6.78 (m, 3H), 5.67 (dd, J=4.0, 11.6 Hz, 1H), 5.32 (dd, J=3.6, 11.6 Hz, 1H), 5.22 (d, J=10.8 Hz, 1H), 5.14-5.08 (m, 4H), 5.01-4.98 (m, 2H), 4.89-4.83 (m, 2H), 4.68-4.04 (m, 2H), 4.39-4.36 (m, 2H), 4.20 (dd, J=4.8, 9.6 Hz, 1H), 3.79 (s, 3H), 3.46 (s, 3H), 3.39 (s, 3H), 3.22 (s, 3H), 3.17 (s, 3H), 3.05 (s, 3H), 2.69 (s, 3H), 2.66 (s, 3H), 2.42-2.30 (m, 2H), 2.12-2.05 (m, 3H), 2.01-1.88 (m, 3H), 1.66-1.58 (m, 5H), 1.54-1.41 (m, 3H), 1.33 (d, J=6.8 Hz, 3H), 1.26 (d, J=6.4 Hz, 3H), 1.21 (d, J=6.4 Hz, 3H), 1.03-1.00 (m, 8H), 0.95-0.91 (m, 9H), 0.88-0.83 (m, 18H), 0.81 (d, J=6.4 Hz, 4H), 0.68 (d, J=6.4 Hz, 3H). Mass (ESI): m/z calcd for $C_{68}H_{115}N_{11}O_{14}$ 1309.86, found 1311.07 [M+H]$^+$.

Compound 82A and Compound 82B: Preparation of [2-((2R,3R)-5-(2-methoxybenzyloxy)-3-methyl-tetrahydrofuran-2-yl)-2-(methylamino)acetic acid]$^1$-cyclosporin A

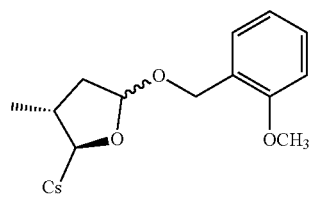

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material and 11 mg (2-methoxyphenyl)methanol were used, and 26 mg compound 82A and 5 mg compound 82B were obtained as white solid. Total yield: 61.3%. $^1$H NMR (CDCl$_3$, 400 MHz):

Compound 82A: δ 8.37 (d, J=10.0 Hz, 1H), 8.04 (d, J=7.2 Hz, 1H), 7.59 (d, J=8.8 Hz, 1H), 7.49 (d, J=8.0 Hz, 1H), 7.31 (d, J=8.0 Hz, 1H), 7.23 (d, J=12.0 Hz, 1H), 6.92 (t, J=7.6 Hz, 1H), 6.84 (d, J=8.4 Hz, 1H), 5.68 (dd, J=4.0, 10.8 Hz, 1H), 5.32 (dd, J=4.0, 11.2 Hz, 1H), 5.24 (d, J=10.8 Hz, 1H), 5.20-5.05 (m, 4H), 5.02 (d, J=4.8 Hz, 1H), 5.00-4.96 (m, 1H), 4.90-4.83 (m, 2H), 4.70 (d, J=12.4 Hz, 1H), 4.65 (d, J=13.6 Hz, 1H), 4.42 (d, J=13.6 Hz, 1H), 4.39 (t, J=7.2 Hz, 1H), 4.19 (dd, J=4.8, 9.6 Hz, 1H), 3.82 (s, 3H), 3.46 (s, 3H), 3.39 (s, 3H), 3.23 (s, 3H), 3.18 (s, 3H), 3.05 (s, 3H), 2.70 (s, 3H), 2.67 (s, 3H), 2.40-2.29 (m, 2H), 2.17-2.06 (m, 3H), 2.06-1.95 (m, 3H), 1.74-1.60 (m, 5H), 1.57-1.42 (m, 3H), 1.34 (d, J=7.2 Hz, 3H), 1.26 (d, J=7.2 Hz, 3H), 1.21 (d, J=6.8 Hz, 3H), 1.03-1.00 (m, 8H), 0.95-0.92 (m, 9H), 0.89-0.85 (m, 18H), 0.82 (d, J=6.4 Hz, 4H), 0.72 (d, J=6.4 Hz, 3H). Mass (ESI): m/z calcd for $C_{68}H_{115}N_{11}O_{14}$ 1309.86, found 1311.07 [M+H]$^+$.

Compound 82B: δ 8.19 (d, J=9.6 Hz, 1H), 7.92 (d, J=7.2 Hz, 1H), 7.42 (d, J=8.8 Hz, 1H), 7.29 (d, J=7.6 Hz, 2H), 7.20-7.25 (m, 1H), 6.93 (t, J=7.2 Hz, 1H), 6.82 (t, J=8.4 Hz, 1H), 5.68 (dd, J=4.0, 11.2 Hz, 1H), 5.30 (dd, J=4.0, 8.8 Hz, 1H), 5.24-5.27 (m, 2H), 5.17-5.19 (m, 2H), 5.09-5.13 (m, 1H), 5.04 (t, J=6.8 Hz, 1H), 4.93-4.97 (m, 1H), 4.84-4.87 (m, 1H), 4.78 (d, J=8.8 Hz, 1H), 4.72-4.75 (m, 1H), 4.69 (d, J=13.2 Hz, 1H), 4.51 (d, J=13.2 Hz, 1H), 4.44 (t, J=7.2 Hz, 1H), 4.06 (t, J=7.2 Hz, 1H), 3.80 (s, 3H), 3.57 (s, 3H), 3.36 (s, 3H), 3.19 (s, 3H), 3.14 (s, 3H), 3.07 (s, 3H), 2.71 (s, 3H), 2.70 (s, 3H), 2.29-2.34 (m, 2H), 2.18-2.24 (m, 2H), 1.94-2.02 (m, 4H), 1.65-1.73 (m, 4H), 1.59-1.63 (m, 2H), 1.41-1.46 (m, 2H), 1.33 (d, J=7.2 Hz, 3H), 1.25 (d, J=6.8 Hz, 3H), 1.24 (d, J=6.8 Hz, 3H), 1.02 (d, J=6.8 Hz, 3H), 0.97-0.99 (m, 3H), 0.95-0.97 (m, 6H), 0.93-0.94 (m, 6H), 0.91-0.92 (m, 5H), 0.89-0.90 (m, 4H), 0.86-0.87 (m, 5H), 0.83-0.84 (m, 4H), 0.81 (d, J=6.4 Hz, 3H), 0.73 (d, J=6.8 Hz, 3H). Mass (ESI): m/z calcd for $C_{68}H_{115}N_{11}O_{14}$ 1309.86, found 1311.35 [M+H]$^+$.

Compound 83A: Preparation of [2-((2R,3R)-5-(4-methoxybenzyloxy)-3-methyltetrahydrofuran-2-yl)-2-(methylamino)acetic acid]$^1$-cyclosporin A

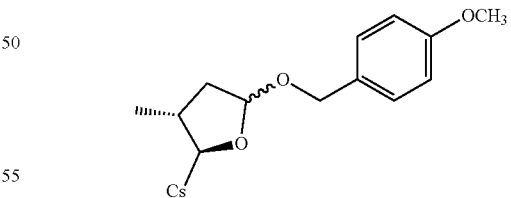

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material and 11 mg (4-methoxyphenyl)methanol (11 mg, 0.0772 mmol) were used, and 24 mg white solid was obtained. Yield: 47.4%. $^1$H NMR (CDCl$_3$, 400 MHz): δ 8.37 (d, J=9.6 Hz, 1H), 8.04 (d, J=6.8 Hz, 1H), 7.59 (d, J=9.2 Hz, 1H), 7.48 (d, J=8.0 Hz, 1H), 7.22 (d, J=8.8 Hz, 2H), 6.85 (d, J=8.8 Hz, 2H), 5.68 (dd, J=4.4, 10.8 Hz, 1H), 5.32 (dd, J=4.0, 11.2 Hz, 1H), 5.23 (d, J=10.8 Hz, 1H), 5.19-5.03 (m, 4H), 5.00-4.96 (m, 2H), 4.88-4.83 (m, 2H), 4.66 (d, J=13.6 Hz, 1H), 4.60 (d, J=11.6 Hz, 1H), 4.39 (t, J=7.2 Hz, 1H), 4.33 (d, J=11.6 Hz, 1H), 4.19 (dd, J=4.8, 10.0 Hz, 1H), 3.79 (s, 3H), 3.48 (s, 3H), 3.40 (s, 3H), 3.22 (s, 3H), 3.18 (s, 3H), 3.05 (s, 3H), 2.70 (s, 3H), 2.67 (s, 3H), 2.40-2.30 (m, 2H), 2.13-2.06 (m, 3H), 2.03-1.87 (m, 3H), 1.75-1.58 (m, 5H), 1.56-1.48 (m, 3H), 1.34 (d, J=7.2 Hz, 3H), 1.25 (d, J=7.2 Hz, 3H), 1.19 (d, J=6.8 Hz, 3H), 1.04-1.00 (m, 8H), 0.95-0.90 (m, 9H), 0.88-0.84 (m, 18H), 0.82 (d, J=6.8 Hz, 4H), 0.69 (d, J=6.8 Hz, 3H). Mass (ESI): m/z calcd for $C_{68}H_{115}N_{11}O_{14}$ 1309.86, found 1311.07 $[M+H]^+$.

Compound 84A: Preparation of [2-((2R,3R)-5-(2-chlorobenzyloxy)-3-methyltetrahydrofuran-2-yl)-2-(methylamino)acetic acid]$^1$-cyclosporin A

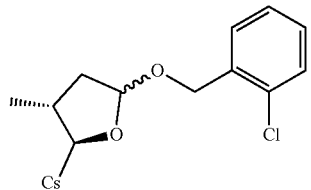

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material 11 mg and (2-chlorophenyl)methanol were used, and 24 mg white solid was obtained. Yield: 47.3%. $^1$H NMR (CDCl$_3$, 400 MHz): δ 8.35 (d, J=9.6 Hz, 1H), 8.03 (d, J=6.8 Hz, 1H), 7.58 (d, J=9.2 Hz, 1H), 7.47 (d, J=8.0 Hz, 1H), 7.42 (d, J=7.2 Hz, 1H), 7.32 (d, J=7.6 Hz, 1H), 7.24-7.18 (m, 2H), 5.68 (dd, J=4.0, 10.8 Hz, 1H), 5.31 (dd, J=3.6, 11.2 Hz, 1H), 5.22 (d, J=10.8 Hz, 1H), 5.18-5.06 (m, 4H), 5.03 (d, J=5.2 Hz, 1H), 5.01-4.95 (m, 1H), 4.87-4.82 (m, 2H), 4.74 (d, J=13.2 Hz, 1H), 4.65 (d, J=14.0 Hz, 1H), 4.51 (d, J=13.2 Hz, 1H), 4.39 (t, J=7.2 Hz, 1H), 4.21 (dd, J=4.8, 9.6 Hz, 1H), 3.43 (s, 3H), 3.39 (s, 3H), 3.23 (s, 3H), 3.17 (s, 3H), 3.05 (s, 3H), 2.70 (s, 3H), 2.66 (s, 3H), 2.40-2.25 (m, 2H), 2.16-2.08 (m, 3H), 2.00-1.87 (m, 3H), 1.75-1.60 (m, 5H), 1.57-1.48 (m, 3H), 1.33 (d, J=6.8 Hz, 3H), 1.25 (d, J=6.8 Hz, 3H), 1.21 (d, J=6.8 Hz, 3H), 1.03-1.00 (m, 8H), 0.94-0.91 (m, 9H), 0.87-0.83 (m, 18H), 0.81-0.79 (d, J=6.4 Hz, 4H), 0.71-0.70 (d, J=6.4 Hz, 3H). Mass (ESI): m/z calcd for $C_{67}H_{112}ClN_{11}O_{13}$ 1313.81, found 1315.10 $[M+H]^+$.

Compound 85A: Preparation of [2-((2R,3R)-5-(3-chlorobenzyloxy)-3-methyltetrahydrofuran-2-yl)-2-(methylamino)acetic acid]$^1$-cyclosporin A

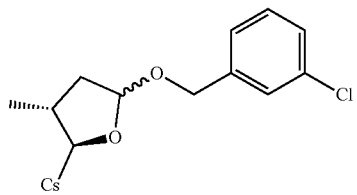

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material and 11 mg (3-chlorophenyl)methanol were used was used, and 26 mg white solid was obtained. Yield: 51.3%. $^1$H NMR (CDCl$_3$, 400 MHz): δ 8.37 (d, J=9.6 Hz, 1H), 8.05 (d, J=6.8 Hz, 1H), 7.59 (d, J=8.8 Hz, 1H), 7.49 (d, J=8.0 Hz, 1H), 7.30 (s, 1H), 7.25-7.23 (m, 2H), 7.17-7.16 (m, 1H), 5.67 (dd, J=4.0, 10.8 Hz, 1H), 5.32 (dd, J=4.0, 11.2 Hz, 1H), 5.20 (d, J=10.8 Hz, 1H), 5.18-5.04 (m, 4H), 5.01-4.96 (m, 2H), 4.86-4.82 (m, 2H), 4.67 (d, J=7.6 Hz, 1H), 4.64 (d, J=6.4 Hz, 1H), 4.40-4.35 (m, 2H), 4.20 (dd, J=4.4, 9.2 Hz, 1H), 3.46 (s, 3H), 3.39 (s, 3H), 3.22 (s, 3H), 3.17 (s, 3H), 3.05 (s, 3H), 2.69 (s, 3H), 2.66 (s, 3H), 2.40-2.28 (m, 2H), 2.16-2.07 (m, 3H), 2.03-1.92 (m, 3H), 1.70-1.57 (m, 5H), 1.54-1.41 (m, 3H), 1.32 (d, J=7.2 Hz, 3H), 1.25 (d, J=7.6 Hz, 3H), 1.20 (d, J=6.4 Hz, 3H), 1.02-1.00 (m, 8H), 0.94-0.91 (m, 9H), 0.88-0.83 (m, 18H), 0.81 (d, J=5.6 Hz, 4H), 0.67 (d, J=6.4 Hz, 3H). Mass (ESI): m/z calcd for $C_{67}H_{112}ClN_{11}O_{13}$ 1313.81, found 1315.56 $[M+H]^+$.

Compound 86A and Compound 86B: Preparation of [2-((2R,3R)-5-(4-chlorobenzyloxy)-3-methyltetrahydrofuran-2-yl)-2-(methylamino)acetic acid]$^1$-cyclosporin A

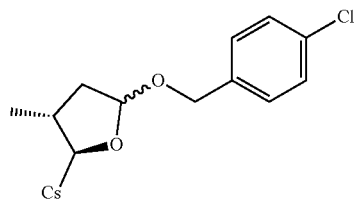

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material and 11 mg (4-chlorophenyl)methanol were used, and 21 mg compound 86A and 10 mg compound 86B were obtained as white solid. Total yield: 61.1%. $^1$H NMR (CDCl$_3$, 400 MHz):

Compound 86A: δ 8.36 (d, J=10.0 Hz, 1H), 8.04 (d, J=7.2 Hz, 1H), 7.59 (d, J=8.8 Hz, 1H), 7.48 (d, J=8.0 Hz, 1H), 7.29 (d, J=8.4 Hz, 2H), 7.23 (d, J=8.4 Hz, 2H), 5.67 (dd, J=4.0, 10.8 Hz, 1H), 5.32 (dd, J=4.0, 11.6 Hz, 1H), 5.20 (d, J=10.8 Hz, 1H), 5.17-5.03 (m, 4H), 4.99-4.95 (m, 2H), 4.87-4.83 (m, 2H), 4.64 (t, J=12.8 Hz, 2H), 4.40-4.35 (m, 2H), 4.18 (dd, J=4.4, 9.6 Hz, 1H), 3.46 (s, 3H), 3.40 (s, 3H), 3.22 (s, 3H), 3.18 (s, 3H), 3.05 (s, 3H), 2.69 (s, 3H), 2.67 (s, 3H), 2.40-2.20 (m, 2H), 2.17-2.06 (m, 3H), 2.03-1.88 (m, 3H), 1.71-1.57 (m, 5H), 1.50-1.41 (m, 3H), 1.33 (d, J=7.2 Hz, 3H), 1.25 (d, J=6.4 Hz, 3H), 1.19 (d, J=6.8 Hz, 3H), 1.04-1.00 (m, 8H), 0.97-0.92 (m, 9H), 0.88-0.83 (m, 18H), 0.82 (d, J=6.4 Hz, 4H), 0.67 (d, J=6.8 Hz, 3H). Mass (ESI): m/z calcd for $C_{67}H_{12}ClN_{11}O_{13}$ 1313.81, found 1315.04 $[M+H]^+$.

Compound 86B: 8.20 (d, J=9.6 Hz, 1H), 7.90 (d, J=7.2 Hz, 1H), 7.42 (d, J=8.8 Hz, 1H), 7.29 (d, J=8.4 Hz, 3H), 7.20 (d, J=8.4 Hz, 2H), 5.67 (dd, J=4.0, 11.2 Hz, 1H), 5.25-5.30 (m, 2H), 5.22 (d, J=10.8 Hz, 1H), 5.09-5.13 (m, 3H), 5.04-5.07 (m, 1H), 4.91-4.96 (m, 1H), 4.83-4.86 (m, 1H), 4.71-4.76 (m, 2H), 4.60 (d, J=12.8 Hz, 1H), 4.40 (d, J=12.8 Hz, 2H), 4.04-4.08 (m, 1H), 3.54 (s, 3H), 3.35 (s, 3H), 3.21

(s, 3H), 3.15 (s, 3H), 3.07 (s, 3H), 2.71 (s, 3H), 2.69 (s, 3H), 2.32-2.37 (m, 2H), 2.13-2.21 (m, 3H), 1.92-2.00 (m, 3H), 1.66-1.71 (m, 3H), 1.58-1.62 (m, 3H), 1.41-1.45 (m, 2H), 1.32 (d, J=7.2 Hz, 3H), 1.29 (d, J=7.2 Hz, 3H), 1.23 (d, J=6.4 Hz, 3H), 1.03 (d, J=6.8 Hz, 3H), 0.98 (d, J=6.8 Hz, 3H), 0.94-0.95 (m, 5H), 0.92-0.93 (m, 4H), 0.90-0.91 (m, 5H), 0.87-0.88 (m, 4H), 0.85-0.87 (m, 6H), 0.82-0.83 (m, 5H), 0.81-0.82 (m, 4H), 0.72 (d, J=6.4 Hz, 3H). Mass (ES): m/z calcd for $C_{67}H_{112}ClN_{11}$ 1313.81, found 1315.44 $[M+H]^+$.

Compound 87A: Preparation of [2-((2R,3R)-5-(4-(2-(dimethylamino)ethoxy)benzyloxy)-3-methyltetrahydrofuran-2-yl)-2-(methylamino)acetic acid]$^1$-cyclosporin A

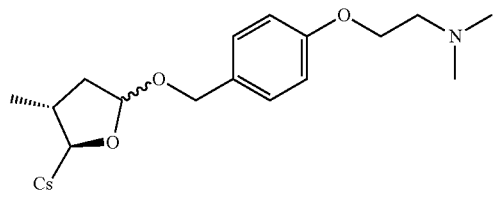

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material and 15 mg (4-(2-(dimethylamino)ethoxy)phenyl)methanol were used, and 8 mg white solid was obtained. Yield: 15.2%. $^1$H NMR (CDCl$_3$, 400 MHz): δ 8.37 (d, J=10.0 Hz, 1H), 8.04 (d, J=7.2 Hz, 1H), 7.62-7.59 (m, 2H), 7.49 (d, J=8.0 Hz, 1H), 7.24 (d, J=8.8 Hz, 1H), 6.84 (d, J=8.8 Hz, 2H), 5.68 (dd, J=4.0, 10.8 Hz, 1H), 5.32 (dd, J=4.0, 11.6 Hz, 1H), 5.22 (d, J=11.2 Hz, 1H), 5.16-5.09 (m, 4H), 5.02-4.96 (m, 2H), 4.88-4.84 (m, 2H), 4.66 (d, J=14.0 Hz, 1H), 4.60 (d, =11.6 Hz, 1H), 4.39 (t, J=7.2 Hz, 1H), 4.36-4.31 (m, 3H), 4.18 (dd, J=4.8, 9.6 Hz, 1H), 3.47 (s, 3H), 3.40 (s, 3H), 3.32-3.28 (m, 2H), 3.23 (s, 3H), 3.19 (s, 3H), 3.06 (s, 3H), 2.80 (s, 6H), 2.70 (s, 3H), 2.68 (s, 3H), 2.38-2.29 (m, 2H), 2.21-2.15 (m, 3H), 2.10-2.02 (m, 3H), 1.67-1.57 (m, 5H), 1.50-1.42 (m, 3H), 1.33 (d, J=7.2 Hz, 3H), 1.26 (d, J=8.0 Hz, 3H), 1.19 (d, J=6.4 Hz, 3H), 1.04-1.01 (m, 8H), 0.97-0.92 (m, 9H), 0.88-0.85 (m, 18H), 0.82 (d, J=6.4 Hz, 4H), 0.71 (d, J=6.8 Hz, 3H). Mass (ESI): m/z calcd for $C_{71}H_{122}N_{12}O_{14}H^+$1366.92, found 1368.80 $[M+H]^+$.

Compound 88A and Compound 88B: Preparation of [2-((2R,3R)-5-(3-chloro-2-methoxybenzyloxy)-3-methyltetrahydrofuran-2-yl)-2-(methylamino)acetic acid]$^1$-cyclosporin A

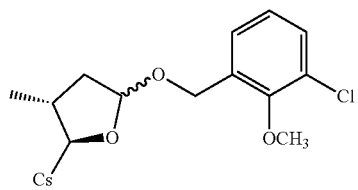

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material and 13 mg (3-chloro-2-methoxyphenyl)methanol were used, and 16 mg compound 88A was obtained as white solid, yield: 30.8%; 5 mg compound 88B was obtained as white solid, yield: 9.6% $^1$H NMR (CDCl$_3$, 400 MHz):

Compound 88A: δ 8.37 (d, J=9.6 Hz, 1H), 8.06 (d, J=6.8 Hz, 1H), 7.59 (d, J=8.8 Hz, 1H), 7.50 (d, J=8.0 Hz, 1H), 7.30-7.28 (m, 2H), 7.03 (d, J=8.0 Hz, 1H), 5.66 (dd, J=4.0, 10.8 Hz, 1H), 5.32 (dd, J=4.0, 11.6 Hz, 1H), 5.24 (d, J=10.8 Hz, 1H), 5.14-5.07 (m, 4H), 5.01 (d, J=4.8 Hz, 1H), 4.99-4.95 (m, 1H), 4.88-4.84 (m, 2H), 4.69-4.64 (m, 2H), 4.52 (d, J=12.4 Hz, 1H), 4.38 (t, J=6.8 Hz, 1H), 4.21 (dd, J=4.8, 9.6 Hz, 1H), 3.84 (s, 3H), 3.46 (s, 3H), 3.40 (s, 3H), 3.22 (s, 3H), 3.18 (s, 3H), 3.05 (s, 3H), 2.69 (s, 3H), 2.66 (s, 3H), 2.40-2.28 (m, 2H), 2.15-2.08 (m, 3H), 2.03-1.94 (m, 3H), 1.66-1.57 (m, 5H), 1.50-1.39 (m, 3H), 1.33 (d, J=7.2 Hz, 3H), 1.25 (d, J=7.6 Hz, 3H), 1.20 (d, J=7.8 Hz, 3H), 1.02-1.00 (m, 8H), 0.95-0.90 (m, 9H), 0.87-0.82 (m, 18H), 0.79 (d, J=6.8 Hz, 4H), 0.67 (d, J=6.8 Hz, 3H). Mass (ESI): m/z calcd for $C_{69}H_{114}ClN_{11}O_{14}$ 1343.82, found 1344.68 $[M+H]^+$.

Compound 88B: δ 8.27 (d, J=9.2 Hz, 1H), 7.96 (d, J=7.2 Hz, 1H), 7.39 (d, J=8.4 Hz, 1H), 7.32 (d, J=7.6 Hz, 1H), 7.28-7.30 (m, 1H), 7.23 (d, J=7.6 Hz, 1H), 7.05 (t, J=7.6 Hz, 1H), 5.69 (dd, J=4.0, 11.2 Hz, 1H), 5.31 (d, J=4.0 Hz, 1H), 5.28 (d, J=4.8 Hz, 1H), 5.24 (d, J=10.8 Hz, 1H), 5.18 (dd, J=4.0, 4.8 Hz, 1H), 5.11 (t, J=5.6 Hz, 1H), 5.06 (t, J=7.2 Hz, 1H), 4.92-4.98 (m, 1H), 4.82-4.89 (m, 2H), 4.72-4.77 (m, 2H), 4.69 (d, J=12.8 Hz, 1H), 4.56 (d, J=12.8 Hz, 1H), 4.44 (t, J=7.2 Hz, 1H), 4.06 (t, J=6.4 Hz, 1H), 3.83 (s, 3H), 3.60 (s, 3H), 3.38 (s, 3H), 3.23 (s, 3H), 3.16 (s, 3H), 3.09 (s, 3H), 2.71 (s, 3H), 2.69 (s, 3H), 2.31-2.37 (m, 1H), 2.20-2.24 (m, 1H), 2.07-2.17 (m, 3H), 1.92-2.00 (m, 3H), 1.60-1.72 (m, 5H), 1.39-1.46 (m, 3H), 1.33 (d, J=7.2 Hz, 3H), 1.26 (d, J=6.8 Hz, 3H), 1.04 (d, J=6.8 Hz, 3H), 0.96-1.00 (m, 8H), 0.92-0.95 (m, 8H), 0.88-0.90 (m, 7H), 0.86-0.87 (m, 9H), 0.81-0.84 (m, 7H), 0.71 (d, J=6.4 Hz, 3H). Mass (ESI): m/z calcd for $C_{68}H_{114}CN_{11}O_{14}$ 1343.82, found 1344.81 $[M+H]^+$.

Compound 89A and Compound 89B: Preparation of [2-((2R,3R)-5-(2,4-dichlorobenzyloxy)-3-methyltetrahydrofuran-2-yl)-2-(methylamino)acetic acid]$^1$-cyclosporin A

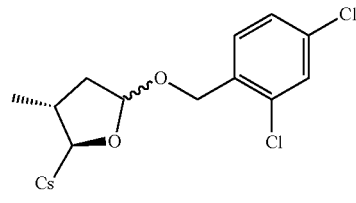

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material and 14 mg (2,4-dichlorophenyl)methanol were used. 26 mg compound 89A and 8 mg compound 89B were obtained as white solid. Yield: 50% and 15.4% respectively. $^1$H NMR (CDCl$_3$, 400 MHz):

Compound 89A: δ 8.34 (d, J=9.6 Hz, 1H), 8.05 (d, J=6.8 Hz, 1H), 7.57 (d, J=9.2 Hz, 1H), 7.47 (d, J=8.0 Hz, 1H), 7.37-7.34 (m, 2H), 7.22 (dd, J=2.0, 8.0 Hz, 1H), 5.67 (dd, J=4.0, 10.8 Hz, 1H), 5.30 (dd, J=3.6, 11.2 Hz, 1H), 5.21 (d, J=10.8 Hz, 1H), 5.16-5.05 (m, 4H), 5.01 (d, J=5.2 Hz, 1H), 4.98-4.94 (m, 1H), 4.86-4.81 (m, 2H), 4.72-4.64 (m, 2H), 4.44 (d, J=13.2 Hz, 1H), 4.39 (t, J=7.2 Hz, 1H), 4.20 (dd, J=4.4, 9.2 Hz, 1H), 3.45 (s, 3H), 3.39 (s, 3H), 3.23 (s, 3H), 3.17 (s, 3H), 3.05 (s, 3H), 2.69 (s, 3H), 2.67 (s, 3H), 2.40-2.28 (m, 2H), 2.15-2.06 (m, 3H), 1.98-1.90 (m, 3H), 1.68-1.56 (m, 5H), 1.53-1.40 (m, 3H), 1.32 (d, J=6.8 Hz, 3H), 1.25 (d, J=7.2 Hz, 3H), 1.19 (d, J=6.8 Hz, 3H), 1.02-1.00 (m, 8H), 0.94-0.91 (m, 9H), 0.86-0.84 (m, 18H), 0.81 (d, J=6.4 Hz, 4H), 0.70 (d, J=6.4 Hz, 3H). Mass (ESI): m/z calcd for $C_{67}H_{111}Cl_2N_{11}O_{13}$ 1347.77, found 1349.30 $[M+H]^+$.

Compound 89B: δ 8.23 (d, J=9.6 Hz, 1H), 7.92 (d, J=7.2 Hz, 1H), 7.44 (d, J=8.8 Hz, 1H), 7.36-7.34 (m, 2H), 7.30 (d, J=8.0 Hz, 1H), 7.23-7.25 (m, 1H), 5.68 (dd, J=4.0, 11.2 Hz, 1H), 5.29-5.26 (m, 1H), 5.21 (d, J=10.8 Hz, 1H), 5.18-5.16 (m, 1H), 5.11-5.03 (m, 3H), 4.97-4.93 (m, 1H), 4.89-4.83 (m, 1H), 4.79-4.74 (m, 2H), 4.70 (d, J=13.2 Hz, 2H), 4.50 (d, J=12.8 Hz, 1H), 4.43 (t, J=6.8 Hz, 1H), 4.07 (t, J=6.8 Hz, 1H), 3.55 (s, 3H), 3.37 (s, 3H), 3.20 (s, 3H), 3.15 (s, 3H), 3.08 (s, 3H), 2.71 (s, 3H), 2.69 (s, 3H), 2.37-2.31 (m, 2H), 2.15-2.12 (m, 3H), 2.03-1.97 (m, 3H), 1.67-1.59 (m, 5H), 1.44-1.38 (m, 3H), 1.33 (d, J=7.2 Hz, 3H), 1.26-1.25 (m, 3H), 1.03 (d, J=6.8 Hz, 3H), 0.99-0.96 (m, 8H), 0.94-0.92 (m, 9H), 0.89-0.84 (m, 18H), 0.83 (d, J=6.8 Hz, 4H), 0.69 (d, J=6.4 Hz, 3H). Mass (ESI): m/z calcd for $C_{67}H_{111}Cl_2N_{11}O_{13}$ 1347.77, found 1349.30 $[M+H]^+$.

Compound 90A and Compound 90B: Preparation of [2-((2R,3R)-5-(2,6-dichlorobenzyloxy)-3-methyl-tetrahydrofuran-2-yl)-2-(methylamino)acetic acid]$^1$-cyclosporin A

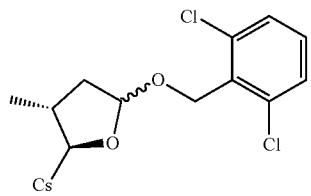

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material and 14 mg (2,6-dichlorophenyl)methanol were used, 25 mg Compound 90A and 8 mg Compound 90B were obtained as white solid, yield: 48.1% and 15.4% respectively. $^1$H NMR (CDCl$_3$, 400 MHz):

Compound 90A: δ 8.36 (d, J=9.6 Hz, 1H), 8.05 (d, J=6.8 Hz, 1H), 7.56 (d, J=9.2 Hz, 1H), 7.50 (d, J=7.6 Hz, 1H), 7.28 (d, J=8.0 Hz, 2H), 7.15 (t, J=8.0 Hz, 1H), 5.67 (dd, J=4.0, 10.8 Hz, 1H), 5.30 (dd, J=4.0, 11.6 Hz, 1H), 5.22 (d, J=10.8 Hz, 1H), 5.16-5.05 (m, 4H), 5.01 (d, J=10.0 Hz, 1H), 4.97-4.91 (m, 2H), 4.87-4.82 (m, 2H), 4.66-4.61 (m, 2H), 4.38 (t, J=7.2 Hz, 1H), 4.16 (dd, J=4.0, 9.6 Hz, 1H), 3.38 (s, 3H), 3.35 (s, 3H), 3.22 (s, 3H), 3.17 (s, 3H), 3.03 (s, 3H), 2.70 (s, 3H), 2.67 (s, 3H), 2.34-2.30 (m, 2H), 2.16-2.09 (m, 3H), 2.08-1.98 (m, 3H), 1.83-1.61 (m, 5H), 1.59-1.56 (m, 3H), 1.33 (d, J=7.2 Hz, 3H), 1.25 (d, J=7.6 Hz, 3H), 1.19 (d, J=6.8 Hz, 3H), 1.04-0.99 (m, 8H), 0.94-0.89 (m, 9H), 0.87-0.82 (m, 18H), 0.81-0.79 (m, 4H), 0.75-0.73 (m, 3H). Mass (ESI): m/z calcd for $C_{67}H_{111}Cl_2N_{11}O_{13}$ 1347.77, found 1349.23 $[M+H]^+$.

Compound 90B: δ 8.05 (brs, 1H), 7.87 (d, J=7.2 Hz, 1H), 7.38 (d, J=8.8 Hz, 1H), 7.28-7.34 (m, 3H), 7.13-7.17 (m, 1H), 5.69 (dd, J=4.0, 10.8 Hz, 1H), 5.35 (d, J=5.2 Hz, 1H), 5.25-5.29 (m, 2H), 5.22 (dd, J=2.0, 5.6 Hz, 1H), 5.10-5.14 (m, 2H), 5.02 (t, J=7.2 Hz, 1H), 4.92-4.96 (m, 2H), 4.86 (t, J=7.2 Hz, 1H), 4.65-4.77 (m, 3H), 4.40-4.47 (m, 1H), 4.09 (dd, J=6.0, 8.0 Hz, 1H), 3.61 (s, 3H), 3.36 (s, 3H), 3.21 (s, 3H), 3.14 (s, 3H), 3.08 (s, 3H), 2.74 (s, 3H), 2.69 (s, 3H), 2.31-2.37 (m, 2H), 2.08-2.17 (m, 3H), 1.92-2.00 (m, 3H), 1.64-1.74 (m, 5H), 1.39-1.45 (m, 3H), 1.33 (d, J=7.2 Hz, 3H), 1.26 (d, J=6.8 Hz, 3H), 1.04 (d, J=6.8 Hz, 3H), 1.00 (d, J=6.4 Hz, 3H), 0.94-0.96 (m, 7H), 0.92-0.93 (m, 7H), 0.86-0.89 (m, 15H), 0.82-0.84 (m, 7H), 0.72 (d, J=6.4 Hz, 3H). Mass (ESI): m/z calcd for $C_{67}H_{111}Cl_2N_{11}O_{13}$ 1347.77, found 1349.30 $[M+H]^+$.

Compound 91A and Compound 91B: Preparation of [2-((2R,3R)-5-(3,5-dichlorobenzyloxy)-3-methyl-tetrahydrofuran-2-yl)-2-(methylamino)acetic acid]$^1$-cyclosporin A

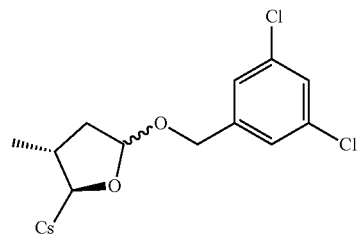

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material and 14 mg (3,5-dichlorophenyl)methanol were used, and 20 mg compound 91A and 6 mg compound 91B were obtained as white solid, yield: 38.5% and 11.6% respectively. $^1$H NMR (CDCl$_3$, 400 MHz):

Compound 91A: δ 8.34 (d, J=10.0 Hz, 1H), 8.05 (d, J=6.8 Hz, 1H), 7.58 (d, J=8.8 Hz, 1H), 7.48 (d, J=8.0 Hz, 1H), 7.25-7.24 (m, 1H), 7.19-7.18 (m, 2H), 5.67 (dd, J=4.0, 10.8 Hz, 1H), 5.32 (dd, J=3.6, 11.2 Hz, 1H), 5.20 (d, J=11.2 Hz, 1H), 5.16-5.04 (m, 4H), 4.99-4.96 (m, 2H), 4.84 (t, J=8.0 Hz, 2H), 4.69-4.61 (m, 2H), 4.39 (t, J=7.2 Hz, 1H), 4.32 (d, J=12.8 Hz, 1H), 4.21 (dd, J=4.4, 9.2 Hz, 1H), 3.47 (s, 3H), 3.39 (s, 3H), 3.22 (s, 3H), 3.18 (s, 3H), 3.05 (s, 3H), 2.69 (s, 3H), 2.67 (s, 3H), 2.38-2.28 (m, 2H), 2.15-2.09 (m, 3H), 2.04-1.97 (m, 3H), 1.67-1.57 (m, 5H), 1.49-1.41 (m, 3H), 1.32 (d, J=6.8 Hz, 3H), 1.25 (d, J=7.6 Hz, 3H), 1.20 (d, J=6.8 Hz, 3H), 1.02-1.00 (m, 8H), 0.95-0.92 (m, 9H), 0.88-0.84 (m, 18H), 0.82 (d, J=6.8 Hz, 4H), 0.69 (d, J=7.2 Hz, 3H). Mass (ESI): m/z calcd for $C_{67}H_{111}Cl_2N_{11}O_{13}$ 1347.77, found 1349.91 $[M+H]^+$.

Compound 91B: 68.21 (d, J=10.0 Hz, 1H), 7.89 (d, J=6.8 Hz, 1H), 7.42 (d, J=8.8 Hz, 1H), 7.27 (d, J=8.8 Hz, 1H), 7.25 (t, J=2.0 Hz, 1H), 7.17 (d, =2.0 Hz, 2H), 5.68 (dd, J=4.0, 11.2 Hz, 1H), 5.27-5.28 (m, 1H), 5.21 (d, J=11.2 Hz, 1H), 5.05-5.13 (m, 4H), 4.92-5.00 (m, 2H), 4.85 (t, J=7.2 Hz, 1H), 4.76 (d, J=4.0 Hz, 1H), 4.73 (d, J=9.2 Hz, 1H), 4.58 (d, J=13.6 Hz, 1H), 4.40-4.45 (m, 2H), 4.07 (t, J=6.4 Hz, 1H), 3.54 (s, 3H), 3.37 (s, 3H), 3.23 (s, 3H), 3.16 (s, 3H), 3.08 (s, 3H), 2.70 (s, 3H), 2.69 (s, 3H), 2.34-2.39 (m, 1H), 2.22-2.25 (m, 1H), 2.09-2.17 (m, 3H), 1.92-2.00 (m, 3H), 1.65-1.76 (m, 5H), 1.42-1.46 (m, 3H), 1.33 (d, J=6.8 Hz, 3H), 1.24 (d, J=7.2 Hz, 3H), 1.04 (d, J=6.4 Hz, 3H), 0.95-0.99 (m, 8H), 0.91-0.95 (m, 9H), 0.86-0.89 (m, 14H), 0.82-0.84 (m, 8H), 0.71 (d, J=6.4 Hz, 3H). Mass (ESI): m/z calcd for $C_{67}H_{111}Cl_2N_{11}O_{13}$ 1347.77, found 1348.97 [M+H]$^+$.

Compound 92A: Preparation of [2-((2R,3R)-5-((S)-1-(3,5-dichlorophenyl)ethoxy)-3-methyltetrahydrofuran-2-yl)-2-(methylamino)acetic acid]$^1$-cyclosporin A

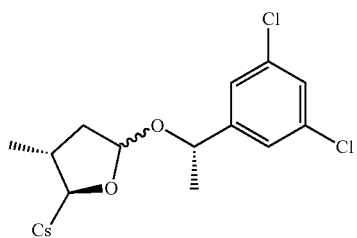

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 70 mg starting material and 21 mg (S)-1-(3,5-dichlorophenyl)ethan-1-ol were used, 13 mg white solid was obtained. Yield: 17.7%. $^1$H NMR (400 MHz, CDCl$_3$): δ 8.35 (d, J=9.6 Hz, 1H), 8.05 (d, J=6.8 Hz, 1H), 7.57 (d, J=9.2 Hz, 1H), 7.48 (d, J=8.0 Hz, 1H), 7.23 (t, J=1.6 Hz, 1H), 7.14 (d, J=1.6 Hz, 2H), 5.66 (dd, J=4.0, 10.8 Hz, 1H), 5.32 (dd, J=4.0, 11.2 Hz, 1H), 5.21 (d, J=11.8 Hz, 1H), 5.05-5.11 (m, 2H), 4.95-5.04 (m, 2H), 4.78-4.87 (m, 3H), 4.73 (d, J=4.8 Hz, 1H), 4.65-4.69 (m, 2H), 4.33-4.40 (m, 1H), 4.24 (dd, J=4.0, 9.6 Hz, 1H), 3.51 (s, 3H), 3.41 (s, 3H), 3.19 (s, 3H), 3.17 (s, 3H), 3.05 (s, 3H), 2.69 (s, 3H), 2.66 (s, 3H), 2.25-2.32 (m, 2H), 2.04-2.11 (m, 3H), 1.93-2.01 (m, 3H), 1.72-1.79 (m, 1H), 1.54-1.66 (m, 6H), 1.47-1.50 (m, 1H), 1.37 (d, J=6.4 Hz, 3H), 1.32 (d, J=7.2 Hz, 3H), 1.25 (d, J=6.0 Hz, 3H), 1.24 (d, J=6.8 Hz, 3H), 0.99-1.04 (m, 10H), 0.93-0.95 (m, 6H), 0.89-0.91 (m, 4H), 0.84-0.88 (m, 11H), 0.81-0.83 (m, 5H), 0.68 (d, J=6.4 Hz, 3H), 0.52 (d, J=6.8 Hz, 3H). Mass (ESI): m/z calcd for $C_{68}H_{113}Cl_2N_{11}O_{13}$ 1361.79, found 1363.24 [M+H]$^+$.

Compound 93A: Preparation of [2-((2R,3R)-5-((R)-1-(3,5-dichlorophenyl)ethoxy)-3-methyltetrahydrofuran-2-yl)-2-(methylamino)acetic acid]$^1$-cyclosporin A

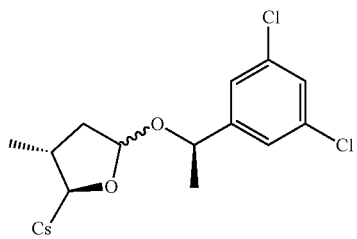

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 70 mg starting material and 21 mg (R)-1-(3,5-dichlorophenyl)ethan-1-ol were used, 60 mg white solid was obtained. Yield: 81.6%. $^1$H NMR (400 MHz, CDCl$_3$): δ 8.33 (d, J=9.6 Hz, 1H), 8.02 (d, J=6.8 Hz, 1H), 7.59 (d, J=8.8 Hz, 1H), 7.49 (d, J=8.0 Hz, 1H), 7.22 (t, J=2.0 Hz, 1H), 7.20 (d, J=2.0 Hz, 2H), 5.67 (dd, J=4.4, 10.8 Hz, 1H), 5.33 (dd, J=4.0, 11.2 Hz, 1H), 5.18 (d, J=11.2 Hz, 1H), 5.06-5.12 (m, 3H), 5.00 (d, J=9.6 Hz, 1H), 4.92-4.96 (m, 1H), 4.78-4.88 (m, 3H), 4.66 (d, J=13.6 Hz, 1H), 4.56 (q, J=6.4 Hz, 1H), 4.34-4.41 (m, 1H), 3.99 (dd, J=4.0, 9.6 Hz, 1H), 3.37 (s, 3H), 3.23 (s, 3H), 3.22 (s, 3H), 3.17 (s, 3H), 3.06 (s, 3H), 2.70 (s, 3H), 2.65 (s, 3H), 2.29-2.35 (m, 1H), 2.07-2.12 (m, 4H), 1.93-2.02 (m, 2H), 1.81-1.88 (m, 1H), 1.67-1.73 (m, 2H), 1.55-1.62 (m, 4H), 1.44-1.51 (m, 2H), 1.35 (d, J=6.4 Hz, 3H), 1.32 (d, J=7.2 Hz, 3H), 1.25 (d, J=7.2 Hz, 3H), 1.20 (d, J=6.8 Hz, 3H), 1.00-1.04 (m, 10H), 0.93-0.95 (m, 7H), 0.89-0.91 (m, 4H), 0.85-0.87 (m, 8H), 0.81-0.84 (m, 7H), 0.79 (d, J=6.4 Hz, 3H), 0.69 (d, J=6.8 Hz, 3H). Mass (ESI): m/z calcd for $C_{68}H_{113}Cl_2N_{11}O_{13}$ 1361.79, found 1363.50 [M+H]$^+$.

Compound 94A and Compound 94B: Preparation of [2-((2R,3R)-5-(3,4-dichlorobenzyloxy)-3-methyltetrahydrofuran-2-yl)-2-(methylamino)acetic acid]$^1$-cyclosporin A

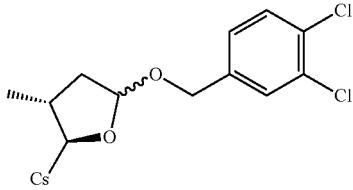

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 50 mg starting material and 14 mg (3,4-dichlorophenyl)methanol were used, and 25 mg Compound 94A and 6 mg Compound 94B were obtained as white solid, yield: 48.1% and 11.5% respectively. $^1$H NMR (CDCl$_3$, 400 MHz):

Compound 94A: 8.33 (d, J=9.6 Hz, 1H), 8.05 (d, J=6.8 Hz, 1H), 7.58 (d, J=8.8 Hz, 1H), 7.48 (d, J=8.0 Hz, 1H), 7.40-7.37 (m, 2H), 7.13 (d, J=8.0 Hz, 1H), 5.66 (dd, J=4.0, 10.8 Hz, 1H), 5.31 (dd, J=4.0, 11.6 Hz, 1H), 5.20 (d, J=11.2 Hz, 1H), 5.14-5.02 (m, 4H), 5.00-4.95 (m, 2H), 4.87-4.82 (m, 2H), 4.68-4.60 (m, 2H), 4.38 (t, J=7.2 Hz, 1H), 4.33 (d, J=12.8 Hz, 1H), 4.20 (dd, J=4.4, 9.2 Hz, 1H), 3.46 (s, 3H), 3.38 (s, 3H), 3.22 (s, 3H), 3.17 (s, 3H), 3.05 (s, 3H), 2.68 (s, 3H), 2.67 (s, 3H), 2.38-2.28 (m, 2H), 2.15-2.07 (m, 3H), 2.02-1.89 (m, 3H), 1.68-1.58 (m, 5H), 1.51-1.40 (m, 3H), 1.32 (d, J=6.8 Hz, 3H), 1.25 (d, J=7.6 Hz, 3H), 1.19 (d, J=6.8 Hz, 3H), 1.02-1.00 (m, 8H), 0.94-0.91 (m, 9H), 0.87-0.83 (m, 18H), 0.82-0.80 (m, 4H), 0.67 (d, J=6.8 Hz, 3H). Mass (ESI): m/z calcd for $C_{67}H_{111}Cl_2N_{11}O_{13}$ 1347.77, found 1349.71 [M+H]$^+$.

Compound 94B: δ 8.20 (d, J=9.2 Hz, 1H), 7.89 (d, J=7.2 Hz, 1H), 7.41-7.43 (m, 2H), 7.37-7.39 (m, 1H), 7.27 (d, J=9.2 Hz, 1H), 7.12 (dd, J=2.0, 8.4 Hz, 1H), 5.68 (dd, J=4.0, 11.2 Hz, 1H), 5.26-5.29 (m, 2H), 5.21 (d, J=10.8 Hz, 1H), 5.05-5.13 (m, 4H), 4.92-4.98 (m, 1H), 4.82-4.89 (m, 11H), 4.76 (d, J=2.0 Hz, 1H), 4.73 (d, J=8.4 Hz, 1H), 4.59 (d, J=13.2 Hz, 1H), 4.39-4.45 (m, 2H), 4.07 (t, J=6.8 Hz, 1H), 3.54 (s, 3H), 3.36 (s, 3H), 3.22 (s, 3H), 3.16 (s, 3H), 3.09 (s, 3H), 2.71 (s, 3H), 2.69 (s, 3H), 2.32-2.37 (m, 1H), 2.21-2.24 (m, 1H), 2.07-2.15 (m, 3H), 1.93-1.99 (m, 3H), 1.65-1.74 (m, 5H), 1.40-1.46 (m, 3H), 1.33 (d, J=7.2 Hz, 3H), 1.24 (d, J=6.8 Hz, 3H), 1.04 (d, J=6.4 Hz, 3H), 0.94-0.97 (m, 13H), 0.90-0.93 (m, 8H), 0.86-0.88 (m, 11H), 0.81-0.83 (m, 7H), 0.72 (d, J=6.8 Hz, 3H). Mass (ESI): m/z calcd for $C_{67}H_{111}Cl_2N_{11}O_{13}$ 1347.77, found 1348.78 [M+H]$^+$.

Compound 96A: Preparation of [2-((2R,3R)-5-((S)-1-(3,4-dichlorophenyl)ethoxy)-3-methyltetrahydrofuran-2-yl)-2-(methylamino)acetic acid]$^1$-cyclosporin A

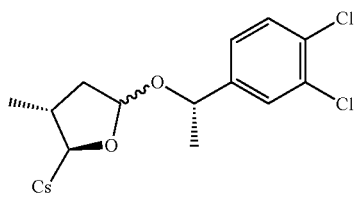

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 70 mg starting material and 21 mg (S)-1-(3,4-dichlorophenyl)ethan-1-ol were used, 50 mg white solid was obtained. Yield: 68.0%. $^1$H NMR (400 MHz, CDCl$_3$): δ 8.34 (d, J=9.6 Hz, 1H), 8.04 (d, J=6.8 Hz, 1H), 7.57 (d, J=8.8 Hz, 1H), 7.47 (d, J=8.0 Hz, 1H), 7.37 (d, J=8.0 Hz, 1H), 7.35 (d, J=2.0 Hz, 1H), 7.10 (dd, J=2.0, 8.4 Hz, 1H), 5.65 (dd, J=4.4, 11.2 Hz, 1H), 5.31 (dd, J=4.4, 11.6 Hz, 1H), 5.20 (d, J=10.8 Hz, 1H), 5.09 (t, J=6.8 Hz, 1H), 5.03-5.05 (m, 2H), 4.94-5.00 (m, 2H), 4.78-4.86 (m, 2H), 4.68-4.71 (m, 2H), 4.66 (t, J=10.0 Hz, 1H), 4.32-4.39 (m, 1H), 4.24 (dd, J=4.0, 9.6 Hz, 1H), 3.50 (s, 3H), 3.40 (s, 3H), 3.18 (s, 3H), 3.17 (s, 3H), 3.04 (s, 3H), 2.70 (s, 3H), 2.65 (s, 3H), 2.26-2.32 (m, 1H), 2.17-2.20 (m, 1H), 2.09-2.14 (m, 3H), 1.91-1.99 (m, 3H), 1.69-1.77 (m, 2H), 1.53-1.65 (m, 6H), 1.36 (d, J=6.4 Hz, 3H), 1.31 (d, J=7.2 Hz, 3H), 1.24 (d, J=6.0 Hz, 3H), 1.23 (d, J=7.2 Hz, 3H), 1.02-1.04 (m, 6H), 0.98-1.00 (m, 4H), 0.92-0.94 (m, 7H), 0.86-0.89 (m, 8H), 0.83-0.85 (m, 7H), 0.80-0.82 (m, 4H), 0.65 (d, J=6.4 Hz, 3H), 0.48 (d, J=6.8 Hz, 3H). Mass (ESI): m/z calcd for $C_{68}H_{113}Cl_2N_{11}O_{13}$ 1361.79, found 1363.17 [M+H]$^+$.

Compound 97A: Preparation of [2-((2R,3R)-5-((R)-1-(3,4-dichlorophenyl)ethoxy)-3-methyltetrahydrofuran-2-yl)-2-(methylamino)acetic acid]$^1$-cyclosporin A

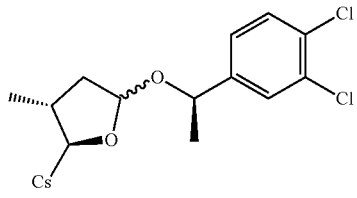

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 70 mg starting material and 21 mg (R)-1-(3,4-dichlorophenyl)ethan-ol were used, 46 mg white solid was obtained. Yield: 62.6%. $^1$H NMR (400 MHz, CDCl$_3$): δ 8.29 (d, J=9.6 Hz, 1H), 8.05 (d, J=6.8 Hz, 1H), 7.59 (d, J=9.2 Hz, 1H), 7.46 (d, J=8.0 Hz, 1H), 7.42 (d, J=2.0 Hz, 1H), 7.38 (d, J=8.4 Hz, 1H), 7.13 (d, J=2.0, 8.4 Hz, 1H), 5.67 (dd, J=4.0, 11.2 Hz, 1H), 5.32 (dd, J=4.0, 11.2 Hz, 1H), 5.15 (d, J=11.2 Hz, 1H), 5.07-5.12 (m, 3H), 5.00 (d, J=9.6 Hz, 1H), 4.90-4.96 (m, 1H), 4.77-4.87 (m, 3H), 4.65 (d, J=14.0 Hz, 1H), 4.56 (q, J=6.8 Hz, 1H), 4.34-4.41 (m, 1H), 3.95 (dd, J=4.4, 9.6 Hz, 1H), 3.35 (s, 3H), 3.23 (s, 3H), 3.17 (s, 6H), 3.05 (s, 3H), 2.69 (s, 3H), 2.65 (s, 3H), 2.27-2.32 (m, 1H), 2.06-2.15 (m, 4H), 1.92-2.00 (m, 2H), 1.82-1.89 (m, 1H), 1.64-1.72 (m, 2H), 1.51-1.59 (m, 3H), 1.38-1.46 (m, 3H), 1.35 (d, J=6.4 Hz, 3H), 1.31 (d, J=7.2 Hz, 3H), 1.25 (d, J=6.8 Hz, 3H), 1.18 (d, J=6.8 Hz, 3H), 1.02-1.04 (m, 4H), 0.98-1.01 (m, 6H), 0.94-0.96 (m, 4H), 0.92-0.93 (m, 3H), 0.88-0.90 (m, 5H), 0.85-0.87 (m, 7H), 0.82-0.83 (m, 5H), 0.79-0.81 (m, 5H), 0.70 (d, J=6.8 Hz, 3H). Mass (ESI): m/z calcd for $C_{68}H_{113}Cl_2N_{11}O_{13}$ 1361.79, found 1363.17 [M+H]$^+$.

Compound 98A: Preparation of [2-((2R,3R)-5-(2,5-dichlorobenzyloxy)-3-methyltetrahydrofuran-2-yl)-2-(methylamino)acetic acid]$^1$-cyclosporin A

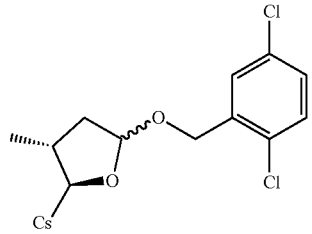

The compound was synthesized from [2-((2R,3R)-5-(3-methoxy-3-oxopropoxy)-3-methyltetrahydrofuran-2-yl)-2-(methylamino)acetic acid]$^1$-cyclosporin A in a manner similar to that described for compound 75A. 70 mg starting material and 19 mg (2,5-dichlorophenyl)methanol were used, 20 mg of pure compound 98A and 5 mg of compound 98A+B(1:1) mixture isomers were obtained as white solid. Total yield: 34.4%. $^1$H NMR (400 MHz, CDCl$_3$): δ 8.32 (d, J=9.6 Hz, 1H), 8.05 (d, J=6.8 Hz, 1H), 7.56 (d, J=8.8 Hz, 1H), 7.46 (d, J=8.0 Hz, 1H), 7.42 (t, J=2.4 Hz, 1H), 7.24 (d, J=8.8 Hz, 1H), 7.16 (dd, J=2.4, 8.4 Hz, 1H), 5.67 (dd, J=4.4, 10.8 Hz, 1H), 5.31 (dd, J=4.0, 11.2 Hz, 1H), 5.22 (d, J=11.2 Hz, 1H), 5.10-5.15 (m, 3H), 5.07-5.09 (m, 1H), 5.05 (d, J=5.2 Hz, 1H), 4.95-5.01 (m, 1H), 4.81-4.85 (m, 2H), 4.73 (d, J=13.6 Hz, 1H), 4.67 (d, J=14.0 Hz, 1H), 4.43 (d, J=14.0 Hz, 1H), 4.36-4.39 (m, 1H), 4.24 (dd, J=4.4, 8.8 Hz, 1H), 3.45 (s, 3H), 3.38 (s, 3H), 3.23 (s, 3H), 3.17 (s, 3H), 3.05 (s, 3H), 2.69 (s, 3H), 2.67 (s, 3H), 2.28-2.35 (m, 2H), 2.05-2.15 (m, 4H), 1.96-2.01 (m, 2H), 1.68-1.76 (m, 2H), 1.57-1.65 (m, 3H), 1.48-1.53 (m, 1H), 1.37-1.45 (m, 2H), 1.33 (d, J=6.8 Hz, 3H), 1.25 (d, J=7.2 Hz, 3H), 1.21 (d, J=6.4 Hz, 3H), 0.99-1.01 (m, 8H), 0.92-0.94 (m, 5H), 0.89-0.91 (m, 4H), 0.86-0.87 (m, 7H), 0.84-0.85 (m, 12H), 0.81 (d, J=6.8 Hz, 3H), 0.72 (d, J=6.4 Hz, 3H). Mass (ESI): m/z calcd for $C_{67}H_{111}Cl_2N_{11}O_{13}$ 1347.77, found 1349.45 [M+H]$^+$.

Compound 99A: Preparation of [2-((2R,3R)-3-methyl-5-(4-morpholinobenzyloxy)tetrahydrofuran-2-yl)-2-(methylamino)acetic acid]¹-cyclosporin A

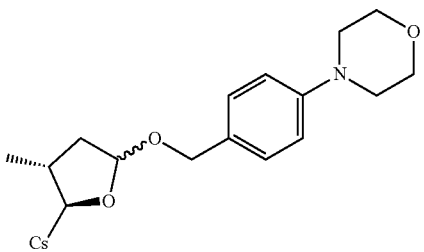

The compound was synthesized from [2-((2R,3R)-5-(3-methoxy-3-oxopropoxy)-3-methyltetrahydrofuran-2-yl)-2-(methylamino)acetic acid]¹-cyclosporin A in a manner similar to that described for compound 75A. 100 mg starting material and 30 mg (4-morpholinophenyl)methanol were used, and 20 mg compound 99A and 12 mg compound 99A+B(1:1.1) were obtained as white solid. Total yield: 30.5%. ¹H NMR (400 MHz, CDCl₃) δ 8.39 (d, J=9.6 Hz, 1H), 8.06 (d, J=6.8 Hz, 1H), 7.60 (d, J=8.8 Hz, 1H), 7.49 (d, J=8.0 Hz, 1H), 7.22 (d, J=8.0 Hz, 2H), 6.88 (s, 2H), 5.67 (dd, J=4.0, 10.8 Hz, 1H), 5.32-5.34 (m, 1H), 5.29-5.31 (m, 1H), 5.22 (d, J=11.2 Hz, 1H), 5.09-5.14 (m, 3H), 4.95-5.01 (m, 2H), 4.83-4.87 (m, 2H), 4.65 (d, J=13.6 Hz, 1H), 4.59 (d, J=11.6 Hz, 1H), 4.38 (t, J=7.2 Hz, 1H), 4.31 (d, J=11.6 Hz, 1H), 4.18 (dd, J=4.8, 9.6 Hz, 1H), 3.85 (brs, 4H), 3.48 (s, 3H), 3.40 (s, 3H), 3.22 (s, 3H), 3.18 (s, 3H), 3.14 (brs, 4H), 3.05 (s, 3H), 2.69 (s, 3H), 2.66 (s, 3H), 2.28-2.37 (m, 1H), 1.98-2.15 (m, 6H), 1.83-1.92 (m, 1H), 1.54-1.69 (m, 6H), 1.37-1.46 (m, 2H), 1.33 (d, J=7.2 Hz, 3H), 1.25 (d, J=6.8 Hz, 3H), 1.19 (d, J=6.8 Hz, 3H), 1.00-1.03 (m, 8H), 0.89-0.95 (m, 9H), 0.84-0.87 (m, 17H), 0.80-0.82 (m, 5H), 0.69 (d, J=6.4 Hz, 3H). Mass (ESI) calcd for $C_{71}H_{120}N_{12}O_{14}$ 1364.90, found 1365.66 [M+H]⁺.

Compound 100A: Preparation of [2-((2R,3R)-5-(benzo[d][1,3]dioxol-5-ylmethoxy)-3-methyltetrahydrofuran-2-yl)-2-(methylamino)acetic acid]¹-cyclosporin A

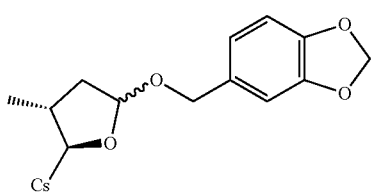

The compound was synthesized from [2-((2R,3R)-5-(3-methoxy-3-oxopropoxy)-3-methyltetrahydrofuran-2-yl)-2-(methylamino)acetic acid]¹-cyclosporin A in a manner similar to that described for compound 75A. 100 mg starting material and 15 mg benzo[d][1,3]dioxol-5-ylmethanol were used, and 36 mg white solid was obtained. Yield: 35.3%. ¹H NMR (400 MHz, CDCl₃) δ 8.38 (d, J=9.6 Hz, 1H), 8.06 (d, J=6.8 Hz, 1H), 7.60 (d, J=8.8 Hz, 1H), 7.50 (d, J=8.0 Hz, 1H), 6.80 (s, 1H), 6.74 (d, J=0.8 Hz, 2H), 5.92 (dd, J=1.6, 2.4 Hz, 2H), 5.67 (dd, J=4.0, 10.8 Hz, 1H), 5.32 (dd, J=4.0, 11.2 Hz, 1H), 5.21 (d, J=10.8 Hz, 1H), 5.04-5.16 (m, 4H), 4.95-4.99 (m, 2H), 4.82-4.86 (m, 2H), 4.66 (d, J=14.0 Hz, 1H), 4.57 (d, J=11.6 Hz, 1H), 4.35-4.42 (m, 1H), 4.29 (d, J=12.0 Hz, 1H), 4.20 (dd, J=4.8, 9.6 Hz, 1H), 3.48 (s, 3H), 3.39 (s, 3H), 3.22 (s, 3H), 3.17 (s, 3H), 3.05 (s, 3H), 2.67 (s, 3H), 2.66 (s, 3H), 2.28-2.36 (m, 1H), 2.01-2.17 (m, 5H), 1.83-1.95 (m, 2H), 1.53-1.69 (m, 6H), 1.39-1.49 (m, 2H), 1.33 (d, J=7.2 Hz, 3H), 1.25 (d, J=6.8 Hz, 3H), 1.19 (d, J=6.8 Hz, 3H), 0.99-1.03 (m, 9H), 0.91-0.94 (m, 10H), 0.84-0.87 (m, 15H), 0.80-0.82 (m, 5H), 0.68 (d, J=6.8 Hz, 3H). Mass (ESI) calcd for $C_{68}H_{113}N_{11}O_{15}$ 1323.84, found 1324.76 [M+H]⁺.

Compound 101A and Compound 101B: Preparation of [2-((2R,3R)-5-(2,4-dichloro-5-fluorobenzyloxy)-3-methyltetrahydrofuran-2-yl)-2-(methylamino)acetic acid]¹-cyclosporin A

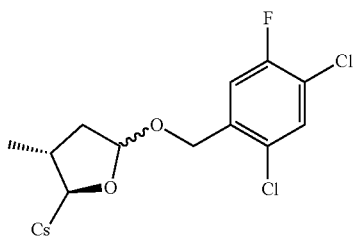

The compound was synthesized from [2-((2R,3R)-5-(3-methoxy-3-oxopropoxy)-3-methyltetrahydrofuran-2-yl)-2-(methylamino)acetic acid]¹-cyclosporin A in a manner similar to that described for compound 75A. 50 mg starting material and 15 mg (2,4-dichloro-5-fluorophenyl)methanol were used, and 31 mg white solid (compound 101A: 25 mg, compound 101B: 6 mg) was obtained. Total yield: 58.8%.

Compound 101A: ¹H NMR (CDCl₃, 400 MHz): δ 8.33 (d, J=9.6 Hz, 1H), 8.03 (d, J=6.8 Hz, 1H), 7.56 (d, J=8.8 Hz, 1H), 7.46 (d, J=8.0 Hz, 1H), 7.37 (d, J=6.4 Hz, 1H), 7.25 (d, J=9.6 Hz, 1H), 5.67 (dd, J=4.0, 10.8 Hz, 1H), 5.31 (d, J=4.0 Hz, 1H), 5.29 (s, 1H), 5.21 (d, J=11.2 Hz, 1H), 5.16 (d, J=9.2 Hz, 1H), 5.12 (t, J=5.2 Hz, 1H), 5.09 (t, J=7.2 Hz, 1H), 5.03 (d, J=4.8 Hz, 1H), 4.95-5.01 (m, 1H), 4.80-4.88 (m, 2H), 4.71 (d, J=14.0 Hz, 1H), 4.67 (d, J=14.0 Hz, 1H), 4.36-4.43 (m, 2H), 4.23 (dd, J=4.8, 9.2 Hz, 1H), 3.47 (s, 3H), 3.39 (s, 3H), 3.23 (s, 3H), 3.17 (s, 3H), 3.05 (s, 3H), 2.69 (s, 3H), 2.67 (s, 3H), 2.29-2.38 (m, 1H), 2.02-2.16 (m, 5H), 1.91-2.01 (m, 2H), 1.69-1.78 (m, 1H), 1.56-1.68 (m, 4H), 1.44-1.54 (m, 2H), 1.38-1.43 (m, 1H), 1.32 (d, J=7.2 Hz, 3H), 1.25 (d, J=7.2 Hz, 3H), 1.19 (d, J=6.4 Hz, 3H), 1.00-1.02 (m, 8H), 0.91-0.96 (m, 9H), 0.84-0.87 (m, 18H), 0.81 (d, J=6.4 Hz, 4H), 0.70 (d, J=6.4 Hz, 3H). Mass (ESI): m/z calcd for $C_{67}H_{110}Cl_2FN_{11}O_{13}$ 1365.76, found 1366.70 [M+H]⁺.

Compound 101B: ¹H NMR (CDCl₃, 400 MHz): δ 8.23 (brs, 1H), 7.92 (d, J=6.8 Hz, 1H), 7.40 (d, J=8.0 Hz, 1H), 7.38 (d, J=6.4 Hz, 1H), 7.28 (d, J=3.6 Hz, 1H), 7.25 (d, J=4.0 Hz, 1H), 5.68 (dd, J=4.0, 11.2 Hz, 1H), 5.30-5.32 (m, 1H), 5.27-5.29 (m, 1H), 5.18-5.21 (m, 1H), 5.16-5.17 (m, 1H), 5.09-5.13 (m, 1H), 5.04-5.08 (m, 1H), 4.92-4.98 (m, 1H), 4.81-4.89 (m, 2H), 4.73-4.78 (m, 2H), 4.69 (d, J=14.4 Hz, 1H), 4.48 (d, J=14.4 Hz, 1H), 4.38-4.44 (m, 1H), 4.08 (t, J=6.4 Hz, 1H), 3.55 (s, 3H), 3.37 (s, 3H), 3.24 (s, 3H), 3.15 (s, 3H), 3.09 (s, 3H), 2.71 (s, 3H), 2.68 (s, 3H), 2.31-2.40 (m, 1H), 2.20-2.23 (m, 1H), 2.08-2.16 (m, 3H), 1.97-2.06 (m, 3H), 1.71-1.79 (m, 3H), 1.59-1.69 (m, 3H), 1.41-1.47 (m, 2H), 1.33 (d, J=7.2 Hz, 3H), 1.25 (d, J=2.8 Hz, 3H), 1.23 (d, J=3.6 Hz, 3H), 1.04 (d, J=6.4 Hz, 3H), 0.99 (d, J=6.4 Hz, 3H), 0.96-0.97 (m, 3H), 0.93-0.94 (m, 6H), 0.91-0.92 (m, 6H), 0.87-0.89 (m, 6H), 0.85-0.86 (m, 5H), 0.83 (d, J=4.0 Hz, 3H), 0.80 (d, J=6.8 Hz, 4H), 0.69 (d, J=6.8 Hz, 3H). Mass (ESI): m/z calcd for $C_{67}H_{110}Cl_2FN_{11}O_{13}$ 1365.76, found 1366.64 [M+H]$^+$.

Compound 95, 102-105: Compound 95, 102-105 would be Prepared According to the Procedure Outlined in Scheme 3

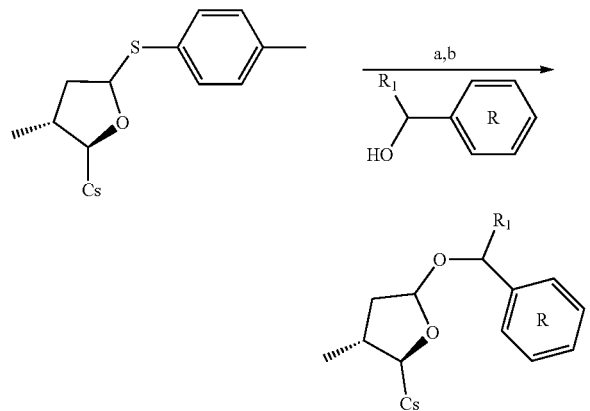

scheme 3: reagent and conditions: (a) silver trifluoromethanesulfonate, activated 3 Å molecular sieves, $CH_2Cl_2$, r.t. (b) NIS, activated 3 Å molecular sieves, $CH_3CN$, r.t.

Compound 91A-s: Preparation of [2-((2R,3R)-5-(3,5-dichlorobenzylthio)-3-methyltetrahydrofuran-2-yl)-2-(methylamino)acetic acid]$^1$-cyclosporin A

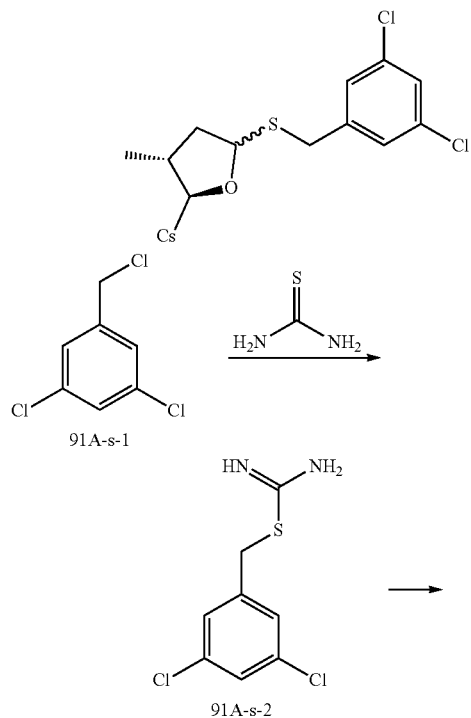

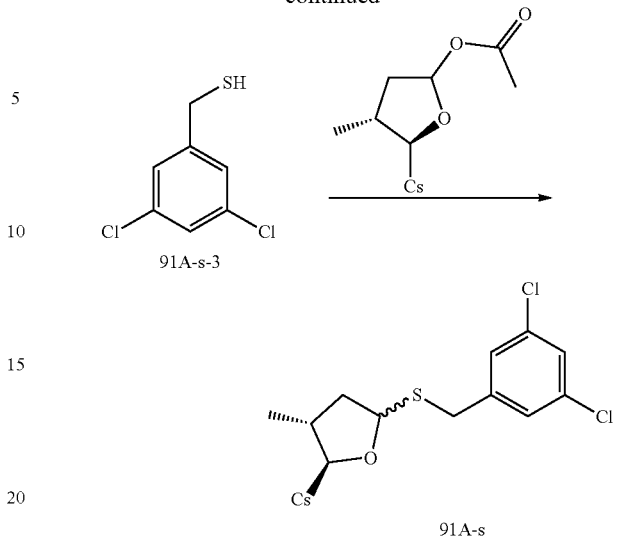

(I) Synthesis of 3,5-dichlorobenzyl carbamimidothioate (91 A-s-1)

A solution of 1,3-dichloro-5-(chloromethyl)benzene (200 mg, 1.03 mmol), in EtOH (20 mL) at 50° C. was added dropwise to a refluxing solution of thiourea (94 mg, 1.24 mmol) in EtOH (2 mL). The mixture was heated at reflux for 3 hrs. The solvent was evaporated to give 309 mg white solid. yield: 100%.

(II) Synthesis of (3,5-dichlorophenyl)methanethiol(91 A-s-2). 2N NaOH (3.2 mL, 6.4 mmol) was added to a solution of 3,5-dichlorobenzyl carbamimidothioate (300 mg, 1.28 mmol) in $CH_3OH$ (6 mL) at 0° C. The mixture was stirred at r.t. for 15 hrs. The solvent was evaporated and the pH was adjusted to 5.0 with 1N HCl. The mixture was extracted with EA (100 mL), dried over $Na_2SO_4$, filtered and concentrated to give 140 mg colorless oil, yield: 56.9%. $^1$H-NMR (400 MHz, $CDCl_3$): δ 7.24-7.25 (m, 1H), 7.22 (d, J=2.0 Hz, 1H), 7.13 (d, J=2.0 Hz, 1H), 3.67 (d, J=8.0 Hz, 1H), 3.55 (s, 1H).

(III) Synthesis of [2-((2R,3R)-5-(3,5-dichlorobenzylthio)-3-methyltetrahydrofuran-2-yl)-2-(methylamino)acetic acid]$^1$-cyclosporin A(91 A-s). The compound was synthesized from [2-((2R,3R)-5-acetoxy-3-methyltetrahydro furan-2-yl)-2-(methylamino)acetic acid]$^1$-cyclosporin A in a manner similar to that described for compound 1B. (3,5-dichlorophenyl)methanethiol was used instead of benzenethiol and 40 mg white solid was obtained. Yield: 24.1% $^1$H NMR ($CDCl_3$, 400 MHz): δ 8.34 (d, J=9.2 Hz, 1H), 8.04 (d, J=6.8 Hz, 1H), 7.63 (d, J=8.8 Hz, 1H), 7.47 (d, J=8.0 Hz, 1H), 7.18-7.20 (m, 3H), 5.66 (dd, J=4.0, 10.8 Hz, 1H), 5.31 (dd, J=4.0, 10.8 Hz, 1H), 5.22 (d, J=9.2 Hz, 1H), 5.18 (d, J=10.8 Hz, 1H), 5.07-5.14 (m, 3H), 4.99 (q, J=8.0 Hz, 2H), 4.89 (t, J=8.0 Hz, 1H), 4.84 (d, J=7.2 Hz, 1H), 4.64 (d, J=13.6 Hz, 1H), 4.34-4.44 (m, 1H), 4.23 (dd, J=7.2, 8.8 Hz, 1H), 3.69 (d, J=4.8 Hz, 2H), 3.48 (s, 3H), 3.37 (s, 3H), 3.20 (s, 3H), 3.16 (s, 3H), 3.04 (s, 3H), 2.67 (s, 3H), 2.66 (s, 3H), 2.26-2.38 (m, 2H), 2.09-2.17 (m, 2H), 1.91-2.06 (m, 4H), 1.61-1.70 (m, 3H), 1.52-1.59 (m, 2H), 1.39-1.48 (m, 3H), 1.32 (d, J=6.8 Hz, 3H), 1.24 (d, J=7.2 Hz, 3H), 1.11 (d, J=6.4 Hz, 3H), 0.98-0.99 (m, 4H), 0.95-0.97 (m, 3H), 0.90-0.93 (m, 11H), 0.83-0.87 (m, 17H), 0.81 (d, J=6.4 Hz, 4H), 0.72 (d, J=6.4 Hz, 3H). Mass (ESI): m/z calcd for $C_{67}H_{111}Cl_2NO_2S$ 1363.75, found 1365.07 [M+H]$^+$.

Compound 74A-s to 90B-s, 91B-s to 105-s:
Compound 74A-s to 90B-s, 91B-s to 105-s are Prepared According to the Procedure Outlined in Scheme 4

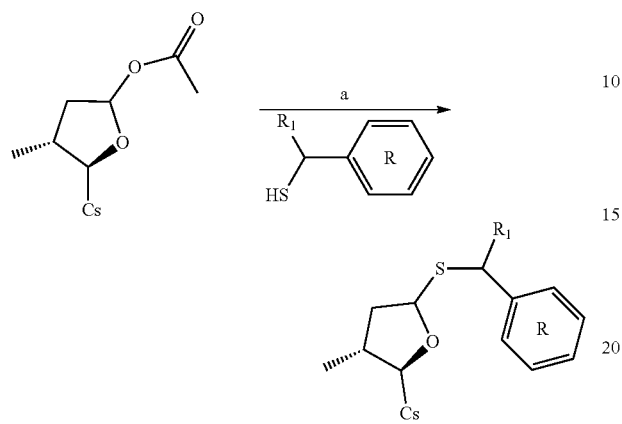

scheme 4: reagent and conditions: (a) BSA, TMSOTf, CH$_3$CN.

IV Bioactivity

| # | IC50 |
|---|---|
| 1B | 1-100 μM |
| 2A | 1-1000 nM |
| 2A + B(1:3.3) | 1-1000 nM |
| 3A | 1-1000 nM |
| 4A | 1-10 μM |
| 5A | 1-10 μM |
| 6A | 1-1000 nM |
| 7A | 1-10 μM |
| 8A | 1-1000 nM |
| 9A | 1-1000 μM |
| 10A | 1-1000 μM |
| 11 | 1-100 μM* |
| 12A | 1-1000 nM |
| 12B | 1-1000 nM |
| 13A | 1-1000 nM |
| 14A | 1-100 μM* |
| 15A | 1-10 μM |
| 16A | 1-10 μM |
| 17A | 1-1000 nM |
| 18A | 1-1000 nM |
| 19A | 1-1000 nM |
| 20A | 1-1000 nM |
| 21A | 1-1000 nM |
| 22A | 1-1000 nM |
| 23A | 1-1000 nM |
| 24A | 1-1000 nM |
| 25A | 1-1000 nM |
| 26A | 1-1000 nM |
| 26B | 1-1000 nM |
| 27A | 1-1000 nM |
| 28A | 1-1000 nM |
| 29A | 1-1000 nM |
| 30A | 1-1000 nM |
| 30B | 1-1000 nM |
| 31A | 1-1000 nM |
| 32A | 1-1000 nM |
| 33A | 1-1000 nM |
| 34A | 1-1000 nM |
| 35A | 1-1000 nM |
| 36A | 1-10 μM |
| 37A | 1-1000 nM |
| 38A | 1-1000 nM |
| 39A | 1-1000 nM |
| 40A | 1-1000 nM |
| 41A | 1-1000 nM |
| 42A | 1-1000 nM |
| 43A | 1-1000 nM |
| 44A | 1-1000 nM |
| 45A | 1-1000 nM |
| 46A | 1-1000 nM |
| 47A | 1-1000 nM |
| 48A | 1-1000 nM |
| 49A | 1-1000 nM |
| 50A | 1-1000 nM |
| 51A | 1 1000 nM |
| 52A | 1-1000 nM |
| 52A + B(1:1.1) | 1-1000 nM |
| 53A | 1-1000 nM |
| 53A + B(1:1.5) | 1-1000 nM |
| 54A | 1-1000 nM |
| 55 | 1-100 μM* |
| 56 | 1-100 μM* |
| 57A | 1-1000 nM |
| 58A | 1-1000 nM |
| 59A | 1-1000 nM |
| 60A | 1-1000 nM |
| 60A + B(1:1.4) | 1-1000 nM |
| 61A | 1-1000 nM |
| 62 | 1-100 μM* |
| 63 | 1-100 μM* |
| 64 | 1-100 μM* |
| 65 | 1-100 μM* |
| 66 | 1-100 μM* |
| 67 | 1-100 μM* |
| 68 | 1-100 μM* |
| 69 | 1-100 μM* |
| 70 | 1-100 μM* |
| 71 | 1-100 μM* |
| 72 | 1-100 μM* |
| 73 | 1-100 μM* |
| 1B-o | 1-100 μM* |
| 2A-o | 1-100 μM* |
| 2A + B(1:3.3)-o | 1-100 μM* |
| 3A-o | 1-100 μM* |
| 4A-o | 1-100 μM* |
| 5A-o | 1-100 μM* |
| 6A-o | 1-100 μM* |
| 7A-o | 1-100 μM* |
| 8A-o | 1-100 μM* |
| 9A-o | 1-100 μM* |
| 10A-o | 1-100 μM* |
| 11-o | 1-100 μM* |
| 12A-o | 1-1000 nM |
| 12B-o | 1-1000 nM |
| 13A-o | 1-100 μM* |
| 14A-o | 1-100 μM* |
| 15A-o | 1-100 μM* |
| 16A-o | 1-100 μM* |
| 17A-o | 1-100 μM* |
| 18A-o | 1-100 μM* |
| 19A-o | 1-100 μM* |
| 20A-o | 1-100 μM* |
| 21A-o | 1-100 μM* |
| 22A-o | 1-100 μM* |
| 23A-o | 1-100 μM* |
| 24A-o | 1-100 μM* |
| 25A-o | 1-100 μM* |
| 26A-o | 1-100 μM* |
| 26B-o | 1-100 μM* |
| 27A-o | 1-100 μM* |
| 28A-o | 1-100 μM* |
| 29A-o | 1-100 μM* |
| 30A-6 | 1-100 μM* |
| 30B-o | 1-100 μM* |
| 31A-o | 1-100 μM* |
| 32A-o | 1-100 μM* |
| 33A-o | 1-100 μM* |
| 34A-o | 1-100 μM* |
| 35A-o | 1-100 μM* |

| # | IC50 |
|---|---|
| 36A-o | 1-100 μM* |
| 37A-o | 1-100 μM* |
| 38A-o | 1-100 μM* |
| 39A-o | 1-100 μM* |
| 40A-o | 1-100 μM* |
| 41A-o | 1-100 μM* |
| 42A-o | 1-100 μM* |
| 43A-o | 1-100 μM* |
| 44A-o | 1-100 μM* |
| 45A-o | 1-100 μM* |
| 46A-o | 1-100 μM* |
| 47A-o | 1-100 μM* |
| 48A-o | 1-100 μM* |
| 49A-o | 1-100 μM* |
| 50A-o | 1-100 μM* |
| 51A-o | 1-100 μM* |
| 52A-o | 1-100 μM* |
| 52A + B(1:1.1)-o | 1-100 μM* |
| 53A-o | 10 μM* |
| 53A + B(1:1.5)-o | 1-100 μM* |
| 54A-o | 1-100 μM* |
| 55-o | 1-100 μM* |
| 56-o | 1-100 μM* |
| 57A-o | 1-100 μM* |
| 58A-o | 1-100 μM* |
| 59A-o | 1-100 μM* |
| 60A-o | 1-100 μM* |
| 60A + B(1:1.4)-o | 1-100 μM* |
| 61A-o | 1-100 μM* |
| 62-o | 1-100 μM* |
| 63-o | 1-100 μM* |
| 64-o | 1-100 μM* |
| 65-o | 1-100 μM* |
| 66-o | 1-100 μM* |
| 67-o | 1-100 μM* |
| 68-o | 1-100 μM* |
| 69-o | 1-100 μM* |
| 70-o | 1-100 μM* |
| 71-o | 1-100 μM* |
| 72-o | 1-100 μM* |
| 73-o | 1-100 μM* |
| 74A | 1-1000 nM |
| 75A | 1-1000 nM |
| 76A | 1-10 μM |
| 77A | 1-10 μM |
| 78A | 1-1000 nM |
| 78B | 1-1000 nM |
| 79A | 1-1000 nM |
| 80A | 1-1000 nM |
| 81A | 1-1000 nM |
| 82A | 1-1000 nM |
| 82B | 1-1000 nM |
| 83A | 1-1000 nM |
| 84A | 1-1000 nM |
| 85A | 1-1000 nM |
| 86A | 1-1000 nM |
| 86B | 1-1000 nM |
| 87A | 1-10 μM |
| 88A | 1-1000 nM |
| 88B | 1-1000 nM |
| 89A | 1-1000 nM |
| 89B | 1-1000 nM |
| 90A | 1-1000 nM |
| 90B | 1-1000 nM |
| 91A | 1-1000 nM |
| 91B | 1-1000 nM |
| 92A | 1-1000 nM |
| 93A | 1-1000 nM |
| 94A | 1-1000 nM |
| 94B | 1-1000 nM |
| 95 | 1-100 μM* |
| 96A | 1-1000 nM |
| 97A | 1-1000 nM |
| 98A | 1-1000 nM |
| 98A + B(1:1) | 1-1000 nM |
| 99A | 1-10 μM |
| 99A + B(1:1.1) | 1-1000 nM |

| # | IC50 |
|---|---|
| 100A | 1-1000 nM |
| 101A | 1-1000 nM |
| 101B | 1-1000 nM |
| 102 | 1-100 μM* |
| 103 | 1-100 μM* |
| 104 | 1-100 μM* |
| 105 | 1-100 μM* |
| 74A-s | 1-100 μM* |
| 75A-s | 1-100 μM* |
| 76A-s | 1-100 μM* |
| 77A-s | 1-100 μM* |
| 78A-s | 1-100 μM* |
| 78B-s | 1-100 μM* |
| 79A-s | 1-100 μM* |
| 80A-s | 1-100 μM* |
| 81A-s | 1-100 μM* |
| 82A-s | 1-100 μM* |
| 82B-s | 1-100 μM* |
| 83A-s | 1-100 μM* |
| 84A-s | 1-100 μM* |
| 85A-s | 1-100 μM |
| 86A-s | 1-100 μM |
| 86B-s | 1-100 μM* |
| 87A-s | 1-100 μM* |
| 88A-s | 1-100 μM* |
| 88B-s | 1-100 μM* |
| 89A-s | 1-100 μM* |
| 89B-s | 1-100 μM* |
| 90A-s | 1-100 μM* |
| 90B-s | 1-100 μM* |
| 91A-s | 1-1000 nM |
| 91B-s | 1-100 μM* |
| 92A-s | 1-100 μM* |
| 93A-s | 1-100 μM* |
| 94A-s | 1-100 μM* |
| 94B-s | 1-100 μM* |
| 95-s | 1-100 μM* |
| 96A-s | 1-100 μM* |
| 97A-s | 1-100 μM* |
| 98A-s | 1-100 μM* |
| 98A + B(1:1)-s | 1-100 μM* |
| 99A-s | 1-100 μM* |
| 99A + B(1:1:1)-s | 1-100 μM* |
| 100A-s | 1-100 μM* |
| 101A-s | 1-100 μM* |
| 101B-s | 1-100 μM* |
| 102-s | 1-100 μM* |
| 103-s | 1-100 μM* |
| 104-s | 1-100 μM* |
| 105-s | 1-100 μM* |

V. Synthesis Method

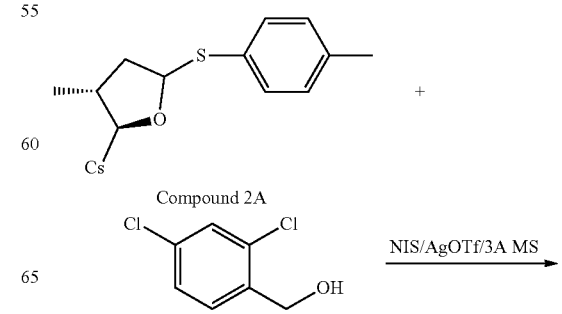

Compound 2A

NIS/AgOTf/3A MS →

-continued

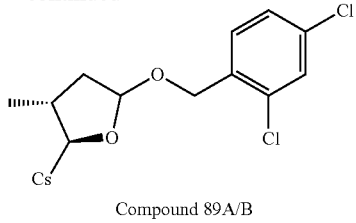

Compound 89A/B

Table

Synthesis of compound 89A/B from compound 2A

| entry | activator | solvent | temp(° C.) | A/B ratio |
|---|---|---|---|---|
| 1 | NIS/AgOTf | CH$_2$Cl$_2$ | rt | 1.7:1 |
| 2 | NIS/AgOTf | DCE | rt | 2.6:1 |
| 3 | NIS/AgOTf | Et$_2$O | rt | 2.7:1 |
| 4 | NIS/AgOTf | MeCN | rt | 2.1:1 |
| 5 | NIS/AgOTf | THF | rt | 1.9:1 |
| 6 | NIS/AgOTf | 1,4-dioxane | rt | 1.4:1 |
| 7 | NIS/AgOTf | toluene | rt | 1.7:1 |
| 8 | NIS/AgOTf | toluene | 50° C. | 2.6:1 |
| 9 | NIS/AgOTf | DMF | rt | 2.6:1 |
| 10 | NIS/AgOTf | acetone | rt | 3.3:1 |

EXAMPLES

The examples herein are provided by way of illustration only and not by way of limitation. Those skilled in the art will readily recognize a variety of noncritical parameters that could be changed or modified to yield essentially similar results.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Results

CsA inhibits HBV infection. We established 4 HBV infection systems in vitro, based on HBV susceptible primary hepatocytes and hepatoma cell lines, which are Primary Tupaia hepatocyte (PTH), primary human hepatocyte (PHH), human hepatoma cell line HepaRG and HepG2-NTCP. We firstly discovered on PTH that when adding CsA into HBV infection system, the HBV infection is hindered, and the infection activity is dose dependent. Later we also found that CsA could dose dependently inhibit HBV infection on PHH and the HepaRG cell lines.

CsA blocks HBV infection at entry level. Comparing the effect of CsA (2 µM) inhibiting HBV infection at different time windows, we found that CsA significantly inhibited infection only when adding CsA at the time of virus and cells incubation, however, if cells were treated by CsA before virus inoculation or after the infection, CsA were not very effective. This result indicates that CsA inhibits HBV infection at an early stage, probably at entry level. Hepatitis D virus has the same envelop protein as HBV, and the entry step of HDV reflects the entry step of HBV. We found that CsA can also inhibit HDV infection in a dose dependent manner.

CsA interferes with HBV binding to target cell. We compared several HBV entry inhibitors (including 17B9, 2D3 and Myr-59) to CsA of their effects on HBV binding to cells. 17B9 and 2D3 are monoclonal antibodies specifically recognizing N terminal of HBV surface protein (S region and pre-S1 region, respectively). Myr-59 is a peptide consisting of 59 amino acids from HBV Large protein pre-S1 region, myristylated. The results indicate that CsA can significantly inhibit the binding between HBV and target cell, and the inhibition is dose dependent.

CsA inhibits the transporting activity of the HBV receptor NTCP. NTCP is a functional receptor for HBV and HDV infections of human hepatocyte. NTCP is a hepatic sodium/bile acid symporter presumed to span the cellular membrane up to 10 times with small extracellular loops, and taurine conjugated bile acid is its natural substrate. We therefore checked if CsA could interfere NTCP uptake of [$^3$H] labeled taurocholate acid ([H]-TCA). The results show that, comparing to the positive control—Tauroursodeoxycholic acid (TUDCA), CsA significantly inhibited NTCP uptake of [$^3$H]-TCA, with a high efficiency up to 90% at 10 µM, indicating CsA inhibits NTCP transporting activity to inhibit HBV infection.

Anti-HBV activity of CsA analogs. We demonstrated the anti-HBV activity of our CsA analogs by in vitro infection assays. The results indicate that our analogs have anti-HBV activity, many with the inhibition rates over 90% at 1 µM. Time course curves of HBV infection demonstrated that our analogs are effective at the early stages of HBV infection. In addition, many of our inhibitors demonstrated better anti-HBV activity than CsA on both HepG2-NTCP cell line and Primary human hepatocyte (PHH) infection system.

Our CsA analogs inhibit the transporting activity of the HBV receptor NTCP without inducing NTCP endocytosis. We compared CsA and representative analogs re their ability to inhibit NTCP uptake of substrates. The results showed that our analogs significantly inhibited NTCP uptake of [$^3$H]-TCA, with a much higher efficiency than CsA. We also performed pan-species tests which indicated that our analogs are able to inhibit substrate uptake of not only human NTCP, but also mouse NTCP, monkey NTCP and treeshrew NTCP, whereas CsA does not inhibit [$^3$H]-TCA uptake of human ASBT—another bile acid transporter of SLC10 family. These data indicate that CsA specifically inhibits the transporting activity of NTCP. We also stained the cells using NTCP specific antibodies after CsA analog treatments. Taurolithocholic acid (TLCA) can significantly induces NTCP endocytosis so we used TLCA here as a positive control. Our results demonstrated that our analogs do not induce NTCP endocytosis.

Immunosuppressive effect of our CsA analogs. CsA is widely used as an immuno-suppressant medication for organ transplantation to avoid rejection. Its immuno-suppressive effect is based on the interaction of the CypA-CsA complex with Calcineurin. This interaction inhibits the expression of IL-2, and consequently inhibits T cell activation. To determine if our analogs provide the immuno-suppressive potential of their prototype, we performed in vitro T cell activation assays. Briefly, spleen T cells from adult C57BL/6 mice were separated and cultured in complete RPMI-1640 medium (Thermo Fisher). The cells were stained by CFSE (Thermo Fisher) following manufacturer's guide. The cells were then cultured in 96 well plates coated by anti-CD3 antibody for 72 hours with the presence of analog and DMSO control. T cells proliferation was determined by FACS. The results indicate that, comparing to CsA prototype and DMSO control, our analogs did not significantly inhibit T cell proliferation.

CsA analogs inhibit NFAT signaling pathway with much lower potency than that of CsA prototype. Jurkat cells were cultured in complete RPMI-1640 medium (Thermo Fisher). For electroporation transfection, the cells were collected and resuspended by 100 μL Buffer R (Thermo Fisher) at a final concentration of $2\times10^7$ cells/ml and then mixed with 2 μg of pGL3-NFAT-LUC plasmid (Addgene). Electroporation transfection was carried by a Neon Transfection System (Thermo Fisher) with parameters following manufacturer's instructions. After electroporation, the cells were quickly transferred to pre-warmed complete RPMI 1640 medium without antibiotics. 24 hours after electroporation, the Jurkat cells were aliquoted into 96-well plate at a concentration of $2\times10^5$ cells/well, and then stimulated by adding 10 ng/ml PMA and 500 nM ionomycin with testing compounds. After 48 hours stimulation period, the cells were collected by centrifuge and then lysed by 20 μL of passive lysis buffer (Promega) on a shaking bed for 15 mins at RT. Luciferase intensity was checked by Centro LB960 Microplate Luminometer (Berthold Tech).

CsA analogs prevent hNTCP mice from HDV infection. HDV invasion into hepatocytes is also NTCP mediated. C57BL/6 mice expressing human NTCP can be infected by HDV, and this hNTCP-C57BL/6 provides a virus infection animal model to evaluate the drug potential of our CsA analogs. Briefly, the mice were injected 30 mg/kg analog and vehicle control each day by two days, and the mice were then challenged by $5\times10^9$ Geq HDV virus 2 hours after the second injection. The mice were sacrificed 6 days after virus challenge, and the livers were then dissected and lysed for RNA extraction. The infection level was determined by qPCR of HDV genome. The result indicates that, compared to vehicle, analog treatments significantly decreased HDV RNA level in mice liver without disturbing the expression of NTCP.

Our CsA analogs/NTCP inhibitors ameliorate liver damage, hepatic inflammation induced by methionine-choline deficient diet in mice. HBV entry into hepatocytes via its receptor NTCP, limited its function of NTCP and thus promoted compensatory BA synthesis and cholesterol provision (9). This result underlines the importance to exploit the possible effects of NTCP inhibition on metabolic benefits. Here, we used our NTCP inhibitors to evaluate their effects on the development of nonalcoholic steatohepatitis (NASH) mouse model induced by methionine-choline deficient (MCD) diet. During the experiments, we monitored food intake and found no difference between MCD/vehicle group and MCD/analog group. Results at end point demonstrated that intervention with representative inhibitors resulted in significant reduction in serum liver functional enzyme ALT activity, indicating the less liver damage. As expected, the level of total bile acids in serum increased significantly. Additionally, liver inflammation was less severe than with MCD control diets.

Our NTCP inhibitors lower serum cholesterol and triglyceride in apoE$^{-/-}$ mice fed a high-fat (45%) diet. We also tested the effects of our NTCP inhibitors in apoE$^{-/-}$ mice fed a high-fat (45%) diet. Male apoE$^{-/-}$ mice (10) (8-10 weeks) were purchased from Beijing Huafukang Bioscience Co. Inc. Mice were divided into 2 experimental groups: (1) vehicle (0.9% saline) once daily i.p. for 8 weeks, or (2) 20 mg/kg inhibitor in vehicle once daily i.p. for 8 weeks. During the study, treatment with representative inhibitors significantly lowered average sera total cholesterol levels and triglyceride levels. As expected, the level of total bile acids in serum increased significantly.

Our NTCP inhibitors lower blood glucose and ameliorate the fatty liver in ob/ob mice. We also tested the effects of our NTCP inhibitors in ob/ob mice with oral administration of the inhibitors. Male ob/ob mice (8-10 weeks) were purchased from Beijing Huafukang Bioscience Co. Inc. Mice were divided into 2 experimental groups: (1) orally chow diet for 2 weeks, or (2) 30 mg inhibitor per kilogram chow diet for 2 weeks. At the end point, oral glucose tolerance test (OGTT) were conducted. 30% sucrose was orally administrated with the dose of 2 g/kg. Results of OGTT demonstrated that treatment with representative inhibitors significantly lowered average sera total glucose levels. Also, results of oil red 0 staining demonstrated that the fat accumulation in liver decreased in CsA-analog treated ob/ob mice. As expected, the level of total bile acids in serum increased significantly.

Methods

HBV and HDV infection assay. HBV and HDV infection assays were performed in 96 well plates. Briefly, PHH, PTH and HepG2-NTCP cells were cultured in PMM for 24 hours to induce NTCP expression. HBV and HDV virus were harvested from the culture medium of transfected Huh-7 cells. To infect cells with virus, the virus-containing medium was mixed with PEG at a final concentration of 5%, and then mixed with DMSO or compounds to be tested. The mixture was then applied to the cells for 24 hours at 37° C. The virus was then removed and fresh medium was added to the cells for every two days. The culture medium from dpi3-dpi5 was collected for HBeAg and HBsAg determination by commercial ELISA kits followed by manufacturer's guide.

[$^3$H]-TCA uptake assay. PTH and HepG2-NTCP cells were cultured in PMM for 24 hours to induce NTCP expression. After treated by DMSO or test compounds for 2 hours, the cells were then incubated with 1 μM [$^3$H]-taurocholate acid dissolved in Na$^+$ Ringer's buffer (the concentration of Na was 145 mM) for 15 minutes at 37° C. Subsequently, the cells were washed once in phosphate-buffered saline (PBS) and lysed in 50 μL 1% TritonX-100 in H$_2$O for 5 minutes at room temperature. The lysate were totally transferred into a liquid scintillation 96 well plate and mixed with 200 μL liquid scintillation cocktail (Ultima Gold XR, PerkinElmer). Liquid scintillation counting was performed on a PerkinElmer 1450 LSC liquid scintillation counter.

T cell activation assay. The spleen T cells were separated from adutC57BL/6 mouse spleen. Red blood cells were lysated by Red blood cell lysis buffer (Sigma). T cells were separated by FACS using specific anti-mouse CD3 antibody. The T cells were then stained with CFSE (Thermo Fisher) to monitor its proliferation. To activate T cell proliferation, $1\times10^5$ cells were plated in a single well of a 96 well plate coated with anti-mouse CD3 antibody. Cells were cultured in complete RPMI-1640 medium with or without tested compounds for 72 hours and analyzed again by FACS.

HDV infection of mice and quantification of HDV RNA assay. The C57-hNTCP-mice were intraperitoneal (i.p.) injected 30 mg/kg CsA-analog or vehicle for 2 days. HDV challenge was performed 2 hours after the second injection. Mice were sacrificed 6 days after virus challenge, and the livers were then dissected and lysed for RNA extraction. HDV RNA and NTCP RNA expression level was determined by qPCR using GAPDH as a reference. A standard curve is also applied to calculate the copy numbers of HDV RNA and NTCP RNA.

Evaluation the effects of CsA-analogs on MCD-diet induced NASH model. Male wild-type C57BL/6J mice were purchased from Beijing Vital River Laboratory Animal Technology Co., Ltd and used to establish the NASH model with MCD diets at age 8-10 wks. Before MCD diet induction, blood collection to analyze the liver function. After 1 week of adaption of MCD diet, mice were divided into 3 experimental groups: (1) normal diet; (2) MCD diet, vehicle (0.9% saline) once daily i.p. for 4 weeks; (3) MCD diet, 20 mg/kg inhibitor in vehicle once daily i.p. for 4 weeks. n=5-6/group. At the end of experiments, mice were sacrificed and blood and livers were collected for pathologic evaluation.

Hematoxylin and eosin staining. Liver tissues were fixed in 4% paraformaldehyde overnight and embedded with paraffin. The embedded liver tissues were cut into 5 μm sections, stained in hematoxylin for 5 minutes, and then blued in 0.3% ammonia water.

Oral glucose tolerance test. Oral glucose tolerance test (OGTT) was assessed after 8 weeks of treatment with inhibitor. Male obob mice were fasted for 4-6 h, and the tests were carried out at 1:30 p.m. Glucose (2 mg/g body weight) was administered via an oral gavage. Blood samples were drawn from the tail vein at 0, 15, 30, 60, and 120 min after glucose administration. Blood glucose levels were measured using a portable glucometer (Accu-check Active, Roche).

Applications.

The disclosed compounds and composition provide virus entry inhibitors, useful for the prevention of new infection and treatment for chronic infection. Additional indications include:

To prevent vertical transmission. Vertical transmission from pregnant women to infants is a main route of transmission in HBV highly epidemic area, especially in Middle Africa and East Asia. Almost 50% of HBV chronic infections are from maternal-neonatal transmission. Current protocol to control vertical transmission is anti-viral treatment for pregnant women before labor and injection of Hepatitis B immunoglobulin (HBIG) and HBV vaccine to neonate within 12 days after birth. By administration of HBIG to neonates labored by an HBeAg positive mother, the vertical transmission chance can be lower down from 90% to 26%. The primary effect of HBIG is to block HBV entry into hepatocytes. Our inhibitors similarly block HBV infection and are applicable to HBV positive pregnant women and their neonates to prevent HBV vertical transmission.

To prevent HBV horizontal transmission. HBV vaccination has been introduced world wide; however, coverage is limited, and 5-10% population has no response to HBV vaccine. Our inhibitors provide a treatment options for these large HBV susceptible populations. Our inhibitors can also be used to prevent HBV horizontal transmission in susceptible populations, including: for HBV susceptible individuals accidentally contacted to HBV, the inhibitors provide emergency prevention after exposure, and for HBV susceptible individuals in intimate contact to HBV carriers, the inhibitors can be used to prevent horizontal transmission.

To prevent HBV relapse after liver transplantation. Preventing HBV relapse after liver transplantation requires long term, high dose HBIG, which is a major cost of transplantation. Our inhibitors have much lower manufacturing cost and provide a cost-effective substitute for HBIG to prevent HBV relapse after liver transplantation.

To treat HBV chronic infection. There are about 240 million chronic HBV infections worldwide. Providing chronic HBV pregnant women HBIG before labor can lower down HBV DNA load by 2 order of magnitude. HBV entry inhibitor Myrcludex B was able to protect animals that were already HBV infected, by blocking the virus spread in the liver. Our inhibitors are also HBV entry inhibitors and provide effective treatments for chronic HBV infection.

To treat HDV infection. HDV has a similar mechanism to invade target cells with HBV. The entry step of HDV is also NTCP mediated. Our inhibitors efficiently blocked HDV infection in both cell and animal models.

To ameliorate hepatocyte damage, hepatic inflammation in liver diseases. NTCP is involved in the inflammation of cholestasis via transport of bile acids into hepatocytes, which in turn release cytokines to recruit lymphocytes to initiate inflammatory responses(11). NTCP inhibition can be used to suppress the inflammatory responses and thus the liver damage. As demonstrated herein, our inhibitors ameliorated liver damage and inhibited hepatic inflammation.

To lower circulation levels of cholesterol and triglyceride in metabolic diseases. Functional inhibition of NTCP by HBV infection can promote compensatory BA synthesis and cholesterol provision (9). Bile acid synthesis is a major pathway for hepatic cholesterol catabolism, and increased bile acid synthesis lowers the level of circulating cholesterol. Treatment with our NTCP inhibitors significantly decreased cholesterol and triglyceride levels.

To ameliorate the glucose intolerance for treatment of diabetes. The bile acid receptor TGR5 (also known as GPBAR1) is a target for the development of pharmacological interventions in T2DM (12). Bile acids stimulate glucagon-like peptide 1 (GLP1) production in the distal small bowel and colon, stimulating insulin secretion (13). The increased BAs level (also the proportion of BAs) after treatment with our inhibitors provides benefits for diabetes patients.

To ameliorate fatty liver. In obese rodents with fatty liver, bile acid sinusoidal transport is preserved and canalicular bile acid transport reduced, resulting in mild cholestasis (14). Consistently, hepatic overexpression of bile salt export pump (BSEP) prevents hepatic lipid accumulation in mice (15). Inhibition of NTCP can achieve the same effect as BSEP overexpression. Treatment of obob mice with our inhibitors also provided the reduction of lipid droplets examined with Oil Red O staining.

To prevent the hepatocarcinogenesis. NTCP variant rs2296651 (Ser267Phe) is reported to inversely associate with chronic hepatitis B and progression to cirrhosis and hepatocellular carcinoma in patients with chronic hepatitis B (HBV) (4). In a long-term experiment of evaluating toxic effects of our NTCP inhibitors, we determined that control mice all developed macroscopically liver tumors, however, all representative inhibitor-treated mice did not.

REFERENCES

1. Chiang J Y. Recent advances in understanding bile acid homeostasis. F1000Res 2017; 6:2029.
2. Arab J P, Karpen S J, Dawson P A, Arrese M, Trauner M. Bile acids and nonalcoholic fatty liver disease: Molecular insights and therapeutic perspectives. Hepatology 2017; 65:350-362.
3. Yan H, et al. Sodium taurocholate cotransporting polypeptide is a functional receptor for human hepatitis B and D virus. eLife 2012; 1.
4. Hu H H, et al. The rs2296651 (S267F) variant on NTCP (SLC10 A1) is inversely associated with chronic hepatitis B and progression to cirrhosis and hepatocellular carcinoma in patients with chronic hepatitis B. Gut 2016; 65:1514-1521.

5. Qiu et al. Sodium taurocholate cotransporting polypeptide (NTCP) deficiency: Identification of a novel SLC10 A1 mutation in two unrelated infants presenting with neonatal indirect hyperbilirubinemia and remarkable hypercholanemia. Oncotarget 2017; 8:106598-106607.
6. Slijepcevic D, Kaufman C, Wichers C G Gilglioni E H, Lempp F A, Duijst S, de Waart D R, et al. Impaired uptake of conjugated bile acids and hepatitis b virus presl-binding in na(+)-taurocholate cotransporting polypeptide knockout mice. Hepatology 2015:62:207-219.
7. Vaz F M, et al. Sodium taurocholate cotransporting polypeptide (SLC10 A1) deficiency: conjugated hypercholanemia without a clear clinical phenotype. Hepatology 2015; 61:260-267.
8. Slijepcevic D, van de Graaf S F. Bile Acid Uptake Transporters as Targets for Therapy.
Dig Dis 2017; 35:251-258.
9. Oehler N, et al. Binding of hepatitis B virus to its cellular receptor alters the expression profile of genes of bile acid metabolism. Hepatology 2014; 60:1483-1493.
10. Zhang S H, Reddick R L, Piedrahita J A, Maeda N. Spontaneous hypercholesterolemia and arterial lesions in mice lacking apolipoprotein E. Science 1992; 258:468-471.
11. Cai S Y, Ouyang X, Chen Y, Soroka C J, Wang J, Mennone A, Wang Y, et al. Bile acids initiate cholestatic liver injury by triggering a hepatocyte-specific inflammatory response. JCI Insight 2017; 2:e90780.
12. van Nierop F S, et al. Clinical relevance of the bile acid receptor TGR5 in metabolism.
Lancet Diabetes Endocrinol 2017; 5:224-233.
13. Tomkin G H, Owens D. Obesity diabetes and the role of bile acids in metabolism. J Transl Int Med 2016; 4:73-80.
14. Pizarro M, et al. Bile secretory function in the obese Zucker rat: evidence of cholestasis and altered canalicular transport function. Gut 2004; 53:1837-1843.
15. Figge A, et al. Hepatic overexpression of murine Abcb11 increases hepatobiliary lipid secretion and reduces hepatic steatosis. J Biol Chem 2004; 279:2790-2799.

The invention claimed is:
1. A compound of formula:

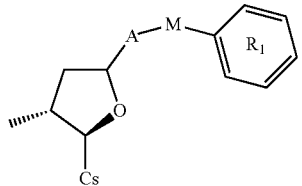

wherein:
A is O or S;
M is an optionally substituted methylene bridge, or a bond;
R1 is optionally substituted phenyl; and
Cs is cyclosporine A at position 1; or
a composition, stereoisomer, hydrate or salt thereof.
2. The compound of claim 1 wherein M is a bond.
3. The compound of claim 1 wherein M is an optionally substituted methylene bridge.
4. The compound of claim 1 wherein M is a substituted or unsubstituted methyl-substituted methylene bridge, wherein the methyl substituents are selected from halogen and an H isotope.

5. The compound of claim 1 wherein A is O.
6. The compound of claim 1 wherein A is S.
7. The compound of claim 1 wherein R1 comprises at ortho positions, independently, H, halogen, OH, Me or OMe, and at meta and para positions, independently, H, halogen, C1-C4 alkyl, C1-C4 alkyloxy or a substituent selected from:

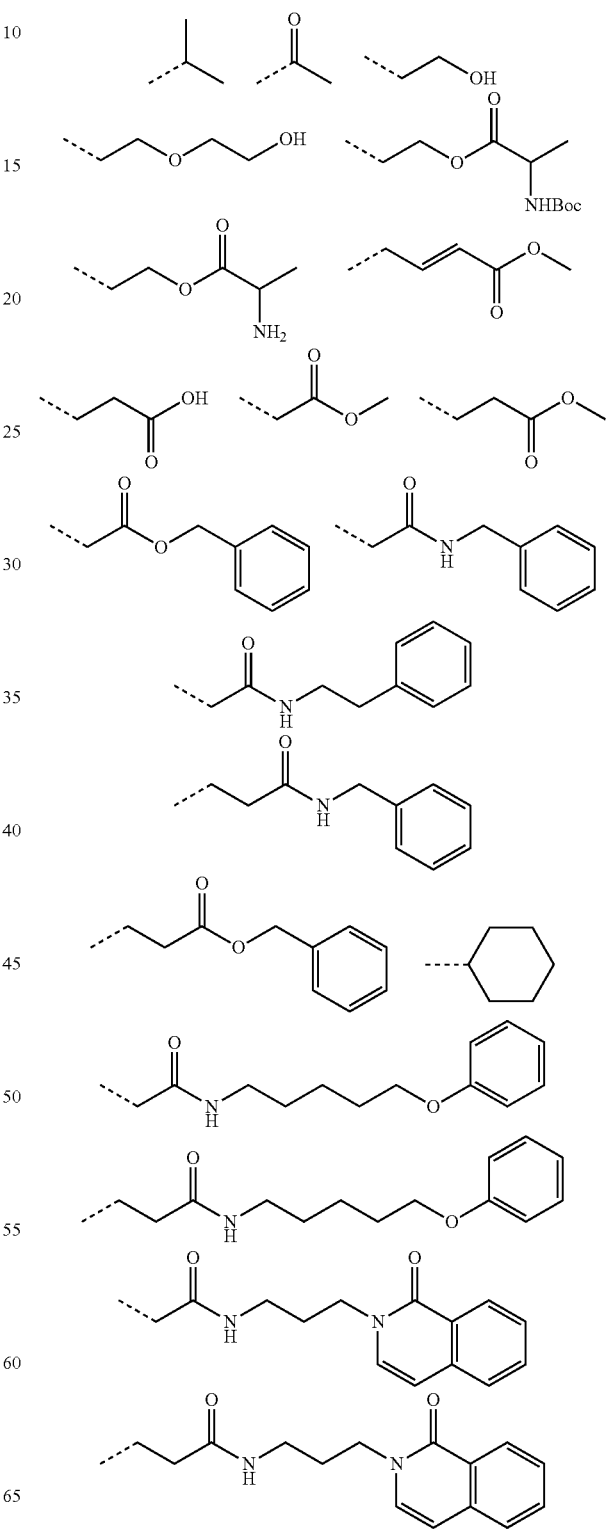

167
-continued
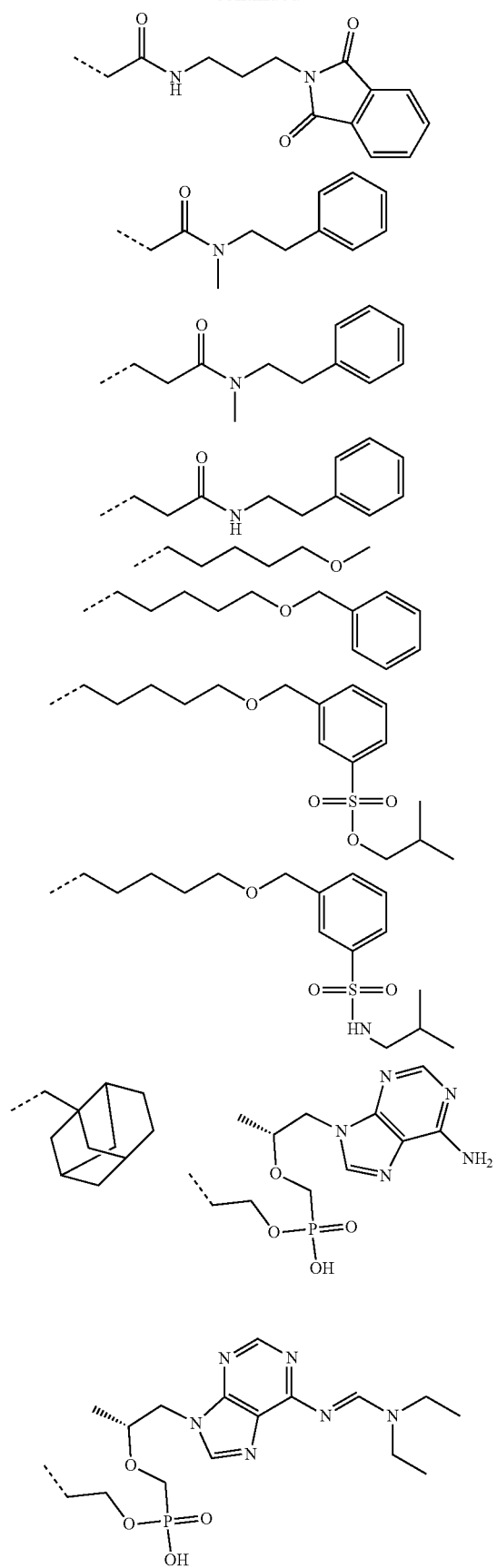
168
-continued
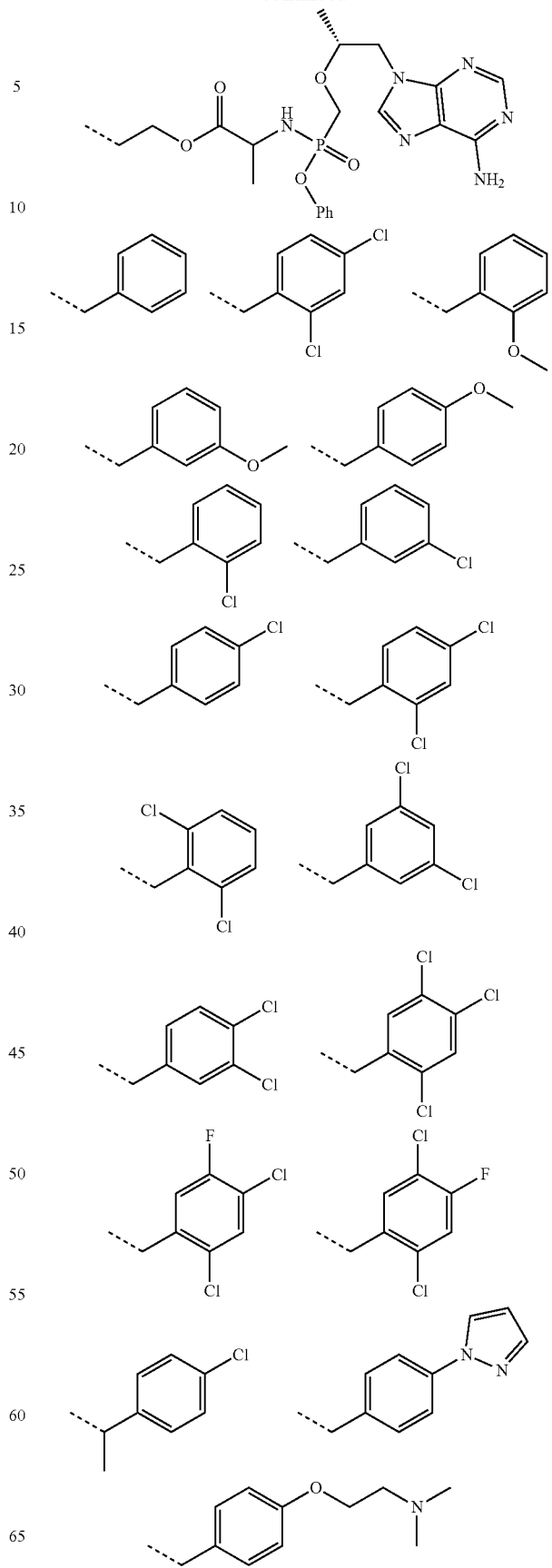

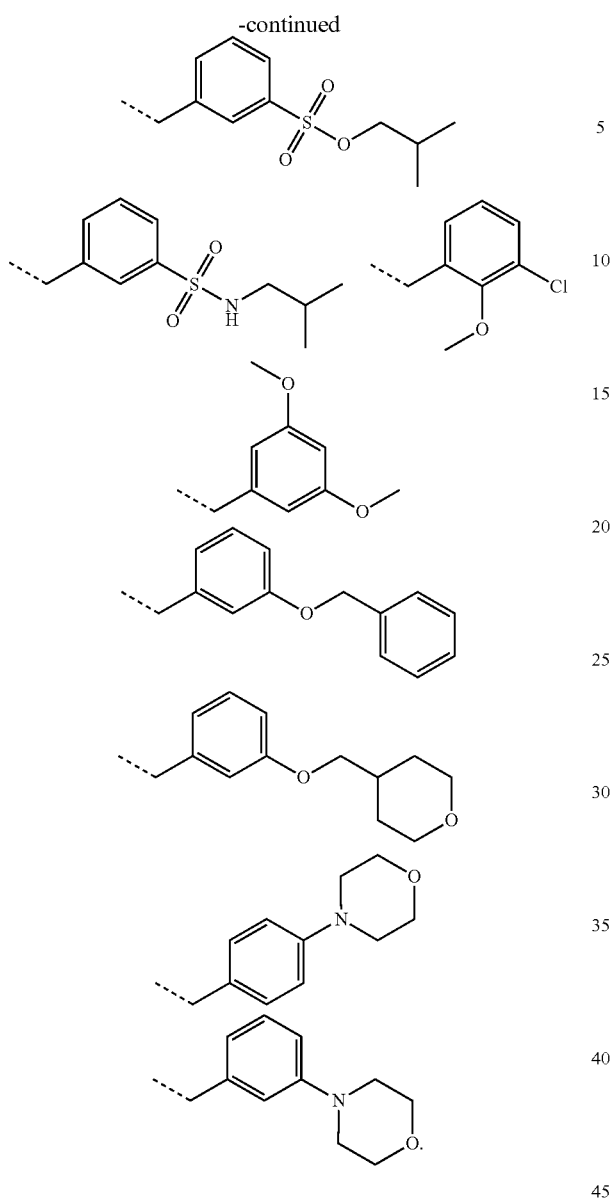

8. The compound of claim 7 wherein M is a bond.

9. The compound of claim 7 wherein M is an optionally substituted methylene bridge.

10. The compound of claim 7 wherein M is a substituted or unsubstituted methyl-substituted methylene bridge, wherein the methyl substituents are selected from halogen and an H isotope.

11. The compound of claim 1 having a phenylthiol structure selected from Table 1:

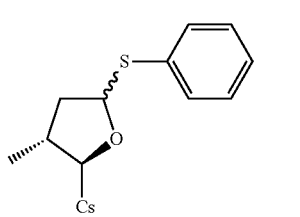

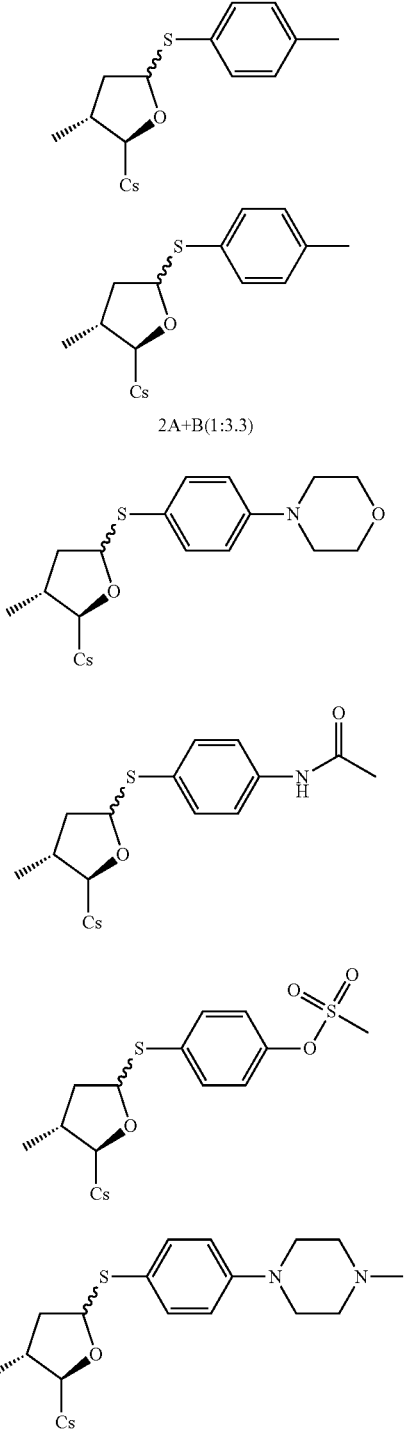

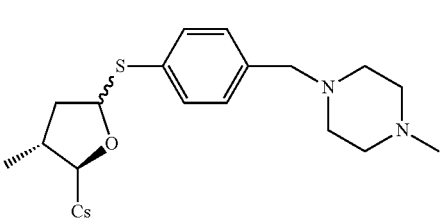

8A
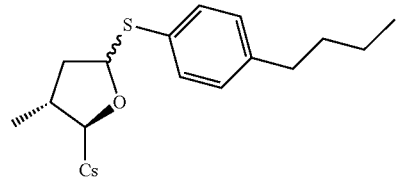
9A
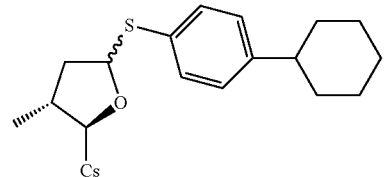
10A
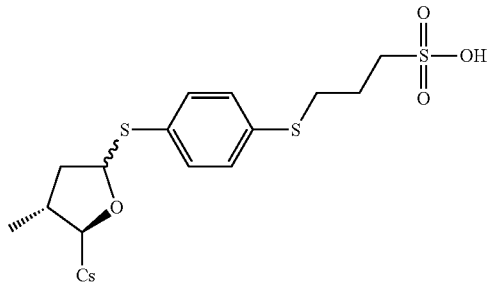
11
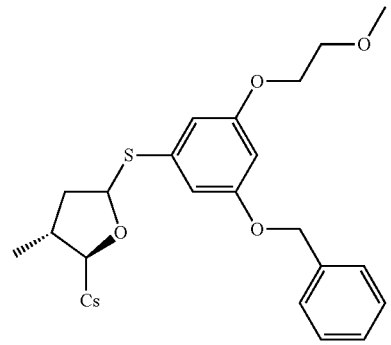
12A
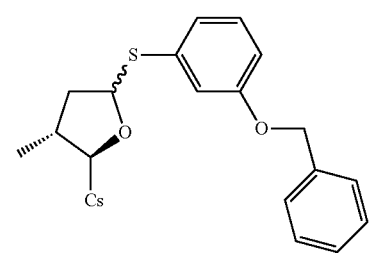
12B
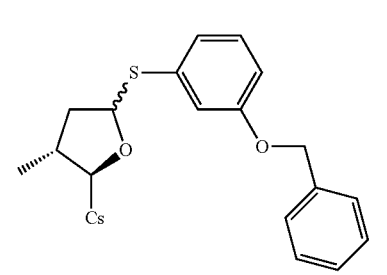
13A
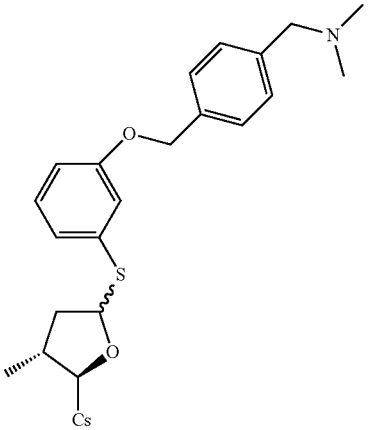
14A
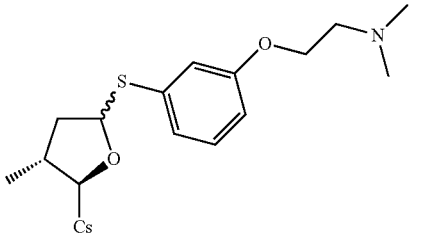
15A
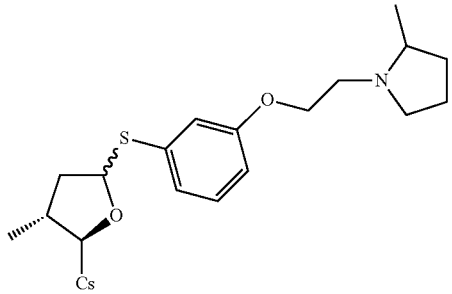
16A
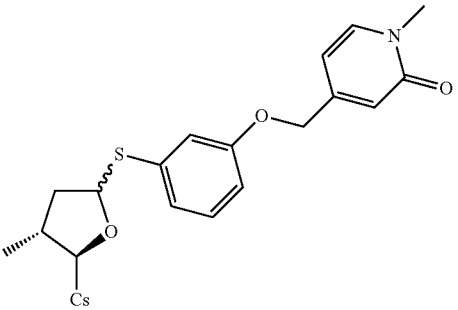

17A
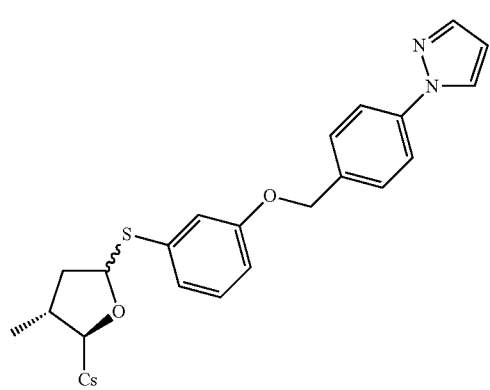
18A
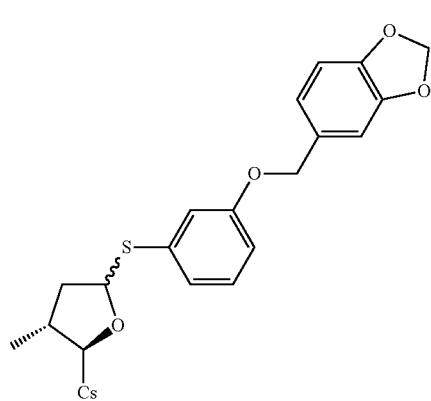
19A
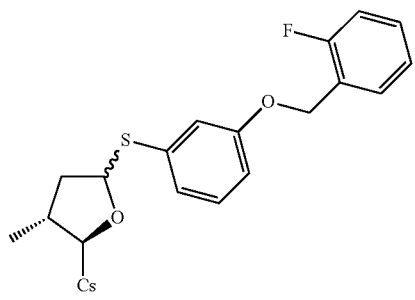
20A
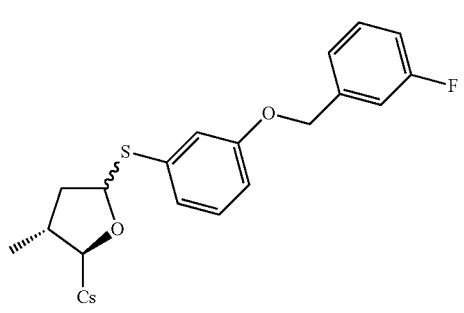
21A
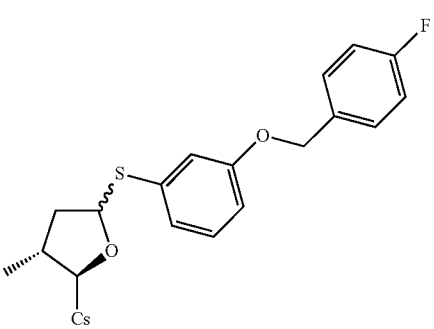
22A
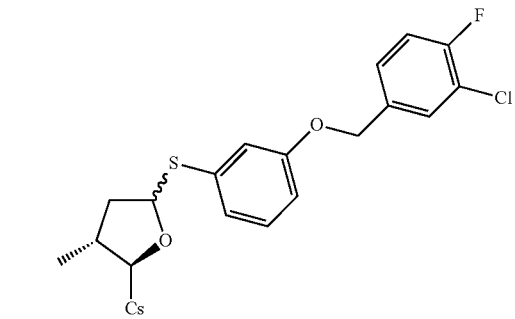
23A
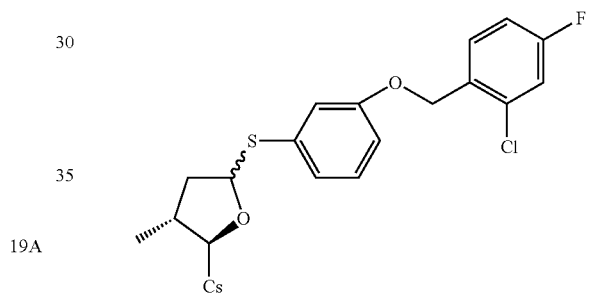
24A
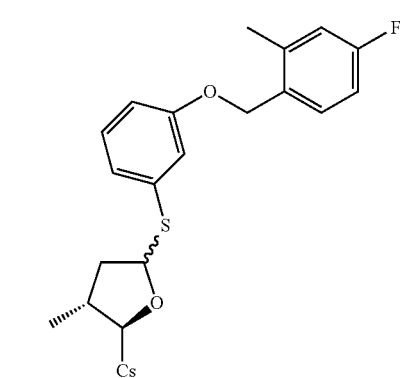
25A
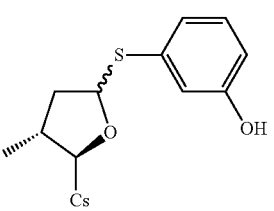

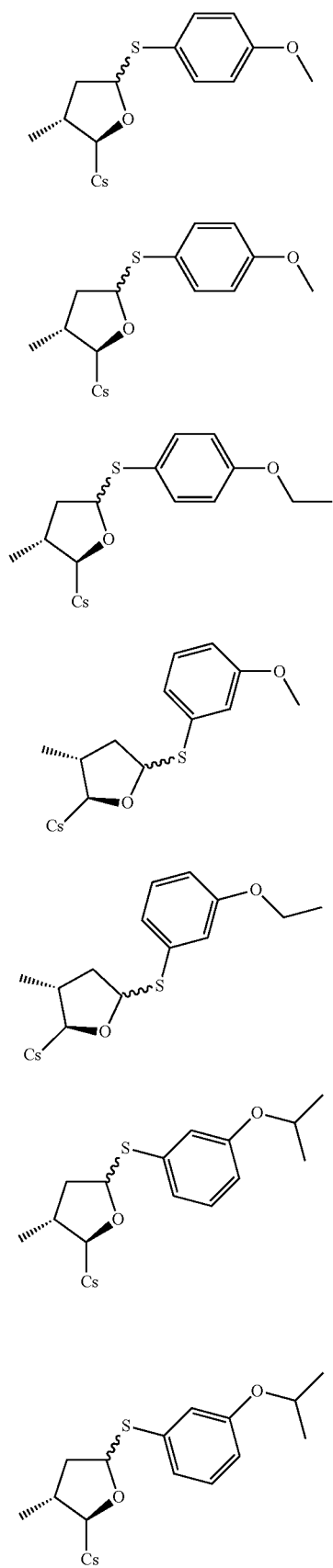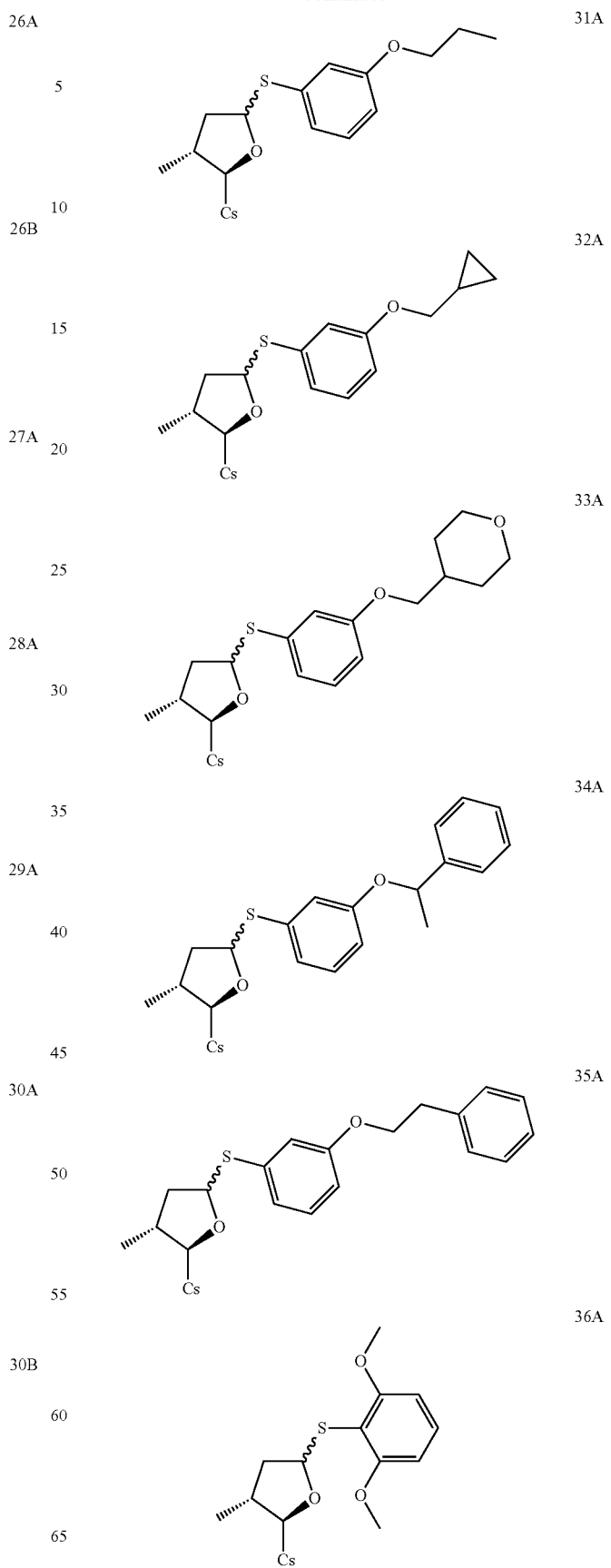

37A 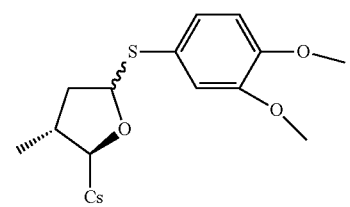
38A 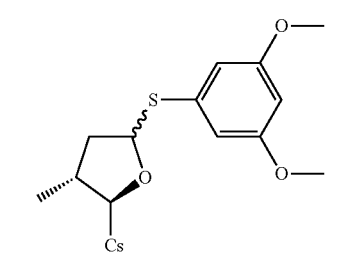
39A 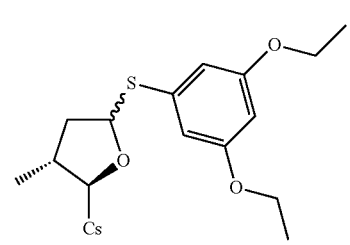
40A 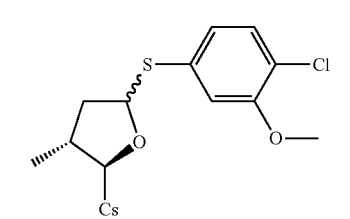
41A 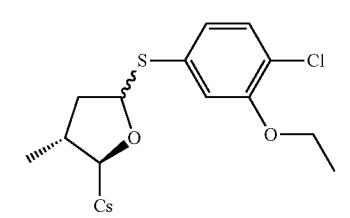
42A 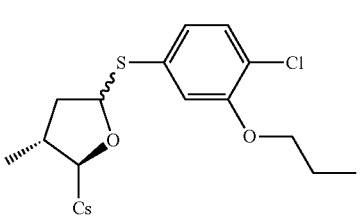
43A 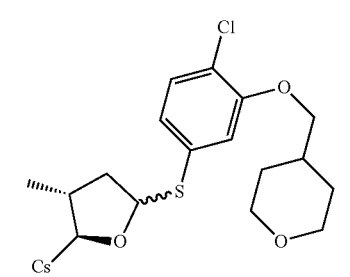
44A 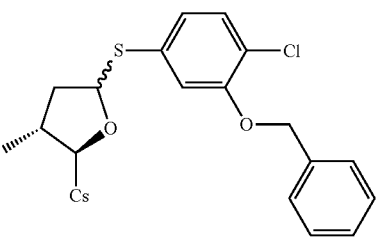
45A 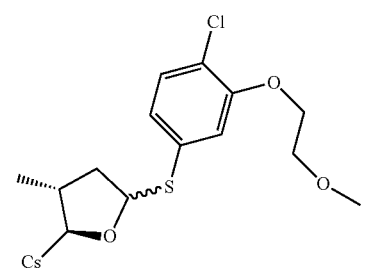
46A 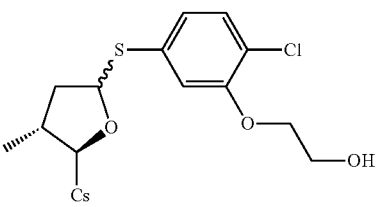
47A 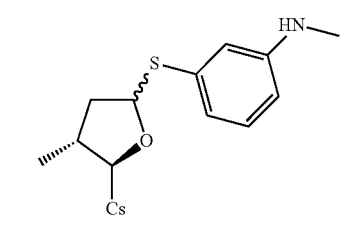
48A 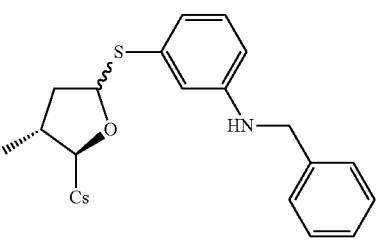
49A

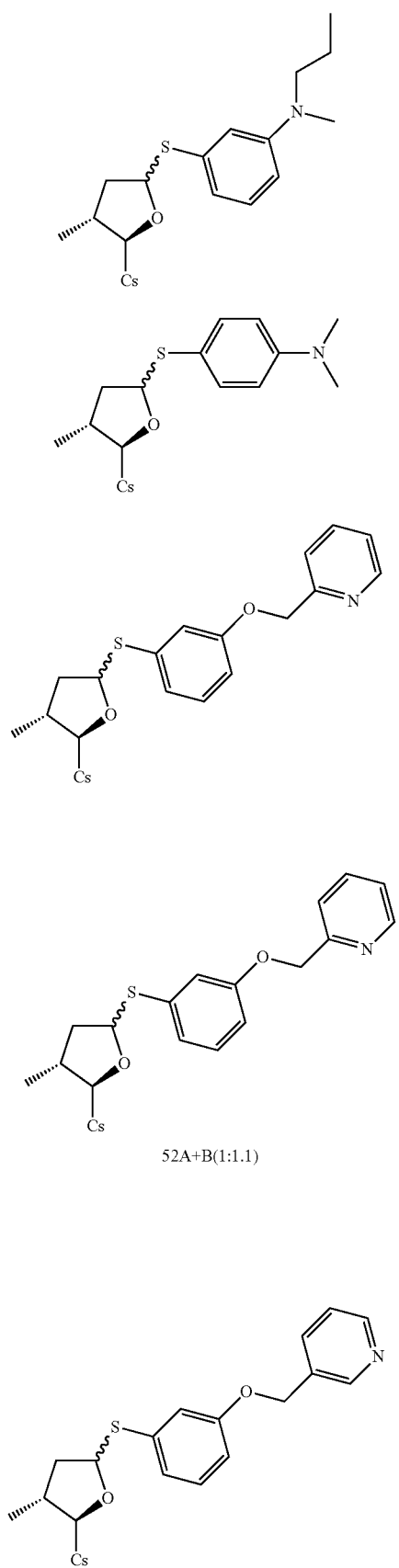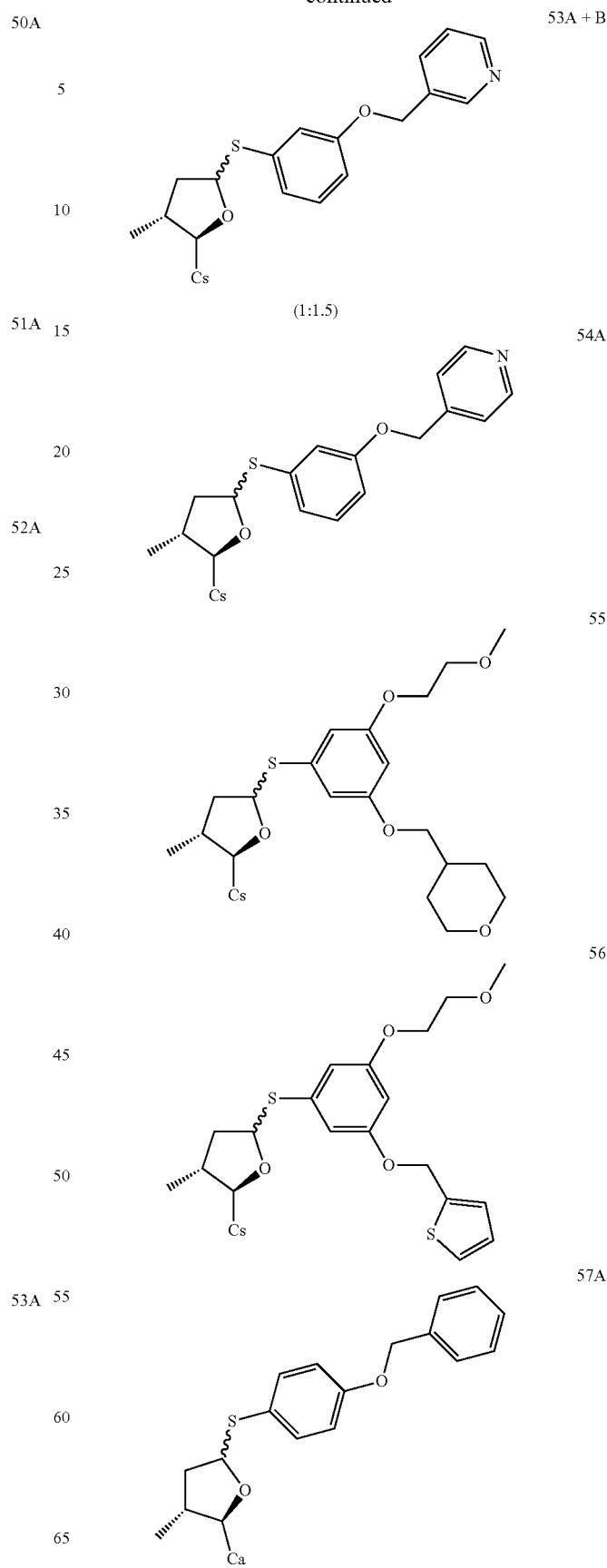

-continued
58A
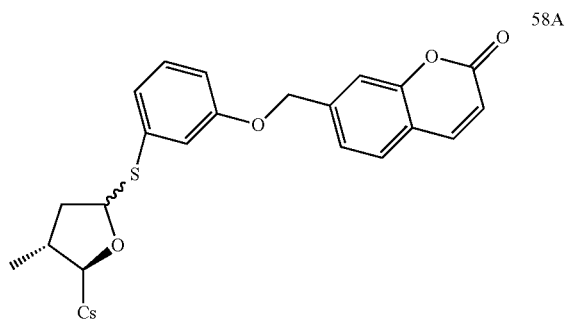
59A
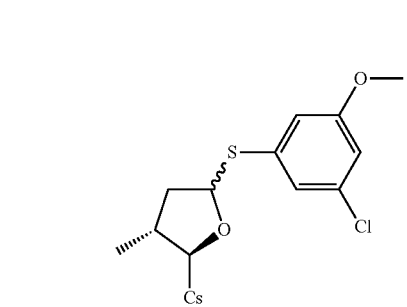
60A
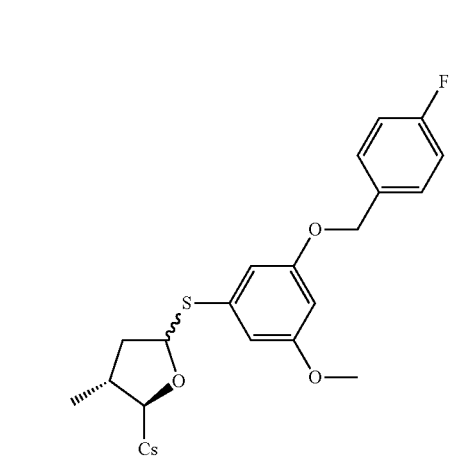
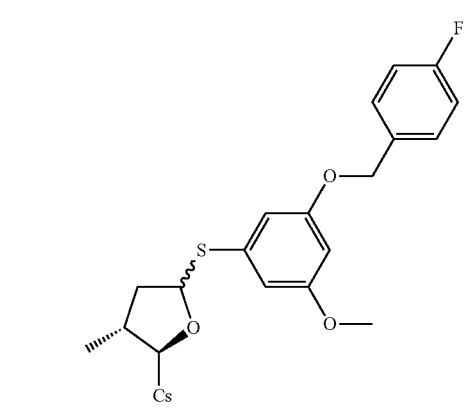
60A+B(1:1.4)
-continued
61A
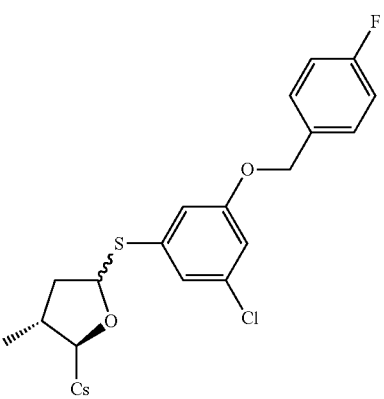
62
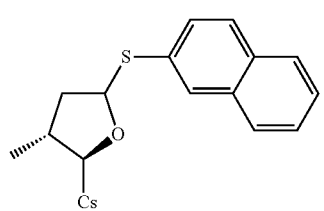
63
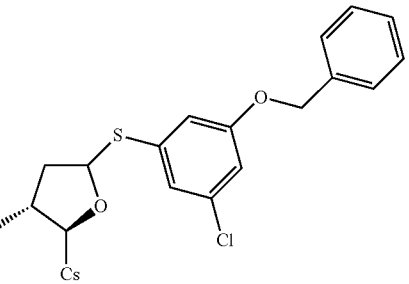
64
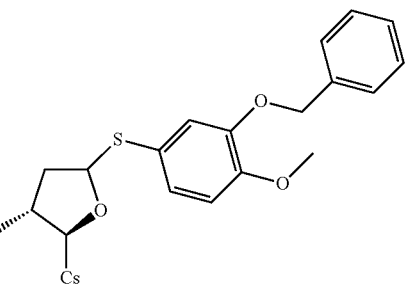
65
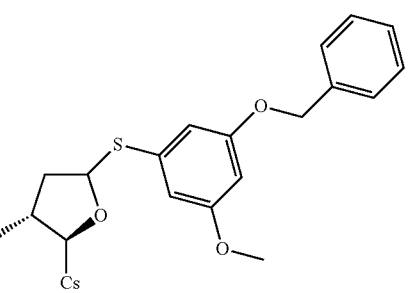

-continued
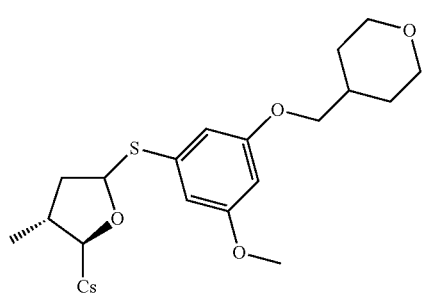
66
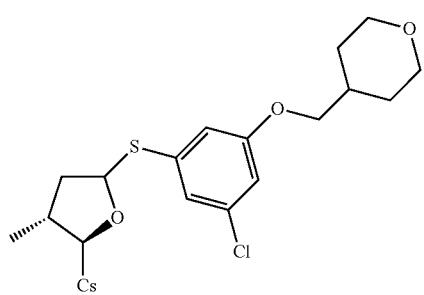
67
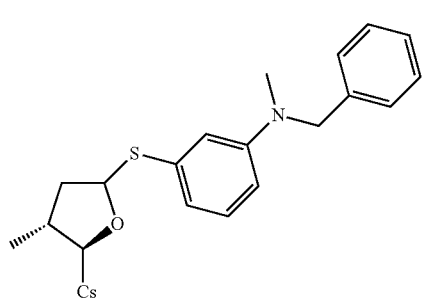
68
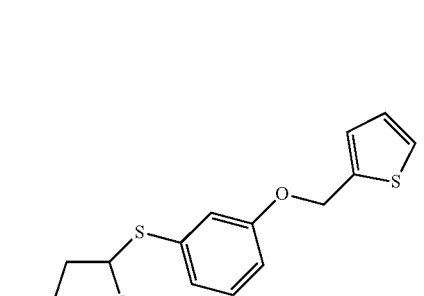
69
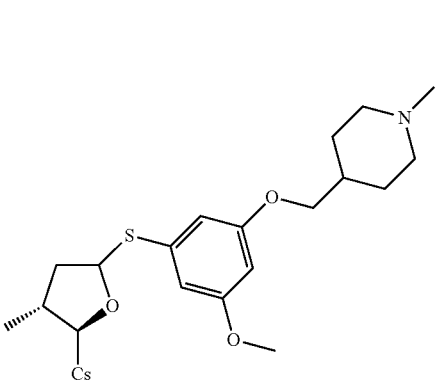
70
-continued
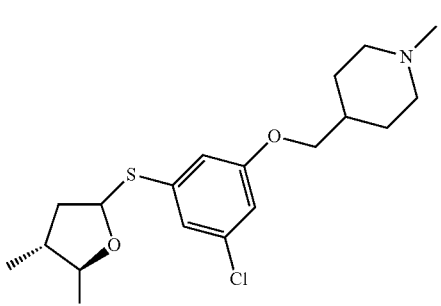
71
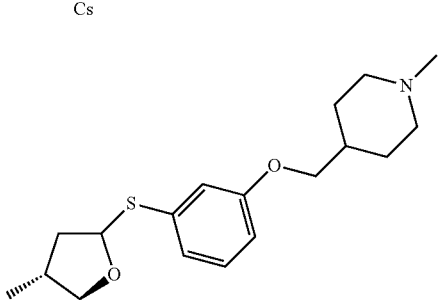
72
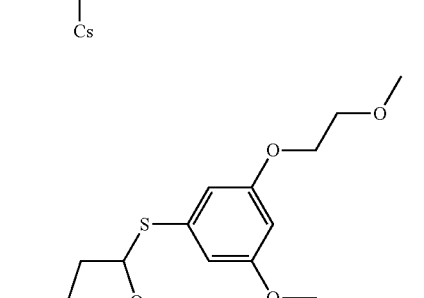
73
12. The compound of claim 1 having a phenyloxy structure selected from Table 2:
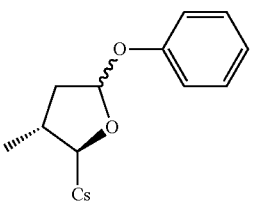
1B-o
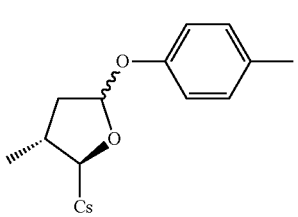
2A-o

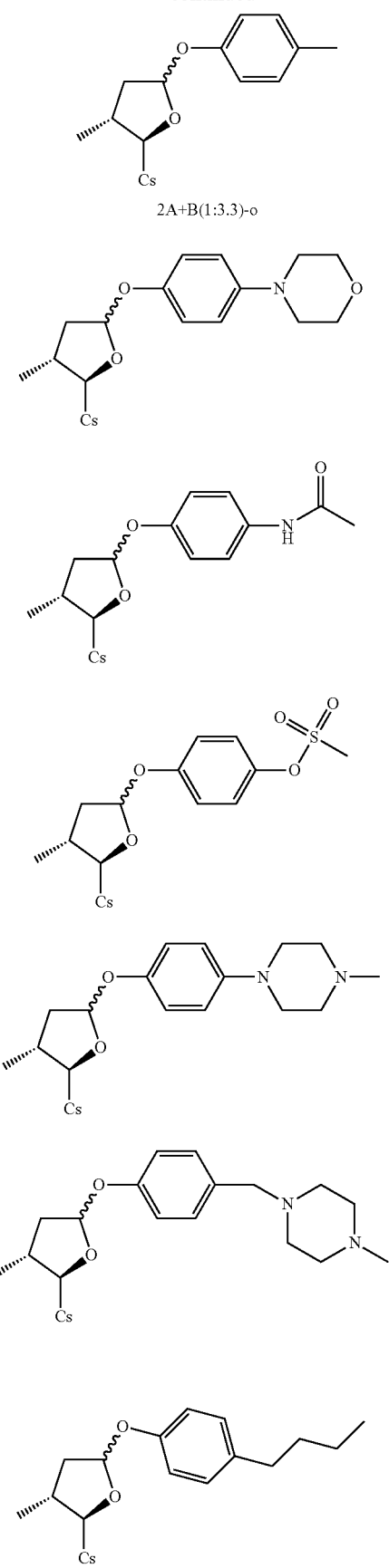

13A-o
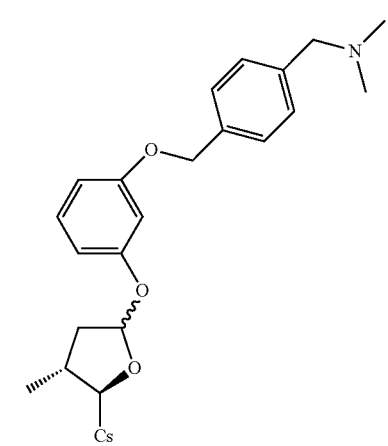
14A-o
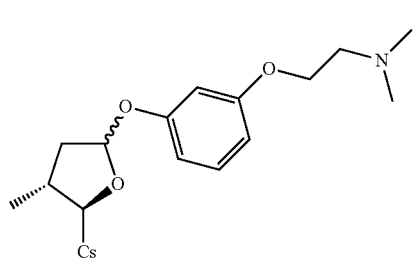
15A-o
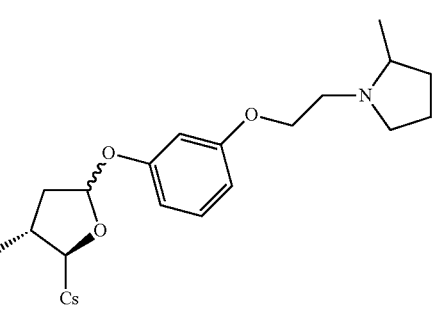
16A-o
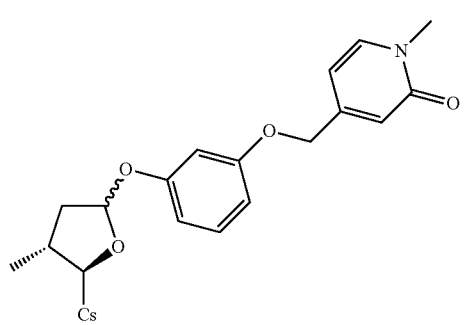
17A-o
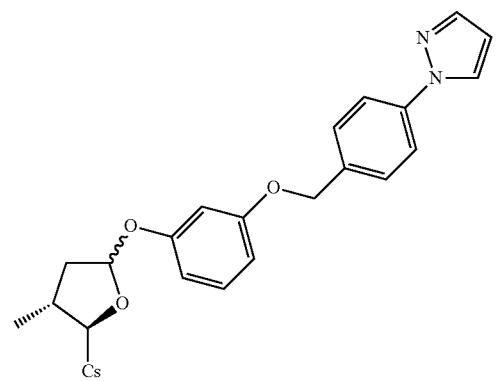
18A-o
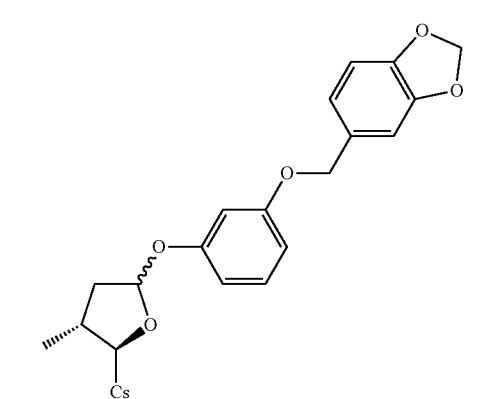
19A-o
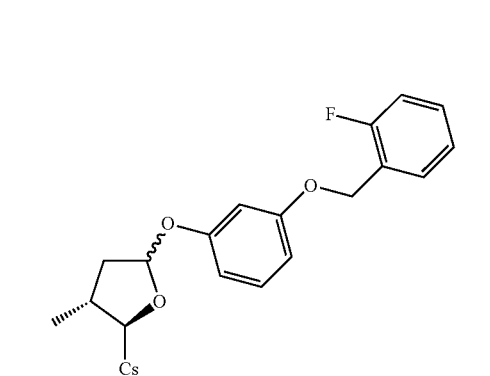
20A-o
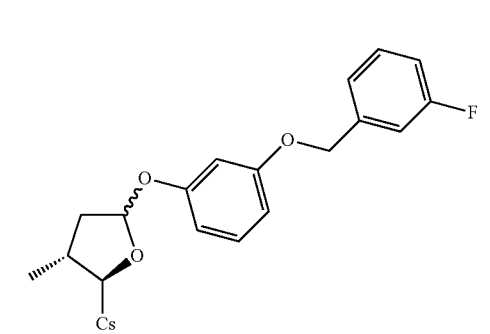

21A-o
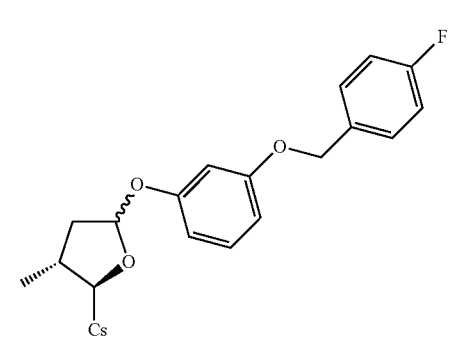
22A-o
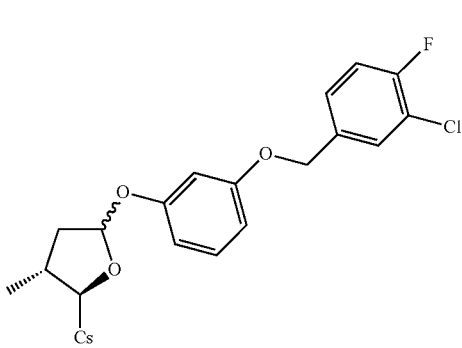
23A-o
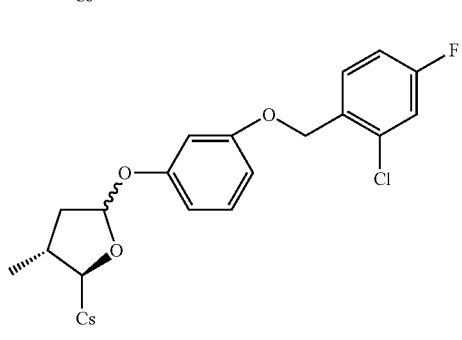
24A-o
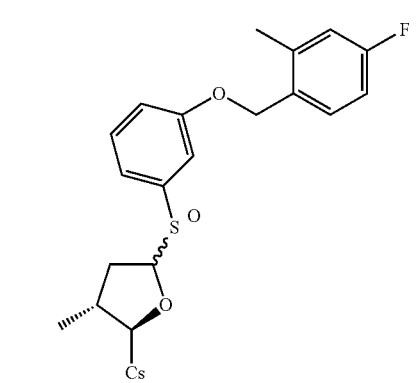
25A-o
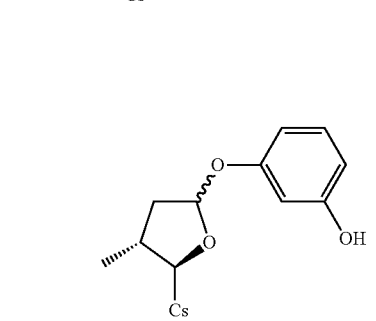
26A-o
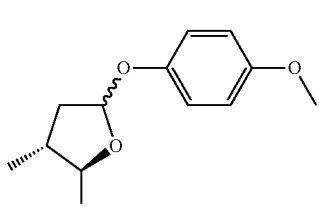
26B-o
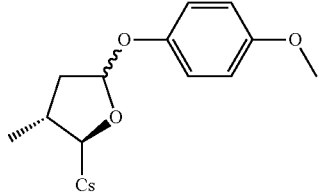
27A-o
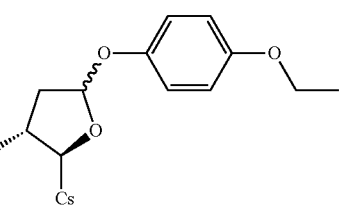
28A-o
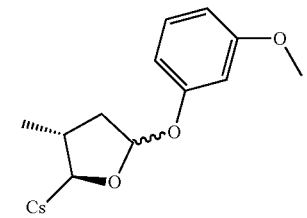
29A-o
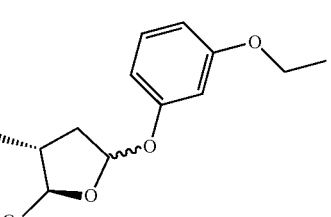
30A-o
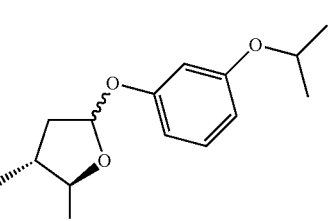
30B-o 31A-o 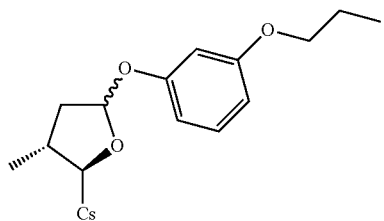
32A-o 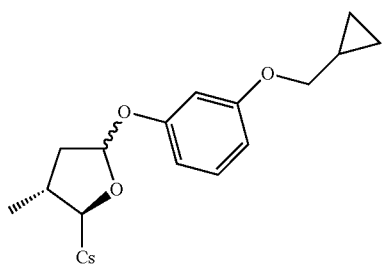
33A-o 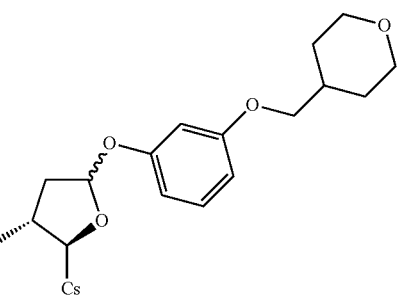
34A-o 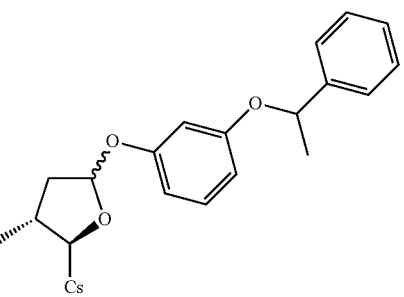
35A-o 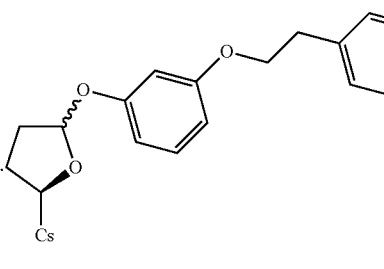
36A-o 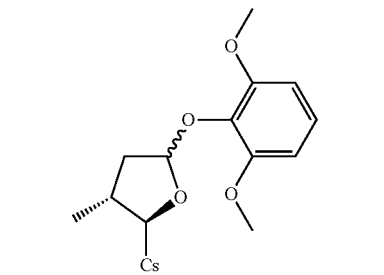
37A-o 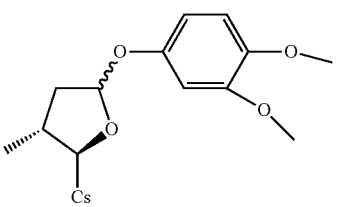
38A-o 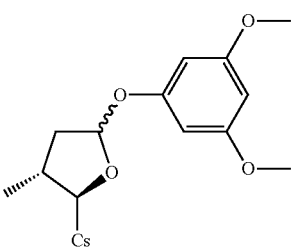
39A-o 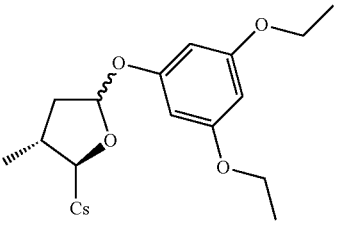
40A-o 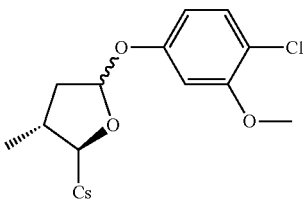
41A-o 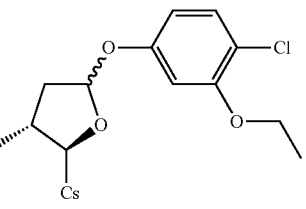
42A-o 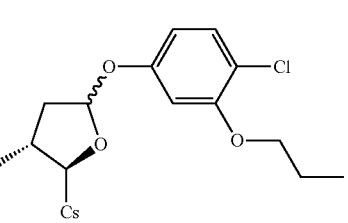
43A-o 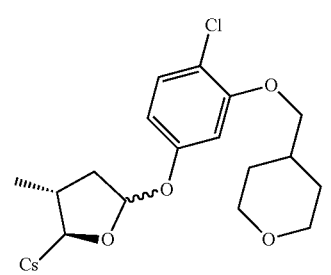

44A-o
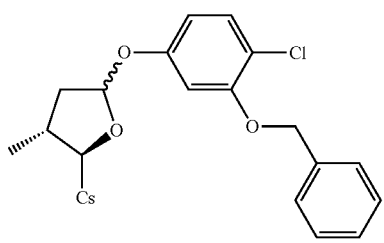
45A-o
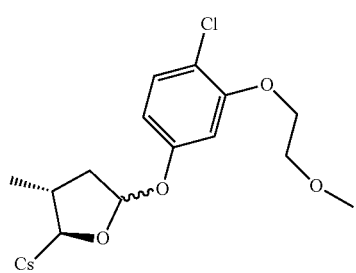
46A-o
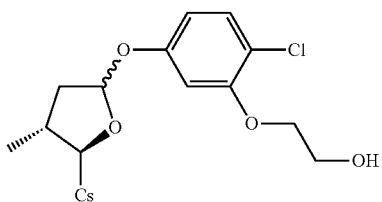
47A-o
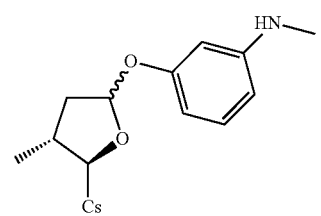
48A-o
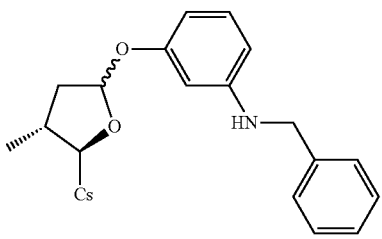
49A-o
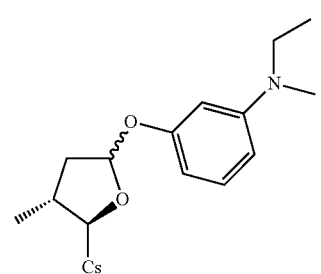
50A-o
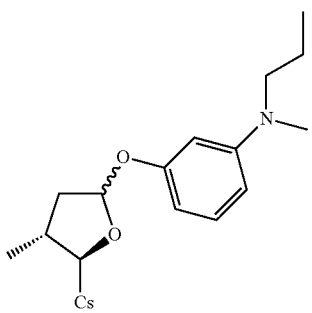
51A-o
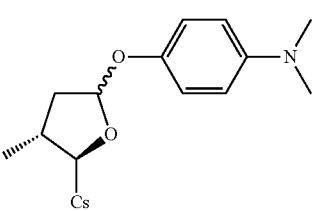
52A-o
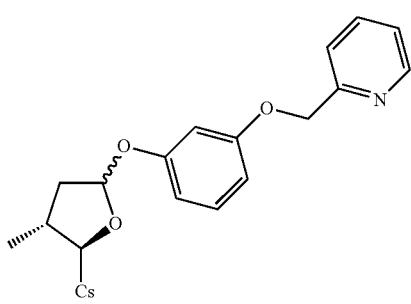
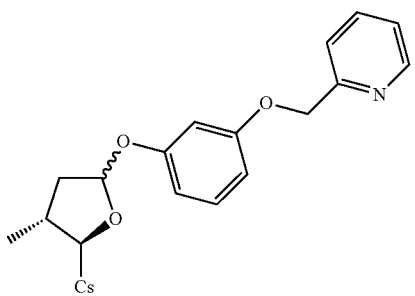
52A+B(1:1.1)-o
53A-o
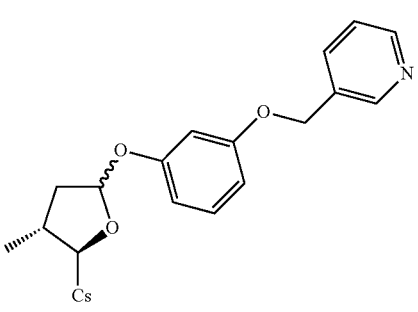

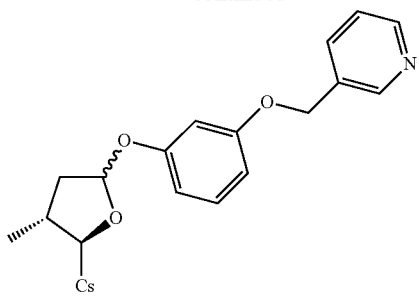
53A+B(1:1.5)-o
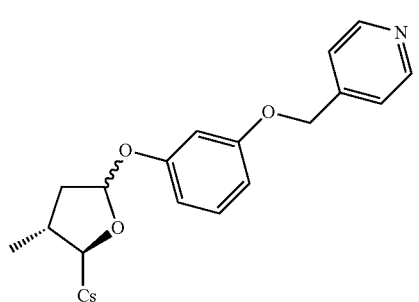
54A-o
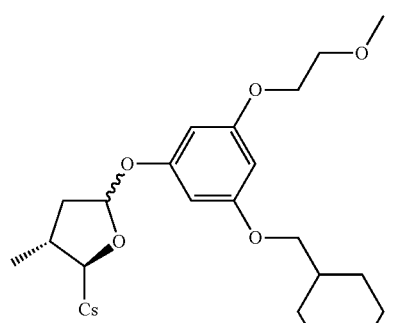
55-o
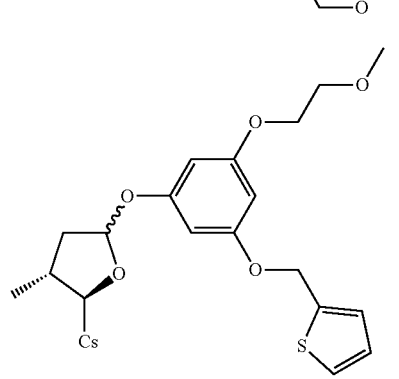
56-o
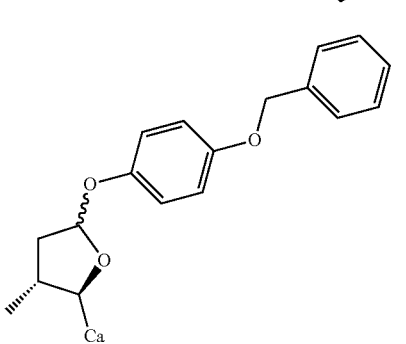
57A-o
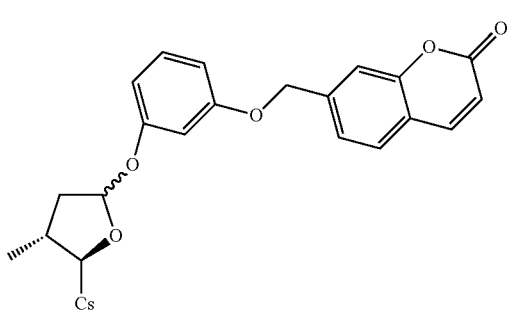
58A-o
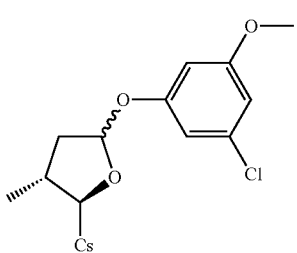
59A-o
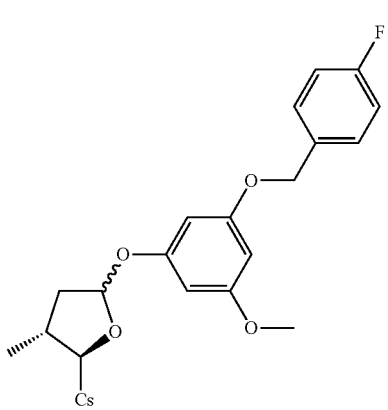
60A-o
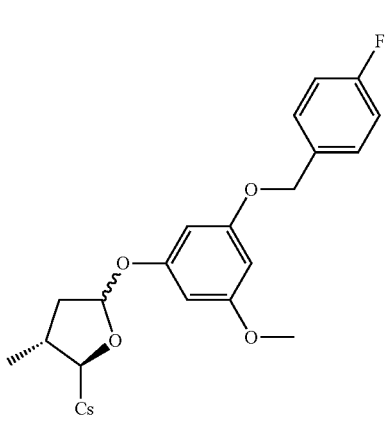
60A + B-o
(1:1.4)

61A-o
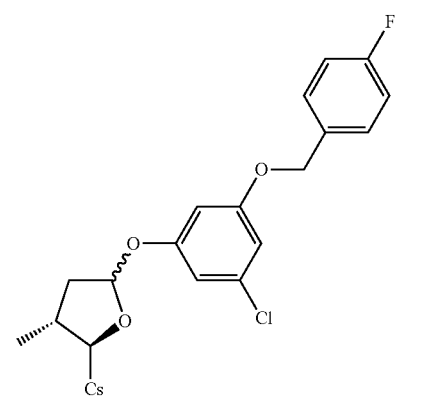
62-o
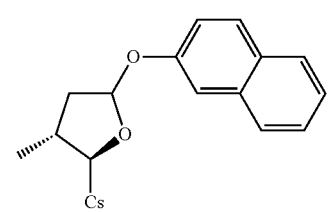
63-o
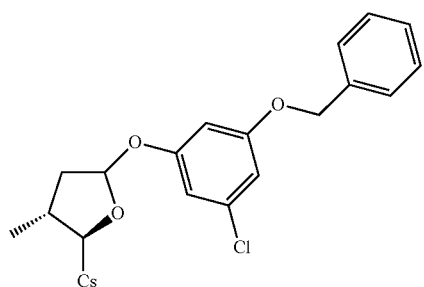
64-o
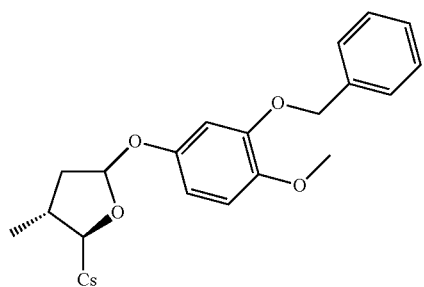
65-o
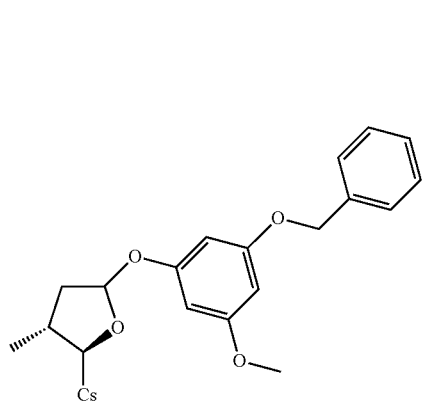
66-o
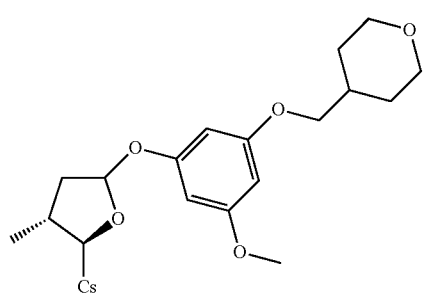
67-o
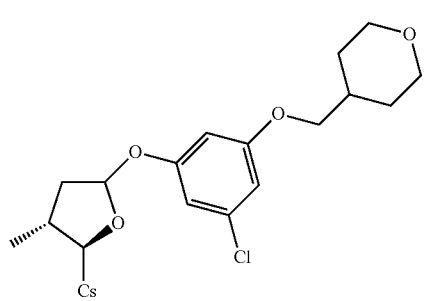
68-o
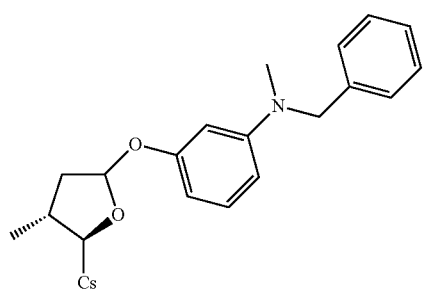
69-o
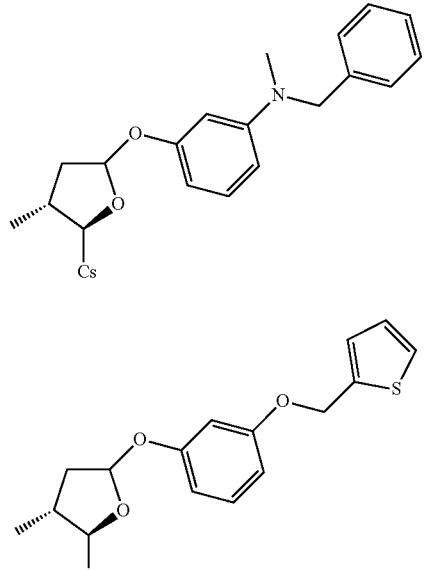
70-o
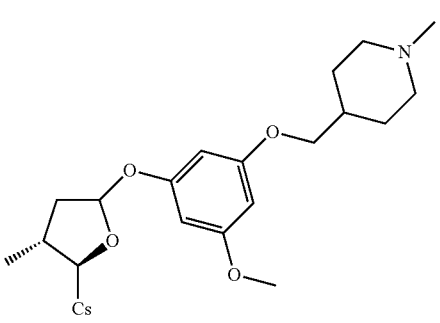

71-o 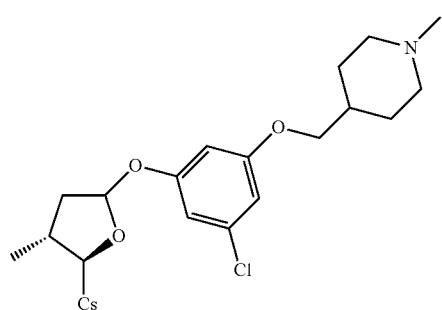
72-o 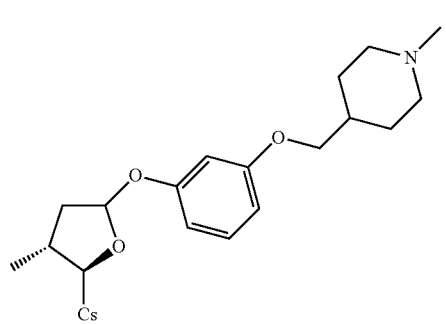
73-o 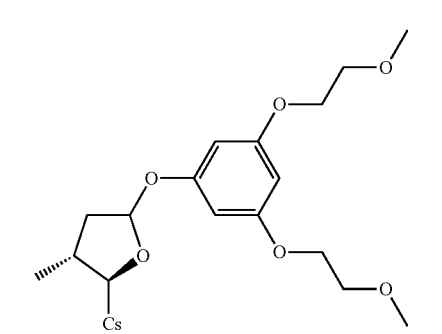
13. The compound of claim 1 having a benzyloxy structure selected from Table 3:
74A 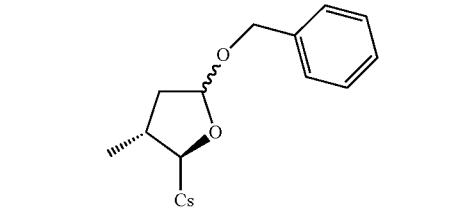
75A 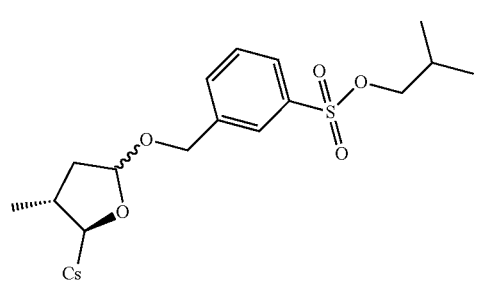
76A 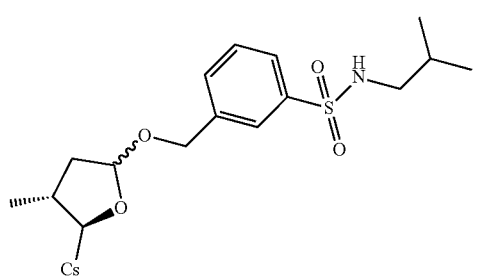
77A 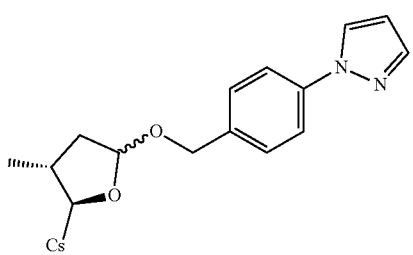
78A 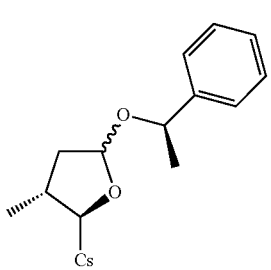
78B 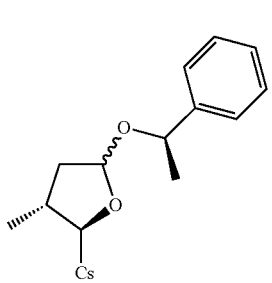
79A 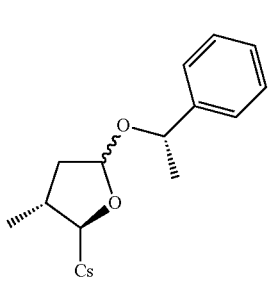
80A 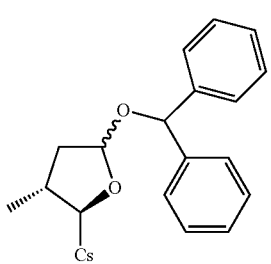

| | |
|---|---|
| 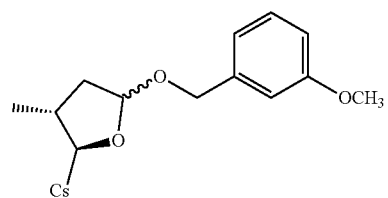 | 81A |
| 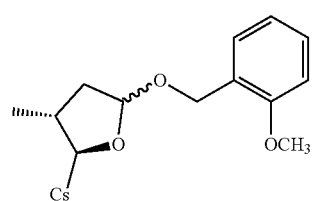 | 82A |
| 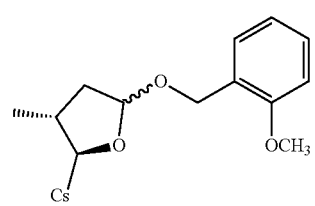 | 82B |
| 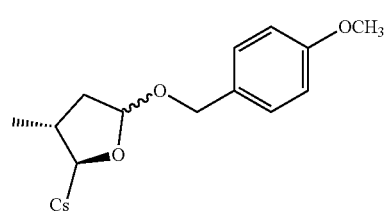 | 83A |
| 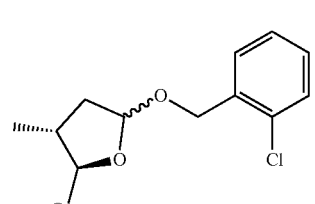 | 84A |
| 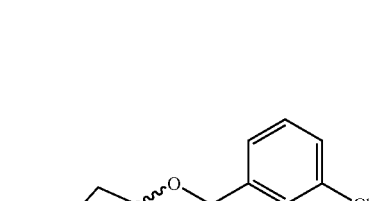 | 85A |
| 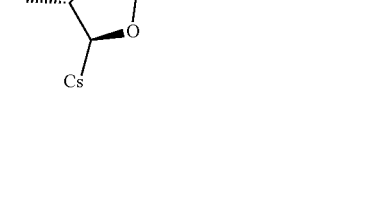 | 86A |
| 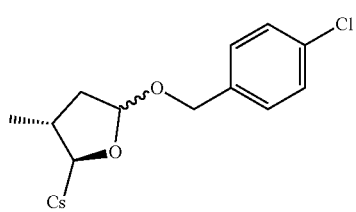 | 86B |
| 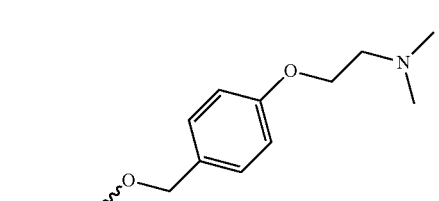 | 87A |
| 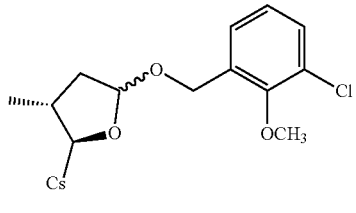 | 88A |
| 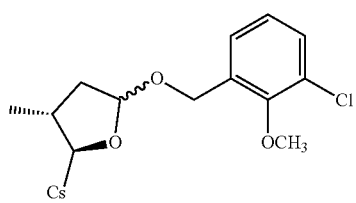 | 88B |
| 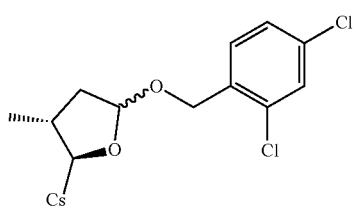 | 89A |
| 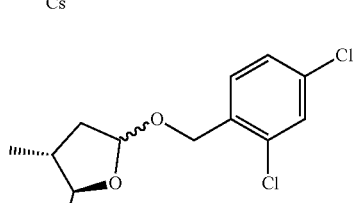 | 89B |
| 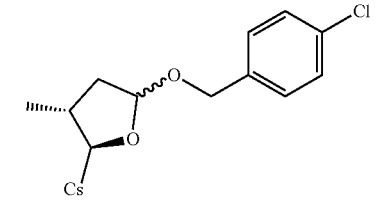 | 90A |

| | |
|---|---|
| 90B 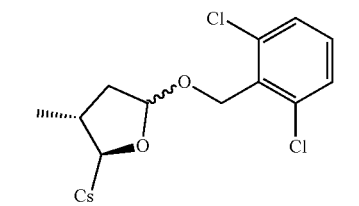 | 95 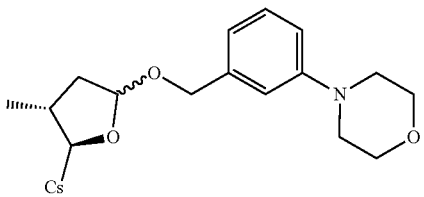 |
| 91A 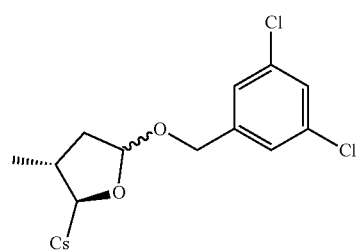 | 96A 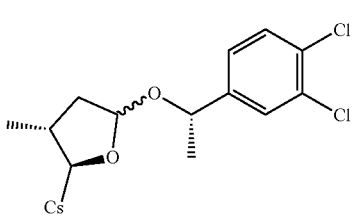 |
| 91B 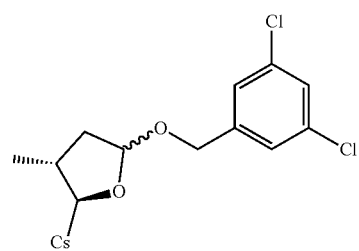 | 97A 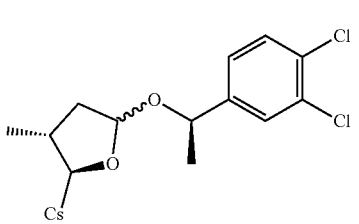 |
| 92A 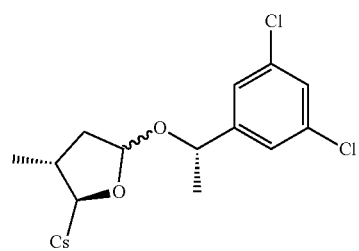 | 98A 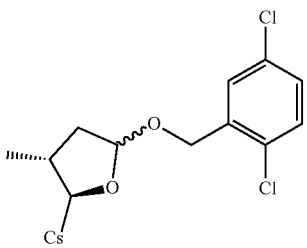 |
| 93A 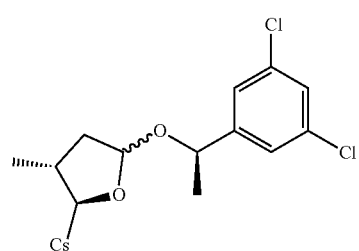 | |
| 94A 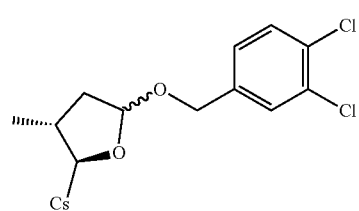 | 98A+B(1:1.1) |
| 94B 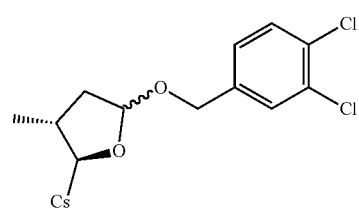 | 99A 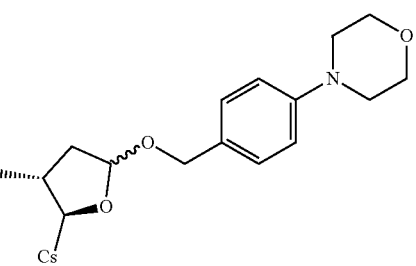 |

99A+B(1:1.1)
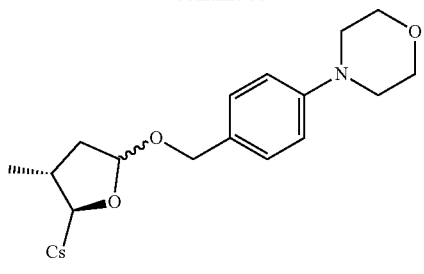
100A
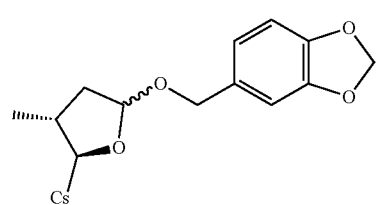
101A
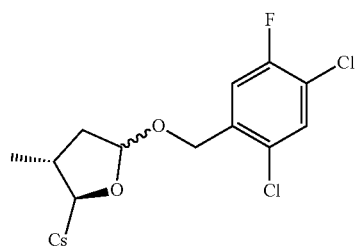
101B
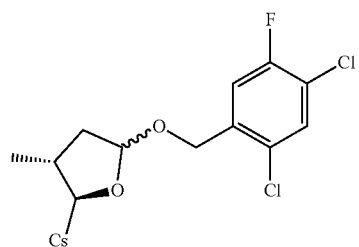
102
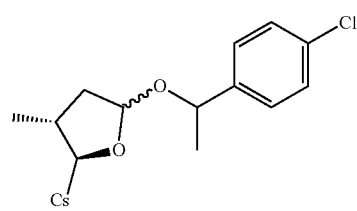
103
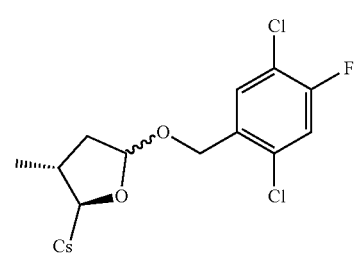
104
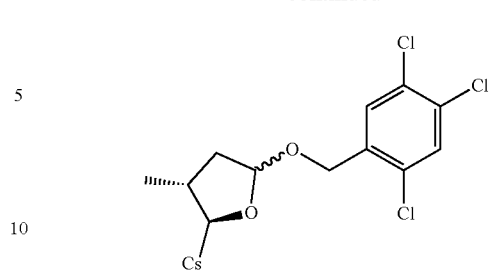
105
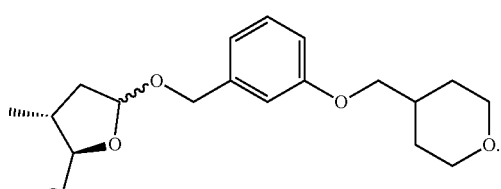
14. The compound of claim 1 having a benzylthiol structure selected from Table 4:
74A-s
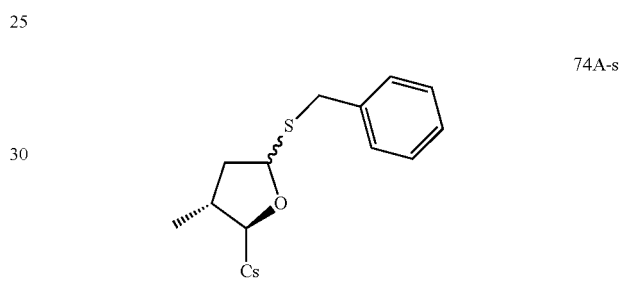
75A-s
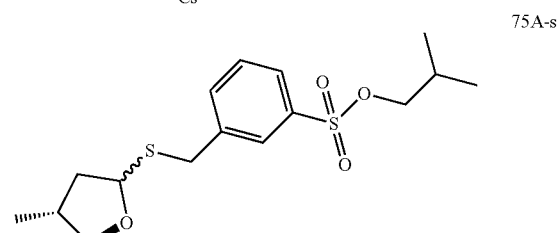
76A-s
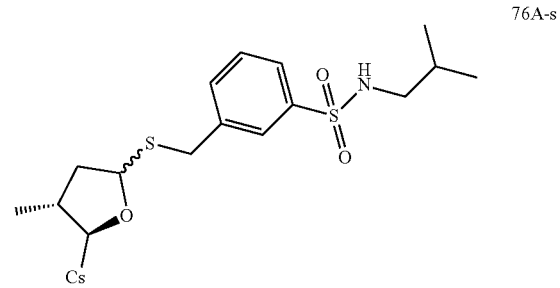
77A-s
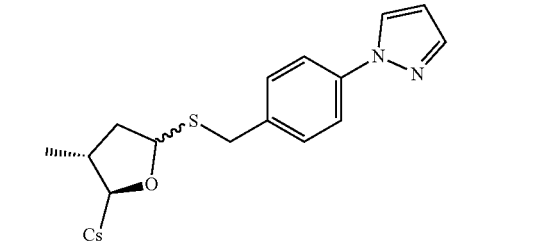

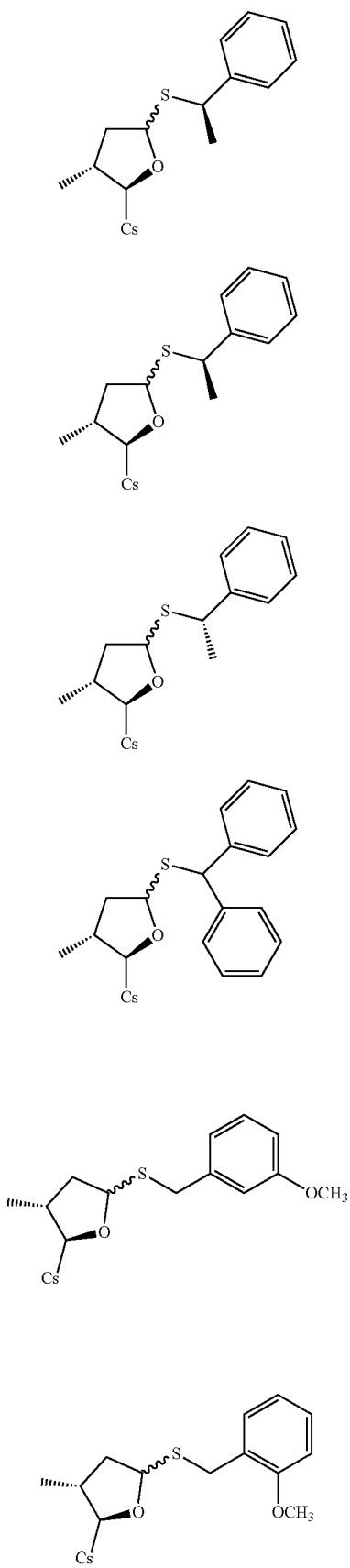
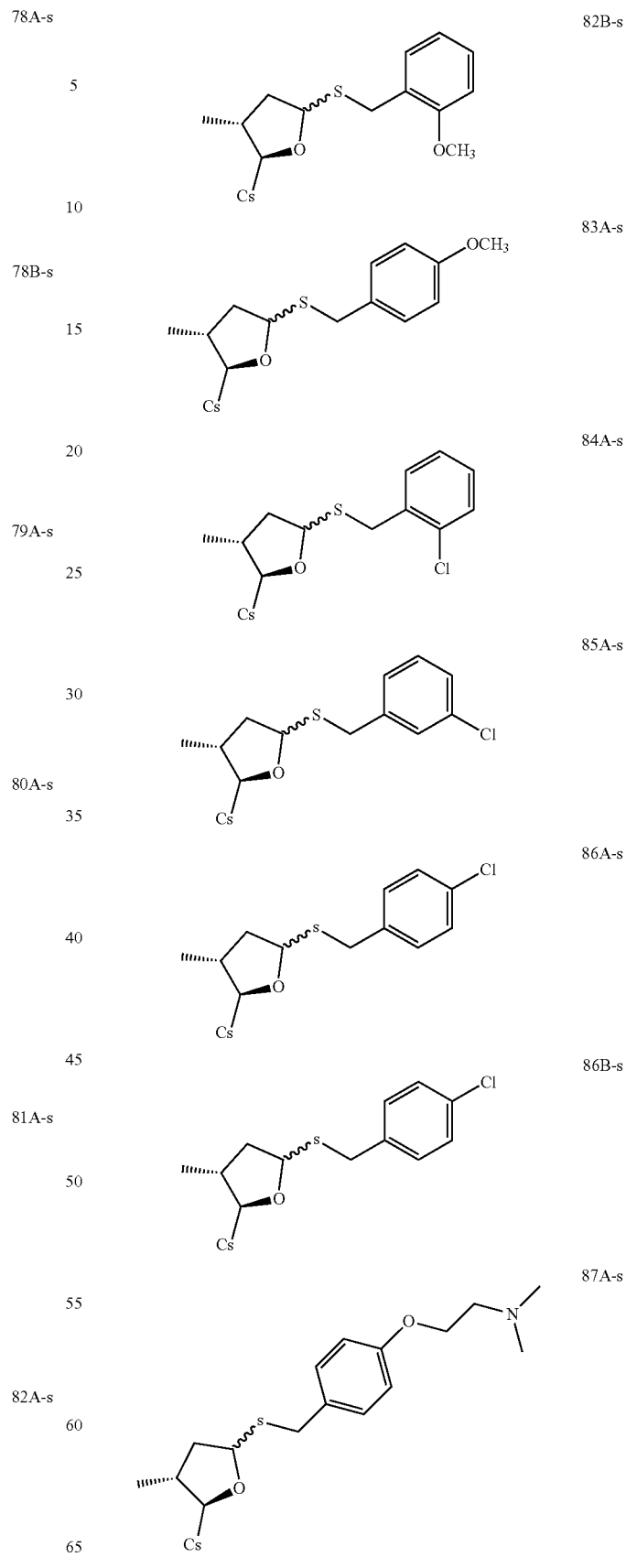

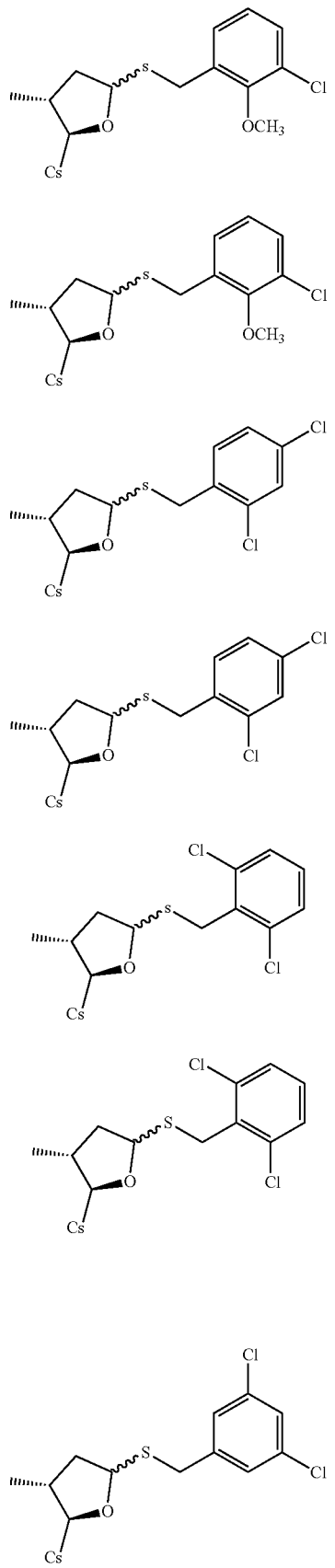
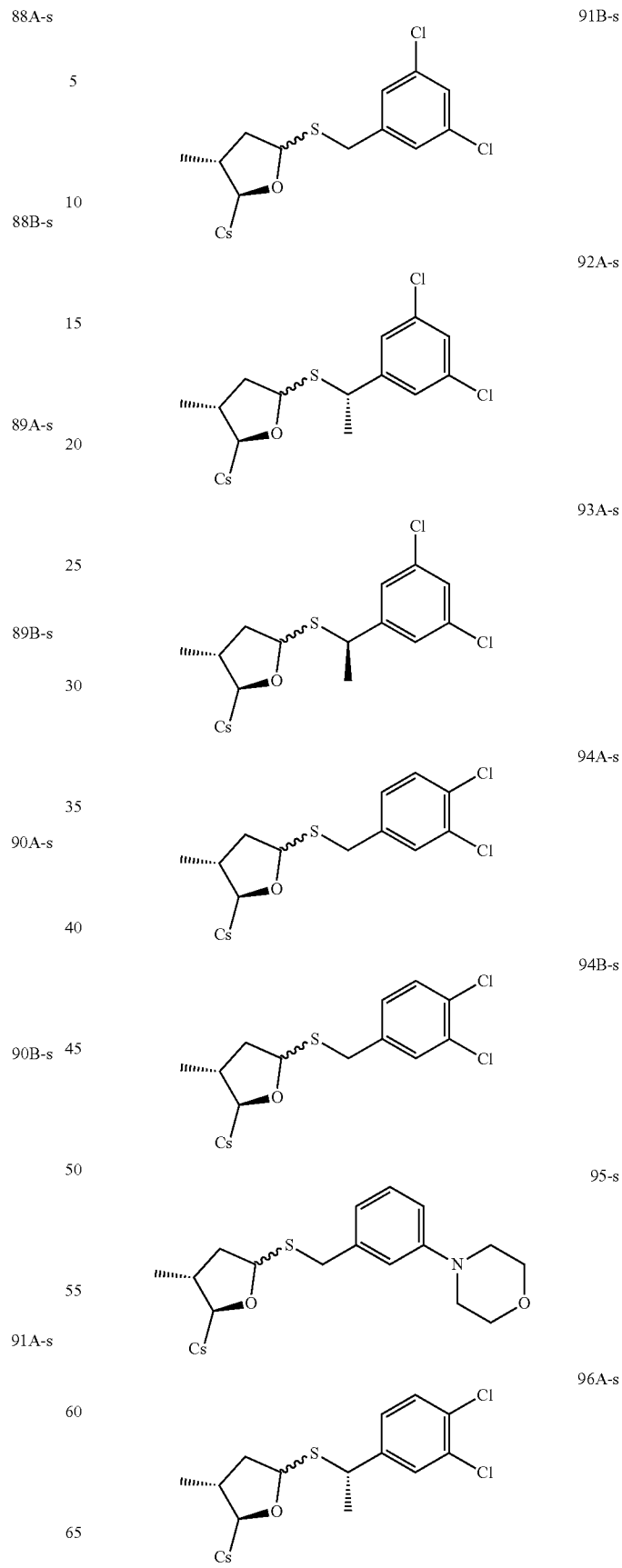

-continued 97A-s 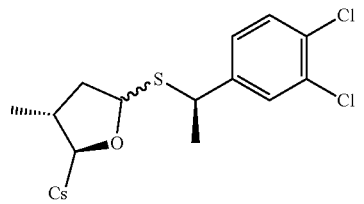

98A-s 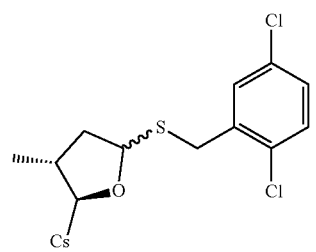

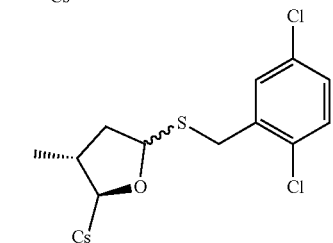
98A+B(1:1.1)-s 99A-s 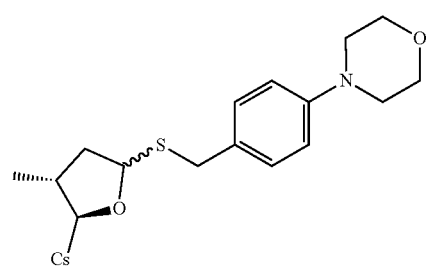

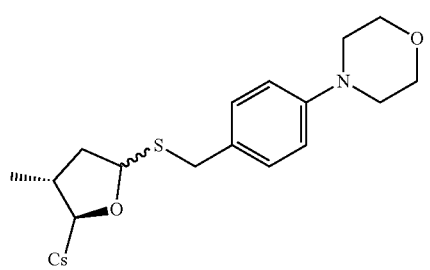
99A+B(1:1.1)

100A-s 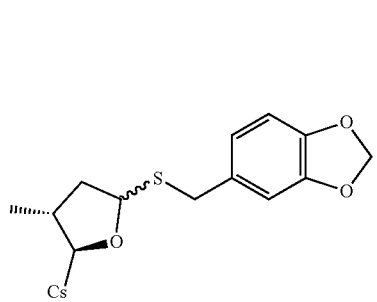

-continued 101A-s 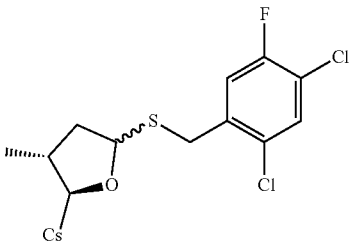

101B-s 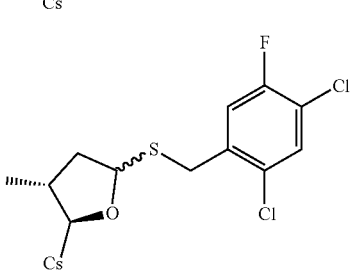

102-s 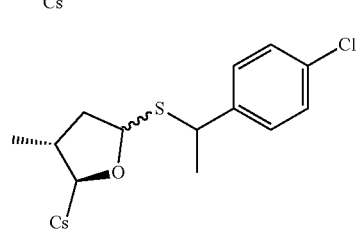

103-s 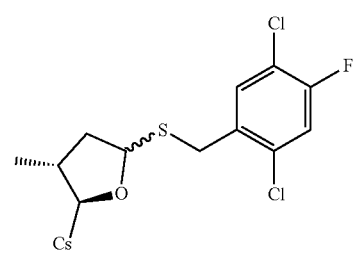

104-s 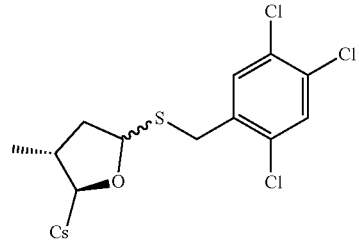

105-s 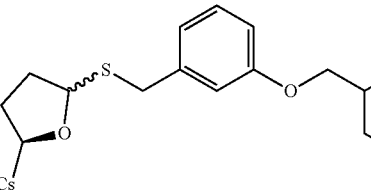

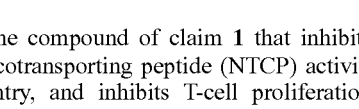

15. The compound of claim 1 that inhibits Na$^+$-Taurocholate cotransporting peptide (NTCP) activity or HBV or HDV entry, and inhibits T-cell proliferation and NFAT signaling pathway less than CsA.

16. The compound of claim 10 that inhibits Na$^+$-Taurocholate cotransporting peptide (NTCP) activity or HBV or HDV entry, and inhibits T-cell proliferation and NFAT signaling pathway less than CsA.

17. A pharmaceutical composition comprising a therapeutically effective amount of a compound of claim 1 in unit dosage form and one or more pharmaceutically acceptable excipients.

18. A pharmaceutical composition comprising a therapeutically effective amount of a compound of claim 1 and a different agent therapeutically active against HBV or HDV.

19. A method of using a compound or composition of claim 1 to treat hepatitis B virus (HBV) or hepatitis D virus (HDV) infection comprising: administering to a cell or person in need thereof an effective amount of a compound of claim 1, or a prodrug thereof.

20. A method of using a compound or composition of claim 1 to inhibit $Na^+$-Taurocholate cotransporting peptide (NTCP) comprising: administering to a cell or person in need thereof an effective amount of a compound of claim 1, or a prodrug thereof.

* * * * *